US008986696B2

(12) United States Patent
Brown et al.

(10) Patent No.: US 8,986,696 B2
(45) Date of Patent: Mar. 24, 2015

(54) TRANS-CAPSULAR ADMINISTRATION OF P38 MAP KINASE INHIBITORS INTO ORTHOPEDIC JOINTS

(75) Inventors: Laura J. Brown, Hamilton Square, NJ (US); Jeffery C. Geesin, Doylestown, PA (US); Carrie H. Fang, Pittstown, NJ (US); John J. Siekierka, Towaco, NJ (US)

(73) Assignee: DePuy Mitek, Inc., Raynham, MA (US)

( * ) Notice: Subject to any disclaimer, the term of this patent is extended or adjusted under 35 U.S.C. 154(b) by 1454 days.

(21) Appl. No.: 12/005,069

(22) Filed: Dec. 21, 2007

(65) Prior Publication Data

US 2009/0162376 A1 Jun. 25, 2009

(51) Int. Cl.
*A61K 31/4439* (2006.01)
*A61K 31/496* (2006.01)
*A61K 31/495* (2006.01)
*A61K 35/28* (2006.01)
*A61K 36/23* (2006.01)
*A61K 36/28* (2006.01)
*A61K 38/18* (2006.01)
*A61K 45/06* (2006.01)
*C07K 16/24* (2006.01)
*A61K 39/00* (2006.01)

(52) U.S. Cl.
CPC ........... *C07K 16/244* (2013.01); *A61K 31/4439* (2013.01); *A61K 31/496* (2013.01); *A61K 35/28* (2013.01); *A61K 36/23* (2013.01); *A61K 36/28* (2013.01); *A61K 38/1841* (2013.01); *A61K 45/06* (2013.01); *A61K 2039/505* (2013.01); *A61K 2300/00* (2013.01); *C07K 16/241* (2013.01); *C07K 2316/96* (2013.01)
USPC ................ 424/158.1; 424/145.1; 514/7.6

(58) Field of Classification Search
None
See application file for complete search history.

(56) References Cited

U.S. PATENT DOCUMENTS

| | | |
|---|---|---|
| 3,678,158 A | 7/1972 | Sussman |
| 4,341,867 A | 7/1982 | Johansen |
| 4,427,649 A | 1/1984 | Dingle et al. |
| 4,435,506 A | 3/1984 | Jackson et al. |
| 4,696,816 A | 9/1987 | Brown |
| 5,095,037 A | 3/1992 | Iwamitsu et al. |
| 5,116,964 A | 5/1992 | Capon et al. |
| 5,194,596 A | 3/1993 | Tischer et al. |
| 5,223,248 A | 6/1993 | McNamara et al. |
| 5,225,538 A | 7/1993 | Capon et al. |
| 5,231,024 A | 7/1993 | Moeller et al. |
| 5,258,371 A | 11/1993 | Golub et al. |
| 5,270,300 A | 12/1993 | Hunziker |
| 5,368,841 A | 11/1994 | Trauner et al. |
| 5,447,851 A | 9/1995 | Beutler et al. |
| 5,510,370 A | 4/1996 | Hock |
| 5,602,156 A | 2/1997 | Kohn et al. |
| 5,656,272 A | 8/1997 | Le et al. |
| 5,656,644 A | 8/1997 | Adams et al. |
| 5,728,396 A | 3/1998 | Peery et al. |
| 5,827,886 A | 10/1998 | Hersh |
| 5,833,984 A | 11/1998 | Eibl et al. |
| 5,842,477 A | 12/1998 | Naughton et al. |
| 5,942,499 A | 8/1999 | Radomsky |
| 5,965,583 A | 10/1999 | Beers et al. |
| 6,015,557 A | 1/2000 | Tobinick et al. |
| 6,049,026 A | 4/2000 | Muschler |
| 6,228,062 B1* | 5/2001 | Howell et al. ................ 604/171 |
| 6,277,969 B1 | 8/2001 | Le et al. |
| 6,284,471 B1 | 9/2001 | Le et al. |
| 6,288,089 B1* | 9/2001 | Zawada et al. ............... 514/341 |
| 6,294,170 B1 | 9/2001 | Boone et al. |
| 6,300,347 B1 | 10/2001 | Révész |
| 6,340,369 B1 | 1/2002 | Ferree |
| 6,352,557 B1 | 3/2002 | Ferree |
| 6,419,944 B2 | 7/2002 | Tobinick |
| 6,541,477 B2 | 4/2003 | Lewicki et al. |
| 6,554,830 B1 | 4/2003 | Chappius |
| 6,590,081 B1 | 7/2003 | Zhang |
| 6,593,310 B1 | 7/2003 | Cullis-Hill |
| 6,623,472 B1 | 9/2003 | Reincke et al. |
| 6,713,246 B1 | 3/2004 | Reinecke et al. |
| 6,756,215 B1 | 6/2004 | Wolfraim et al. |
| 7,067,144 B2 | 6/2006 | Demopulos et al. |
| 7,097,834 B1 | 8/2006 | Boyle |
| 7,344,716 B2 | 3/2008 | DiMauro et al. |
| 7,429,378 B2 | 9/2008 | Serhan et al. |
| 7,553,827 B2 | 6/2009 | Attawia et al. |
| 7,727,954 B2 | 6/2010 | McKay |
| 7,741,273 B2 | 6/2010 | McKay |
| 7,799,782 B2 | 9/2010 | Munson et al. |
| 8,067,397 B2 | 11/2011 | Attawia et al. |

(Continued)

FOREIGN PATENT DOCUMENTS

| | | |
|---|---|---|
| AU | 2003/263340 A1 | 3/2004 |
| EP | 0 218 868 A2 | 4/1987 |

(Continued)

OTHER PUBLICATIONS

Schaible et al, The role of proinflammatory cytokines in the generation and maintenance of joint pain, Ann. N.Y. Acad. Sci. 1193 (2010) 60-69.*
Bullington et al, Inhibitors of unactivated p38 MAP Kinase, Biorganic and Medicinal Chemistry Letters 16 (2006) 6102-6106.*
Bullington et al, Inhibitors of unactivated p38 MAP kinase, Bioorganic & Medicinal Chemistry Letters 16 (2006) 6102-6106.*
Abbas-Ghaleb, K., et al., "Preconcentration of Selenium Compounds on a Porous Graphitic Carbon Column in View of HPLC-ICP-AES Speciation Analysis," *Anal. Bioanal. Chem.*, 377: 1026-1031 (2003).
Ahn, N., et al., "Effect of Nutrient Concentration and OP-1 on the Metabolism of Intervertebral Disc: In Vitro Organ Culture Study," 28, *Abstracts of the 30th Annual Meeting of the International Society for the Study of the Lumbar Spine*, Vancouver, Canada (May 2003).

(Continued)

*Primary Examiner* — Maria Marvich
(74) *Attorney, Agent, or Firm* — Hamilton, Brook, Smith & Reynolds, P.C.

(57) ABSTRACT

The present invention relates to trans-capsularly administering into a diseased joint an inhibitor of p38 MAP kinase or a different therapeutic agent.

12 Claims, 69 Drawing Sheets

(56) References Cited

U.S. PATENT DOCUMENTS

| | | | |
|---|---|---|---|
| 8,361,467 B2 | 1/2013 | DiMauro et al. | |
| 8,481,064 B2 | 7/2013 | McKay | |
| 8,728,523 B2 | 5/2014 | Attawia et al. | |
| 2001/0006948 A1 | 7/2001 | Kang et al. | |
| 2001/0016195 A1 | 8/2001 | Tobinick | |
| 2001/0026801 A1 | 10/2001 | Tobinick | |
| 2002/0010471 A1 | 1/2002 | Wironen et al. | |
| 2002/0019351 A1 | 2/2002 | Ke et al. | |
| 2002/0026244 A1 | 2/2002 | Trieu | |
| 2002/0032155 A1 | 3/2002 | Ferree | |
| 2002/0082697 A1 | 6/2002 | Damien | |
| 2002/0107200 A1 | 8/2002 | Chang et al. | |
| 2002/0169162 A1 | 11/2002 | Smith et al. | |
| 2002/0198599 A1 | 12/2002 | Haldimann | |
| 2003/0007972 A1 | 1/2003 | Tobinick | |
| 2003/0008817 A1 | 1/2003 | Sander et al. | |
| 2003/0039651 A1 | 2/2003 | Olmarker | |
| 2003/0049256 A1 | 3/2003 | Tobinick | |
| 2003/0069639 A1 | 4/2003 | Sander et al. | |
| 2003/0134792 A1 | 7/2003 | Pike et al. | |
| 2003/0207827 A1 | 11/2003 | Boyle et al. | |
| 2003/0220692 A1 | 11/2003 | Shapiro et al. | |
| 2003/0235585 A1 | 12/2003 | Fischkoff et al. | |
| 2003/0235589 A1 | 12/2003 | Demopulos et al. | |
| 2004/0022864 A1 | 2/2004 | Freyman et al. | |
| 2004/0126372 A1 | 7/2004 | Banerjee et al. | |
| 2004/0193274 A1 | 9/2004 | Trieu | |
| 2004/0228853 A1 | 11/2004 | Serhan et al. | |
| 2004/0229786 A1 | 11/2004 | Attawia et al. | |
| 2004/0229878 A1 | 11/2004 | DiMauro et al. | |
| 2005/0025765 A1* | 2/2005 | DiMauro et al. | 424/145.1 |
| 2005/0038001 A1 | 2/2005 | Attawia et al. | |
| 2005/0054595 A1 | 3/2005 | Binette et al. | |
| 2005/0080113 A1* | 4/2005 | Ohkawa et al. | 514/342 |
| 2005/0090501 A1* | 4/2005 | Collis et al. | 514/252.01 |
| 2005/0100538 A1 | 5/2005 | Mohamed et al. | |
| 2005/0112091 A1 | 5/2005 | DiMauro et al. | |
| 2005/0208095 A1* | 9/2005 | Hunter et al. | 424/423 |
| 2005/0282783 A1 | 12/2005 | Bujoli et al. | |
| 2006/0122150 A1* | 6/2006 | Argentieri et al. | 514/54 |
| 2006/0193920 A1* | 8/2006 | Bosch et al. | 424/489 |
| 2006/0210552 A1 | 9/2006 | Demopulos et al. | |
| 2007/0237777 A1 | 10/2007 | DiMauro et al. | |
| 2007/0243228 A1* | 10/2007 | McKay | 424/426 |
| 2007/0269413 A1 | 11/2007 | Serhan et al. | |
| 2007/0299043 A1 | 12/2007 | Hunter et al. | |
| 2008/0019969 A1 | 1/2008 | Gorman | |
| 2008/0019970 A1 | 1/2008 | Gorman | |
| 2008/0019975 A1 | 1/2008 | Gorman | |
| 2008/0213261 A1 | 9/2008 | DiMauro et al. | |
| 2009/0068270 A1 | 3/2009 | Attawia et al. | |
| 2009/0155364 A1 | 6/2009 | Serhan et al. | |
| 2009/0162351 A1 | 6/2009 | Brown et al. | |
| 2009/0162376 A1 | 6/2009 | Brown et al. | |
| 2009/0175943 A1 | 7/2009 | Attawia et al. | |
| 2009/0324558 A1 | 12/2009 | Attawia et al. | |
| 2009/0324559 A1 | 12/2009 | Sakurada et al. | |
| 2010/0040609 A1 | 2/2010 | Gorman | |
| 2010/0047235 A1 | 2/2010 | Gorman | |
| 2010/0093829 A1 | 4/2010 | Gorman | |
| 2010/0158800 A1 | 6/2010 | McKay | |
| 2010/0189757 A1 | 7/2010 | McKay | |

FOREIGN PATENT DOCUMENTS

| | | |
|---|---|---|
| EP | 0 288 088 B1 | 10/1988 |
| EP | 0 438 234 A1 | 7/1991 |
| EP | 0 950 417 A2 | 10/1999 |
| EP | 1 133 995 A2 | 9/2001 |
| EP | 1 153 607 A2 | 11/2001 |
| EP | 1 464 307 A1 | 10/2004 |
| WO | WO 91/02078 A1 | 2/1991 |
| WO | WO 92/07076 A1 | 4/1992 |
| WO | WO 92/16553 A1 | 10/1992 |
| WO | WO 93/16099 A2 | 8/1993 |
| WO | WO 97/28828 A1 | 8/1997 |
| WO | WO 98/24477 A1 | 6/1998 |
| WO | WO 99/45923 A1 | 9/1999 |
| WO | WO 00/18409 | 4/2000 |
| WO | WO 00/50079 | 8/2000 |
| WO | WO 01/85179 A2 | 11/2001 |
| WO | WO 02/057240 A1 | 7/2002 |
| WO | WO 02/100387 A1 | 12/2002 |
| WO | WO 03/000190 A2 | 1/2003 |
| WO | WO 2004/022078 A1 | 3/2004 |
| WO | WO 2004/039248 | 5/2004 |
| WO | WO 2005/000283 A2 | 1/2005 |
| WO | WO 2005/011689 A2 | 2/2005 |
| WO | WO 2005/049055 A1 | 6/2005 |
| WO | WO 2005/053795 A2 | 6/2005 |
| WO | WO 2005/110276 A1 | 11/2005 |
| WO | WO 2006/031376 A2 | 3/2006 |
| WO | WO 2007/121288 | 10/2007 |

OTHER PUBLICATIONS

Alini, M., et al., "A Biological Approach in Treating Disc Degeneration: Not for Today, but Maybe for Tomorrow," *Eur. Spine J.*, 11(Supp.2): S215-S220 (2002).

Allali, F., et al., "Increase in Bone Mineral Density of Patients with Spondyloarthropathy Treated with Anti-tumour Necrosis Factor β," *Ann. Rheum. Dis.*, 62: 347-349 (2003).

Andonopoulos, A., et al., "Intra-articular Anti-tumor Necrosis Factor α Antibody in Recalcitrant Arthritis of Behcet's Disease," *Clinical and Experimental Rheumatology*, 21(4 Suppl 30): S57-S58 (Jul.-Aug. 2003).

Aoki, Y., et al., "Local Application of Disc-related Cytokines on Spinal Nerve Roots," *Spine*, 27(15): 1614-1617 (2002).

Arai, I., et al., "Pretreatment with Loxoprofen Sodium, 6-OHDA or Anti TNF-alpha Antibody Reduce Fos-like Immunoreactivity in Rat Experimental Lumber Disc Herniation," 111, *Abstracts of the 30th Annual Meeting of the International Society for the Study of the Lumbar Spine*, Vancouver, Canada (May 2003).

Ariga, K., et al., "Mechanical Stress-induced Apoptosis of Endplate Chondrocytes in Organ-cultured Mouse Intervertebral Discs," *Spine*, 28(14): 1528-1533 (2003).

Ashkenazi, A., et al., "Protection Against Endotoxic Shock by a Tumor Necrosis Factor Receptor Immunoadhesin," *Proc. Natl. Acad. Sci. USA*, 88: 10535-10539 (1991).

Awasthi, Y., et al., "Purification and Properties of Human Erythrocyte Glutathione Peroxidase," *J.Biol. Chem.*, 250(13): 5144-5149 (1975).

Baker, D., et al., "Control of Established Experimental Allergic Encephalomyelitis by Inhibition of Tumor Necrosis Factor (TNF) Activity Within the Central Nervous System Using Monoclonal Antibodies and TNF Receptor-immunoglobulin Fusion Proteins," *Eur. J. Immunol.*, 24: 2040-2048 (1994).

Benjamin, L., et al., "A Plasticity Window for Blood Vessel Remodelling is Defined by Pericyte Coverage of the Preformed Endothelial Network and is Regulated by PDGF-B and VEGF," *Development*, 125: 1591-1598 (1998).

Biemond, P., et al., "Protective Factors Against Oxygen Free Radicals and Hydrogen Peroxide in Rheumatoid Arthritis Synovial Fluid," *Arthritis Rheum.*, 27(7): 760-765 (1984).

Biskobing, D., "Novel Therapies for Osteoporosis," *Expert Opinion Invest. Drugs*, 12(4): 611-621 (2003).

Boehm, J., et al., "New Inhibitors of p38 Kinase," *Exp. Opin, Ther. Patents*, 10(1): 25-37 (2000).

Bokarewa, M., et al., "Local Infusion of Infliximab for the Treatment of Acute Joint Inflammation," *Ann. Rheum Dis.*, 62: 783-784 (2003).

Braun, J., et al., "Anti-tumour Necrosis Factor α Therapy for Ankylosing Spondylitis: International Experience," *Ann. Rheum. Dis.*, 61(Supp. III): iii51-iii60 (2002).

Braun, J., et al., "Overview of the Use of the Anti-TNF Agent Infliximab in Chronic Inflammatory Diseases," *Expert Opin. Biol. Ther.*, 3(1): 141-168 (2003).

Bringman, T., et al., "Monoclonal Antibodies to Human Tumor Necrosis Factors Alpha and Beta: Application for Affinity Purification, Immunoassays, and as Structural Probes," *Hybridoma*, 6(5): 489-507 (1987).

(56) References Cited

OTHER PUBLICATIONS

Brown, K., et al., "Gelatin/Chondroitin 6-sulfate Microspheres for the Delivery of Therapeutic Proteins to the Joint," *Arthritis. & Rheum.*, 41(12): 2185-2195 (1998).
Burke, J., et al., "Human Nucleus Pulposus Secretes Transforming Growth Factor Beta-1 and Basic Fibroblast Growth Factor," 189, *Abstracts of the 30th Annual Meeting of the International Society for the Study of the Lumbar Spine*, Vancouver, Canada (May 2003).
Burke, J., et al., "Intervertebral Discs Which Cause Low Back Pain Secrete High Levels of Proinflammatory Mediators," *J. of Bone and Joint Surg.* [*Br*], 84-B: 196-201 (2002).
Butler, D., et al., "TNF Receptor Fusion Proteins are Effective Inhibitors of TNF-mediated Cytotoxicity on Human KYM-1D4 Rhabdomyosarcoma Cells," *Cytokine*, 6(6): 616-623 (1994).
Capon, D., et al., "Designing CD4 Immunoadhesins for AIDS Therapy," *Nature*, 337: 525-531 (1989).
Cardone, D., et al., "Diagnostic and Therapeutic Injection of the Hip and Knee," *Family Medicine*, 67(10): 2147-2152 (2003).
Castro, R., et al., "Failure of Bone Marrow Cells to Transdifferentiate Into Neural Cells in Vivo," *Science*, 297: 1299 (2002).
Čeponis, A., et al., "Effects of Low-dose, Noncytotoxic, Intraarticular Liposomal Clodronate on Development of Erosions and Proteoglycan Loss in Established Antigen-induced Arthritis in Rabbits," *Arthritis and Rheum.*, 44(8): 1908-1916 (2001).
Chae, H., et al., "The p38 Mitogen-activated Protein Kinase Pathway Regulates Interleukin-6 Synthesis in Response to Tumor Necrosis Factor in Osteoblasts," *Bone*, 28(1): 45-53 (2001).
Chan, J., et al., "Intraarticular Gene Transfer of TNFR:Fc Suppresses Experimental Arthritis with Reduced Systemic Distribution of the Gene Product," *Mol. Ther.*, 6(6): 727-736 (2002).
Cirillo, P., et al., "The Non-diaryl Heterocycle Classes of p38 MAP Kinase Inhibitors," *Current Topics in Medicinal Chemistry*, 2: 1021-1035 (2002).
CN 1 569 039 A (Niu X) Jan. 26, 2005 (abstract) World Patents Index [online]. London, GB: Derwent Publications, Ltd., Week 200577, Class B04, Accession No. 2005-749289.
CN 1 647 808 A (Zhou C) Aug. 3, 2005 (abstract) World Patents Index [online]. London, GB: Derwent Publications, Ltd., Week 200621, Class B04, Accession No. 2006-194507.
Connolly, J., et al., "Development of an Osteogenic Bone-marrow Preparation," *The Journal of Bone and Joint Surgery, Inc.*, 71-A(5): 684-691 (1989).
Conti, F., et al., "Successful Treatment with Intraarticular Infliximab for Resistant Knee Monarthritis in a Patient with Spondylarthropathy," *Arthritis & Rheumatism*, 52(4): 1224-1226 (2005).
Corcoran, A., et al., "Characterization of Ligand Binding by the Human p55 Tumour-necrosis-factor Receptor," *Eur. J. Biochem.*, 223: 831-840 (1994).
Cornefjord, M., et al., "Cerebrospinal Fluid Biomarkers in Experimental Spinal Nerve Root Injury," 38, *Abstracts of the 30th Annual Meeting of the International Society for the Study of the Lumbar Spine*, Vancouver, Canada (May 2003).
Crandall, C., "Combination Treatment of Osteoporosis: a Clinical Review," *J. of Women's Health & Gender-Based Medicine*, 11(3): 211-224 (2002).
Crevensten, G., et al., "Intervertebral Disc Cell Therapy for Regeneration: Mesenchymal Stem Cell Implantation in Rat Intervertebral Discs," *Ann. Biomed. Eng.*, 32(3): 430-434 (2004).
Dayer, J., "The Pivotal Role of Interleukin-1 in the Clinical Manifestations of Rheumatoid Arthritis," *Rheumatology*, Oxford University Press, London, GB, 42(Suppl 2): ii3-ii10 (2003).
Desai, S., et al., "Coated Microwell Plate-based Affinity Purification of Antigens," *Anal. Biochem.*, 328: 162-165 (2004).
DeSantis, A., et al., "Current and Emerging Therapies in Osteoporosis," *Expert Opin. Pharmacother.*, 3(7): 835-843 (2002).
Diwan, A., et al., "Current Concepts in Intervertebral Disk Restoration," *Tissue Engineering in Orthopedic Surgery*, 31(3): 453-464 (2000).
Edwards, S., et al., "Radiographic Assessment of Posterolateral Spine Fusion With and Without Platelet Rich Plasma," 117, *Abstracts of the 30th Annual Meeting of the International Society for the Study of the Lumbar Spine*, Vancouver, Canada (May 2003).
El-Khoury, G., et al., "Percutaneous Procedures for the Diagnosis and Treatment of Lower Back Pain: Diskography, Facet-joint Injection, and Epidural Injection," *AJR Am. J. Roentgenol.*, 157(4): 685-691 (1991).
Engelmann, H., et al., "Two Tumor Necrosis Factor-binding Proteins Purified From Human Urine," *J. Biol. Chem.*, 265(3): 1531-1536 (1990).
Eustice, C., et al., "What is Viscosupplementation?" [online] <http://arthritis.com/od/kneetreatments/g/viscosupplement_p.htm, Dec. 9, 2005>.
Ezra, A., et al., "Administration Routes and Delivery Systems of Bisphosphonates for the Treatment of Bone Resorption," *Adv. Drug Del. Rev.*, 42: 175-195 (2000).
Fendly, B., et al., "Murine Monoclonal Antibodies Defining Neutralizing Epitopes on Tumor Necrosis Factor," *Hybridoma*, 6: 359-370 (1987).
Földes, I., et al., "Trace Elements in Tissues of Normal and Vitamin $D_2$-treated Rats," *ACTA Biol. Acad. Sci. Hung.*, 26(3-4): 141-150 (1975).
Frain, J., et al., "Use of cDNA Microarrays to Investigate Cytokine Expression in Intervertebral Disc Degeneration," 126, *Abstracts of the 30th Annual Meeting of the International Society for the Study of the Lumbar Spine*, Vancouver, Canada (May 2003).
Gabay, C., "IL-1 Trap," *Curr. Opin. Invest. Drugs, Curr. Drugs*, London, GB, 4(5): 593-597 (2003).
Ganey, T., et al., "A Potential Role for Cell-based Therapeutics in the Treatment of Intervertebral Disc Herniation," *Eur. Spine J.*, 11(Suppl. 2): S206-S214 (2002).
Goodman, S., et al., "Effects of Local Infusion of TGFβ on Bone Ingrowth in Rabbit Chambers," *J. Biomed. Mat. Res.* (*Appl Biomater*), 53: 475-479 (2000).
Gordon, J., et al., "Metalloproteinase Inhibitors as Therapeutics," *Clin. Exp. Rheumatol.*, 11(Suppl. 8): S91-S94 (1993).
Gori, A., et al., "Tumor Necrosis Factor-α Increased Production During Thalidomide Treatment in Patients With Tuberculosis and Human Immunodeficiency Virus Coinfection," *The Journal of Infectious Diseases*, 182: 639 (2000).
Goupille, P., et al., "Matrix Metalloproteinases: the Clue to Intervertebral Disc Degeneration?," *Spine*, 23(14): 1612-1626 (1998).
Guillen, C., et al., "The Effects of Local Administration of Lactoferrin on Inflammation in Murine Autoimmune and Infectious Arthritis," *Arthritis Rheum.*, 43(9): 2073-2080 (2000).
Haro, H., et al., "Matrix Metalloproteinase-7-dependent Release of Tumor Necrosis Factor-α in a Model of Herniated Disc Resorption," *J. Clin. Invest.*, 105(2): 143-150 (2000).
Hawks, D., "Alternative Medicine: Musculoskeletal System," *Clin. Tech. Small Anim. Pract.*, 17(1): 41-49 (2002).
Hayashida, K., et al., "Lactoferrin Enhances Peripheral Opioid-mediated Antinociception via Nitric Oxide in Rats," *Eur. J. Pharmacol.*, 484: 175-181 (2004).
Hayashida, K., et al., "Oral Administration of Lactoferrin Inhibits Inflammation and Nociception in Rat Adjuvant-induced Arthritis," *J. Vet. Med. Sci.*, 66(2): 149-154(2004).
Hirai, M., et al., "Production and Characterization of Monoclonal Antibodies to Human Tumor Necrosis Factor," *J. Immunol. Meth.*, 96: 57-62 (1987).
Hunter, C., et al., "Functional Behavior of Notochordal Cell Clusters in the Canine Nucleus Pulposus: Cell Communication and Survival," 70, *Abstracts of the 30th Annual Meeting of the International Society for the Study of the Lumbar Spine*, Vancouver, Canada (May 2003).
*Hydrogels*, Encyclopedia of Polymer Science and Technology, vol. 2, (Wiley and Sons, 2003).
Igarashi, A., et al., "Inflammatory Cytokines Release From Facet Joint Tissue in Degenerative Lumbar Disorders," 262, *Abstracts of the 30th Annual Meeting of the International Society for the Study of the Lumbar Spine*, Vancouver, Canada (May 2003).
Imai, Y., et al., "Effect of Recombinant Human Osteogenic Protein-1 on Extracellular Matrix Metabolism by Human Annulus Fibrosus

(56) References Cited

OTHER PUBLICATIONS and Nucleus Pulposus Cells," 205, *Abstracts of the 30th Annual Meeting of the International Society for the Study of the Lumbar Spine*, Vancouver, Canada (May 2003).
Imai, Y., et al., "The Quantification of Cytokine-induced Matrix Catabolism in Tissue Engeneered Intervertebral Discs," 67, *Abstracts of the 30th Annual Meeting of the International Society for the Study of the Lumbar Spine*, Vancouver, Canada (May 2003).
Inui, Y., et al., "Fas-ligand Expression on Nucleus Pulposus Cells Begins in Developing Embryo," 42, *Abstracts of the 30th Annual Meeting of the International Society for the Study of the Lumbar Spine*, Vancouver, Canada (May 2003).
Johnson, W., et al., "Collagenase Inhibitors: Their Design and Potential Therapeutic Use," *J. Enzyme Inhib.*, 2: 1-22 (1987).
Kamanh, A., et al., "Plasma Lipid Peroxidation and Antioxidant Levels in Patients with Rheumatoid Arthritis," *Cell Biochem. Funct.*, 22: 53-57 (2004).
Karppinen, J., et al., "Tumor Necrosis Factor-α Monoclonal Antibody, Infliximab, Used to Manage Severe Sciatica," *Spine*, 28(8): 750-754 (2003).
Kato, H., et al., "The Effect of IL-1 on the Rabbit Intervertebral Disc in Vivo," 199, *Abstracts of the 30th Annual Meeting of the International Society for the Study of the Lumbar Spine*, Vancouver, Canada (May 2003).
Kawakami, M., et al., "Possible Mechanism of Painful Radiculopathy in Lumbar Disc Herniation," *Clin. Orthop.*, 351: 241-251 (1998).
Kawakami, M., et al., "Role of IL-8, MCP-1 and PH in Neuropathic Pain Enhanced by Degenerative Nucleus Pulposus," 127, *Abstracts of the 30th Annual Meeting of the International Society for the Study of the Lumbar Spine*, Vancouver, Canada (May 2003).
Khot, A., et al., "The Use of Intradiscal Steroid Therapy for Lumbar Spinal Discogenic Pain—A Randomized Controlled Trial," *Spine*, 29(8): 833-837 (2004).
Kilic, B., et al., "Effects of Intra-articular Vitamin E and Corticosteroid Injection in Experimental Hemarthrosis in Rabbits," *Pediatr. Hematol. Oncol.*, 15(4): 339-346 (1998).
Kim, S., et al., "Ex Vivo Gene Delivery of IL-1Ra and Soluble TNF Receptor Confers a Distal Synergistic Therapeutic Effect in Antigen-induced Arthritis," *Mol. Ther.*, 6(5): 591-600 (2002).
Kimble, R., et al., "Estrogen Deficiency Increases the Ability of Stromal Cells to Support Murine Osteoclastogenesis Via an InterLeukin-1 and Tumor Necrosis Factor-mediated Stimulation of Macrophage Colony-stimulating Factor Production," *J. Biol. Chem.*, 271(46): 28890-28897 (1996).
Kimble, R., et al., "The Functional Block of TNF but Not of IL-6 Prevents Bone Loss in Ovariectomized Mice," *J. Bone Min. Res.*, 12(6): 935-941 (1997).
Koch, H., et al., "Spontaneous Secretion of Interleukin 1 Receptor Antagonist (IL-1Ra) by Cells Isolated from Herniated Lumbar Discal Tissue After Discectomy," *Cytokine*, 10(9): 703-705 (1998).
Kolls, J., et al., "Prolonged and Effective Blockade of Tumor Necrosis Factor Activity Through Adenovirus-mediated Gene Transfer," *Proc. Natl. Acad. Sci. USA*, 91: 215-219 (1994).
Korhonen, T., et al., "Efficacy of Infliximab for Disc Herniation-induced Sciatica One-year Follow-up," 14, *Abstracts of the 30th Annual Meeting of the International Society for the Study of the Lumbar Spine*, Vancouver, Canada (May 2003).
Kozbor, D., et al., "The Production of Monoclonal Antibodies from Human Lymphocytes," *Immunol. Today*, 4(3): 72-79 (1983).
Kurz, B., et al., "Dietary Vitamins and Selenium Diminish the Development of Mechanically Induced Osteoarthritis and Increase the Expression of Antioxidative Enzymes in the Knee Joint of STR/1N Mice," *Osteoarthritis Cartilage*, 10: 119-126 (2002).
Kwon, U., et al., "Dexamethasone Stimulates Cellular Proliferation While Downregulates Matrix Synthesis in Intervertebral Disc Cells," 29, *Abstracts of the 30th Annual Meeting of the International Society for the Study of the Lumbar Spine*, Vancouver, Canada (May 2003).
Lane, N., et al., "Basic Fibroblast Growth Factor Forms New Trabeculae that Physically Connect with Pre-existing Trabeculae, and This New Bone is Maintained With an Anti-resorptive Agent and Enhanced with an Anabolic Agent in an Osteopenic Rat Model," *Osteoporos. Int.*, 14: 374-382 (2003).
LaVan, D., et al., "Small-scale Systems for in Vivo Drug Delivery," *Nature Biotechnology*, 21(10): 1184-1191 (2003).
Le Maitre, C., et al., "Expression of the IL-1 Family in Human Intervertebral Disc," 217, *Abstracts of the 30th Annual Meeting of the International Society for the Study of the Lumbar Spine*, Vancouver, Canada (May 2003).
Le Maitre, C., et al., "Response of Human Intervertebral Disc Cells to IL-1," 216, *Abstracts of the 30th Annual Meeting of the International Society for the Study of the Lumbar Spine*, Vancouver, Canada (May 2003).
Le Visage, C., et al., "Interaction of Human Mescenchymal Stem Cells with Disc Cells: Changes in Biosynthesis of Extracellular Matrix," 25, *Abstracts of the 30th Annual Meeting of the International Society for the Study of the Lumbar Spine*, Vancouver, Canada (May 2003).
Lee, C., et al., "A Single Period of Hyperphysiologic Stretch Induces IL-6, TGF-beta and Cell Proliferation in Anulus Fibrosus Cells," 215, *Abstracts of the 30th Annual Meeting of the International Society for the Study of the Lumbar Spine*, Vancouver, Canada (May 2003).
Lee, J., et al., "Inhibition of p38 MAP Kinase as a Therapeutic Strategy," *Immunopharmacology*, 47: 185-201 (2000).
Lehman, T., et al., "Thalidomide Theraphy for Recalcitrant Systemic Onset Juvenile Rheumatoid Arthritis," *J. Pediatrics*, 140: 125-7 (2002).
Lesslauer, W., et al., "Recombinant Soluble Tumor Necrosis Factor Receptor Proteins Protect Mice From Lipopolysaccharide-induced Lethality," *Eur. J. Immunol.*, 21: 2883-2886 (1991).
Li, J., et al., "The Effects of Bone Morphogenetic Protein 2 (BMP-2) and Cartilage-derived Morphogentic Protein 2 (CDMP-2) on Aggrecan Gene Expression in Chondrocytes," 30, *Abstracts of the 30th Annual Meeting of the International Society for the Study of the Lumbar Spine*, Vancouver, Canada (May 2003).
Liang, C., et al., "Production and Characterization of Monoclonal Antibodies Against Recombinant Human Tumor Necrosis Factor/Cachectin," *Biochem. Biophys. Res. Comm.*, 137: 847-854 (1986).
Loetscher, H., et al., "Molecular Cloning and Expression of the Human 55 kd Tumor Necrosis Factor Receptor," *Cell*, 61: 351-359 (1990).
Lotz, J., et al., "Cytokines in Normal, Degenerated, and Nucleoplasty-treated Porcine Discs," 157, *Abstracts of the 30th Annual Meeting of the International Society for the Study of the Lumbar Spine*, Vancouver, Canada (May 2003).
Lubberts, E., et al., "Intra-articular IL-10 Gene Transfer Regulates the Expression of Collagen-induced Arthritis (CIA) in the Knee and Ipsilateral Paw," *Clin. Exp. Immunol.*, 120: 375-383 (2000).
Maddipati, K., et al., "Characterization of the Major Hydroperoxide-reducing Activity of Human Plasma," *J. Biol. Chem.*, 262(36): 17398-17403 (1987).
Maeda, S., et al., "Changes With Age in Proteoglycan Synthesis in Cells Cultured in Vitro From the Inner and Outer Rabbit Annulus Fibrosus," *Spine*, 25(2): 166-169 (2000).
Marriott, J., et al., "CC-3052: A Water-soluble Analog of Thalidomide and Potent Inhibitor of Activation-induced TNF-α Production," *J. Immunol.*, 161: 4236-4243 (1998).
Martinez, J., et al., "Blood Platelet Glutathione Peroxidase: Some Properties and Partial Purification," *Thromb. Res.*, 19: 73-83 (1980).
McMillan, D., et al., "Intra-operative Autologous Blood Management," *Transfusion and Apheresis Science*, 27(1): 73-81 (2002).
Meager, A., et al., "Preparation and Characterization of Monoclonal Antibodies Directed Against Antigenic Determinants of Recombinant Human Tumour Necrosis Factor (rTNF)," *Hybridoma*, 6(3): 305-311 (1987).
Meijer, H., et al., "The Production of Anti-inflammatory Cytokines in Whole Blood by Physico-chemical Induction," *Inflamm. Res.*, 52: 404-407 (2003).
Miyamoto, H., et al., "The Effect of Mechanical Stress on the Production of Inflammatory Agents by Disc Cells," 110, *Abstracts of the 30th Annual Meeting of the International Society for the Study of the Lumbar Spine*, Vancouver, Canada (May 2003).

(56) References Cited

OTHER PUBLICATIONS

Möller, A., et al., "Monoclonal Antibodies to Human Tumor Necrosis Factor: in Vitro and in Vivo Application," *Cytokine*, 2(3): 162-169 (1990).

Molloy, T., et al., "The Roles of Growth Factors in Tendon and Ligament Healing," *Sports Med.*, 33(5): 381-394 (2003).

Moreira, A., et al., "Thalidomide Exerts Its Inhibitory Action on Tumor Necrosis Factor α by Enhancing mRNA Degradation," *J. Exp. Med.*, 177: 1675-1680 (1993).

Moroney, P., "PH and Anti-inflammatory Agents Modulate Nucleus Pulposus Cytokine Secretion," *The Spine Journal*, 2(5 Suppl): 49S-50S (2002) (abstract).

Muller, G., et al., "Amino-substituted Thalidomide Analogs: Potent Inhibitors of TNF-α Production," *Bioorg. Med. Chem. Lett.*, 9: 1625-1630 (1999).

Müller, R., "Determination of Affinity and Specificity of Anti-hapten Antibodies by Competitive Radioimmunoassay," *Meth. Enzymol.*, 92: 589-601 (1983).

Nakamura, K., et al., "Local Application of Basic Fibroblast Growth Factor into the Bone Increases Bone Mass at the Applied Site in Rabbits," *Arch. Orthop. Trauma Surg.*, 115: 344-346 (1996).

Nakamura, K., et al., "Stimulation of Endosteal Bone Formation by Local Intraosseous Application of Basic Fibroblast Growth Factor in Rats," *Rev. Rhum. [Engl. Ed.]*, 64(2): 101-105 (1997).

Niccoli, L., et al., "Intraarticular Injection of Infliximab in Relapsing Knee Effusion in Psoriatic Arthritis: A Pilot Study," *Ann. Rheum. Dis.*, 62(1): 239-240 (2003) and EULAR—Annual European Congress of Rheumatology, Lisbon, Portugal (2003) (abstract).

Nikas, S., et al., "Treatment of Resistant Rheumatoid Arthritis by Intra-articular Infliximab Injections: A Pilot Study," *Ann Rheum Dis.*, 63: 102-103 (2004).

Nikas, S., et al., "Treatment of Resistant Rheumatoid Arthritis by Intra-articular Injections with Infliximab: A Pilot Study," *Ann. Rheum. Dis.*, 62(1): 408 (2003) and EULAR—Annual European Congress of Rheumatology, Lisbon, Portugal (2003) (abstract).

Ohno, K., et al., "Transdiscal Lumbar Sympathetic Block: A New Technique for a Chemical Sympathectomy," *Anesth. Analg.*, 85: 1312-1316 (1997).

Ohtori, S., et al., "TNF-α and TNF-α Receptor 1 Upregulation in GLIA and Neurons After Nerve Injury. Studies in Murine DRG and Spinal Cord," 13, *Abstracts of the 30th Annual Meeting of the International Society for the Study of the Lumbar Spine*, Vancouver, Canada (May 2003).

Ohtori, S., et al., "TNF-α-Deficient Mice Have Fewer Macrophages in Injured Nerve and Reduced Glial Activation in DRG and Spinal Cord," 250, *Abstracts of the 30th Annual Meeting of the International Society for the Study of the Lumbar Spine*, Vancouver, Canada (May 2003).

Okuma, M., et al., "Rotary Cell Culture System Stimulates Annulus Fibrosus Cell Proliferation but Suppresses Proteoglycan Metabolism," 164, *Abstracts of the 30th Annual Meeting of the International Society for the Study of the Lumbar Spine*, Vancouver, Canada (May 2003).

Olmarker, K., et al., "Selective Inhibition of Tumor Necrosis Factor-α Prevents Nucleus Pulposus-induced Thrombus Formation, Intraneural Edema, and Reduction of Nerve Conduction Velocity," *Spine*, 26(8): 863-869 (2001).

Pacifici, R., "Editorial: Cytokines, Estrogen, and Postmenopausal Osteoporosis—The Second Decade," *Endocrinology*, 139(6): 2659-2661 (1998).

Pargellis, C., et al., "Inhibition of p38 MAP Kinase by Utilizing a Novel Allosteric Binding Site," *Nature Structural Biology*, 9(4): 268-272 (2002).

Pederson, A., et al., "Thermal Assembly of a Biomimetic Mineral/Collagen Composite," *Biomaterials*, 24: 4881-4890 (2003).

Peppel, K., et al., "A Tumor Necrosis Factor (TNF) Receptor-IgG Heavy Chain Chimeric Protein as a Bivalent Antagonist of TNF Activity," *J. Exp. Med.*, 174: 1483-1489 (1991).

Raucci, A., et al., "Activation of the ERK1/2 and p38 Mitogen-activated Protein Kinase Pathways Mediates Fibroblast Growth Factor-induced Growth Arrest of Chondrocytes," *J. Biol. Chem.*, 279(3): 1747-1756 (2004).

Richardson, S., et al, "Human Bone Marrow Mesenchymal Stromal Cells as a Source of Chondrocytes for Treatment of Intervertebral Disc Degeneration," 27, *Abstracts of the 30th Annual Meeting of the International Society for the Study of the Lumbar Spine*, Vancouver, Canada (May 2003).

Risbud, M., et al., "Mesenchymal Stem Cells Respond to Their Microenvironment in Vitro to Assume Nucleus Pulposus-like Phenotype," 26, *Abstracts of the 30th Annual Meeting of the International Society for the Study of the Lumbar Spine*, Vancouver, Canada (May 2003).

Rodan, G., et al., "Therapeutic Approaches to Bone Diseases," *Science*, 289: 1508-1514 (2000).

Sakai, D., et al., "Autologous Transplantation of Mesenchymal Stem Cells for Disc Repair," 24, *Abstracts of the 30th Annual Meeting of the International Society for the Study of the Lumbar Spine*, Vancouver, Canada (May 2003).

Sakai, D., et al., "Transplantation of Mesenchymal Stem Cells Embedded in Atelocollagen® Gel to the Intervertebral Disc: A Potential Therapeutic Model for Disc Degeneration," *Biomaterials*, 24: 3531-3541 (2003).

Salin, M., et al., "Free Radicals and Inflammation: Protection of Phagocytosing Leukocytes by Superoxide Dismutase," *J. Clin. Invest.*, 56: 1319-1323 (1975).

Sampaio, E., et al., "Thalidomide Selectively Inhibits Tumor Necrosis Factor α Production by Stimulated Human Monocytes," *J. Exp. Med.*, 173: 699-703 (1991).

Schalkwijk, J., et al., "Cationization of Catalase, Peroxidase, and Superoxide Dismutase," *J. Clin. Invest.*, 76: 198-205 (1985).

Schall, T., et al., "Molecular Cloning and Expression of a Receptor for Human Tumor Necrosis Factor," *Cell*, 61: 361-370 (1990).

Schatteman, L., et al., "Treatment of Refractory Inflammatory Monoarthritis in Ankylosing Spondylitis by Intraarticular Injection of Infliximab," *The Journal of Rheumatology*, 33: 182-85 (2006).

Shiel, W., "Ankylosing Spondylitis," MedicineNet.com [online], Sep. 2005 [retrieved on Jun. 20, 2006]. Retrieved from the Internet <URL: http://www.medicinenet.com/script/main/artasp?articlekey=274&pf=3&page=2>.

Sobajima, S., et al., "Stem Cell Therapy for Degenerative Disc Disease: An In-vitro Feasibility Study," 43, *Abstracts of the 30th Annual Meeting of the International Society for the Study of the Lumbar Spine*, Vancouver, Canada (May 2003).

Steer, J., et al., "Altered Leucocyte Trafficking and Suppressed Tumour Necrosis Factor α Release from Peripheral Blood Monocytes After Intra-articular Glucocorticoid Treatment," *Ann. Rheum. Dis.*, 57(12): 732-737 (1998).

Stepanik, T., et al., "Coisolation of Glutathione Peroxidase, Catalase and Superoxide Dismutase From Human Erythrocytes," *J. Biochem. Biophys. Methods*, 20: 157-169 (1990).

Stern, S., et al., "Human Intervertebral Disc Cell Culture for Disc Disorders," *Clin. Orthop.*, 419: 238-244 (2004).

Takada, T., et al., "IL-6 Production was Upregulated by Interaction Between Disc Tissue and Macrophages," 41, *Abstracts of the 30th Annual Meeting of the International Society for the Study of the Lumbar Spine*, Vancouver, Canada (May 2003).

Takegami, K., et al., "Osteogenic Protein-1 Enhances Matrix Replenishment by Intervertebral Disc Cells Previously Exposed to Interleukin-1," *Spine*, 27(12): 1318-1325 (2002).

Tanny, G., et al., "Improved Filtration Technique for Concentrating and Harvesting Bacteria," *Appl. Environ. Microbiol.*, 40(2): 269-273 (1980).

Teo, S., "Properties of Thalidomide and its Analogues: Implications for Anticancer Therapy," *AAPS Journal*, 7(1): E14-E19 (2005).

Tiku, M., et al., "Aggrecan Degradation in Chondrocytes is Mediated by Reactive Oxygen Species and Protected by Antioxidants," *Free Radic. Res.*, 30: 395-405 (1999).

Tiku, M., et al., "Evidence Linking Chondrocyte Lipid Peroxidation to Cartilage Matrix Protein Degradation," *J. Biol. Chem.*, 275(26): 20069-20076 (2000).

(56) References Cited

OTHER PUBLICATIONS

Tobinick, E., et al., "Perispinal TNF-alpha Inhibition for Discogenic Pain," *Swiss Med. Wkly.*, 133: 170-177 (2003).
Tobinick, E., "Targeted Etanercept for Discogenic Neck Pain: Uncontrolled, Open-label Results in Two Adults," *Clin. Thera.*, 25(4): 1211-1218 (2003).
Tobinick, E., "Targeted Etanercept for Treatment-refractory Pain Due to Bone Metastasis: Two Case Reports," *Clinical Therapeutics.*, 25(8): 2279-2288 (2003).
Tracey, K., et al., "Tumor Necrosis Factor in Metabolism of Disease: Hormonal Actions Versus Local Tissue Effects," *Nouv. Rev. Fr. Hematol.*, 34 Suppl: S37-42 (1992) (abstract).
Trif, M., et al., "Liposomes as Possible Carriers for Lactoferrin in the Local Treatment of Inflammatory Diseases," *Exp. Biol. Med.*, 226(6): 559-564 (2001).
Tsuji, T., et al., "Age-Related Changes in M-RNA Expression of Various Regulatory Factors in Rabbit Intervertebral Disc," 81, *Abstracts of the 30th Annual Meeting of the International Society for the Study of the Lumbar Spine*, Vancouver, Canada (May 2003).
Vahle, J., et al., "Skeletal Changes in Rats Given Daily Subcutaneous Injections of Recombinant Human Parathyroid Hormone (1-34) for 2 Years and Relevance to Human Safety," *Toxicol. Pathol.*, 30(3): 312-321 (2002).
Vukicevic, S., et al., "Induction of Nephrogenic Mesenchyme by Osteogenic Protein 1 (Bone Morphogenetic Protein 7)," *Proc. Natl. Acad. Sci.*, 93: 9021-9026 (1996).
Weiler, C., et al., "Expression of TNF-α in Autopsy and Biopsy Specimens of Intervertebral Discs of Various Age and Degeneration," 233, *Abstracts of the 30th Annual Meeting of the International Society for the Study of the Lumbar Spine*, Vancouver, Canada (May 2003).
Williams, A., et al., "Amelioration of Rat Antigen-induced Arthritis by Liposomally Conjugated Methotrexate is Accompanied by Down-regulation of Cytokine mRNA Expression," *Rheumatology*, 40: 375-383 (2001).
Wittenberg, R., et al., "In Vitro Release of Prostaglandins and Leukotrienes from Synovial Tissue, Cartilage, and Bone in Degenerative Joint Diseases," *Arthritis & Rheumatism*, 36(10): 1444-1450 (Oct. 1993).
Xie, X., et al., "Treatment of Spondylodiscitis Intravenous Versus Percutaneous Intradiscal Applications of Antibiotics: An Experimental Study in Rabbits," 120, *Abstracts of the 30th Annual Meeting of the International Society for the Study of the Lumbar Spine*, Vancouver, Canada (May 2003).
Yabuki, S., et al., "Prevention of Compartment Syndrome in Dorsal Root Ganglia Caused by Exposure to Nucleus Pulposus," *Spine*, 26(8): 870-875 (2001).
Yaffe, A., et al., "Combined Local Application of Tetracycline and Bisphosphonate Reduces Alveolar Bone Resorption in Rats," *J. Periodontol.*, 74(7): 1038-1042 (2003).
Yang, J., et al., "Purification and Quantitation of a Rat Plasma Selenoprotein Distinct from Glutathione Peroxidase Using Monoclonal Antibodies," *J. Biol. Chem.*, 262(27): 13372-13375 (1987).
Yoon, S., et al., "LMP-1 Upregulates Proteoglycan Synthesis in Intervertebral Disc Cells Through a BMP Mediated Process," 31, *Abstracts of the 30th Annual Meeting of the International Society for the Study of the Lumbar Spine*, Vancouver, Canada (May 2003).
Zhang, C., et al., "Mitogen-activated Protein (MAP) Kinase Regulates Production of Tumor Necrosis Factor-α and Release of Arachidonic Acid in Mast Cells," *J. Biol. Chem.*, 272(20): 13397-13402 (1997).
Ando, N., et al., "An Immunohistochemical Study of the Degenerative Lumbar Disc," Orthopedics & Traumatology 44(1): 176-178 (1995) (Published in Japanese with English Abstract).
Blight, A.R., "Miracles and molecules—progress in spinal cord repair," Nature Neuroscience Supplement 5:1051-1054 (Nov. 2002).
Höke, A., "Mechanisms of Disease: what factors limit the success of peripheral nerve regeneration in humans?," Nature Clinical Practice Neurology, 2(8): 448-454 (Aug. 2006).
Marzo-Ortega, H., et al., "Bone mineral density improvement in spondyloarthropathy after treatment with etanerecept," Ann. Rheum. Dis.62: 1020-1021 (2003).
Muthumani, K., et al., "Suppression of HIV-1 viral replication and cellular pathogenesis by a novel p38/JNK kinase inhibitor," AIDS 18:730-748 (2004).
Schmidt, C.E. and Leach, J.B., "Neural Tissue Engineering: Strategies for Repair and Regeneration," Annu. Rev. Biomed. Eng. 5:293-347 (Jun. 2003).
't Hart, B.A. and Amor, S., "The use of animal models to investigate the pathogenesis of neuroinflammatory disorders of the central nervous system," Curr. Opin. Neurol. 16:375-383 (2003).
Yorimitsu, E., "A Comparative Study on the Pathological Changes of Intervertebral Discs after Intradiscal Injection of Various Kinds of Steroid Materials: An Experimental Study," Journal Keio Medical Society 74(5): 303-315 (1997) (Published in Japanese with English Abstract).
McIntyre, C.J., et al., "Pyridazine Based Inhibitors of p38 MAPK," Bioorg. Med. Chem. Lett. 12:689-692 (2002).
Rupert, K.C., et al., "Imidazopyrimidines, Potent Inhibitors of p38 MAP Kinase," Bioorg. Med. Chem. Lett. 13:1347-350 (2003).
Séguin, C.A., et al., "Tumor Necrosis Factor a Modulates Matrix Production and Catabolism in Nucleus Pulposus Tissue," Spine 30(17): 1940-1948 (Sep. 1, 2005).
Brekke, O.H. and Sandlie, I, "Therapeutic Antibodies for Human Diseases at the Dawn of the Twenty-First Century," *Nature Reviews*, 2: 52-62 (2003).
Rheumatoid Arthritis, MedicineNet.com http://www.medicinenet.com/script/main/art.asp?articlekey=466&pf=3&page=1.
Weinblatt, M.E., et al., "Adalimumab, a Fully Human Anti-Tumor Necrosis Factor Alpha Monoclonal Antibody, for the Treatment of Rheumatoid Arthritis in Patients Taking Concomitant Methotrexate," *Arthritis andRheumatism*, 48(1), 35-45 (2003).
Hayashi, Y., et al., "Direct Single Injection of p38 Mitogen-Activated Protein Kinase Inhibitor Does Not Affect Calcitonin Gene-Related Peptide Expression in Dorsal Root Ganglion Neurons Innervating Punctured Discs in Rats", Spine, 34(26): 2843-2847 (2009).
Van Beuningen, H.M., et al., "Differential Effects of Local Application of BMP-2 or TGF-B1 on Both Articular Cartilage Composition and Osteophyte Formation," *Osteoarthritis and Cartilage*, 6: 306-317 (1998).
Bertolini, D.R., et al., "Stimulation of Bone Resorption and Inihibition of Bone Formation in vitro by Human Tumour Necrosis Factors," Nature, 319:516-518 (1986).
Brandt, J., et al., "Successful Treatment of Active Ankylosing Spondylitis With the Anti-Tumor Necrosis Factor α Monoclonal Antibody Infliximab," Arthritis & Rheumatism, 43(6):1346-1352 (Jun. 2000).
Dernis, E., et al., "Infliximab in spondylarthropathy-influence on bone density," Clin. Exp. Rheumatol., 20 (6 Suppl 28): S185-6 (2002).
Hashizume, H., et al., "Role of IL-8, MCP-1 and PH in Neuropathic Pain Enhanced by Degenerative Nucleus Pulposus," 127, Abstracts of the 30th Annual Meeting of the International Society for the Study of the Lumbar Spine, Vancouver, Canada (May 2003).
Hotten et al., "Recombinant Human Growth Differentiation Factor 5 Stimulates Mesenchyme Aggregation and Chondrogenesis Responsible for the Skeletal Development of Limbs Growth Factors," 13: 65-74 (1996).
Kitazawa, R., et al., "Interleukin-1 Receptor Antagonist and Tumor Necrosis Factor Binding Protein Decrease Osteoclast Formation and Bone Resorption in Ovariectomized Mice," J. Clin. Invest. 94:2397-2406 (1994).

\* cited by examiner

SD-469

TRANS-CAPSULAR ADMINISTRATION OF P38 MAP KINASE INHIBITORS INTO ORTHOPEDIC JOINTS

BACKGROUND OF THE INVENTION

The natural articulating joint (diarthrodal joint) comprises adjacent bones having opposing hyaline cartilage surfaces held together by a fibrous collagenous capsule defining a joint space. The inner wall of this capsule is lined with synovial cells. Contained within the capsular joint space is an acellular synovial fluid. The function of the synovial fluid is to provide lubrication for the articulating surfaces.

In a healthy joint, cells within the articular cartilage produce an extracellular matrix (ECM) containing a high percentage of proteoglycans. These proteoglycans contain sulfated functional groups that retain water, thereby providing the cartilage with its lubricating qualities. These cells may also secrete small amounts of cytokines as well as matrix metalloproteinases ("MMPs"). These cytokines and MMPs help regulate the metabolism of the hyaline cartilage cells.

There appear to be many causes of degenerative joint disease (DJD). For example, gradual degeneration of the joint may be caused by wear, by trauma, by misalignment, by genetics, or by mechanical instabilities in other portions of the body. In many instances, gradual wear of the hyaline cartilage cause the cells therein (or invading macrophages) to emit larger than normal amounts of the above-mentioned cytokines. In other instances of DJD, genetic factors, such as programmed cell death, or apoptosis can also cause the cells within the hyaline cartilage to emit abnormally large amounts of these cytokines into the extracellular matrix of the hyaline cartilage and synovial fluid.

Although the progression of DJD (also called "osteoarthritis", or "OA") is largely dependent upon etiology, it is often the case that the high levels of the cytokines present in the hyaline cartilage begin to mediate the degradation of the extracellular matrix of the cartilage. Concurrently, enzymes in the synovial fluid both upregulate MMPs and downregulate MMP inhibitors. The MMPs (under mediation by the cytokines) begin cleaving the water-retaining portions of the proteoglycans, thereby reducing their water-retaining and lubricious qualities. This degradation leads to a less lubricious hyaline cartilage, thereby increasing the wear upon the hyaline cartilage. This degenerative cascade also often leads to inflammation of the synovial lining, which often produces a thickening and fibrillation of the synovium, and the creation of finger-like villae with the synovium. When the natural regeneration of these cartilage layers is slower than this degenerative process, these changes cause even more mechanical instability, thereby causing the hyaline cartilage cells, the synovium cells and the invading macrophages to emit even more cytokines, thereby typically upregulating MMPs. In sum, osteoarthritis is a degenerative disease that degrades cartilage, which results in pain, restriction of motion and deformity.

In addition to the foregoing, posterior elements of the spine called the "facet joints" help to support axial, torsional and shear loads that act on the spinal column. Furthermore, the facet joints are diarthroidal joints that provide both sliding articulation and load transmission features. The facet's articular surfaces contact in extension, limiting rotation and increasing compressive load. The articular surfaces also contact on one side of the spine in lateral bending and axial rotation, also limiting rotation and transferring load. Early facet osteoarthrosis is relatively mild and is confined to the articular cartilage, capsule, and synovium, but eventually involves the subchondral bone and the margins equally on both sides of a motion segment. With advancing degeneration, the joint capsule undergoes significant changes including increasing fibrosis and vascularization, which has been reported to become hyperemic with infiltration of inflammatory cells, enlargement, and fibrosis.

The posterior zygo-apophyseal joints (facet joints) may be a significant source of spinal disorders and, in many cases, debilitating pain. The articular cartilaginous surfaces can degenerate due to mechanical or biological factors and cause pain as with other joint osteoarthritis. Synovial cysts of the facet joints occur most commonly in association with degenerative disease of the spine in older individuals. The association of these cysts with trauma, rheumatoid arthritis, spondylosis and kissing spinous processes also has been reported. These cysts can cause symptoms and signs from direct compression of the dura. For example, a patient may suffer from arthritic facet joints, severe facet joint tropism or otherwise deformed facet joints, facet joint injuries, etc. There is currently a lack of suitable intervention procedures for facet joint disorders. Facet blocks with anesthetic and cortisone, facet denervation procedures, radiofrequency ablation of the nerve supply to the joint, or even spinal fusions have been recommended. In the early stages of degeneration, pain may be controlled by blocking the medial branch of the lumbar zygapophyseal (facet) joints (kryorhizotomy). However, this treatment mode of treatment is considered for temporary relief of pain. Facetectomy, or the removal of the facet joints, may provide some relief, but is also believed to significantly decrease the stiffness of the spinal column (i.e., hypermobility) in all planes of motion: flexion and extension, lateral bending, and rotation. Furthermore, problems with the facet joints can also complicate treatments associated with other portions of the spine. By way of example, contraindications for artificial joints include arthritic, deformed, unstable, or painful facet joints. Accordingly, there is a need for a facet joint treatment that addresses these concerns.

Accordingly, there is a need for effective prevention treatment of joint damage.

SUMMARY OF THE INVENTION

The present inventors have developed a number of localized procedures for efficaciously treating degenerative joint disease by drug therapy.

The present inventors believe that pro-inflammatory molecules within a joint capsule may contribute to degeneration of and/or pain within the joint in at least one of the following ways:
 a) chemical sensitization of nerve fibrils contained within the collagenous ligaments of the joint capsule;
 b) chemical sensitization of nerve fibrils contained within the synovium;
 c) mediation of and/or direct degeneration of the hyaline articular surfaces; and
 d) chemical sensitization of nerve fibrils adjacent or in close proximity to a joint capsule.

In accordance with the present invention, the present inventors have developed a method of treating inflamed joints in which an effective amount of an antagonist of a pro-inflammatory molecule (e.g., a p38 MAP kinase inhibitor) is administered locally, for example trans-capsularly (i.e., directly into an inflamed capsule).

Since p38 mitogen-activated protein (MAP) kinase plays a central role in inflammation, trans-capsular injection of p38 MAP kinase inhibitors blocks the production of pro-inflammatory cytokines, such as, for example, TNF-α, IL-1, IL-6 and IL-8 and blocks nitric oxide (NO) production, $PGE_2$ production and proteoglycan degradation. It is believed that the p38 MAP kinase site regulates the production of TNF-α, IL-1 and COX-2 enzyme.

There are several advantages to directly administering these therapeutic inhibitors trans-capsularly over systemic treatments.

Since a highly specific antagonist such as a p38 MAP kinase inhibitor inhibits only the specific molecule of interest, not only will unwanted side effects be reduced, but also the p38 MAP kinase inhibitor may be combined with other therapeutic agents (such as TGF-β, or mesenchymal stem cells) that can also be injected into the capsule without the p38 MAP kinase reducing the effectiveness of those other agents.

Since cytokines such as p38 MAP kinase, interleukins, and TNF-α play roles in mediating inflammatory reactions within the synovium or degradation of hyaline articular cartilage, injecting an antagonist or inhibitor of these proteins directly into a capsule prevents the target cytokine from inducing any inflammation. In effect, the intra-capsular administration of the cytokine antagonist arrests the inflammation process begun within the joint and the degeneration of the hyaline cartilage.

Nerve ending nociceptors are present both within the subchondral endplates of the joint and in the wall of the surrounding peripheral capsule. Additionally, dorsal root ganglion (DRG) neurons having dichotomizing axons are considered to be related to referred pain. Clinically, pain from the lumbar facet joint is sometimes referred to the lower extremities innervated by the sciatic nerve. This is primarily due to DRG neurons innervating the lumbar facet joints. Cytokines such as TNF-α, as well as prostaglandins and nitric oxide ("NO") irritate or mediate the irritation of such nerves. It is believed that locally administering a highly specific antagonist, such as a p38 MAP kinase antagonist of these molecules into the capsule also prevents the target pro-inflammatory molecule from causing intracapsular nerve irritation. Thus, the pain attributed to irritation of these nerves can be efficiently eliminated or reduced.

It is further believed that transcapsular administration of an effective amount of an antagonist of the NO synthase enzyme would also help provide therapy to the patient having DJD. It is believed that the NO synthase enzyme regulates the production of NO, which is known to have pro-inflammatory effects and has been implicated in pain generation. Some antagonists of NO synthase are N-iminoethyl-L-lysine (L-NIL), and $N^G$-monomethyl-L-arginine.

It is further believed that transcapsular administration of an effective amount of an anti-oxidant would also help provide therapy to the patient having DJD. It is believed that oxidants degrade the hyaline cartilage extra-cellular matrix. Typical anti-oxidants include free radical scavengers and superoxide dismutase enzymes.

It is believed that transcapsular administration of an effective amount of an anti-proliferative agent as an additional therapeutic agent would also help provide therapy to the patient having DJD. It is believed that antiproliferative agents may have an effect on inflammation by effecting inflamed synovial tissues which would limit the production of inflammatory cytokines.

Further, it is believed that transcapsular administration of an effective amount of an antagonist of the $PLA_2$ enzyme would also help provide therapy to the patient having DJD. It is believed that the $PLA_2$ enzyme is a regulator of the production of prostaglandin, which itself has been implicated in pain generation. At least one antagonist of $PLA_2$ is disclosed in Kawakami, *Clin. Orthop.*, 351: 241-51 (1998), the contents of which are incorporated by reference herein in its entirety.

Since the surrounding capsule portion of the joint comprises a relatively dense collagenous structure, this outer component of the joint may provide a suitable depot for the antagonist, thereby increasing its half-life in the capsule.

The disintegration of articular cartilage induces production of pro-inflammatory cytokines (interleukin 1α—IL-1α, interleukin 1β—IL-1β, tumor necrosis factor α—TNF-α, interleukin 6—IL-6, leukaemic inhibitor factor—LIF, interleukin 8—IL-8, interleukin 17—IL-17, interleukin 18—IL-18 and others) through the synovial membrane. Cytokines diffuse into the articular cartilage, which produces matrix metalloproteinases (MMPs). MMPs play an important role in the destruction of proteoglycans, collagen and cartilage matrix. The above-mentioned cytokines take part in the inflammatory and catabolic process of OA because they inhibit cartilage collagen and aggrecan production, stimulate chondrocytes to produce MMPs and inducible NO-synthase (iNO), induce nitric oxide (NO) production (which induces $PGE_2$ production), increase the amount of inflammatory cells in the joint, induce and decrease a proliferation of chondrocytes, inhibit proteoglycan synthesis and stimulate their disintegration (which stimulates glycosaminoglycan (GAG) release), induce apoptosis of chondrocytes and decrease their viability. The p38 MAP kinase inhibitors are a class of drugs that target the p38 MAP kinase pathway and can inhibit NO and $PGE_2$ production.

Accordingly, in one embodiment, the invention includes a method of treating an inflamed orthopedic joint, said joint comprising i) opposing hyaline cartilage articular surfaces, ii) a peripheral collagenous capsule defining a central joint space and iii) synovial fluid contained within the joint space, comprising locally, e.g., trans-capsularly administering into the joint space a formulation comprising an effective amount of a p38 MAP kinase inhibitor.

The p38 MAP kinase inhibitors can be one or more of the p38 MAP kinase inhibitors disclosed herein. For example, in one embodiment, the p38 MAP kinase inhibitor is selected from the group consisting of:

| | |
|---|---|
| i) | diaryl imidazole; |
| ii) | N,N'-diaryl urea; |
| iii) | N,N-diaryl urea; |
| iv) | benzophenone; |
| v) | pyrazole ketone; |
| vi) | indole amide; |
| vii) | diamides; |
| viii) | quinazoline; |
| ix) | pyrimido [4,5-d]pyrimidinone; |
| x) | pyridylamino-quinazolines; |
| xi) | JNJ 3026582 (RWJ 67657); |
| xii) | JNJ 17089540 (RWJ 669307); |
| xiii) | JNJ 7583979 (RWJ 351958); |
| xiv) | SCIO-282 (SD 282); and |
| xv) | SCIO-469 (SD 469). |

In one embodiment, the p38 MAP kinase inhibitor is selected from the group consisting of:
a) JNJ 3026582 (RWJ 67657),
b) JNJ 17089540 (RWJ 669307),
c) JNJ 7583979 (RWJ 351958),
d) SCIO-282 (SD 282), and
e) SCIO-469 (SD 469).

In one embodiment, the p38 MAP kinase inhibitor has at least 3 cyclic groups. In one embodiment, the p38 MAP kinase inhibitor is substantially water insoluble. In another embodiment, the p38 MAP kinase inhibitor is water soluble.

In one embodiment, in the p38 MAP kinase inhibitor is an aryl-pyridinyl heterocyle, e.g., a 1-aryl-2-pyridinyl heterocycle. For example, the 1-aryl-2-pyridinyl heterocycle can be selected from the group consisting of:
a) 4,5 substituted imidazole;
b) 1,4,5 substituted imidazole;
c) 2,4,5 substituted imidazole;
d) 1,2,4,5 substituted imidazole; and
e) non-imidazole 5-membered ring heterocycle.

In one embodiment, the formulation is administered in an amount of less than about 2 ccs. In one embodiment, the p38 MAP kinase inhibitor is administered in a dosage to produce a local tissue concentration of between about 1 to about 50 µM. In one embodiment, the p38 MAP kinase inhibitor is present in the formulation in an amount of at least about 1 microgram/ml to about 5 milligram/ml, for example, about 5 mg/ml. In some embodiments, the range is about 1 µg/ml-1.2 mg/ml.

In one embodiment, the formulation is administered in an amount effective to reduce pain.

In one embodiment, the administration comprises providing the formulation in a patch attached to an outer wall of the capsule. In one embodiment, the administration comprises providing the formulation in a depot at a location closely adjacent to an outer wall of the capsule. In one embodiment, the administration comprises providing the formulation in a depot at a location closely adjacent to an endplate of an adjacent bony body.

In one embodiment, the administration is performed through a needle.

In one embodiment, the formulation is administered through a drug pump.

IN one embodiment, more than one p38 MAP kinase inhibitor is administered. For example, the formulation can contain more than one p38 MAP kinase inhibitor.

In one embodiment, an additional therapeutic agent is administered. In one embodiment, the administered formulation further comprises at least one additional therapeutic agent.

In one embodiment, the additional therapeutic agent can include one or more of the following agents:

| | |
|---|---|
| i) | a growth factor, |
| ii) | PPDCs, mesenchymal stem cells, adult stem cells and embryonic stem cells, |
| iii) | an MMP antagonist (inhibitor), |
| iv) | a TNFα antagonist, |
| v) | rapamycin, |
| vi) | a COX-2 antagonist, |
| vii) | an antagonist of nitric oxide synthase, |
| viii) | an anti-oxidant, |
| ix) | an anti-proliferative agent, |
| x) | an anti-apoptotic agent, |
| xi) | a non-steroidal anti-inflammatory agent, |
| xii) | glycosaminoglycans, |
| xiii) | microparticles |
| xiv) | a caspase inhibitor, |
| xv) | an inhibitor of pro-inflammatory interleukin, |
| xvi) | an inhibitor of $PLA_2$ enzyme, |
| xvii) | tetracycline analogs, and |
| xviii) | IGF I or II. |

In one embodiment, the additional therapeutic agent is a growth factor. In one embodiment, the growth factor is provided by platelet concentrate.

In one embodiment, the additional therapeutic agent is viable mesenchymal stem cells. In one embodiment, the mesenchymal stem cells are autologous. In one embodiment, the mesenchymal stem cells are provided in a concentrated form. In one embodiment, the additional therapeutic agent is plasmid DNA.

In one embodiment, the additional therapeutic agent is postpartum-derived cells (PPDCs), which are also known as postpartum cells. The PPDCs can be placenta-derived cells (PDCs) or human Umbilical Tissue-derived Cells (hUTCs). Methods for isolating and collecting PPDCs are described in U.S. patent application Ser. Nos. 10/877,446 and 10/877,012, which are incorporated by reference herein in their entirety.

In one embodiment, the additional therapeutic agent is suprofen. In another embodiment, the additional therapeutic agent is an antagonist of COX-2 enzyme. In another embodiment, the additional therapeutic agent is an antagonist of NO synthase. In one embodiment, the antagonist of NO synthase is selected from the group consisting of N-iminoethyl-L-lysine (L-NIL), and $N^G$-monomethyl-L-arginine. In one embodiment, the antagonist is an inhibitor of $PLA_2$.

In one embodiment, the additional therapeutic agent is an anti-proliferative agent. In some embodiments, the anti-proliferative agent is selected from the group consisting of a) rapamycin; b) an inhibitor of cyclin dependent kinase (CDK); and c) statins (such as mevastatin and lovastatin).

In one embodiment, the anti-proliferative agent is a CDK inhibitor. A CDK inhibitor may directly effect the proliferation and subsequent immune reaction of synoviocytes. CDK inhibitors may also have a direct effect on chondrocyte clustering which is known to be a characteristic osteoarthritic event. Exemplary CDK inhibitors include flavopiridol, roscovitine, and compounds disclosed in PCT Patent Publication No. WO 02/057240 (Lin) and U.S. provisional patent application 60/257,703, the specifications of which are incorporated by reference herein in their entirety. In some embodiments, the CDK inhibitor is JNJ 7706621.

In one embodiment, the CDK inhibitor is provided in an about 0.1 to about 10 µM dose. In one embodiment, when rapamycin is selected, a dosage producing a local tissue concentration of between about 0.5 ug/kg and 50 ug/kg is preferred.

In one embodiment, the anti-proliferative agent is rapamycin. In one embodiment, the rapamycin is provided in an about 0.1 to about 10 µM dose. Rapamycin is a potent inhibitor of downstream signaling of TOR (target of Rapamycin) proteins. As such, it is responsible for coordinating the balance between protein synthesis and protein degradation. Osteoarthritis is known to be propagated by a loss of balance between extracellular matrix synthesis and degradation. Since TOR proteins regulate multiple metabolic pathways, it is believed that rapamycin may stabilize the balance of the cycle. Rapamycin may also directly effect the proliferation and subsequent immune reaction of synoviocytes. In addition, it is known that osteoarthritic chondrocytes demonstrate a low level of proliferative activity by contrast to normal articular chondrocytes which show no activity. This is thought to lead to chondrocyte clustering within the cartilage. Rapamycin could function to eliminate the atypical chondrocyte proliferation. In one embodiment, the anti-proliferative agent is selected from the group consisting of rapamycin and JNJ 7706621.

JNJ 7706621 (RWJ 387252) is (4-[5-Amino-1-(2,6-difluoro-benzoyl)-1H-[1,2,4]triazol-3-ylamino]-benzene-sulfonamide) (developed by Johnson & Johnson) that blocks cell cycle progression through inhibition of cyclin-dependent kinases (CDKs, e.g., CDK 1, 2 and 9) and Aurora kinases. The molecular weight for JNJ 7706621 is 394. JNJ 7706621 has a solubility of 0.006 mg/ml at pH 2 and solubility of 0.017 mg/ml at pH 7.4. JNJ 7706621 exhibits activity against Aurora ($IC_{50}$=11 nM) and VEGFR2 (IC50=154 nM). It is very potent towards CDK1 and CDK2 ($IC_{50}$ 9 and 4 nM, respectively), and inhibits proliferation of many different human cancer cell lines. JNJ 7706621 shows single agent antitumor activity in human tumor xenograft models. JNJ 7706621 inhibits cell proliferation in culture ($IC_{50}$=337±123 nM in 9 cell lines). JNJ 7706621 can induce G2M arrest, endoreduplication and apoptosis. JNJ 7706621 is represented by the structure in FIG. 13B. In one embodiment, the anti-inflammatory agent is selected from the group consisting of tolmetin, tepoxalin, suprofen, tiaprofenic acid, centella (ETCA), madecassoside, rhein, diacerein, feverfew, batimastat and ORC (Interceed).

In some embodiments, the therapeutic agent is an anti-apoptotic agent, such as a highly specific anti-apoptosis molecule. It is believed these molecules will serve to protect against chondrocyte apoptosis. In some embodiments, compounds include EPO erythropoietin mimetic peptides, EPO mimetibodies, IGF-I, IGF-II, and caspase inhibitors.

In some embodiments, the therapeutic agent is an anti-matrix metalloproteinase (HAAMMP), e.g., a highly specific. Preferably, the HAAMMP is administered in an amount effective to inhibit the specific action of MMPs released by cells during the degenerative process.

In some embodiments, the HAAMMP is a natural inhibitor of MMPs (TIMP). Preferably, the TIMP is selected from the group consisting of TIMP-1 and TIMP-2. In some embodiments, the TIMP is autologous and is concentrated by filtration, centrifugation or by immuno-attachment processes. In other embodiments, the TIMP is manufactured recombinantly, and is preferably present in a concentration of at least 1000 times that found in the patient.

In some embodiments, the HAAMP comprises a chelating group that binds tightly to the zinc component present in the active site of the MMP. Such HAAMMPs may be selected from the materials disclosed in Gordon, *Clin. Exp. Rheumatol.*, (1993), 11(Supp 8): S91-4; and Johnson, J., *Enzyme Inhib.*, 2:1-22 (1987), which is incorporated by reference herein in its entirety.

In some embodiments, the therapeutic substance is a specific antagonist of a collagenase MMP. In some embodiments, the therapeutic substance is a specific antagonist of a stromelysin MMP. In some embodiments, the therapeutic substance is a specific antagonist of a gelatinase MMP. In some embodiments, the therapeutic substance is a specific antagonist of a membrane MMP.

Preferably, the targeted MMP is selected from the group consisting MMP-2, MMP-3, MMP-13 and MMP-8. MMP-3, MMP-8, and MMP-13 are all known to be present in higher levels in osteoarthritic cells. Targeting MMP-2 and/or MMP-3 is desirable because these MMPs are believed to degrade proteoglycans. Targeting MMP-8 is desirable because this MMP is believed to degrade aggrecans.

In one embodiment, the therapeutic agent is selected from the group consisting of: anti-proliferative agents, anti-inflammatory agents, and antibodies.

In one embodiment, the anti-inflammatory agent is selected from the group consisting of tolmetin, tepoxalin, suprofen, tiaprofenic acid, centella (ETCA), madecassoside, rhein, diacerein, feverfew, batimastat, suprofen and ORC (Interceed).

In one embodiment the therapeutic agent is an inhibitor of a pro-inflammatory interleukin. In one embodiment the interleukin is IL-1β. In one embodiment the interleukin is IL-2. In one embodiment the interleukin is IL-6. In one embodiment the interleukin is IL-8. In one embodiment the interleukin is IL-12. In one embodiment the interleukin is IL-19.

In one embodiment the therapeutic agent is an inhibitor of membrane-bound TNF-α. In one embodiment the therapeutic agent is also an inhibitor of soluble TNF-α.

In one embodiment the therapeutic agent is an inhibitor of TNF-α synthesis. In one embodiment wherein the agent is an inhibitor of a natural receptor of TNF-α.

In one embodiment, the therapeutic agent is an anti-apoptotic agent. In one embodiment, the anti-apoptotic agent is selected from the group consisting of EPO, erythropoetin mimetic peptides, IGF-I, IGF-II, and caspase inhibitors.

In one embodiment, the formulation further comprises a sustained release device. In one embodiment, the sustained release device comprises a hydrogel. In one embodiment, the sustained release device provides controlled release. In one embodiment, the sustained release device provides continuous release. In one embodiment, the sustained release device provides intermittent release. In one embodiment, the sustained release device comprises a biosensor. In one embodiment, the sustained release device comprises a plurality of microspheres. In one embodiment, the sustained delivery device is a polymer. In one embodiment, the sustained release device comprises an inflammatory-responsive delivery system.

In one embodiment, the antagonist is predominantly released from the sustained delivery device by its diffusion through the sustained delivery device. In one embodiment, the antagonist is predominantly released from the sustained delivery device by biodegradation of the sustained delivery device.

In one embodiment, the invention includes a method of preventing or therapeutically treating an inflamed orthopedic joint, comprising the steps of:
  a) determining a level of a pro-inflammatory protein within the inflamed orthopedic joint,
  b) comparing the level against a pre-determined level of the pro-inflammatory protein, and
  c) injecting a p38 MAP kinase inhibitor into the inflamed orthopedic joint.

In one embodiment, the pro-inflammatory protein is an interleukin. For example, the predetermined level for the interleukin is at least 100 pg/ml. In one embodiment, the pro-inflammatory protein is p38 MAP kinase, an interleukin-6. In one embodiment, the pro-inflammatory protein is p38 MAP kinase, an interleukin-1. In one embodiment, the pre-determined level for the interleukin-6 is at least 100 pg/ml. For example, the predetermined level for the interleukin-6 is at least 250 pg/ml. In one embodiment, the pro-inflammatory protein is an interleukin-8. For example, the predetermined level for the interleukin-8 is at least 500 pg/ml. In one embodiment, the pro-inflammatory protein is $PGE_2$. For example, the predetermined level for $PGE_2$ is at least 1000 pg/ml. In one embodiment, the pro-inflammatory protein is TNF-α. For example, the predetermined level for TNF-α can be at least 20 pg/ml, at least 30 pg/ml or at least 1000 pg/ml.

In one embodiment, the invention includes a method of preventing an inflamed orthopedic joint in a human individual, comprising:
  a) determining a genetic profile of the individual,
  b) comparing the profile of the individual against a pre-determined genetic profile level of at-risk humans,
  c) determining that the individual is an at-risk patient, and
  d) injecting a formulation comprising an effective amount of a p38 MAP kinase inhibitor into an inflamed orthopedic joint of the individual.

In one embodiment, the invention includes a method of treating an inflamed orthopedic joint, comprising trans-capsularly administering an effective amount of a formulation comprising p38 MAP kinase inhibitor into an inflamed orthopedic joint, wherein said p38 MAP kinase inhibitor is selected from the group consisting of: JNJ 3026582 (RWJ 67657), JNJ 17089540 (RWJ 669307), JNJ 7583979 (RWJ 351958), SCIO-282 (SD 282) and SCIO-469 (SD 469). In one embodiment, the p38 MAP kinase inhibitor is JNJ 17089540 (RWJ 669307).

In one embodiment, the invention includes a method of inhibiting GAG degradation in an inflamed orthopedic joint comprising trans-capsularly administering an effective amount of a formulation comprising p38 MAP kinase inhibitor into an inflamed orthopedic joint, wherein said p38 MAP kinase inhibitor is selected from the group consisting of: JNJ 3026582 (RWJ 67657), JNJ 17089540 (RWJ 669307), JNJ 7583979 (RWJ 351958), SCIO-282 (SD 282) and SCIO-469 (SD 469).

In one embodiment, the invention includes a method of inhibiting NO production in an inflamed orthopedic joint comprising trans-capsularly administering an effective amount of a formulation comprising p38 MAP kinase inhibitor into an inflamed orthopedic joint, wherein said p38 MAP kinase inhibitor is selected from the group consisting of: JNJ 3026582 (RWJ 67657), JNJ 17089540 (RWJ 669307), JNJ 7583979 (RWJ 351958), SCIO-282 (SD 282) and SCIO-469 (SD 469).

In one embodiment, the invention includes a method of inhibiting $PGE_2$ synthesis in an inflamed orthopedic joint comprising trans-capsularly administering an effective amount of a formulation comprising p38 MAP kinase inhibitor into an inflamed orthopedic joint, wherein said p38 MAP kinase inhibitor is selected from the group consisting of: JNJ 3026582 (RWJ 67657), JNJ 17089540 (RWJ 669307), JNJ 7583979 (RWJ 351958), SCIO-282 (SD 282) and SCIO-469 (SD 469).

The invention described herein also encompasses formulations comprising at least one p38 MAP kinase inhibitor and at least one an additional therapeutic agent. For example, the additional therapeutic agent or agents can be any of the agents disclosed herein. In some embodiments, the agents can be present in any of the amounts and/or dosages disclosed herein.

In one embodiment, the joint is a knee joint. In one embodiment, the joint is a hip joint. In one embodiment the joint is a spinal facet joint. In one embodiment, the joint is a sacro-iliac joint.

In one embodiment, the additional therapeutic agent can be administered prior to, simultaneously with, or subsequent to administration of the p38 MAP kinase inhibitor.

The invention also includes a method of treating an inflamed orthopedic joint, comprising transcapsularly administering an effective amount of a formulation comprising at least one of: an anti-proliferative agent, an anti-inflammatory agent, a cytokine antagonist, an antibody, an IL-6 antibody, or a MMP inhibitor or antagonist, a growth factor, mesenchymal stem cells, a monoclonal anti-TNFα antibody, rapamycin, a COX-2 antagonist, an antagonist of NO synthesis, an antioxidant, an anti-apoptotic agent, non-steroidal anti-inflammatory agent, glycosaminoglycans, mesenchymal stem cells, a TNFα antagonist, batimastat, rhein, diacerein, or rhGDF-5.

The invention also encompasses methods of inhibiting proteoglycan degradation in an inflamed orthopedic joint, comprising transcapsularly administering an effective amount of a formulation comprising diacerein or rhein into the joint. It also encompasses methods of inhibiting nitric oxide production in an inflamed orthopedic joint, comprising transcapsularly administering an effective amount of a formulation comprising diacerein or rhein into the joint.

The invention also encompasses methods of inhibiting glycosaminoglycan release in an inflamed orthopedic joint, comprising transcapsularly administering an effective amount of a formulation comprising an antiproliferative compound (for example, any such compound described herein) into the joint. It also encompasses methods of inhibiting nitric oxide production in an inflamed orthopedic joint, comprising transcapsularly administering an effective amount of a formulation comprising an antiproliferative compound into the joint.

The invention also encompasses methods of inhibiting TNFα-induced nitric oxide production in an inflamed orthopedic joint, comprising transcapsularly administering an effective amount of a formulation comprising a TNFα antagonist into the joint. It also encompasses methods of inhibiting TNFα-induced $PGE_2$ synthesis in an inflamed orthopedic joint, comprising transcapsularly administering an effective amount of a formulation comprising a TNFα antagonist into the joint.

The invention also encompasses methods of inhibiting glycosaminoglycan release in an inflamed orthopedic joint, comprising transcapsularly administering an effective amount of a formulation comprising an IL-6 antibody into the joint. It also encompasses methods of inhibiting nitric oxide production in an inflamed orthopedic joint, comprising transcapsularly administering an effective amount of a formulation comprising an IL-6 antibody into the joint. It also encompasses methods of inhibiting $PGE_2$ synthesis in an inflamed orthopedic joint, comprising transcapsularly administering an effective amount of a formulation comprising an IL-6 antibody into the joint.

The invention also encompasses methods of inhibiting nitric oxide production in an inflamed orthopedic joint, comprising transcapsularly administering an effective amount of a formulation comprising batimastat into the joint.

In one embodiment, batimastat can be administered in a dose of about 1 to about 10 µM.

The invention also encompasses methods of inhibiting TNFα-induced glycosaminoglycan release in an inflamed orthopedic joint, comprising transcapsularly administering an effective amount of a formulation comprising an antiproliferative compound into the joint.

In one embodiment, diacerein can be administered in a dose of about 0.054 to about 54 µM.

In one embodiment, rhein can be administered in a dose of about 0.035 to about 35 µM.

The invention also encompasses methods of treating an inflamed orthopedic joint, wherein inflammation of the orthopedic joint results in ankylosing spondylitis, said joint comprising i) opposing hyaline cartilage articular surfaces, ii) a peripheral collagenous capsule defining a central joint space and iii) synovial fluid contained within the joint space, comprising trans-capsularly administering into the joint space a formulation comprising an effective amount of an inhibitor of TNF-α synthesis such that an inflamed joint is treated. In one embodiment, the growth factor is a bone morphogenetic protein. In one embodiment, the growth factor is a growth differentiation factor.

The invention also encompasses methods of preserving cartilage in an inflamed joint, comprising trans-capsularly administering an effective amount of a formulation comprising a p38 MAP kinase inhibitor into a joint, wherein said p38 MAP kinase inhibitor is selected from the group consisting of: JNJ 3026582 (RWJ 67657), JNJ 17089540 (RWJ 669307), JNJ 7583979 (RWJ 351958), SCIO-282 (SD 282) and SCIO-469 (SD 469).

The invention also encompasses methods of preventing deterioration in an inflamed joint, comprising trans-capsularly administering an effective amount of a formulation comprising a p38 MAP kinase inhibitor into a joint, wherein said p38 MAP kinase inhibitor is selected from the group consisting of: JNJ 3026582 (RWJ 67657), JNJ 17089540 (RWJ 669307), JNJ 7583979 (RWJ 351958), SCIO-282 (SD 282) and SCIO-469 (SD 469).

Also encompassed within the scope of the invention are kits comprising one or more p38 MAP kinase inhibitors and/or formulations disclosed herein.

BRIEF DESCRIPTION OF THE DRAWINGS

FIG. 5A is a bar graph of the effects of REMICADE® on inhibition of $PGE_2$ synthesis. The Y axis represents $PGE_2$ in pg/ml and the X axis represents REMICADE® concentration in ng/ml. FIG. 5B is a bar graph of the effects of REMICADE® on inhibition of NO production. The Y axis represents NO in μM and the X axis represents REMICADE® concentration in ng/ml. FIG. 5C is a bar graph of the effects of REMICADE® on inhibition of GAG degradation. The Y axis represents GAG in μg/ml and the X axis represents REMICADE® concentration in ng/ml.

FIG. 9A is a bar graph of the effect of SCIO-282 (SD 282) on inhibition of GAG degradation. FIG. 9B is a bar graph of the effect of JNJ 17089540 (RWJ 669307) on inhibition of GAG degradation. FIG. 9C is a bar graph of the effect of JNJ 3026582 (RWJ 67657) on inhibition of GAG degradation. In FIG. 9A-C, the Y axis represents GAG levels in μg/ml and the X axis represents drug concentration in μM.

FIG. 10A is a bar graph of the cytotoxicity of SCIO-282 (SD 282) and JNJ 17089540 (RWJ 669307) in the presence of 10 ng/ml of Il-1β or absence of Il-1β. FIG. 10B is a bar graph of the cytotoxicity of JNJ 7583979 (RWJ 351958) in the presence of 10 ng/ml of Il-1β or absence of Il-1β. FIG. 10C is a bar graph of the cytotoxicity of JNJ 3026582 (RWJ 67657) in the presence of 10 ng/ml of Il-1β or absence of Il-1β.

FIG. 18A is a bar graph demonstrating the effect of JNJ 17089540 (RWJ 669307) on inhibition of GAG degradation. The Y axis represents GAG in μg/ml and the X axis represents JNJ 17089540 (RWJ 669307) in μM concentrations. FIG. 18B is a bar graph demonstrating the effect of SCIO-282 (SD 282) on inhibition of GAG degradation. The Y axis represents GAG in μg/ml and the X axis represents SCIO-282 (SD 282) in μM concentrations. FIG. 18C is a bar graph demonstrating the effect of JNJ 17089540 (RWJ 669307) on inhibition of NO production. The Y axis represents NO in μM and the X axis represents JNJ 17089540 (RWJ 669307) in μM. FIG. 18D is a bar graph demonstrating the effect of SCIO-282 (SD 282) on inhibition of NO production. The Y axis represents NO in μg/ml and the X axis represents SCIO-282 (SD 282) in μM concentrations. FIG. 18E is a bar graph demonstrating the effect of JNJ 17089540 (RWJ 669307) on inhibition of $PGE_2$ synthesis. The Y axis represents $PGE_2$ in pg/ml and the X axis represents JNJ 17089540 (RWJ 669307) in μM. FIG. 18F is a bar graph demonstrating the effect of SCIO-282 (SD 282) on inhibition of $PGE_2$ synthesis. The Y axis represents $PGE_2$ in pg/ml and the X axis represents SCIO-282 (SD 282) in μM concentrations.

Figure 1A:
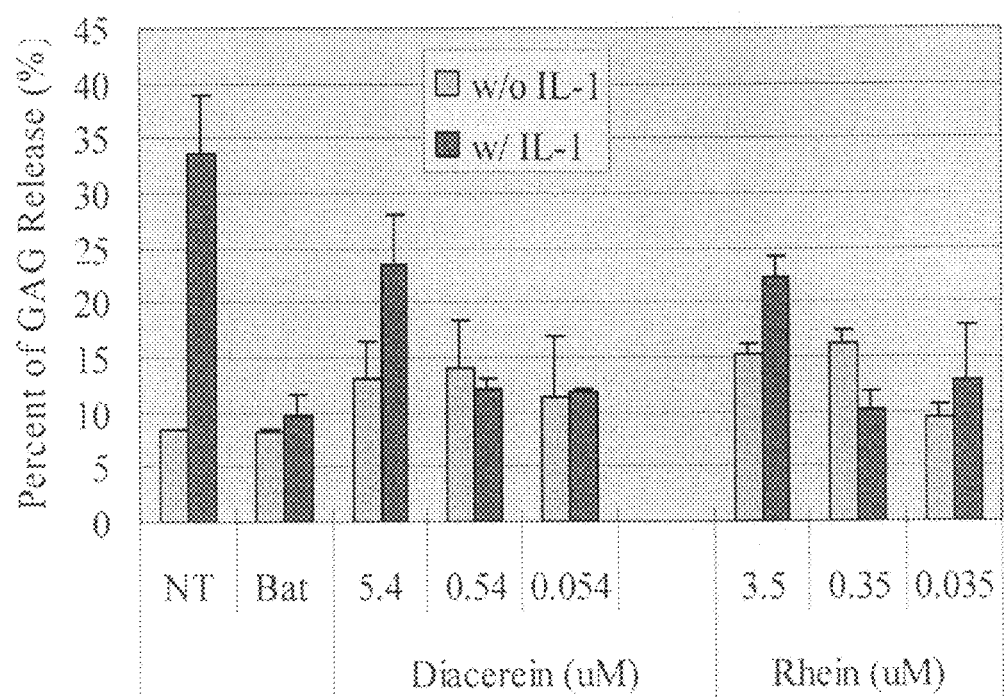
FIG. 1A is a bar graph of the effects of diacerein and rhein on inhibition of GAG degradation in the presence or absence of 10 ng/ml of IL-1β. The Y axis represents percent of GAG inhibition and the X axis represents diacerein and rhein in μM. In addition, non-treated (NT) and Batimastat (Bat) treated tissues were tested.

The foregoing will be apparent from the following more particular description of example embodiments of the invention, as illustrated in the accompanying drawings.

DETAILED DESCRIPTION OF THE INVENTION

For the purposes of the present invention, the terms "inhibitor" and "antagonist" are used interchangeably. A protein may be inhibited at the synthesis level, at the translation level, by shedding, by antibodies, or, in some cases, by soluble receptors. The term "patient" refers to a human having an inflamed joint, such as a hip, knee, toe, finger, ankle, elbow, wrist, shoulder, sacro-iliac and/or spinal facet joint.

Veterinary uses are also encompassed within the scope of the invention. For example, agents disclosed herein can be administered as described herein, to an animal, such as a mammal, for example, a dog, cat or horse.

For the purposes of the present invention "Transcapsular administration" includes, but is not limited to:
 a) injecting a formulation into the capsule of a degenerating joint,
 b) providing the formulation in a patch attached to the outer wall of the capsule,
 c) providing the formulation in a depot at a location outside but closely adjacent to the outer wall of the capsule,
 d) providing the formulation in a depot at a location within at least one of the adjacent bony bodies (hereinafter, "trans-endplate administration"), and
 e) providing the formulation in a depot at a location inside the capsule or within the capsular wall.

As each of the hip, knee, shoulder, ankle, elbow, wrist, toe, finger, sacro-iliac and spinal facet joints may become inflamed due to wear and the presence of pro-inflammatory molecules, the present invention may be beneficially directed to any or all of these joints. In general, each of these joints comprises:
 a) opposing bones having respective opposing hyaline cartilage articular surfaces,
 b) a peripheral, collagenous ligamentous capsule connecting the articular surfaces and defining a central joint space,
 c) a synovium lining upon an inner wall of the capsule, and
 d) synovial fluid contained within the joint space.

In some preferred embodiments, the target joint is a spinal facet joint. The spinal facet joint capsule may contribute to back or leg pain in at least one of the following ways:
 a) chemical sensitization of nerve fibrils contained within the collagenous ligaments of the spinal facet joint capsule,
 b) mediation of and/or direct degeneration of the hyaline articular surfaces, and/or
 c) chemical sensitization of nerve fibrils adjacent or in proximity to a facet joint due to exudation of inflammatory molecules from the capsule during mechanical capsular hydraulic pumping.

Accordingly, the present inventors believe that intra-capsular administration of p38 MAP kinase inhibitors and, optionally, additional therapeutic agents may therapeutically benefit the spinal facet joint capsule by i) preventing cytokine binding to the nerve fibrils within the ligament portion of the spinal facet joint capsule, ii) preventing further degradation of the hyaline cartilage portion of the spinal facet joint, and/or iii) preventing cytokine binding to the extra-capsular nerve fibrils.

Braun, *Expert Opin. Biol. Ther.* 3(1):141-168 (2003) ("Braun I") reviews the efficacy of infliximab, a high specificity antagonist of TNF-α, in treating chronic inflammatory diseases. Braun reports that infliximab is delivered through essentially systemic administration routes. Braun does not report any local administration routes.

Braun, *Ann. Rheum. Dis.,* 61 (Supp. III): iii51-iii60 (2002), reviews the international experience of the use of anti-TNF-α therapy for ankylosing spondylitis. Braun II reports that anti-TNF-α drugs are delivered through essentially systemic administration routes. Braun II does not report any local administration routes.

Olmarker, *Spine,* 26(8):863-9 (2001) ("Olmarker I") and Aoki, *Spine,* 27(15):1614-17 (2002) teach that TNF-α appears to play a role in the producing the pain associated with the nucleus pulposus contacting nerve roots of the spinal cord.

U.S. Published Patent Application No. US 2003/0039651 ("Olmarker II") teaches a therapeutic treatment of nerve disorders comprising administration of a therapeutically effective dosage of at least two substances selected from the group consisting of TNF inhibitors (both specific and non-specific), IL-1 inhibitors, IL-6 inhibitors, IL-8 inhibitors, FAS inhibitors, FAS ligand inhibitors, and IFN-gamma inhibitors. In the examples of Olmarker II, it is taught that these substances are to be administered through systemic pathways. In particular, Olmarker II teaches that "the major contribution of TNF-alpha may be derived from recruited, aggregated and maybe even extravasated leukocytes, and that successful pharmacologic block may be achieved only by systemic treatment".

U.S. Pat. No. 6,419,944 ("Tobinick I") discloses treating herniated discs with cytokine antagonists, including infliximab. However, Tobinick teaches that local administration involves an extradiscal injection between the disc and spinal cord. Accordingly, Tobinick does not teach a procedure involving directly administering a specific cytokine antagonist (such as infliximab) into a capsuled space.

U.S. Published Patent Application No. 2003/0049256 (Tobinick II) discloses that injection of such therapeutic molecules to the anatomic area adjacent to the spine is accomplished by interspinous injection, and preferably is accomplished by injection through the skin in the anatomic area between two adjacent spinous processes of the vertebral column.

Tobinick II discloses several spine and orthopaedic applications: Spinal Cord Injury (#12); neuropathic pain (#14); lumbar and Cervical Radiculopathy (#15); low back pain (#17), and Vertebral Disc Disease (#19). Tobinick teaches a parenteral/perispinal route of administration for spinal cord injuries; a perispinal route of administration for neuropathic pain; a perispinal route of administration for lumbar and Cervical Radiculopathy; a parenteral/perispinal route of administration for low back pain; and a perispinal route of administration for Vertebral Disc Disease. In each of applications Nos. 14, 15, 17 and 19, Tobinick appears to teach that the disc must be herniated, torn or leaking and so an extruded nucleus pulposus is the target tissue.

Tobinick II further teaches that TNF antagonists may be administered by interspinous injection in the human and that the dosage level is in the range of 1 mg to 300 mg per dose, with dosage intervals as short as two days. Tobinick II further discloses that Interleukin-1 antagonists are administered in a therapeutically effective dose, which will generally be 10 mg to 200 mg per dose, and their dosage interval will be as frequent as once daily.

Tobinick, *Swiss Med. Weekly,* 133:170-77 (2003), ("Tobinick III") teaches both perispinal and epidural administration of TNF inhibitors for spine related therapies.

Alini, *Eur. Spine J.,* 11(Supp.2):S215-220 (2002), teaches therapies for early stage disc degeneration disease, DDD, including injection of inhibitors of proteolytic enzymes or biological factors that stimulate cell metabolic activity (i.e., growth factors) in order to slow down the degenerative process. Alini does not teach any similar injections into joints having synovial fluid.

U.S. Published Patent Application US2002/0026244 ("Trieu") discloses an intervertebral disc nucleus comprising a hydrogel that may deliver desired pharmacological agents. Trieu teaches that these pharmacological agents may include growth factors such as TGF-B and anti-inflammatory drugs, including steroids. Trieu further teaches that these pharmacological agents may be dispersed within the hydrogel having an appropriate level of porosity to release the pharmacological agent at a desired rate. Trieu teaches that these agents may be released upon cyclic loading or upon resorption. Trieu does not teach any similar injections into joints having synovial fluid.

Maeda et al. *Spine*, 25(20): 166-169 (2000), reports on the in vitro response to interleukin-1 receptor antagonist protein (IRAP) of rabbit annulus fibrosus exposed to IL-1. Maeda suggests that IRAP could be useful in inhibiting the degradation of the disc. Maeda does not teach any similar utility for joints having synovial fluid.

Igarashi et al., ISSLS Abstract #262 (May 13-17, 2003), sought to quantify the levels of various cytokines present within the facet joints of patients suffering from low back pain and sciatica. Igarashi appears to report that the levels of TNF-α were below the detection limits of the assay, but that the higher levels of IL-1β (for the patients with lumbar canal stenosis), and IL-6 were each statistically significant.

EP 1153607 A2 ("Dunn") discloses injecting anti-cytokines (and in particular, an anti-TNF antibody fusion protein called "Enbrel™" which binds only soluble TNF), anti-kinases, anti-proteases, and anti-growth factors into orthopaedic joints, including those of the vertebrae. Dunn also discloses that these agents may be administered with a lubricant, such as hyaluronic acid.

U.S. Pat. No. 5,095,037 ("Iwamitsu") discloses local administration of a composition comprising (a) an effective amount of hyaluronic acid or its salt, and (b) an effective amount of an anti-inflammatory agent. Iwamitsu particularly discloses Diclofenac, a COX-2 enzyme inhibitor, as one suitable anti-inflammatory agent.

WO 03/000190 A2 ("Thompson") discloses a composition comprising glycosaminoglycans encapsulated in a liposomal delivery system for intra-articular administration for the treatment of osteoarthritis. Thompson further teaches that the composition may further include additional benefit agents such as p38 MAP kinase inhibitors, TNF inhibitors, and inhibitors of enzymes that are involved in the destruction of articulating joints and synovial fluid components (such as hyaluronidase inhibitors, MMP inhibitors, aggrecanase inhibitors, or apoptosis inhibitors such as EPO), and cartilage enhancing factors such as TGF-β and BMP. Thompson does not specifically teach p38 MAP kinase inhibitors having high specificity towards p38 MAP kinase.

Certain molecules, such as tetravalent guanylhydrazone, non-specifically inhibit p38 MAP kinase.

Wittenberg et al., *Arthritis Rheum.*, 36(10):1444-50 (Oct. 1993) investigated the major source of eicosanoid release in arthritic joint tissues. Release of prostaglandin E2 (PGE2), 6-keto-PGF1 alpha, leukotriene B4 (LTB4), and LTC4 were measured. Wittenberg reported in vitro experiments showing that the PG release was significantly inhibited by the addition of indomethacin or diclofenac (a COX-2 enzyme inhibitor) at either $10^{-5}$ moles/liter or $10^{-7}$ moles/liter. Wittenberg concluded that synovial tissue appears to be the major source of eicosanoids in synovial fluid, and that indomethacin and diclofenac inhibit the release of PG, but not LT, from various joint tissues.

The present invention is directed to providing directly into an inflamed joint at least one antagonist, including a highly specific antagonist capable of specifically inhibiting pro-inflammatory processes in the joint, such as a cytokine antagonist. In some embodiments, the antagonist is a p38 MAP kinase inhibitor. In the instant specification and figures, p38, p38 kinase and p38 MAP kinase are used interchangeably. Preferably, the p38 MAP kinase inhibitor specifically inhibits the action of a pro-inflammatory molecule released by local hyaline cartilage cells, local synovial cells or invading macrophages during the degenerative joint process.

In some embodiments, the agent (e.g., p38 MAP kinase inhibitor) is specific to two cytokines. In some embodiments, the antagonist is specific to one cytokine.

In some embodiments, the agent (e.g., cytokine antagonist) is capable of specifically inhibiting a pro-inflammatory cytokine selected from the group consisting of TNF-α, an interleukin (preferably, IL-1β, Il-6 and IL-8), FAS, an FAS ligand, and IFN-gamma. Some of these specific inhibitors include those identified on pages 5-18 of U.S. Published Patent Application No. 2003/0039651 ("Olmarker II"), which is incorporated by reference in its entirety.

In some embodiments, the agent inhibits the pro-inflammatory molecule by preventing its production. In some embodiments, the agent inhibits the pro-inflammatory molecule by binding to a membrane-bound pro-inflammatory molecule. In others, the agent inhibits the pro-inflammatory molecule by binding to a solubilized, e.g., soluble, pro-inflammatory molecule. In some embodiments, the agent inhibits the pro-inflammatory molecule by both binding to membrane bound pro-inflammatory molecules and to solubilized pro-inflammatory molecules. In some embodiments, the agent is a monoclonal antibody ("mAb"). The use of mAbs is highly desirable since they bind specifically to a certain target protein and to no other proteins. In some embodiments, the agent inhibits the pro-inflammatory molecule by binding to a natural receptor of the target pro-inflammatory molecule. In some embodiments, the pro-inflammatory molecule is a pro-inflammatory cytokine.

P38 MAP Kinase Inhibitors

Trans-capsular administration of an effective amount of an antagonist of p38 MAP kinase would help provide therapy to a patient having osteoarthritis. Therefore, in accordance with an embodiment of the present invention, there is provided a method of treating an inflamed orthopedic joint, comprising trans-capsularly administering an effective amount of a formulation comprising an antagonist of p38 MAP kinase into an inflamed orthopedic joint.

The inhibition of p38 MAP kinase is believed to inhibit (e.g., block production) of pro-inflammatory cytokines such as TNF-α. p38 MAP kinase inhibitors also inhibit production of IL-1, IL-6 and IL-8, but not IL-2. Without wishing to be tied to a theory, it is believed that inhibition of p38 MAP kinase should not block TGF signaling nor TGF activity. p38 MAP kinase inhibitors may also block induction of some metalloproteinases, COX2 and NO synthetase, but they do not inhibit interleukins involved in immune cell proliferation such as IL-2. Both p38 MAP kinases and JNK MAP kinases play important roles in mediating proinflammatory cytokine stimulation and synthesis, for cytokines such as interleukin 1 and tumor necrosis factor alpha, maintaining the chronicity of chondrocyte anabolism and catabolism and mediating tissue damage. The availability of potent and selective p38 MAP kinase mitogen activated protein kinase inhibitors provides a means for further dissecting the pathways implicated in cytokine production.

In some embodiments, the antagonist is a small molecule inhibitor of p38 MAP kinase. The small molecule inhibitors of p38 MAP kinase are potent (~nM). Preferably, they are provided in a about 5-100 microgram dose. In one embodiment, the inhibitors are provided in a dose (or doses) of less than about 2 ccs. For in vitro assays, the "dose" can be about 5-100 nM (nanomolar). In some embodiments, the dose can be about 0.02-50 μM (micromolar). In some embodiments, the p38 MAP kinase inhibitor is present in the formulation in an amount of at least about 1 microgram/ml to about 5 milligram/ml, for example, about 5 mg/ml. In some embodiments, the range is about 1 μg/ml-1.2 mg/ml. Some antagonists of p38 MAP kinase are disclosed in Zhang, *J. Biol. Chem.*, 272(20): 13397-402 (May 16, 1997); Pargellis, *Nature Structural Biology*, 9(4): 268-272 (April 2002); and Chae, *Bone*, 28(1): 45-53 (January 2001), and in U.S. Pat. No. 6,541,477 ("Goehring"), U.S. Pat. No. 5,965,583 ("Beers"), and U.S. Pat. No. 7,244,441 ("Schreiner"), which are hereby incorporated by reference in their entirety.

In some embodiments, the p38 MAP kinase inhibitor is selected from the group consisting of JNJ 7583979 (RWJ 351958), JNJ 3026582 (RWJ 67657), JNJ 17089540 (RWJ 669307), SCIO-469 (SD 469) (Scios) and SCIO-282 (SD 282) (Scios).

Figure 9A:
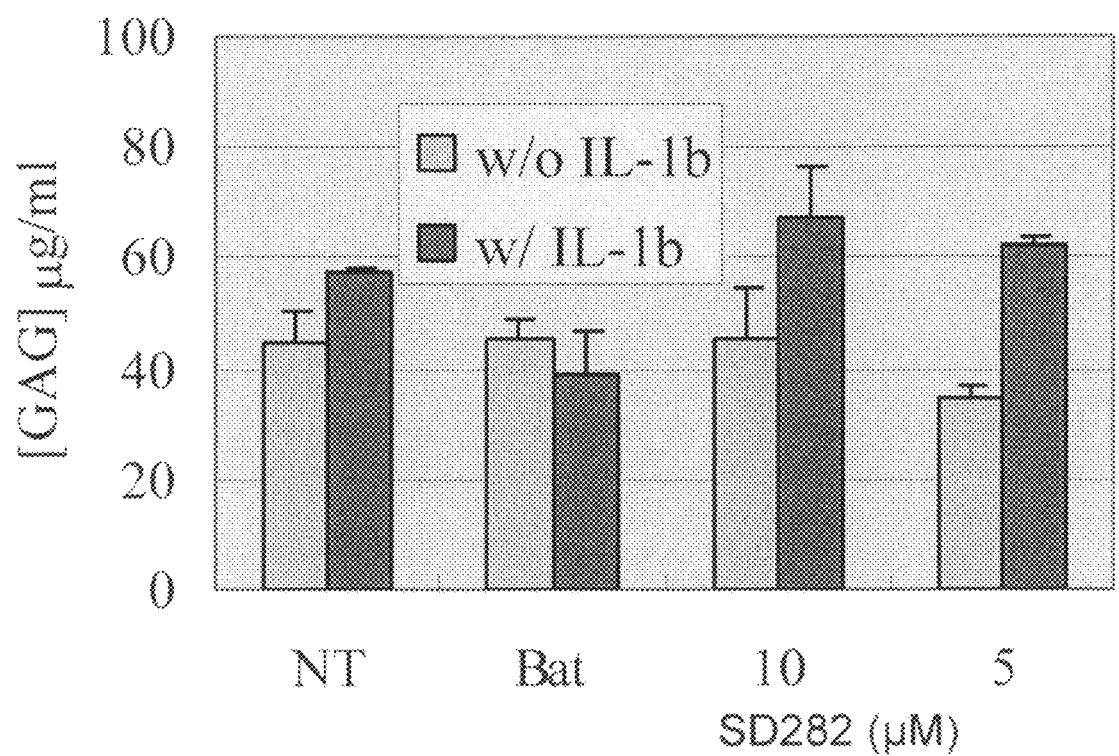
FIG. 9A-C are bar graphs of the effects of p38 MAP kinase inhibitors on inhibition of GAG degradation. Bovine ARC tissues were treated with test compounds at indicated concentrations (μM) in the absence (left bars) or presence (right bars) of 7.5 ng/ml of IL-1β.
Figure 9B:
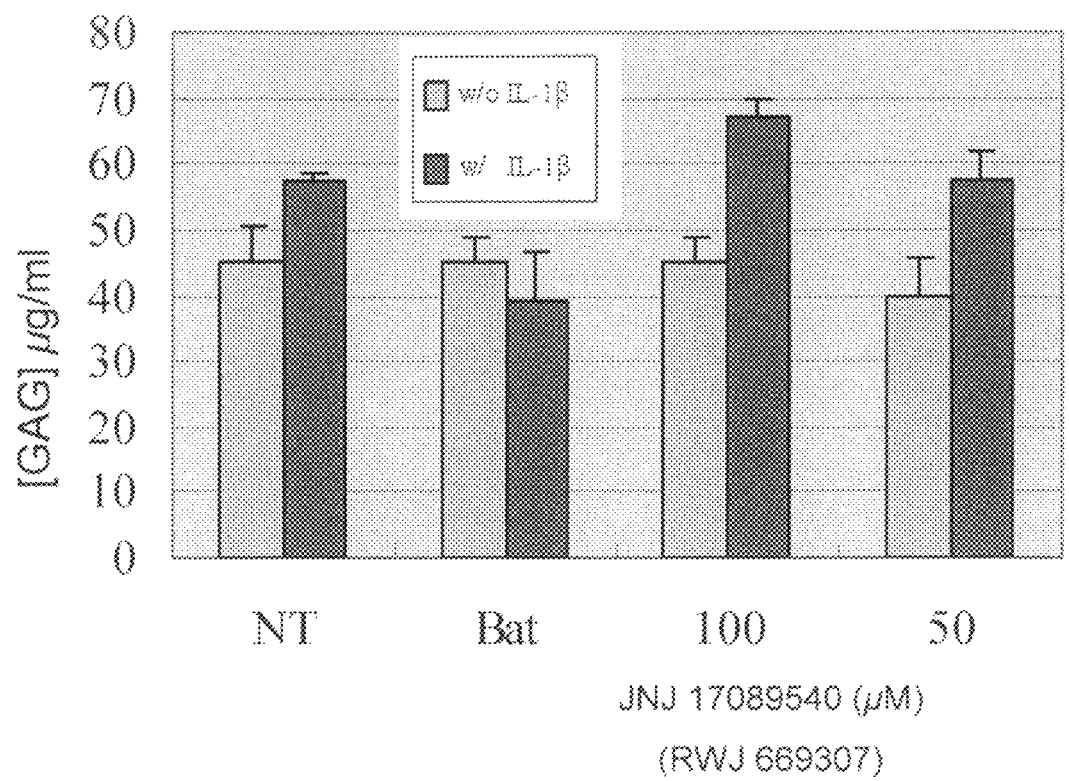
Figure 9C:
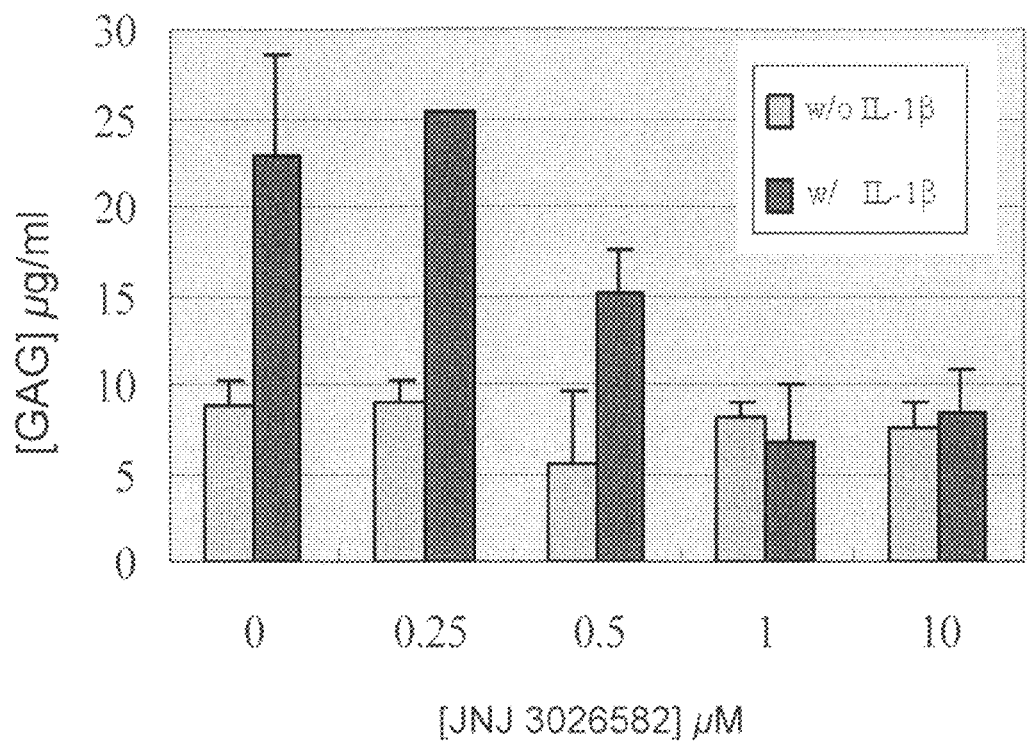
Figure 12A:
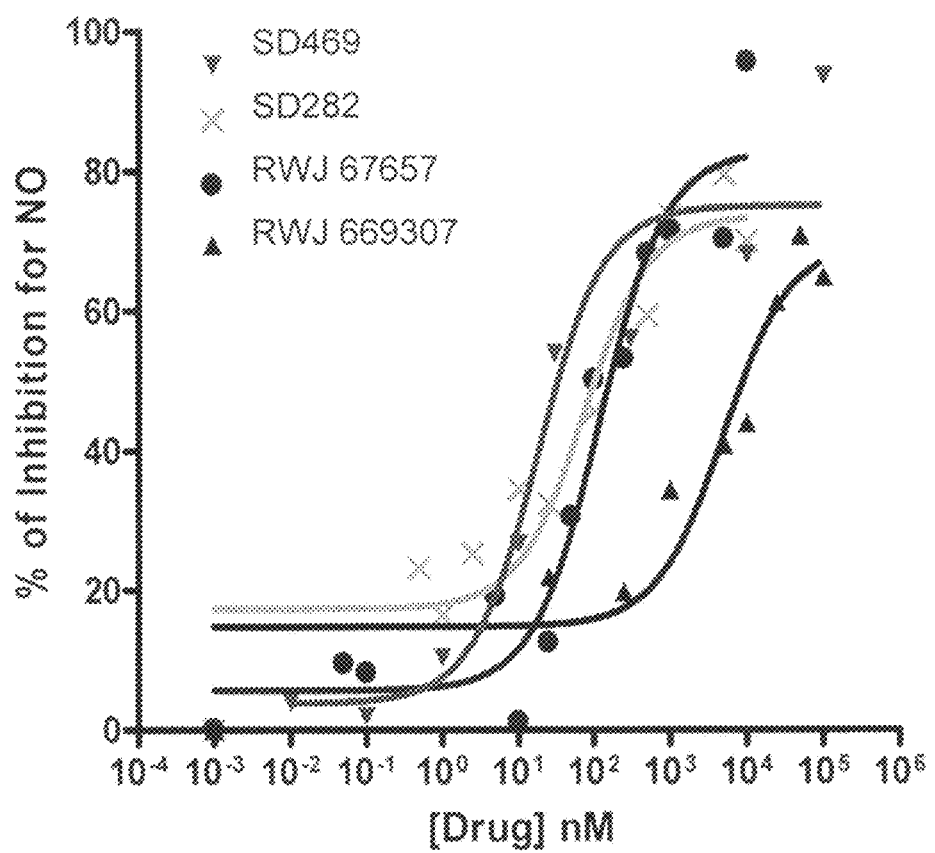
FIG. 12A is a dose-response curve of SCIO-469 (SD 469); SCIO-282 (SD 282); JNJ 3026582 (RWJ 67657); and JNJ 17089540 (RWJ 669307) for percent of inhibition of NO production in bovine ARC tissues in the presence of 10 ng/ml of Il-1β or absence of Il-1β.
Figure 12B:
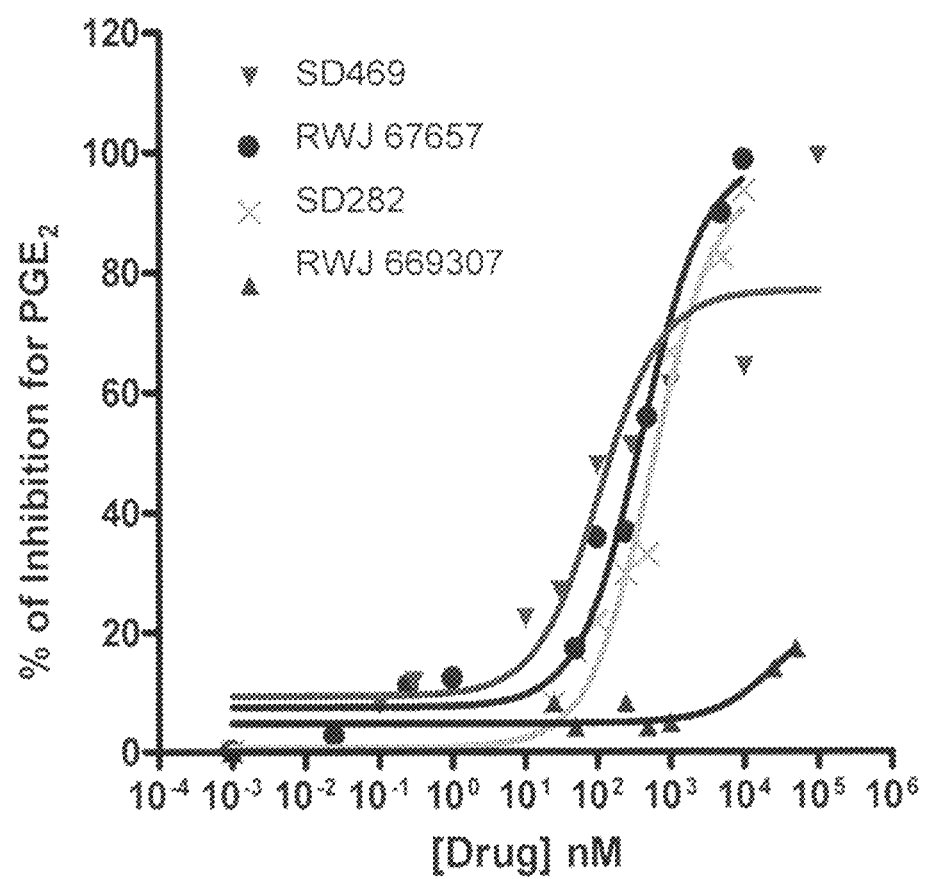
FIG. 12B is a dose-response curve of SCIO-469 (SD 469); SCIO-282 (SD 282); JNJ 3026582 (RWJ 67657); and JNJ 17089540 (RWJ 669307) for percent of inhibition of $PGE_2$ synthesis. The Y axis represents percent of inhibition and the X axis represents the test compounds in μM concentrations.
Figure 13A:
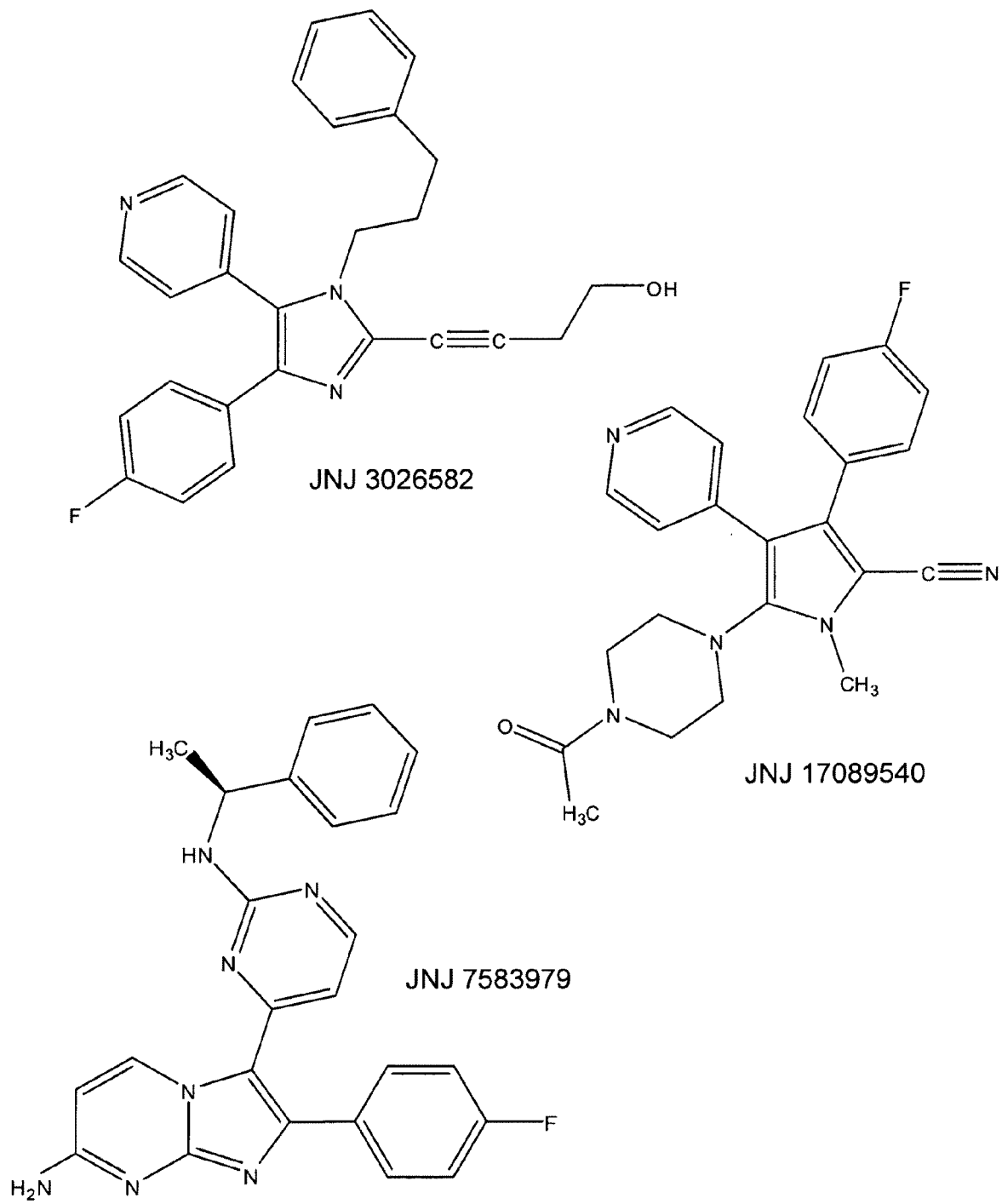
FIG. 13A shows the chemical structures for JNJ 3026582 (RWJ 67657); JNJ 17089540 (RWJ 669307); and JNJ 7583979 (RWJ 351958).

JNJ 3026582 (RWJ 67657) has the following properties: inhibitor of p38 MAP kinase α with an $IC_{50}$ 20 nM; binds p38 MAP kinase α with a Kd of 9 nM; inhibitor of JNK2 with an $IC_{50}$ 80 nM; inhibitor of LPS-induced TNF human peripheral blood mononuclear cells (hPBMC) with an $IC_{50}$ 4 nM; inhibitor of COX1 with an $IC_{50}$>10 μM; and inhibitor of COX2 with an $IC_{50}$>10 μM; molecular weight 425.51; poor water solubility (soluble in 0.1 M HCl); and soluble at pH<2. JNJ 3026582 (RWJ 67657) is a potent dual inhibitor of both p38 MAP kinase and c-Jun N-terminal kinase (JNK MAP kinase). The structure of JNJ 3026582 (RWJ 67657) is represented in FIG. 13A. As seen in Example III, JNJ 3026582 (RWJ 67657) significantly inhibited GAG degradation (FIG. 9C) and inhibited NO production and $PGE_2$ synthesis (FIGS. 12A and 12B and Table 3B) in a chondrocyte pellet culture model. As seen in Example IV, JNJ 3026582 (RWJ 67657) dose-dependently inhibited NO production and $PGE_2$ synthesis (FIGS. 17B and 17C and Table 4) in a drop tower model. As seen in Example VII, JNJ 3026582 (RWJ 67657) demonstrated a dose response curve favoring the low dose group in an ACLT model. JNJ 3026582 (RWJ 67657) is a 2-ethylynyl imidazole derivative.

JNJ 17089540 (RWJ 669307) has the following properties: inhibitor of p38α MAP kinase with an $IC_{50}$ 2 μM; binds to inactivated p38 MAP kinase with a Kd 100 nM; inhibitor of LPS-induced TNF hPBMC with an $IC_{50}$ 220 nM; inhibitor of LPS-induced IL-1 in hPBMC with an $IC_{50}$ of 250 nM; and inhibitor of COX1 and COX2 with an $IC_{50}$>10 μM; molecular weight 403.46; and water solubility>100 mg/ml of HCl salt. JNJ 17089540 (RWJ 669307) is a weak inhibitor of p38 MAP kinase and it is a TNFα modulator. Its mechanism of action is based on binding to unactivated p38 MAP kinase and preventing its phosphorylation activity. JNJ 17089540 (RWJ 669307) does not inhibit active p38 MAP kinase directly, but rather binds to unactivated p38 MAP kinase and prevents its activation by upstream kinases. The term "modulator" of TNF production means that it prevents p38 MAP kinase from becoming activated. The structure of JNJ 17089540 (RWJ 669307) is represented in FIG. 13A. As seen in Example VII, JNJ 17089540 (RWJ 669307) was efficacious in reducing the clinical scores across multiple endpoints. As seen in Example IX, JNJ 17089540 (RWJ 669307) demonstrated a trend towards improvement in a therapeutic drop tower model. JNJ 17089540 is a 3,4 aryl or heteroaryl substituted pyrrole derivative.

JNJ 7583979 (RWJ 351958) has the following properties: inhibitor of p38α MAP kinase with an $IC_{50}$ 1 nM; inhibitor of JNK with an $IC_{50}$ 12 nM; inhibitor of TNF human whole blood (HWB) with an $IC_{50}$ 5 nM; inhibitor of COX1 and COX2 with an $IC_{50}$>10 μM; molecular weight 425.47; and poor water solubility (>1 mg/ml at pH 2). The structure of JNJ 7583979 (RWJ 351958) is represented in FIG. 13A. As seen in Example III, JNJ 7583979 (RWJ 351958) significantly inhibited NO production and $PGE_2$ synthesis (FIGS. 7A and 7B and Table 3B) and significantly inhibited GAG degradation (FIG. 8) in a chrondrocyte pellet culture model. JNJ 7583979 is a 2,3 aryl or heteroaryl substituted imidazopyrimidine derivative.

Figure 18A:
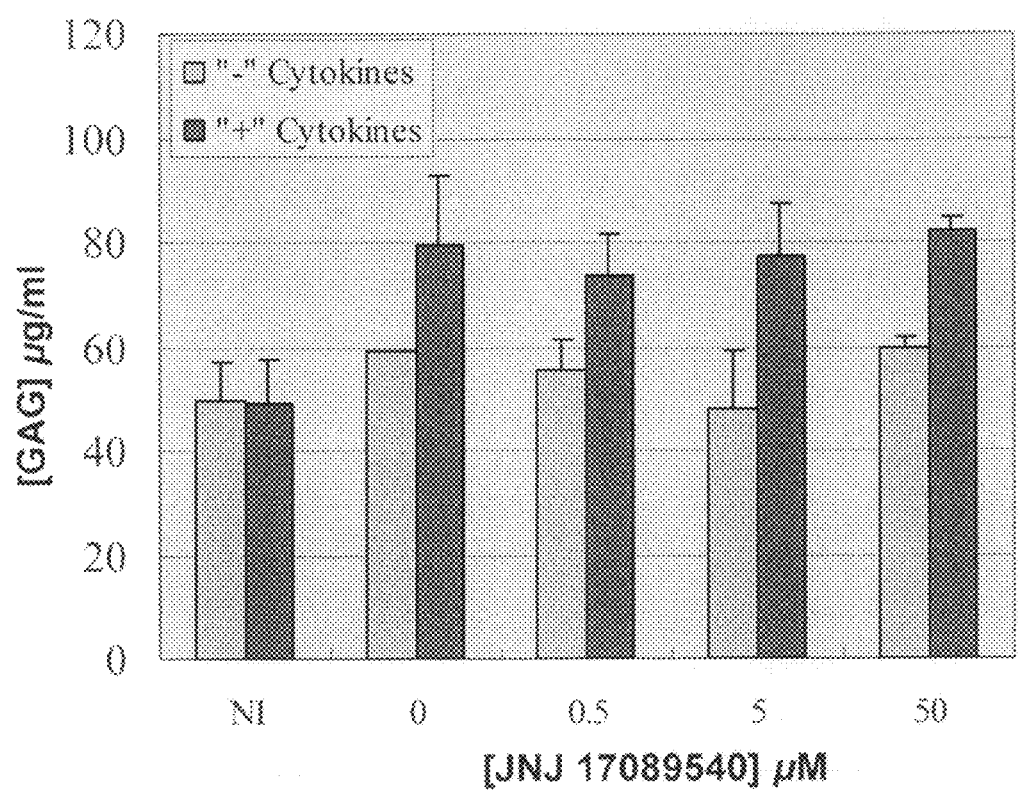
FIGS. 18A-F are bar graphs demonstrating the effects of p38 MAP kinase inhibitors on GAG degradation, NO production and $PGE_2$ synthesis in injured cartilage explants in the presence ("+") or absence ("−") of a cocktail of cytokines (10 ng/ml of IL-1β, 10 ng/ml IL-6 and 100 ng/ml of TNFα). "NI" is the non-injured cartilage specimen.
Figure 18B:
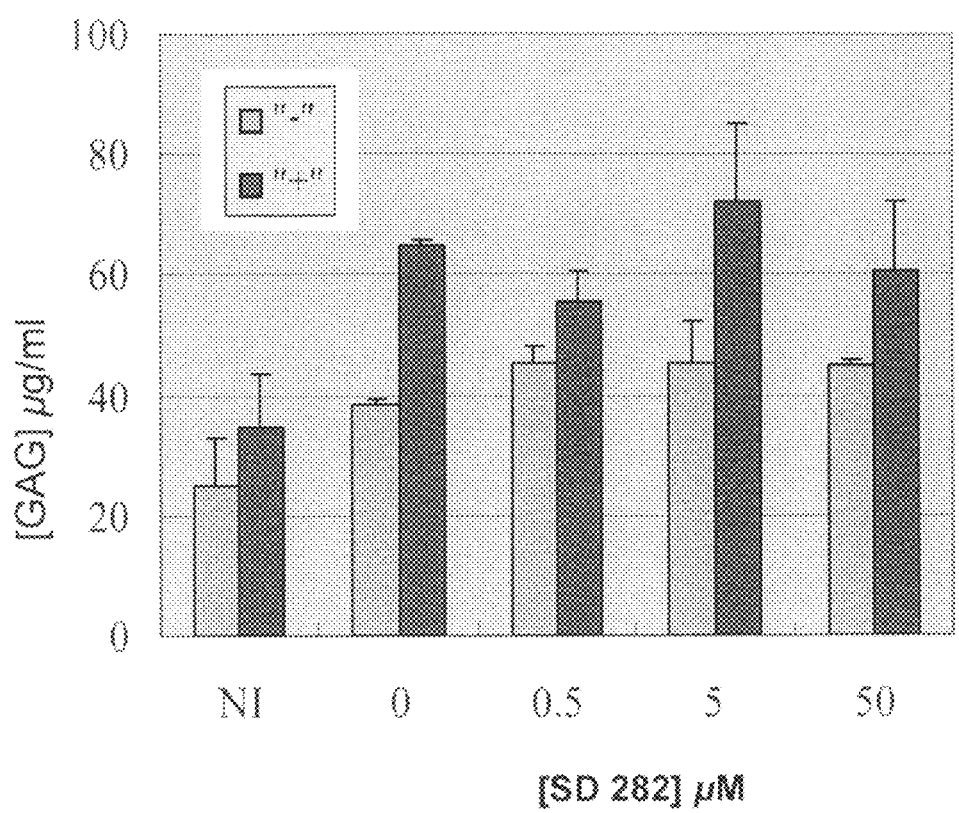
Figure 18C:
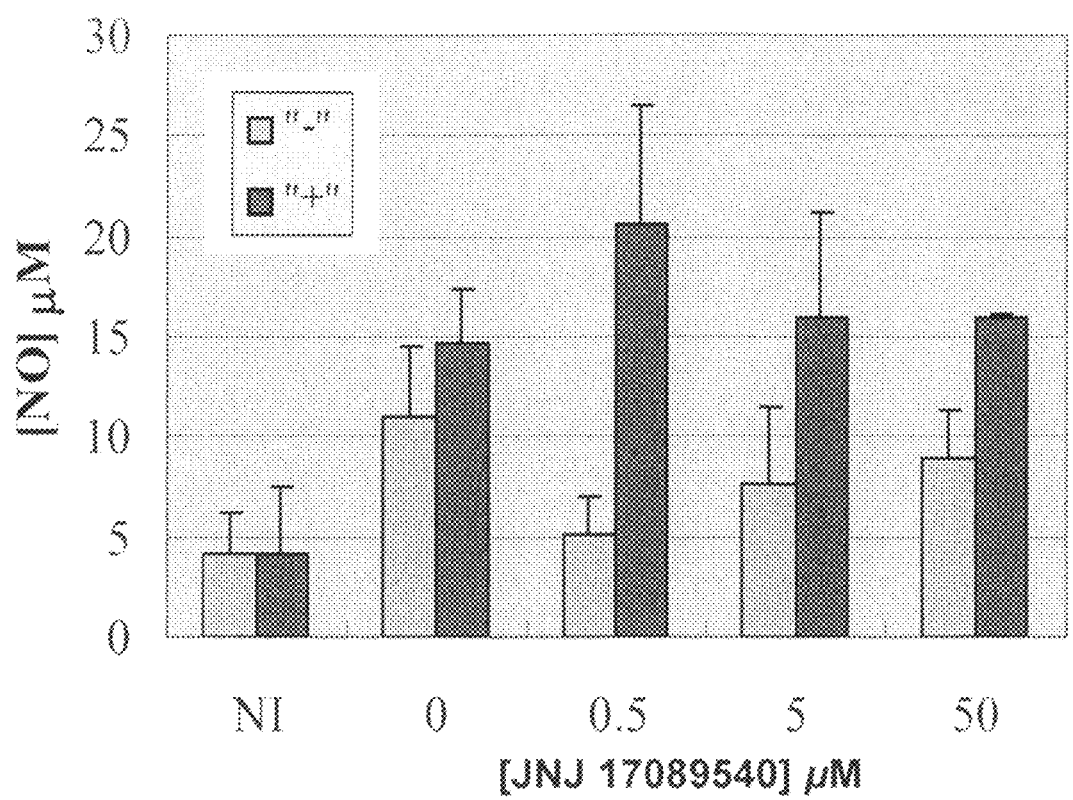
Figure 18D:
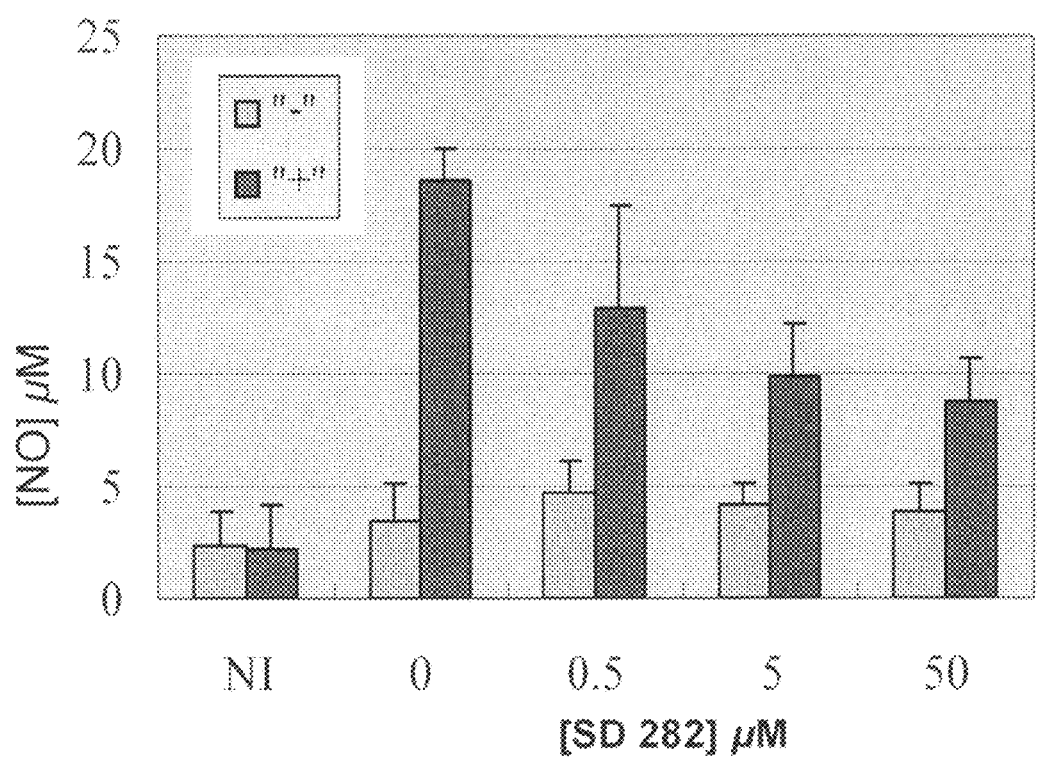
Figure 18E:
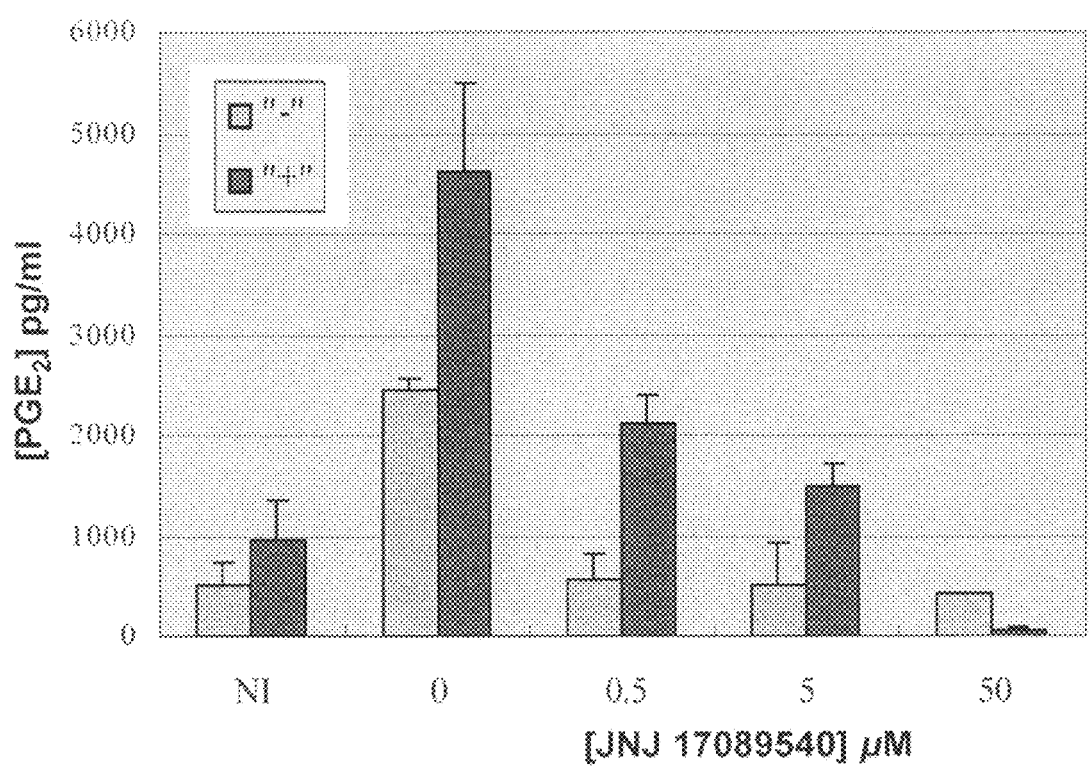
Figure 18F:
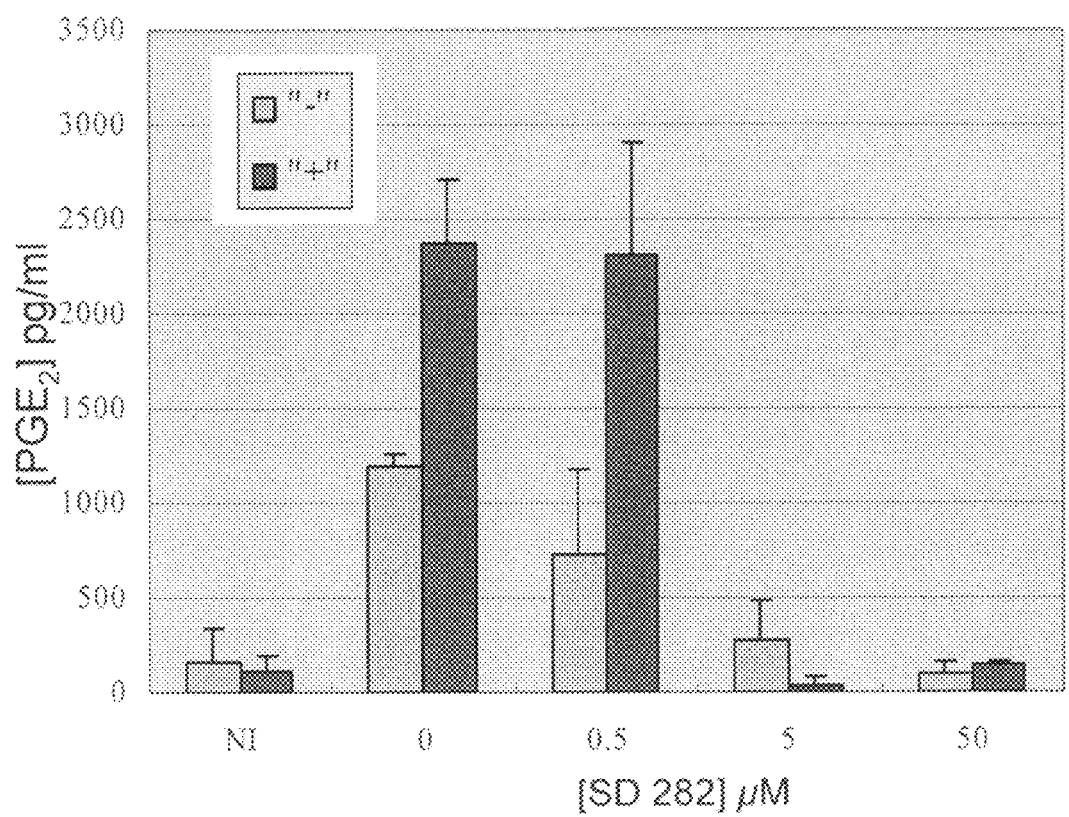

SCIO-282 (SD 282) has the following properties: inhibitor of p38α MAP kinase with an $IC_{50}$ 1.6 nM; inhibitor of p38β MAP kinase with an $IC_{50}$ of 23 nM; selectivity for p38α MAP kinase and p38β MAP kinase β of approximately 15; CYP2C9 with an $IC_{50}$ of 0.5 μM; inhibits TNFα h-WBA (EC50), of 0.07 μM (10× diluted); Rat (F) PK (F %, t1/2) of 46%; and limited water solubility. SCIO-282 (SD 282) is a direct inhibitor or selective inhibitor of p38 MAP kinase alpha and it has limited water solubility. SCIO-282 (SD 282) has the identical chemical structure as SCIO-469 (SD 469) except that the indole nitrogen has a hydrogen instead of a methyl substituent. As seen in Example IV, SCIO-282 (SD 282) dose-dependently inhibited NO production and $PGE_2$ synthesis (FIGS. 18D and 18F). SD-282 has the identical chemical structure as SD-469 except that the indole nitrogen has a hydrogen instead of a methyl substituent.

Figure 13B:
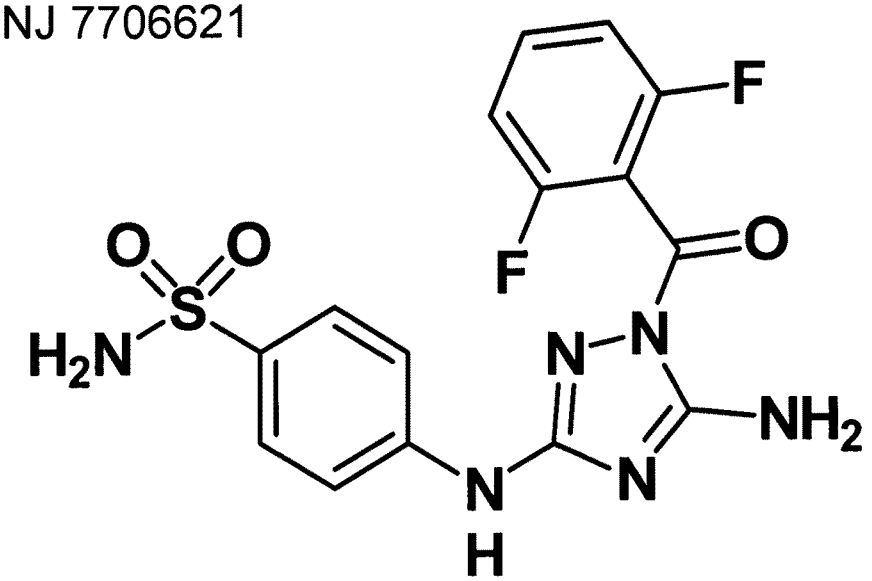
FIG. 13B shows the chemical structure for JNJ 7706621.
Figure 13C:
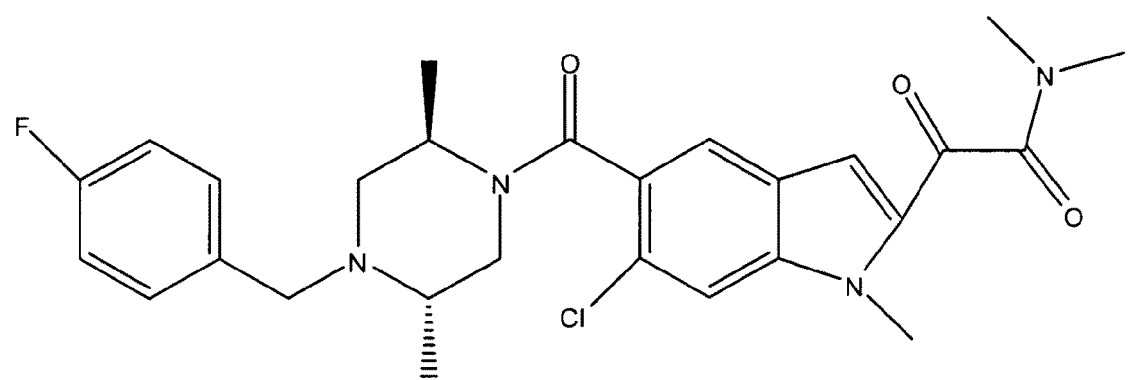
FIG. 13C shows the chemical structure for SD-469.

SCIO-469 (SD 469) has the following properties: inhibitor of p38 MAP kinase α with an $IC_{50}$ 9 nM; inhibitor of p38 MAP kinase β with an $IC_{50}$ of 98 nM; selectivity for p38 MAP kinase α and p38 MAP kinase β of approximately 10; 6 CYP450 with an $IC_{50}$ of >1 μM; inhibits TNFα h-WBA (EC50), of 1.6 μM (10× diluted); Rat (F) PK (F %, t1/2) of 1 h; Rat (M) PK (F %, t1/2) of 15%, 0.5 h; Monkey (F) PK (F %, t1/2) of 12%, 1.3 h; and Monkey (F) PK (F %, t1/2) of 12%, 1.3 h; formula $C_{27}H_{30}N_4O_3F_1Cl_1$; molecular weight is 513.01; molecular volume (cm$^3$) is 273.3; surface area (cm$^2$/mol×10$^9$) is 33.84; Log P is 2.82; molar volume (cm$^3$/mol) is 356.8; HLB is 11.55; Hansen's solubility parameter (delta/sqr (Mpa)) is 23.9 (11.72H); % hydrophilic surface is 48.8; water solubility (mg/mL) is 0.00004; H bond acceptor is 0.95; H bond donor is 0.43; polarity is 8.15; dipole moment (debyes) is 4.89; and max charge on N is −0.40226. SCIO-469 (SD 469) is a p38 MAP kinase inhibitor specific for the a unit. As seen in Example VIII, SCIO-469 (SD 469) demonstrated a trend towards improvement in the therapeutic model. As seen in Example IV, SCIO-469 (SD 469) inhibited NO production and $PGE_2$ synthesis (FIGS. 12A and 12B) in a drop tower model. The structure of SD-469 is represented in FIG. 13C.

SCIO-282 and SCIO-469 are indole based heterocyclic inhibitors. See Mavunkel, B., et al., "Indole-Based Heterocyclic Inhibitors of p38 MAP Kinase: Designing a Conformationally Restricted Analogue," *Bioorganic & Medicinal Chemistry Letters*, 13: 3087-3090 (2003) is incorporated herein by reference in its entirety.

Figure 10A:
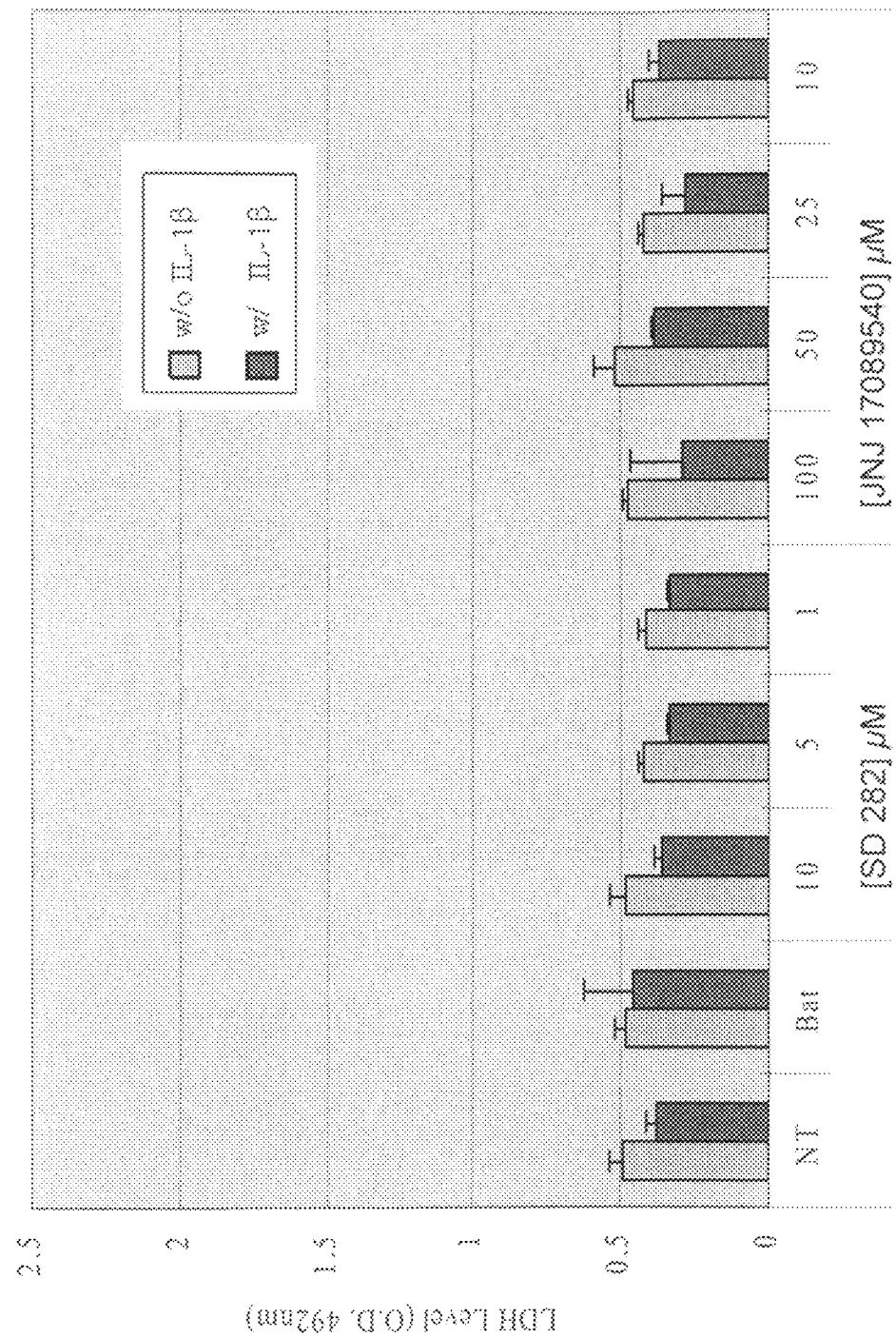
FIG. 10A-C are bar graphs of the cytotoxicity of p38 MAP kinase inhibitors. The Y axis represents LDH level (O.D. 492 nm) and the X axis represents the test compound in μM concentrations. The scales of Y axis were intentionally set at a larger value usually observed for a pellet with more than 80% of cell death to demonstrate the low toxicity of this class of molecules. In addition, non-treated (NT) and Batimastat (Bat) treated tissues were tested as controls. The same culture media was used as in FIGS. 7A-B, 8 and 9A-C.
Figure 10B:
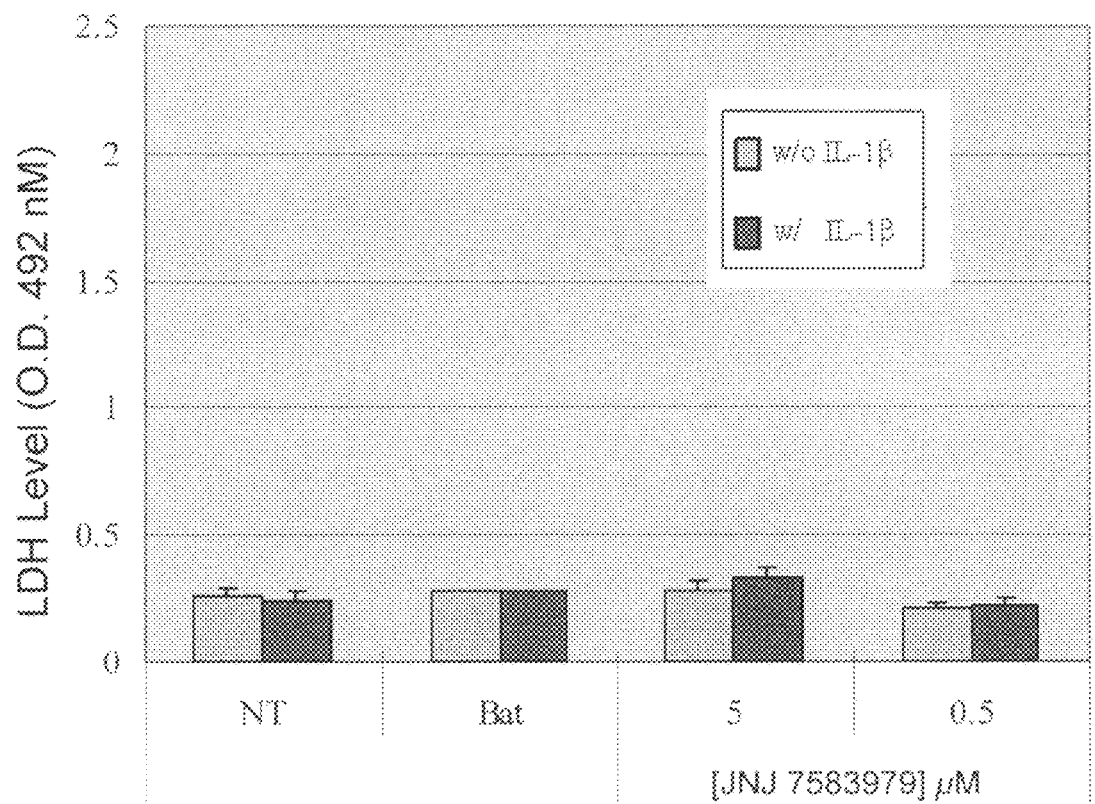
Figure 10C:
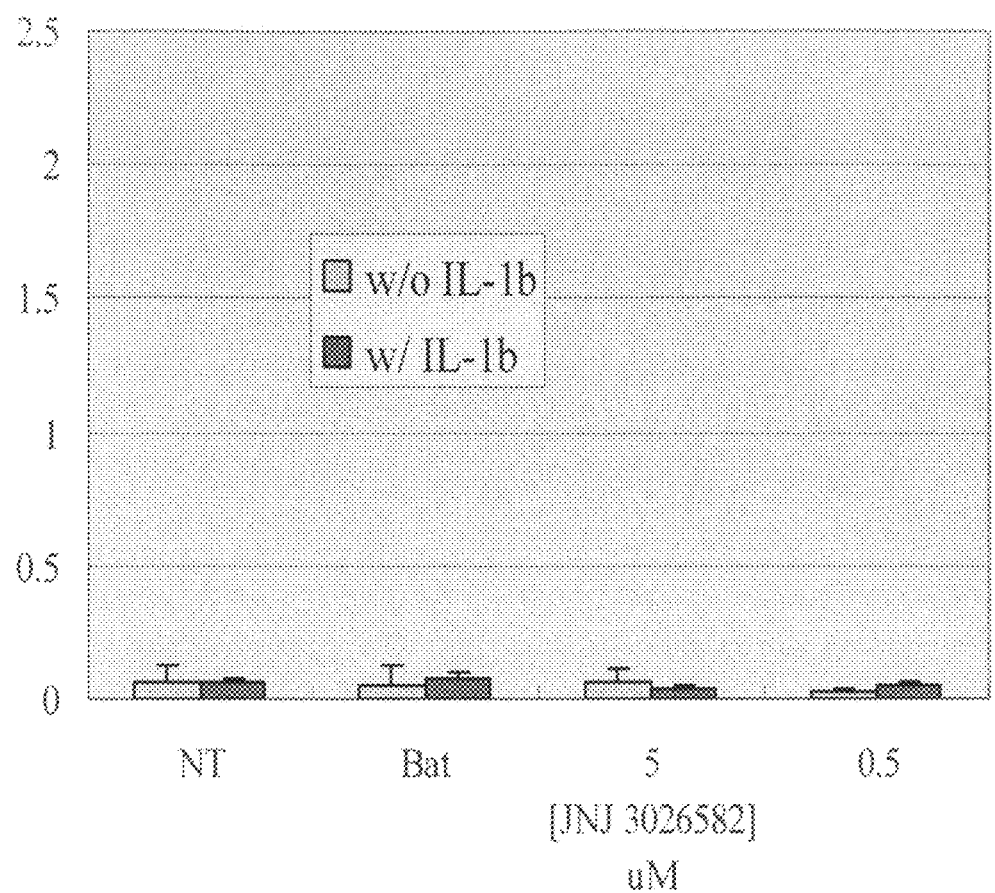

Further, as seen in Example III, FIGS. 10A-C, JNJ 7583979 (RWJ 351958), JNJ 3026582 (RWJ 67657), JNJ 17089540 (RWJ 669307) and SD282 all showed little cytoxicity to chondrocytes within the tested concentrations.

The JNJ 7583979 (RWJ 351958), JNJ 3026582 (RWJ 67657), and JNJ 17089540 (RWJ 669307) compounds are Aryl-pyridyl heterocycles. The SCIO-282 (SD 282) and SCIO-469 (SD 469) compounds are indol-5-carboxamides.

In some embodiments, the p38 MAP kinase inhibitor is selected from the group consisting of:
a) diaryl imidazole;
b) N,N'-diaryl urea (developed by Bayer, Boehringer Ingelheim and Vertex);
c) N,N-diaryl urea (developed by Vertex);
d) benzophenone (developed by Leo Pharmaceuticals);
e) pyrazole ketone (developed by Hoffman-LaRoche);
f) indole amide (developed by GlaxoSmithKline and Scios);
g) diamides (developed by AstraZeneca);
h) quinazoline (developed by GlaxoSmithKline);
i) pyrimido [4,5-d]pyrimidinone (developed by GlaxoSmithKline and Hoffman LaRoche); and
j) pyridylamino-quinazolines (developed by Scios).

Members of this group are further described, for example, in Zhang et al., supra, Pargellis et al., supra, Chae et al., supra, and Cirillo et al., *Current Topics in Medicinal Chemistry*, 2: 1021-1035 (2002), Boehm et al, *Exp. Opin, Ther. Patents*, 10(1):25-38 (2000), and Lee et al., *Immunopharmacology*, 47: 185-2001 (2000), which are incorporated by reference in their entirety.

In some embodiments, the p38 MAP kinase inhibitor is characterized as a 1-aryl-2-pyridinyl heterocycle. In some embodiments, the 1-aryl-2-pyridinyl heterocycle is selected from the group consisting of:
a) 4,5 substituted imidazole,
b) 1,4,5 substituted imidazole;
c) 2,4,5 substituted imidazole;
d) 1,2,4,5 substituted imidazole; and
e) non-imidazole 5-membered ring heterocycle.

In some embodiments, the p38 MAP kinase inhibitor has at least 3 cyclic groups.

In some embodiments, the p38 MAP kinase inhibitor is selected from the group consisting of a molecule that is readily soluble in water and a substantially water insoluble molecule. In some embodiments, the p38 MAP kinase inhibitor is a substantially water insoluble molecule. The substantially water insoluble p38 MAP kinase inhibitor may be advantageous in that, if injected into the nucleus pulposus or capsule, it may remain in the nucleus pulposus or capsule as a solid and only slightly solubilize over time, thereby providing sustained release.

In some embodiments, the p38 MAP kinase inhibitor is selected from the group consisting of:
a) SK&F 86002;
b) SB 203580;
c) L-167307;
d) HEP 689;
e) SB220025;
f) VX-745;
g) SU4984;
h) RWJ 68354;
i) ZM336372;
j) PD098059;
k) SB235699;
l) SB220025;
m) JNJ 3026582 (RWJ 67657) (Johnson & Johnson);
n) JNJ 17089540 (RWJ 669307) (Johnson & Johnson);
o) JNJ 7583979 (RWJ 351958) (Johnson & Johnson);
p) SCIO-282 (SD 282) (developed by Scios); and
q) SCIO-469 (SD 469) (developed by Scios).

Additional details regarding a number of these inhibitors are found in Table 1.

TABLE 1

P38 MAP KINASE INHIBITORS

| Name | Chemical Formula |
|---|---|
| JNJ3026582 (RWJ 67657) | 4-[4-(4-fluorophenyl)-1-(3-phenylpropyl)-5-(4-pyridinyl)-1H-imidazol-2-yl]-3-butyn-1-ol |
| SK&F86002 | 6-(4'-fluorophenyl)-5-(4'-pyridyl)-2,3-dihydroimadazo(2,1-b)-thiazole |
| SB203580 | 4-(4-fluorophenyl)-2-(4-methylsulfinylphenyl)-5-(4-pyridyl)imidazole |
| L-167307 | 3-(4-pyridyl-2-(4-fluoro-phenyl)-5-(4-methylsulfinylphenyl)-pyrrole |
| HEP689 | Aminobenzophenone compound |
| SB220025 | 5-(2amino-4-pyrimidinyl)-4-(4-fluorophenyl)-1-(4-piperidinyl)imidazole |
| VX-745 | 5-(2,6-Dichlorophenyl)-2-(phenylthio)-6H-pyrimido[1,6-b]pyridazin-6-one |
| SU4984 | 4-[4-(2-Oxo-1,2-dihydro-indol-3-ylidenemethyl)-phenyl]-piperazine-1-carbaldehyde |
| RWJ-68354 | 6-Amino-2-(4-fluorophenyl)-4-methoxy-3-(4pyridyl)-1H-pyrrolo[2,3-b]pyridine |
| ZM336372 | N-[5-(dimethyl-aminobensamido)-2-methylphenyl]-4-hydroxybenzamide |
| PD098059 | 2'-Amino-3'-methoxyflavone |
| SB220025 | 5-(2-Amino-4-pyrimidinyl)-4-(fluorophenyl)-1-(4-piperidinyl)imidazole |
| PD169316 | 4-(4-Fluorophenyl)-2-(4-nitrophenyl)-5-(4-pyridyl)-1H-imidazole |
| ML3403 | (RS)-{4-[5-(4-Fluorophenyl)-2-methylsulfanyl-3H-imidazol-4-yl]pyridin-2-yl}-(1-phenylethyl)amine] |
| ML3163 | 4-[5-(4-Fluorophenyl)-2-(4-methanesulfinyl-benzylsulfanyl)-3H-imidazol-4-yl]pyridine |
| SB242235 | 1-(4-piperidinyl)-4-(4-fluorophenyl)-5-(2-methoxy-4-pyrimidinyl)imidazole |
| SB239063 | trans-1-(4-Hydroxycyclohexyl)-4-(4-fluorophenyl)-5-(2-methoxypyrimidin-4-yl)imidazole |

TABLE 1-continued

P38 MAP KINASE INHIBITORS

| Name | Chemical Formula |
| --- | --- |
| M39 | Aminopyridine-based inhibitor |
| SD-169 | Indole-5-carboxamide |
| EO-1428 | |
| SC-68376 | 2-Methyl-4-phenyl-5-(4-pyridyl)oxazole |
| PD169316 | 4-(4-Fluorophenyl)-2-(4-nitrophenyl)-5-(4-pyridyl)-1H-imidazole |
| SB202190 | 4-(4-Fluorophenyl)-2-(4-hydroxyphenyl)-5-(4-pyridyl)1H-imidazole |
| TAK-715 | N-[4-[2-ethyl-4-(3-methylphenyl)-1,3-thiazol-5-yl]-2-pyridyl]benzamide |
| VX-702 | |
| RPR 200765A | A 2-(2-dioxanyl)imidazole |
| BIRB-796 | Non-diaryl imidazole inhibitor |
| AMG-548 | Structure undisclosed |
| Ro-320-1195 | S-[5-Amino-1-(4-fluorophenyl)-1H-pyrazol-4-yl]-[3-(2,3-dihydroxypropoxy)phenyl]methanone |

Tumor Necrosis Factor Inhibitors

In some embodiments, the agent is a highly specific inhibitor of TNF-α. In some embodiments, the p38 MAP kinase inhibitor is a TNF-α inhibitor. In some embodiments, the inhibitor of TNF-α is an inhibitor of p38 MAP kinase, preferably, a small molecule inhibitor of p38 MAP kinase.

In some embodiments, the TNF-α inhibitor inhibits the TNF-α by binding to membrane-bound TNF-α in order to prevent its release from membrane. In others, the TNF-α inhibitor inhibits the TNF-α by binding to solubilized TNF-α. One example thereof is etanercept. In some embodiments, the TNF-α inhibitor inhibits the TNF-α by both binding to membrane bound TNF-α and to solubilized TNF-α. One example thereof is REMICADE® infliximab. In some embodiments, the TNF-α inhibitor inhibits the TNF-α by preventing its production. In some embodiments, the cytokine antagonist inhibits the cytokine (e.g., TNF-α) by binding to a natural receptor of the target cytokine. In some embodiments, the TNF-α inhibitor is an inhibitor of TNF-α synthesis.

Preferred TNF antagonists include, but are not limited to, the following: etanercept (ENBREL®, Amgen); infliximab (REMICADE®, Johnson & Johnson); D2E7, a human anti-TNF monoclonal antibody (Knoll Pharmaceuticals, Abbott Laboratories); CDP 571 (a humanized anti-TNF IgG4 antibody); CDP 870 (an anti-TNF alpha humanized monoclonal antibody fragment), both from Celltech; soluble TNF receptor Type I (Amgen); pegylated soluble TNF receptor Type I (PEGs TNF-R1) (Amgen); onercept, a recombinant TNF binding protein (r-TBP-1) (Serono); and CNTO 148 (Centocor/Johnson & Johnson), which is a fully human antibody and disclosed in U.S. Pat. No. 7,250,165, the contents of which are hereby incorporated by reference in their entirety.

TNF antagonists suitable for compositions, combination therapy, co-administration, devices and/or methods of the present invention (optionally further comprising at least one antibody, specified portion and/or variant thereof, of the present invention), include, but are not limited to, anti-TNF antibodies (e.g., at least one TNF antagonist (e.g., but not limited to a TNF chemical or protein antagonist, e.g., an anti-TNF antibody, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, REMICADE® infliximab, ENBREL® etanercept, HUMIRA™ adalimumab, CDP-571, CDP-870, afelimomab, lenercept, and the like); antigen-binding fragments thereof, receptor molecules which bind specifically to TNF; compounds which prevent and/or inhibit TNF synthesis, TNF release or its action on target cells, such as thalidomide, tenidap, phosphodiesterase inhibitors (e.g. pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody", "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNF-alpha (TNFα). A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

In one embodiment, the antagonist is REMICADE®, infliximab, or cA2. Chimeric monoclonal antibody cA2 consists of the antigen binding variable region of the high-specificity neutralizing mouse anti-human TNFα IgG1 antibody, designated A2, and the constant regions of a human IgG 1, kappa immunoglobulin. The human IgG 1 Fc region improves allogeneic antibody effector function, increases the circulating serum half-life and decreases the immunogenicity of the antibody. The avidity and epitope specificity of cA2 is derived from the variable region of A2. A preferred source for nucleic acids encoding the variable region of the murine antibody A2 is the A2 hybridoma cell line designated c134A. Chimeric antibody cA2 is produced by a cell line designated c168A.

Chimeric A2 (cA2) neutralizes the cytotoxic effect of both natural and recombinant human TNFα in a dose dependent manner. Preferred methods for determining monoclonal antibody specificity and specificity by competitive inhibition can be found in Harlow et al., *Antibodies. A Laboratory Manual*, Cold Spring Harbor Laboratory Press, Cold Spring Harbor, N.Y. (1988); Colligan et al., eds., *Current Protocols in Immunology*, Greene Publishing Assoc. and Wiley Interscience, New York, (1992-2000); Kozbor et al., *Immunol. Today,* 4:72-79 (1983); Ausubel et al., eds. *Current Protocols in Molecular Biology*, Wiley Interscience, New York (1987-2000); and Muller, *Meth. Enzymol.,* 92:589-601 (1983), which references are entirely incorporated herein by reference.

In one embodiment, the TNF antibody is selected from the group of compounds disclosed in U.S. Pat. No. 6,277,969, which is entirely incorporated by reference herein. In some embodiments, the TNF antibody is delivered to produce a formulation having an antibody concentration of between about 1 ug/ml and about 30 ug/ml. In some embodiments, the antibody is delivered in a formulation having an an antibody concentration of between about 30 mg/ml and about 60 mg/ml.

In some embodiments, the antibody binds to human TNFα with an affinity of $1\times10^8$ liter/mole, measured as an association constant (Ka). In some embodiments, the affinity constant of the antibody is $1.0^4\times10^{10}$ $M^{-1}$. Additional examples of monoclonal anti-TNF antibodies that can be used in the present invention are described in the art (see, e.g., U.S. Pat. No. 5,231,024; Möller, A. et al., *Cytokine* 2(3):162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang et al., *Biochem. Biophys. Res. Comm.* 137:847-854 (1986); Meager et al., *Hybridoma* 6:305-311 (1987); Fendly et al., *Hybridoma* 6:359-369 (1987); Bringman et al., *Hybridoma* 6:489-507 (1987); and Hirai, et al., *J. Immunol. Meth.* 96:57-62 (1987), which references are entirely incorporated herein by reference).

Preferred TNF receptor molecules useful in the present invention are those that bind TNFα with high specificity (see, e.g., Feldmann et al., International Publication No. WO 92/07076 (published Apr. 30, 1992); Schall et al., *Cell,* 61:361-370 (1990); and Loetscher et al, *Cell,* 61:351-359 (1990), which references are entirely incorporated herein by reference) and, optionally, possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high specificity, as well as other undefined properties, can contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al, U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116, 964; Capon et al., U.S. Pat. No. 5,225,538; and Capon et al., *Nature* 337:525-531(1989), which references are entirely incorporated herein by reference.

A functional equivalent, derivative, fragment or region of a TNF receptor molecule refers to the portion of the TNF receptor molecule, or the portion of the TNF receptor molecule sequence which encodes the TNF receptor molecule, that is of sufficient size and sequences to functionally resemble TNF receptor molecules that can be used in the present invention (e.g., bind TNFα with high specificity and possess low immunogenicity). A functional equivalent of a TNF receptor molecule also includes modified TNF receptor molecules that functionally resemble TNF receptor molecules that can be used in the present invention (e.g., bind TNFα with high specificity and possess low immunogenicity). For example, a functional equivalent of a TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1987-2003).

In some embodiments, the monoclonal antibody that inhibits a cytokine (e.g., TNF-α) is selected from the group consisting of monoclonal rodent-human antibodies, rodent antibodies, human antibodies or any portions thereof, having at least one antigen binding region of an immunoglobulin variable region, which antibody binds TNF. In one embodiment, this monoclonal antibody is selected from the group of compounds disclosed in U.S. Pat. No. 6,277,969, the specification of which is entirely incorporated by reference.

Degenerative joint disease ("DJD") involves the progressive degeneration of a joint in which many factors are involved. In many of these instances, simply providing a single dose or even a regimen of the agent (e.g., the p38 MAP kinase antagonist) over the space of a few days may not be sufficient to resolve the DJD. For example, if DJD were caused in part by mechanical instability or wear in the joint, then simply providing a one-time therapy for the joint cells and fibrils will likely only delay the onset of the DJD. Therefore, there is a need to provide a long-term drug therapy treatment of DJD that does not require multiple injections.

Because it is believed that the target molecules of interest may both produce pain and degrade the joint when present within the capsule, it is desirable for the antagonist to remain within the joint as long as possible in a pharmaceutically effective amount. The half-life of the antagonist within the joint will depend upon many factors, including the size of the antagonist and its charge. In general, the larger the molecular weight of the antagonist, the more likely it is to remain contained by the capsule portion of the joint.

When using an antagonist whose half-life is relatively short, it would be desirable for a relatively large dose of the antagonist to be administered into the joint. In this condition, quick depletion of the antagonist would not cause the antagonist to fall below therapeutically effective levels until an extended period.

Although a large dose of the antagonist would be desirable in such instances, it is also known that nociceptors present within the inner wall of the capsule react to increased pressure and produce pain, and that one avenue for increasing the pressure in the capsule is to inject a critical volume of water. In some cases, and in the relatively small spinal facet joint in particular, an added amount of as little as a few cc's by volume could produce pain. Accordingly, if a dilute concentration of an antagonist is added to the synovial fluid to provide a large dose, the resulting pressure increase caused by this added volume could be sufficient to cause acute pain.

For example, if it were determined that 100 mg of an antagonist was needed to therapeutically affect a joint, and that antagonist was provided in concentrations of 30-60 mg/ml, then at least 1.5 ml of the antagonist would need to be injected into the capsule in order to provide the desired therapeutic effect. However, when injecting volumes into the capsule, and in particular a spinal facet joint capsule, it is often desirable that the volume of drug delivered be no more than about 1 ml, preferably no more than 0.5 ml, more preferably between about 0.1 and 0.3 ml. When injected in these smaller quantities, it is believed the added volume will not cause an appreciable pressure increase in the capsule. In one embodiment, the antagonist is injected into the knee in a volume of about 1-3 ml.

Accordingly, in some embodiments, the concentration of the antagonist (preferably, the p38 MAP kinase or TNF-α antagonist) in the administered drug is at least about 100 mg/ml. In this condition, no more than about 1 ml of the drug need be injected. For example, the concentration of TNF-α antagonist in the administered drug is at least 200 mg/ml. In this condition, no more than about 0.5 ml of the drug need be injected. Preferably, the concentration of TNF-α antagonist in the administered drug is at least 500 mg/ml. In this condition, between about 0.1 and about 0.3 ml of the drug need be injected. For example, the range of about about 5 mg/kg to about 50 mg/kg is an appropriate range when JNJ 3026582 (RWJ 67657) is placed into DMSO solution to be solubilized. In some preferred embodiments, the antagonist is combined in the formulation with a viscosupplement. The viscosupplement has a viscosity and elasticity substantially similar to that of natural healthy synovial fluid.

Preferably, the viscosupplement comprises glycosaminoglycans (GAGS). GAGS are biopolymers consisting of repeating polysaccharide units, and are present in nature on the cell surface as well as in the extracellular matrix of animals. GAGS are long unbranched polysaccharides containing a repeating disaccharide unit. The disaccharide unit contains either of two modified sugars, N-acetylgalactosamine or N-acetylglucosamine and a uronic acid such as glucuronate or iduronate. GAGS are highly negatively charged molecules, with extended conformation that imparts high viscosity to the solution. In addition to high viscosity, GAGS routinely possess low compressability, which makes these molecules ideal for a lubricating fluid in the joints. At the same time, their rigidity provides structural integrity to cells and provides passageways between cells, allowing for cell migration.

Hyaluronic acid (HA) is a high molecular weight polysaccharide of N-acetyl glucosamine and glucuronic acid molecules that is naturally occurring in all mammals in a variety of tissue and some bacterial species. For the purposes of this invention, HA includes any derivatives such as hyaluronan and hyaluronic acid itself with $H^+$ ion attached to the $COO^-$ group, and salts of hyaluronic acid whereby another positive ion replaces the H+ ion, as for example, with $Na^+$ which forms sodium hyaluronate. Also included in the definition of HA is any physically or chemically cross-linked hyaluronic acid or derivative. HA is unique among the GAGS in that it does not contain any sulphate and is not found covalently attached to proteins as a proteoglycan. HA polymers are very large with molecular weights of between about 100,000 and 10,000,000 and can displace a large volume of water. For the purposes of the present invention, a preferred embodiment includes a non-cross linked HA with a molecular weight of 0.5-10 M Dalton.

Preferably, the viscosupplement is selected from the group consisting of hyaluronic acid and hyaluronate (either cross-linked or uncross-linked).

In some embodiments, the antagonist is provided in a sustained release device (or "sustained delivery device"). The sustained release device is adapted to remain within the joint for a prolonged period and slowly release the antagonist contained therein to the surrounding environment. This mode of delivery allows an antagonist to remain in therapeutically effective amounts within the joint for a prolonged period.

Preferably, the sustained release device comprises a bioresorbable material whose gradual erosion causes the gradual release of the antagonist to the joint environment. In some embodiments, the sustained release device comprises a bioresorbable polymer. Preferably, the bioresorbable polymer has a half-life of at least one month, more preferably at least two months, more preferably at least 6 months. In some embodiments, the sustained release device comprises GAGS.

In some embodiments, the sustained release device provides controlled release. In others, it provides continuous release. In others, it provides intermittent release. In others, the sustained release device comprises a biosensor.

In some embodiments, the sustained delivery device comprises bioerodable macrospheres. The antagonist is preferably contained in a gelatin (or water or other solvent) within the macrosphere, and is released to the joint environment when the outer shell has been eroded. The device can include a plurality of macrospheres having outer shells of varying thickness, so that the sequential breakdown of the outer shells provides periodic release of the antagonist.

In some embodiments, the sustained delivery device comprises an inflammatory-responsive delivery system, preferably comprising bioerodable microspheres that are eroded by invading macrophages. This technology provides a high correspondence between physiologic inflammation of joint environment and the release of the antagonists into that environment. Preferably, the technology disclosed in Brown et al., *Arthritis. Rheum.*, 41(12):2185-95 (December 1998) is selected.

In some embodiments, the sustained delivery device comprises a device disclosed in U.S. Pat. No. 5,728,396 ("Peery"), the specification of which is incorporated by reference in its entirety.

In some embodiments, the sustained delivery device comprises a liposomal delivery system, such as that disclosed in WO 03/000190. Liposomes are small spheres whose walls are layers of lipids with water. As they form, liposomes entrap water and any water soluble solutes that are present. Because of this entrapping ability, they are useful as delivery systems. For the purposes of the present invention, a preferred embodiment includes the use of a multilamellar vesicle, and any naturally occurring phospholipid, such as dipalmitoylphosphatidylcholine (DPPC).

A liposome may be a vesicle having at least one lipid bilayer surrounding an inner liquid phase (a lipid bilayer surrounding either a liquid core or a liquid phase dispersed between it and another lipid bilayer). The liposome may have various structures such as multilamellar (MLVs), unilamellar (ULVs) and paucilamellar (PLVs) vesicles. The resulting structure of the liposome is dependent, in part, on the choice of materials forming the hydrophobic phase and the manufacturing parameters, such as temperature and incubation time.

Some liposomes comprise at least one amphiphilic bilayer-forming substance. The therapeutic substances contained therein may be contained either within the lipid bilayer or the hydrophilic compartments of the liposome. The amphiphilic bilayer-forming substance comprises both a hydrophilic and a lipophilic group and is capable of forming, either alone or in combination with other lipids, the bilayer of a liposome. The lipid can have single or multiple lipophilic side chains being either saturated or unsaturated in nature and branched or linear in structure. The amphiphilic bilayer-forming substance can be a phospoholipid or a ceramide.

In some embodiments, the sustained delivery device comprises a plurality (preferably at least one hundred) of water-containing chambers, each chamber containing the antagonist. Each chamber is defined by bilayer lipid membranes comprising synthetic duplicates of naturally occurring lipids. The release of the drug can be controlled by varying at least one of the aqueous excipients, the lipid components, and the manufacturing parameters. Preferably, the formulation comprises no more than 10% lipid. In some embodiments, the DEPOFOAM™ technology of Skyepharma PLC (located in London, United Kingdom) is selected.

In some embodiments, the sustained delivery device comprises a delivery system disclosed in U.S. Pat. No. 5,270,300 ("Hunziker"), the specification of which is incorporated by reference in its entirety.

In some embodiments, the sustained delivery device comprises the co-polymer poly-DL-lactide-co-glycolide (PLG). Preferably, the formulation is manufactured by combining the HSA, the co-polymer and a solvent to form a droplet, and then evaporating the solvent to form a microsphere. The plurality of microspheres are then combined in a biocompatible diluent. Preferably, the antagonist is released from the co-polymer by its diffusion therethrough and by the biodegradation of the co-polymer. In some embodiments hereof, the Pro-Lease technology of Alkermes (located in Cambridge, Mass.) is selected.

Hydrogels can also be used as a sustained release device to deliver the antagonist in a time-release manner to the joint environment. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the antagonist at the application site, thereby eliminating undesired migration from the joint. The hydrogels are also biocompatible, e.g., not toxic, to any cells suspended in the hydrogel.

A "hydrogel-antagonist composition" is a suspension of a hydrogel containing desired HSA. The hydrogel-HSA composition forms a uniform distribution of antagonist with a well-defined and precisely controllable density. Moreover, the hydrogel can support very large densities of antagonist.

Hydrogels suitable for use in the present invention include water-containing gels, i.e., polymers characterized by hydrophilicity and insolubility in water. See, for instance, "Hydrogels", pages 458-459 in *Concise Encyclopedia of Polymer Science and Engineering*, Eds. Mark et al., Wiley and Sons (1990), the disclosure of which is incorporated herein by reference. Although their use is optional in the present invention, the inclusion of hydrogels is highly preferred since they tend to contribute a number of desirable qualities. By virtue of their hydrophilic, water-containing nature, hydrogels can:

a) house viable cells, such as mesenchymal stem cells, and
b) assist with load bearing capabilities of the joint.

In a preferred embodiment, the hydrogel is a fine, powdery synthetic hydrogel. Suitable hydrogels exhibit an optimal combination of such properties as compatibility with the matrix polymer of choice, and biocompatibility. The hydrogel can include any of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

In some embodiments, the sustained delivery device includes a polymer selected from the group consisting of PLA, PGA, PCL, and mixtures thereof.

When using an antagonist, e.g., a p38 MAP kinase antagonist, having a relatively long half-life within the joint, then it may be assumed that a relatively small dose of the antagonist can be administered into the joint. In this condition, the slow depletion of the antagonist would not cause the antagonist to fall below therapeutically effective levels until an extended period of time has elapsed.

In some embodiments in which administered agents (e.g., cytokine antagonists) have long half-lives within the joint, the dose administered can be very small. For example, if it is believed that an antagonist is effective when present in the target tissue in the range of about 1-10 mg/kg or about 1-10 ppm (as is the case for the TNF-α antagonist REMICADE® (infliximab), and since a typical spinal facet joint has a volume of about 3 ml (or 3 cc, or 3 g) of synovial fluid, then only about 3-30 μg of the antagonist need be administered to the joint in order to provide a long lasting effective amount of the drug. In some embodiments, it is administered to the knee at a range of about 1 to 3 ml. As a point of reference, Tobinick discloses that at least 1 mg of cytokine antagonist should be administered perispinally in order to cure back pain. The smaller amounts available by this route reduce the chances of deleterious side effects of the antagonist.

For example, suppose a clinician administered 0.3 ml of 60 mg/ml infliximab into a 2.7 cc facet joint, thereby producing a infliximab concentration in the joint of about 6 mg/ml, or 6 parts per thousand. Without wishing to be tied to a theory, if infliximab has the same half-life within the synovial fluid of the joint as it does when administered systemically (i.e., about 1 week), then the concentration of infliximab would remain above about 10 ppm for about 9 weeks. Therefore, if another dose were needed, the clinician would only need to provide the second dose after about two months.

In one embodiment, the cytokine antagonist is effective when present in the range of about 5 mg/kg to about 50 mg/kg. In one embodiment, the cytokine antagonist is provided in a dose of about 5 μg to about 100 μg. In one embodiment, the cytokine antagonist is provided in a concentration of about 25 μg to about 50 μg.

Therefore, in some embodiments, the agent is provided in a dose of less than 1 mg, e.g., in a maximum amount of 0.5 mg, preferably, less than 0.5 mg, more preferably, less than 0.1 mg, more preferably less than 0.01 mg, more preferably less than about 0.01 mg, e.g., less than about 0.001 mg. In one embodiment, a formulation comprising the antagonist is administered in a volume of between 0.03 ml and 0.3 ml. The smaller amounts available by this route reduce the chances of deleterious side effects of the antagonist.

In one embodiment, for local delivery, for example local delivery with a hydrogel or local delivery device, the amount of compound or agent in the tissue can be 0.02 to 50 μM (micro-molar) or per ml of fluid in the cavity to be injected.

In one embodiment, for in vitro assays, the dose can be 5-100 nM (nano-molar). In some embodiments, the dose can be about 0.02-50 μM (micromolar). In one embodiment, for an in vivo dose, the dose can be about 1 microgram/ml to about 5 milligram/ml, for example, about 5 mg/ml. In some embodiments, the range is about 1 g/ml-1.2 mg/ml.

It is understood that the clinician will consider the weight, age and other factors typically considered and well-known to one of skill in the art when determining appropriate dosage for clinical use.

In preferred embodiments, the formulation of the present invention is administered directly into the joint through the outer wall of the capsule. More preferably, the direct administration includes depositing the agent in the synovial fluid-containing portion of the joint. In this condition, the fibrous nature of the capsule that surrounds and contains the synovial fluid will help keep the antagonist contained within the capsule.

Preferably, the formulation of the present invention is injected into the joint through a small bore needle. More preferably, the needle has a bore diameter of 22 gauge or less, so that the possibilities of producing a rupture are mitigated. More preferably, the needle has a bore of 24 gauge or less, so that the possibilities of producing a rupture are even further mitigated.

If the volume of the direct injection of the formulation is sufficiently high so as to cause a concern of overpressurizing the capsule, then it is preferred that at least a portion of the synovial fluid be removed prior to direct injection. Preferably, the volume of removed synovial fluid is substantially similar to the volume of the formulation to be injected. More preferably, the volume of removed synovial fluid is within 80-120% of the volume of the formulation to be injected.

In other embodiments, the formulation is delivered into the joint space through the cartilage endplate of an adjacent joint bone. This avenue eliminates the need to puncture the capsule, and so eliminates the possibility of its capsule rupture.

In some embodiments, the formulation is administered through a drug pump.

Although the antagonists may therapeutically treat the joint by binding the target pro-inflammatory molecule, and thereby reducing pain and arresting degradation of the extracellular matrix (ECM), it is believed that at least some of these antagonists do not help repair the damage done by the target molecule to the ECM. Therefore, there may be a need to provide a therapy that also helps repair the ECM.

Therapeutic Agents

In accordance with one aspect of the invention, both the agent (e.g., antagonist, e.g., p38 MAP kinase inhibitor) and at least one additional therapeutic agent (for example, a second therapeutic agent) are locally administered into the capsule. Because the p38 MAP kinase inhibitor is specific, it does not interfere with the locally administered second therapeutic agent, and so each drug may independently work to provide therapy to the diseased joint. More than one additional therapeutic agent can be administered. For example, there can be third, fourth, fifth or more therapeutic agents.

In some embodiments, the p38 MAP kinase inhibitor and additional therapeutic agent are administered simultaneously. In others, the p38 MAP kinase inhibitor is administered first. In still others, the additional therapeutic agent is administered first.

Also included in the scope of the present invention are methods of treating or preventing an inflamed joint comprising the administration of one or more of the therapeutic agents described herein.

Other compounds which may be administered include, but are not limited to: any agent recited herein; vitamins and other nutritional supplements; hormones; glycoproteins; fibronectin; peptides and proteins; carbohydrates (both simple and/or complex); proteoglycans; oligonucleotides (sense and/or antisense DNA and/or RNA); bone morphogenic proteins (BMPs); antibodies (for example, to infectious agents, tumors, drugs or hormones); gene therapy reagents; anticancer agents; anti-proliferative compounds (agents) (for example, rapamycin and JNJ 7706621); additional cytokine antagonists (for example, TNFα inhibitors such as REMICADE®, IL-6 inhibitors and Il-1β inhibitors); (MMP inhibitors, e.g., batimastat) (BB94, British Biotech Pharmaceuticals, Ltd.); non-steroidal anti-inflammatory drugs (NSAIDS) such as tolmetin, tepoxalin, diacerein and rhein; PPDCs, anti-inflammatory agents such as centella (ETCA), madecassoside; feverfew; ORC (interceed); suprofen; and tiaprofenic acid. Genetically altered cells and/or other cells may also be included in the matrix of this invention. If desired, substances such as pain killers and narcotics may also be admixed with a polymer for delivery and release to the joint space.

In one embodiment, the anti-proliferative agent is selected from the group consisting of rapamycin and JNJ 7706621. JNJ 7706621 is represented by the structure in FIG. 13B.

In another embodiment, the agent is selected from the group consisting of tolmetin, tepoxalin, suprofen, tiaprofenic acid; centella (ETCA), madecassoside, rhein, diacerein, feverfew, batimastat and ORC (INTERCEED®).

In some embodiments, healthy cells are introduced into the joint that have the capability of at least partially repairing any damage done to the hyaline articular cartilage or capsule during the degenerative process. In some embodiments, these cells are introduced into the synovial fluid and ultimately produce new extracellular matrix for the hyaline articular cartilage. In others, these cells are introduced into the capsule and produce new extracellular matrix for the capsule.

In some embodiments, these cells are obtained from another human individual (allograft), while in others, the cells are obtained from the same individual (autograft). In some embodiments, the cells are taken from articular hyaline cartilage, while in others, the cells are taken from a non-joint tissue (and may be mesenchymal stem cells). In others, autograft chondrocytes may be used (such as from the hip, knee, shoulder, fingers, or ear).

In some embodiments, when viable cells are selected as the second agent or therapeutic substance, the viable cells comprise mesenchymal stem cells (MSCs). MSCs provide a special advantage for administration into a degenerating joint because it is believed that they can more readily survive the relatively harsh environment present in the degenerating joint; that they have a desirable level of plasticity; and that they have the ability to proliferate and differentiate into the desired cells.

In some embodiments, the cells are obtained from bone marrow, preferably autologous bone marrow. In others, the mesenchymal stems cells are obtained from adipose tissue, preferably autologous adipose tissue.

In some embodiments, the mesenchymal stem cells injected into the joint are provided in an unconcentrated form. In others, they are provided in a concentrated form. When provided in concentrated form, they are preferably uncultured. Uncultured, concentrated cells can be readily obtained by centrifugation, filtration, or immuno-absorption. When filtration is selected, the methods disclosed in U.S. Pat. No. 6,049,026 ("Muschler"), which is incorporated by reference in its entirety, are preferably used. In some preferred embodiments, the matrix used to filter and concentrate the cells is also administered into the joint space. If this matrix has suitable lubricating properties, it can be used to restore the lubrication qualities of the joint that were lost during the degradation process.

In some embodiments, cartilage cells (which may be from either an allogeneic or autologous source) or mesenchymal stem cells may be genetically modified to produce a cartilage anabolic agent which can be chosen from the list of growth factors named below. The production of these chondroprotective agents and, differentiation promoting agents would lead to tissue repair.

Recent work has shown that plasmid DNA will not elicit an inflammatory response as does the use of viral vectors. Genes encoding cartilage (anabolic) agents such as BMP, etc. may be efficacious if injected into the joint. In addition, overexpression of any of the growth factors listed under growth factor delivery or other agents such as TIMP which would limit local MMP activity would have positive effects on chondrocyte and ECM protection. Preferably, the plasmid contains the genetic code for human TGF-β or EPO.

In one embodiment, the additional therapeutic agent is postpartum-derived cells (PPDCs), which are also known as postpartum cells. The PPDCs can be placenta-derived cells (PDCs) or human Umbilical Tissue-derived Cells (hUTCs). Methods for isolating and collecting PPDCs are described in U.S. application Ser. Nos. 10/877,446 and 10/877,012, which are incorporated by reference herein in their entirety.

As used herein, the term "growth factors" encompasses any cellular product that modulates the growth or differentiation of other cells, particularly connective tissue progenitor cells. Preferably, growth factors are delivered after the inhibition of the pro-inflammatory molecules has taken effect. The growth factors that may be used in accordance with the present invention include, but are not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 and 3; osteoid-inducing factor (OIF); angiogenin(s); endothelins; hepatocyte growth factor and keratinocyte growth factor; members of the bone morphogenetic proteins (BMP's) BMP-1, BMP-3, BMP-2; OP-1, BMP-2A, BMP-2B, and BMP-7; HBGF-1 and HBGF-2; growth differentiation factors (GDF's); members of the hedgehog family of proteins, including indian, sonic and desert hedgehog; ADMP-1; other members of the interleukin (IL) family; and members of the colony-stimulating factor (CSF) family, including CSF-1, G-CSF, and GM-CSF, and isoforms thereof; and VEGF.

In some embodiments, the growth factor is selected from the group consisting of TGF-B, bFGF, and IGF-1. These growth factors are believed to promote regeneration of the hyaline articular cartilage. In some embodiments, the growth factor is TGF-B. More preferably, TGF-B is administered in an amount of between about 10 ng/ml and about 5000 ng/ml, more preferably between about 50 ng/ml and about 500 ng/ml, more preferably between about 100 ng/ml and about 300 ng/ml.

In some embodiments, the growth factor is a growth differentiation factor. In some embodiments, the growth factor is MP-52. In some embodiments, the growth factor is GDF-5. The protein encoded by this gene is a member of the bone morphogenetic protein (BMP) family and the TGF-beta superfamily. This group of proteins is characterized by a polybasic proteolytic processing site which is cleaved to produce a mature protein containing seven conserved cysteine residues. The members of this family are regulators of cell growth and differentiation in both embryonic and adult tissues.

In some embodiments, platelet concentrate is provided as an additional therapeutic agent. Preferably, the growth factors released by the platelets are present in an amount at least two-fold (more preferably, four-fold) greater than the amount found in the blood from which the platelets were taken. More preferably, the platelet concentrate is autologous. In some embodiments, the platelet concentrate is platelet rich plasma (PRP). PRP is advantageous because it contains growth factors that can restimulate the growth of the ECM, and because its fibrin matrix provides a suitable scaffold for new tissue growth.

In addition, non-steroidal anti-inflammatory drugs (NSAIDs) may also be selected as additional therapeutic agents. In some embodiments, the NSAID is anabolic, and is preferably selected from the group consisting of tolmetin (available from Ortho-McNeil) and Tiaprofenic acid, (available from Roussel Labs). Preferably, the anabolic NSAID is administered in a dosage sufficient to produce an initial local tissue concentration of between about 5 ug/kg and about 500 ug/kg. In some embodiments, the NSAID is a dual inhibitor of both the COX and LOX pathways, and is preferably tepoxalin (available from Johnson & Johnson).

In addition, anti-cathepsins may also be used in accordance with the present invention. It is believed that inhibition of these enzymes inhibits the breakdown of the extracellular matrix. Preferably, the antagonists inhibits a cathepsin selected from the group consisting of cathepsin B, cathepsin L and cathepsin K.

In addition, cycline compounds may also be used as an additional therapeutic agent in accordance with the present invention. Preferably, the cycline compound is administered in an amount effective to inhibit the action of a pro-inflammatory cytokine (such as TNF-α) or MMP. Preferably, the cycline compound is administered in an amount effective to inhibit the action of an MMP released by cells during the degenerative process. More preferably, the cycline compound is administered in an amount effective to both a) inhibit the action of a specific pro-inflammatory cytokine (such as TNF-α), and b) inhibit the action of an ECM-degrading MMP released by cells during the degenerative process.

In some embodiments, the cycline compound is selected from the group of cycline compounds consisting of doxycycline, lymecycline, oxicycline compound, tetracycline, minocycline, chemically modified cycline compound (CMT) and KB-R7785. Preferably, doxycycline is selected.

In some embodiments, anti-inflammatory agents such as an antagonist of PPAR-α, are selected.

Since it is known that many pro-inflammatory molecules play a role in joint degeneration, and that the antagonists of the present invention are highly specific, it is further believed that injecting at least two of the highly specific antagonists of the present invention directly into the joint space would be advantageous.

In accordance with the present invention, there is provided a method of treating degenerative joint disease, comprising trans-capsularly administering a formulation comprising a p38 MAP kinase inhibitor and at least two additional therapeutic agents selected from the group consisting of:
  i) an inhibitor of a pro-inflammatory interleukin;
  ii) an inhibitor of TNF-α synthesis;
  iii) an inhibitor of membrane-bound TNF-α;
  iv) an inhibitor of a natural receptor of TNF-α;
  v) an inhibitor of NO synthase;
  vi) an inhibitor of $PLA_2$ enzyme;
  vii) an anti-proliferative agent;
  viii) an anti-oxidant;
  ix) an apoptosis inhibitor selected from the group consisting of EPO mimetic peptides, IGF-I, IGF-II, and caspase inhibitors; and
  x) an inhibitor of MMPs.

Preferably, at least one of the substances is an antagonist of TNF-α. Preferably, the other substance is an antagonist of an interleukin.

In some embodiments, the formulation comprises a suitable biocompatible carrier such as saline. In some embodiments, the carrier is selected from the carriers disclosed in U.S. Pat. No. 6,277,969 ("Le"), the specification of which is incorporated by reference in its entirety. In some embodiments, the formulation includes a solvent, preferably selected from the group consisting of DMSO and ethanol.

Also in accordance with one embodiment of the present invention, there is provided a formulation for treating degenerative joint disease, comprising:
  a) a first therapeutic agent selected from the group consisting of:
    i) an inhibitor of a pro-inflammatory interleukin;
    ii) an inhibitor of TNF-α synthesis;
    iii) an inhibitor of membrane-bound TNF-α;
    iv) an inhibitor of a natural receptor of TNF-α;
    v) an inhibitor of NO synthase;
    vi) an inhibitor of $PLA_2$ enzyme;
    vii) an anti-proliferative agent;
    viii) an anti-oxidant;
    ix) an apoptosis inhibitor selected from the group consisting of EPO mimetic peptides, EPO mimetibodies, IGF-I, IGF-II, and caspase inhibitors;
    x) an inhibitor of MMPs; and
    xi) a cytokine antagonist, such as p38 MAP kinase inhibitor;
  and
  b) a second therapeutic agent selected from the group consisting of:
    i) a growth factor
    ii) viable cells, and
    iii) plasmid DNA.

In some embodiments of this formulation, the antagonist is selected from the group consisting of antagonists of TNF and antagonists of an interleukin.

Because the causes of joint pain may be myriad, and because of the significant cost of many of these specialized antagonists, it would be useful for the clinician to first perform a diagnostic test in order to confirm that the targeted joint in fact possesses high levels of the targeted cytokine prior to providing the injection.

In one embodiment, the diagnostic test comprises a non-invasive diagnostic test comprising using an MRI.

Preferably, the clinician would perform an invasive or non-invasive test upon the synovial fluid of the targeted joint in order to confirm the presence of or quantify the level of the pro-inflammatory cytokine.

In one embodiment, the diagnostic test comprises an invasive test in which a portion of the joint is removed and analyzed. In some embodiments, the clinician removes a portion of the synovial fluid. In others, the clinician removes a portion of the capsule. Preferably, the removed material is a portion of the synovial fluid. The presence of pro-inflammatory cytokines in the removed material may detected by procedures including but not limited to electrophoresis, or an enzyme-linked immunoabsorbent assay (as per Burke, Br. JBJS, 84-B (2) (2002)). In some embodiments, the invasive test may be performed during arthroscopy.

In some embodiments, the diagnostic methods disclosed in U.S. Pat. No. 6,277,969 ("Le"), the specification of which is incorporated by reference in its entirety, are selected. In these methods, high specificity anti-cytokine (e.g., anti-TNF-α) compounds are used as diagnostic tools for detecting the cytokine in the patient known or suspected to have a high level of the cytokine.

In some embodiments, a bioMEMS device containing a "lab on a chip" used in the diagnostic test.

In another embodiment, the diagnostic test comprises evaluating the genetic makeup of the patient and forecasting whether that patient will have a degenerative joint in the future.

After determining the levels of the different pro-inflammatory cytokine in the degenerating joint, the clinician will preferably proceed to compare these diagnosed levels against pre-determined levels of the pro-inflammatory cytokines. If the diagnosed level of the pro-inflammatory cytokine exceeds the pre-determined level, then the clinician may conclude that these higher levels are causing unwanted inflammatory action and proceed to inject directly a specific antagonist into the joint capable of inhibiting the targeted protein.

In some embodiments, the predetermined level for an interleukin is 10 pg/ml. In some embodiments, the predetermined level for IL-6 is 10 pg/ml. In other embodiments, the predetermined level for IL-6 is at least 100 pg/ml, e.g., at least 250 pg/ml. In some embodiments, the predetermined level for IL-8 is 10 pg/ml. In other embodiments, the predetermined level for IL-8 is at least 500 pg/ml. In some embodiments, the predetermined level for non-cytokine PGE2 is 10 pg/ml. In some embodiments, the predetermined level for TNF-α is 10 pg/ml (or, in other embodiments, at least 20 pg/ml, or at least 30 pg/ml). In others, the predetermined level for TNF-α is 1 ng/ml. In others, the predetermined level for TNF-α is 1 ng/joint (or, in other embodiments, at least 1000 pg/joint).

It would also be useful to be able to determine whether directly administering the therapeutic substances of the present invention is, in fact, efficacious. Accordingly, one can measure the level of cytokine remaining in the joint after administration.

It is further believed that the present invention can also be used to prevent degeneration of a joint in a human individual, namely, by following a procedure comprising the steps of:
a) determining a genetic profile of the individual,
b) comparing the profile of the individual against a pre-determined genetic profile level of at-risk humans,
c) determining that the individual is an at-risk patient, and
d) injecting an antagonist of the pro-inflammatory protein into a joint of the individual.

In some embodiments, additional therapeutic agents can include one or more of the following: anti-proliferating compounds (for example, rapamycin and JNJ 7706621); additional cytokine antagonists (for example, TNFα inhibitors such as REMICADE®; IL-6 inhibitors and Il-1β inhibitors); batimastat; diacerein; rhein; centella (ETCA), madecassoside; feverfew; ORC (interceed); tolmetin; tepoxalin; suprofen; suprofen; and tiaprofenic acid.

Further information regarding the invention may be found in the patent application Ser. No. 12/005,060, entitled "Transdiscal Administration Of Inhibitors Of p38 MAP Kinase" by Laura J. Brown, et al. filed December 2007, the contents of which are incorporated herein by reference in their entirety.

In addition, the following U.S. applications are incorporated herein by reference in their entirety: U.S. Ser. Nos. 10/456,948; 10/610,355; 10/631,487; and 10/630,227.

The teachings of all patents, patent applications and references cited herein are incorporated by reference in their entirety.

Example I

Saline

This non-limiting prophetic example describes how to administer transcapsularly a formulation comprising an agent, such as a p38 MAP kinase inhibitor, and saline into the synovium of a degenerating joint or capsule.

Optionally, the clinician uses a diagnostic test to verify that a particular joint has high levels of a particular pro-inflammatory cytokine, such as p38 MAP kinase, in excess of normal levels.

Next, the clinician provides a local anesthetic (such as 5 ml lidocaine) to the region above the joint of concern to reduce subcutaneous pain.

Next, the clinician punctures the skin of the patient above the joint of concern with a relatively large (e.g., 18-19 gauge) needle having a stylet therein, and advances the needle through subcutaneous fat, ligaments and muscles to the outer edge of the capsule.

In the case of antagonist injections, the clinician may aspirate a volume of synovial fluid before injection.

Next, the stylet is removed from the needle.

Next, the clinician receives a syringe having a smaller gauge needle adapted to fit within the larger gauge needle. This needle is typically a 22 or 24 gauge needle. The barrel of the syringe contains the formulation of the present invention.

In one example, the formulation contains REMICADE® infliximab, and has an infliximab concentration of between about 30 mg/ml and about 60 mg/ml. In another example, the formulation contains a p38 MAP kinase inhibitor at a concentration of about 100 nanograms/ml. In another embodiment, the p38 MAP kinase inhibitor is administered in a dose of 50 μg/kg.

Next, the physician advances the smaller needle co-axially through the larger needle and past the distal end of the larger needle, thereby puncturing the capsule. The smaller needle is then further advanced into the center of the synovium. Finally, the clinician depresses the plunger of the syringe, thereby injecting between about 0.1 and 1 ml of the formulation.

Example II

Sustained Release

This non-limiting prophetic example is substantially similar to that of Example I, except that the formulation comprises a sustained release device comprising the co-polymer poly-DL-lactide-co-glycolide (PLG). In one example, the formulation contains infliximab as the antagonist, and has an infliximab concentration of between about 30 mg/ml and about 60 mg/ml. In another embodiment, the formulation contains a p38 MAP kinase inhibitor at a concentration of about 100 nanograms/ml. In another embodiment, the p38 MAP kinase inhibitor is administered in a dose of 50 μg/kg.

Example III

Chondrocyte Pellet Culture Model

Cytokines, such as IL-1β, have significant effects on matrix molecule expression by articular chondrocytes, decreasing type II collagen and aggrecan expression. In addition, such cytokines also have effects on apoptosis, inducible nitric oxide (NO) synthase expression, and matrix metalloproteinase expression. Cytokines also blunt chondrocyte compensatory synthesis pathways required to restore the integrity of the degraded extracellular matrix (ECM). The inventors have demonstrated herein that, in the presence of IL-1β, a chondrocyte pellet undergoes proteoglycan degradation that mimics in vivo the osteoarthritis (OA) condition. This process was fully inhibited by the presence of aggrecanase inhibitors such as batimastat and this model was successfully used for screening aggrecanase inhibitors and other agents.

A chondrocyte pellet culture model was developed for in vitro high throughput screening of therapeutic compounds for inhibition of IL-1β-stimulated matrix degradation. The chondrocyte pellet culture model can be used to detect various potential therapeutic compounds effective in blocking different processes caused by IL-1β stimulation. For example, IL-1β stimulation results in increased glycosaminoglycan (GAG) degradation, prostaglandin $E_2$ ($PGE_2$) synthesis and total nitrite/nitrate production. Compounds with different mechanisms of action may inhibit the increase of one or two or all three of these parameters. For this reason, screening by, for example, measuring only GAG release would be limited to detection of a specific class of inhibitors and may not detect compounds with diversified mechanisms of function which may be involved in inhibition of the IL-1 stimulated inflammatory process. The development of the chondrocyte pellet culture assay system in a 96-well plate made possible large-scale screening of potential therapeutic compounds with different mechanisms of action.

In addition, human chondrocytes also release nitric oxide (NO) and prostaglandin $E_2$ ($PGE_2$) during OA pathogenesis. Since both NO and $PGE_2$ have modulating effects on matrix synthesis, cytokine-induced production of both molecules can represent mediators of cartilage degeneration and human knee joints. Therefore, measurement of NO and $PGE_2$ levels in addition to assessment of GAG release allows for detection of potential therapeutic compounds with different mechanism of actions other than inhibition of proteases directly involved in matrix degradation.

The following in vitro parameters were evaluated using this model:
a) GAG release in the media—a measurement of proteoglycan degradation which indicates cartilage extracellular matrix breakdown,
b) Total Nitric Oxide (NO) production—a measurement of NO production which indicates the presence of inflammatory response or mitogenic stimuli, and
c) $PGE_2$ levels (by Enzyme-linked Immunosorbent Assay (ELISA))—$PGE_2$ is a primary product of arachidonic acid metabolism that is synthesized and released upon cell activation, and whose presence indicates an inflammatory response.

Materials and Methods
Materials.

Dulbecco's Modified Eagle Medium (DMEM) with high glucose (Cat. No 10564011), Antibiotic-Antimycotic (100×) containing penicillin, streptomycin, amphotericin B, and neomycin (10000 U/ml, 10 μg/ml, 25 mg/ml and 5 μg/ml, respectively) (Cat. No. 15240062), MEM Non-Essential Amino Acids Solution 10 mM (100×), liquid (Cat. No. 11140-050) and phosphate buffered saline (PBS, Cat. No. 14130-144) were purchased from Invitrogen Life Technology. Dimethylethylene (341088), ascorbic acid (A-4403), L-proline (P-5607), tolmetin sodium salt dihydrate (T-6779), diacerein (D9302), rhein (R-7269), indomethacin (1-7378), lipopolysaccharide (L-6529), insulin-transferrin-sodium selenite media supplement (Cat. No. I-1884), trypan blue (T-8154), and chondroitin 6-sulfate sodium salt from shark cartilage (C-4384), were purchased from Sigma-Aldrich (St. Louis, Mo.). Recombinant human interleukin-1β (IL-1β, Cat. No: 201-LB), recombinant human tissue necrosis factor α (TNF-α) (Cat. No. 210-TA), recombinant interferon-γ (Cat. No. 285-IF), and recombinant human IL-6 (Cat. No. 1609-CL-025/CF) were purchased from R&D Systems (Minneapolis, Minn.). Nitrate/Nitrite Colorimetric Assay Kit (Cat. No. 780001), and a prostaglandin E2 detection kit (Cat. No. 514131) were purchased from Cayman Chemicals (Ann Arbor, Mich.). A Cytotoxicity Detection Kit (LDH) (Cat. No. 1 644 793) was purchased from Roche (Nutley, N.J.). Fetal calf serum (FCS), Cat. No. SH30070.03, Lot No. ANF19047) was purchased from Hyclone (Logan, Utah). Collagenase (3.4.24.3) and papain (3.4.22.2) were purchased from Worthington Biochemical Corp (Lakewood, N.J.). BD FALCON™ cell strainers 40 μm (Cat. No. 352340) was purchased from Becton, Dickinson and Company (Franklin Lakes, N.J.). Ninety-six deep-well plates (73520-474) were purchased from VWR International, Inc. (West Chester, Pa.). Alginate Recovered Chondrocyte (ARC) tissues were purchased from Articular Engineering Inc., LLC (Northbrook, Ill.).

Culture Media:

Chondrocyte medium was prepared with DMEM supplemented with 50 μM ascorbic acid, 20 μM L-Proline, 1× non-essential amino acids and 10% (v/v) FCS. The Chondrocyte Stimulation Medium is a defined medium containing DMEM supplemented with 1% FCS, 1× insulin-transferrin-sodium selenite media supplement and Antibiotics-Antimycotics in the presence or absence of IL-1β.

Chondrocyte Isolation and Pellet Culture and Alginate Recovered Chondrocytes:

Calf articular cartilage was obtained from the knee joints of eight to twelve month old animals and was processed within twenty-four hours after sacrifice. After removal of muscle and ligament, the cartilage was kept moist using phosphate buffer solution (PBS) to prevent tissue dehydration, and was aseptically peeled off from subchondral bone with a scalpel, and the cartilage pieces were further minced into smaller pieces (~0.3-0.5×~0.2-0.5 cm cubes). The cartilage tissue was then washed 3× one hour with PBS containing 10× Antibiotic-Antimycotic followed by a 1× 0.5 hour wash in PBS with 1× Antibiotic-Antimycotic. Chondrocytes were then enzymatically isolated from the tissue by incubation for overnight at 37° C. with gentle agitation in 0.2% collagenase in Dulbecco's modified eagle media (DMEM). After removal of tissue debris by filtration through cell strainer and the residual collagenase by 3× wash in PBS, cells were finally resuspended at a density of $2.5 \times 10^6$ cells/ml in chondrocyte medium. A 1 ml aliquot of the cell suspension was dispensed into either a 15 ml Falcon centrifuge tube or a 96 deep-well plate and centrifuged at 2000×g for five minutes. The chondrocyte pellets were incubated at 37° C. in a humidified atmosphere of 5% $CO_2$ for two to three weeks with a medium change every other day.

As an alternative to using calf articular cartilage, a commercial Alginate Recovered Chondrocytes (ARC) system was also used (Articular Engineering, LLC (Northbrook, Ill.)). Use of the commercial system cut down on labor and time in producing chondrocyte pellet. This system produced cartilaginous tissue in vitro using bovine chondrocytes. The first step consisted of culturing chondrocytes in alginate under conditions optimal for the formation of a cell-associated matrix (CM). The second step allowed these cells with their CM, after recovery, to rapidly form and become integrated into a solid mass of cartilage on a porous insert within two weeks. This tissue is rich in cells surrounded by a cell-associated matrix that is degraded rapidly when the cells are exposed to IL-1. ARC tissues in 3 mm punches at delivery were first dispensed into a 96 deep-well plate, one punch per well, for compound treatment. The subsequent procedures were the same as those used for the chondrocyte pellets.

Treatment of Pellet Cultures:

Chondrocyte pellets were washed once with 1 ml of Chondrocyte Stimulation Medium and equilibrated in the same medium at room temperature for fifteen to thirty minutes. Compounds were dissolved in $H_2O$, Ethanol or dimethyl sulfoxide (DMSO) ($10^{-2}$ M) according to suppliers' instructions and further diluted with Chondrocyte Stimulation Medium to the required concentrations. DMSO concentrations in the culture media should not exceed 1%; this concentration of DMSO has no effect on cartilage proteoglycan metabolism in response to cytokines.

The pellets were first treated with compounds at desired concentrations at 37° C. for one hour and then incubated for three to five days in the absence or presence of 10 ng/ml of IL-1β. At the end of the incubation, media and pellets were harvested and frozen for further analysis. Pellets were also fixed as needed in 4% (w/v) paraformaldehyde in PBS for histology analysis.

GAG Degradation Assay:

Glycosaminoglycan (GAG) levels in the culture media were determined by measuring the amount of polyanionic material reacting with 1,9-dimethylmethylene blue (DME) as detected by absorbance at 525 nm, using shark chondroitin sulfate as a standard. The DME blue dye-binding solution was prepared by dissolving 16 mg of DME blue in a solution containing 0.304% glycine, 0.23% sodium chloride (NaCl), 9.5 mM hydrochloric acid (HCl), pH=3.0 with absorbance at 525 equal to 0.31. Proteoglycans and proteoglycan metabolites in chondrocyte pellet were released by digesting the pellet with 125 µg/ml of papain in 0.1 M PBS, pH 6.0, 5 mM cysteine, 5 mM ethylene-diamine-tetra-acetic acid disodium salt ($Na_2EDTA$) at 50° C. for overnight. Results are reported as either micrograms of GAG per milliliter or percent of total GAG released into culture medium.

Total Nitrite and Nitrate Assay:

Nitrate/Nitrite levels were measured using the Griess reaction (Green L. C. et al., "Analysis of Nitrate, Nitrite, and [15N]nitrate in Biological Fluids," *Anal. Biochem.* 126: 131-138 (1982)) with aNitrate/Nitrite Colorimetric Assay Kit (Cayman Chemicals), the contents of which are incorporated herein by reference. The assay involved a simple two-step process. The first step involved conversion of nitrate in 50 µl of culture medium to nitrite utilizing nitrate reductase in a reaction volume of 100 µl at room temperature for two hours. The second step involved the addition of 50 µl of both Griess Reagent 1 and 2, which converted nitrite into a deep purple azo compound in ten minutes. Photometric measurement of the absorbance at 540 or 550 nm due to this azo chromophore accurately determined nitrite concentration. This assay kit cannot be used for RPMI (Roswell Park Memorial Institute) derived tissue culture medium due to interference with the colorimetric reaction.

Prostaglandin $E_2$ Assay:

Prostaglandin $E_2$ ($PGE_2$) was measured with a STAT-Prostaglandin $E_2$ EIA ELISA kit (Cayman Biochemicals). This assay is based on the competition between $PGE_2$ from 50 µl samples and a $PGE_2$-alkaline phosphatase conjugate for a limited amount of $PGE_2$ monoclonal antibody in a reaction volume of 150 µl at room temperature for one hour. The antibody-$PGE_2$ complex bound to a goat polyclonal anti-mouse IgG that had been previously attached to the well. After washing to remove any unbound reagents, para-nitrophenyl phosphate (pNPP) was added to the well. The product of this enzymatic reaction absorbs strongly at 412 nm. Because of the large range in response to IL-1β and other cytokines, $PGE_2$ values were converted to log scale prior to doing t-tests.

Assessment of Cytotoxicity:

Cell death was assessed by measuring the amount of lactate dehydrogenase (LDH) in the culture supernatant. 10-20 µl of culture medium was incubated with the reaction mixture from the Cytotoxicity Detection Kit (Cat No. 11 644 793 001, Roche). The LDH activity was determined colorimetrically in an enzymatic test based on the conversion of lactic acid to pyruvate in the presence of chromagenic substrate tetrazolium salt INT that was reduced to formazan. The amount of formazan formed was measured at 500 nm, which is proportional to the number of dead cells. Since no purified LDH was available for a standard curve at each measurement, the LDH level for 100% dead cells was measured in each experiment. The lysate for the dead cells was prepared as follows: Chondrocytes were enzymatically isolated as described above and about 0.1 million cells that are equivalent to the number of cells contained in a 3-mm punch of fresh cartilage explant were lysed in 1 ml of PBS with 1% Triton-100. 10-20 µl of the lysate was used in the assay as killed cell control.

All assays were done with triplicate or quadruplicate pellets for each dose.

Results

Effects of IL-1β, 8 Stimulation on $PGE_2$ Synthesis, NO Production and GAG Degradation IL-1β stimulation resulted in increased glycosaminoglycan (GAG) degradation (1.7-4.5 fold increase), prostaglandin $E_2$ ($PGE_2$) synthesis (2-200 fold increase) and total nitrite/nitrate production (10-20 fold increase).

Effects of Diacerein and Rhein on $PGE_2$ Synthesis, NO Production, GAG Degradation and LDH Toxicity The chondrocyte pellet culture model was validated with known IL-1 inhibitors (diacerein and rhein (its active metabolite)). Therapeutic levels of diacerein and rhein have been shown to inhibit the synthesis and activity of IL-1β and increase expression of soluble IL-1 receptor, as well as to stimulate anabolic processes. Chondrocyte pellets were prepared as described herein. The pellets were treated for five days with or without diacerein or rhein at indicated concentrations in the presence or absence of 10 ng/ml of IL-1β. Culture media were collected for GAG, $PGE_2$, NO and lactate dehydrogenase (LDH) measurement.

Figure 1B:
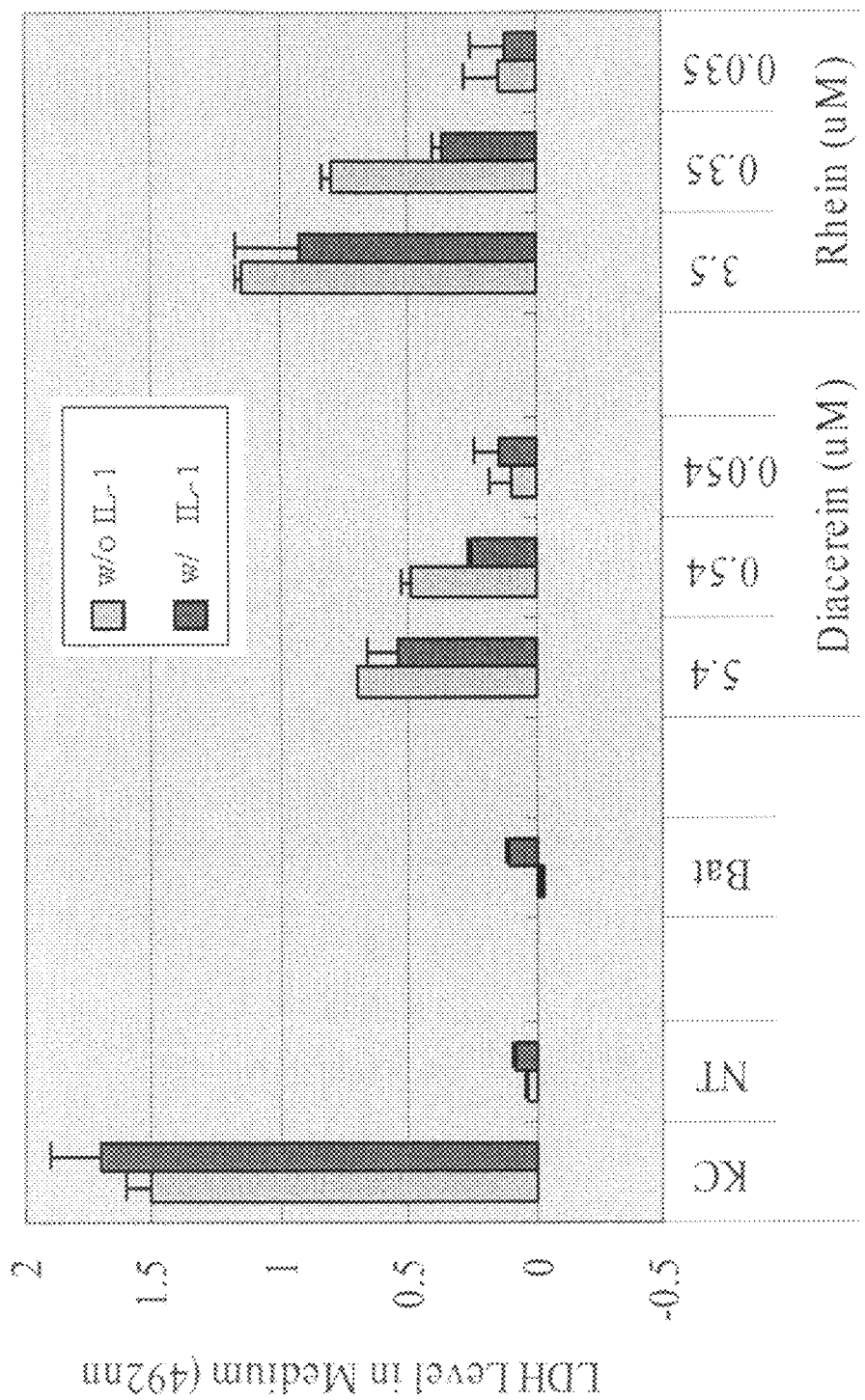
FIG. 1B is a bar graph of the effects of diacerein and rhein on inhibition of cytotoxicity in the presence or absence of 10 ng/ml of IL-1β. The Y axis represents LDH level (492 nm) and the X axis represents diacerein and rhein in μM. In addition, non-treated (NT), killed chondrocytes $2 \times 10^6$ cells/ml (KC) and Batimastat (Bat) treated tissues were tested.
Figure 1C:
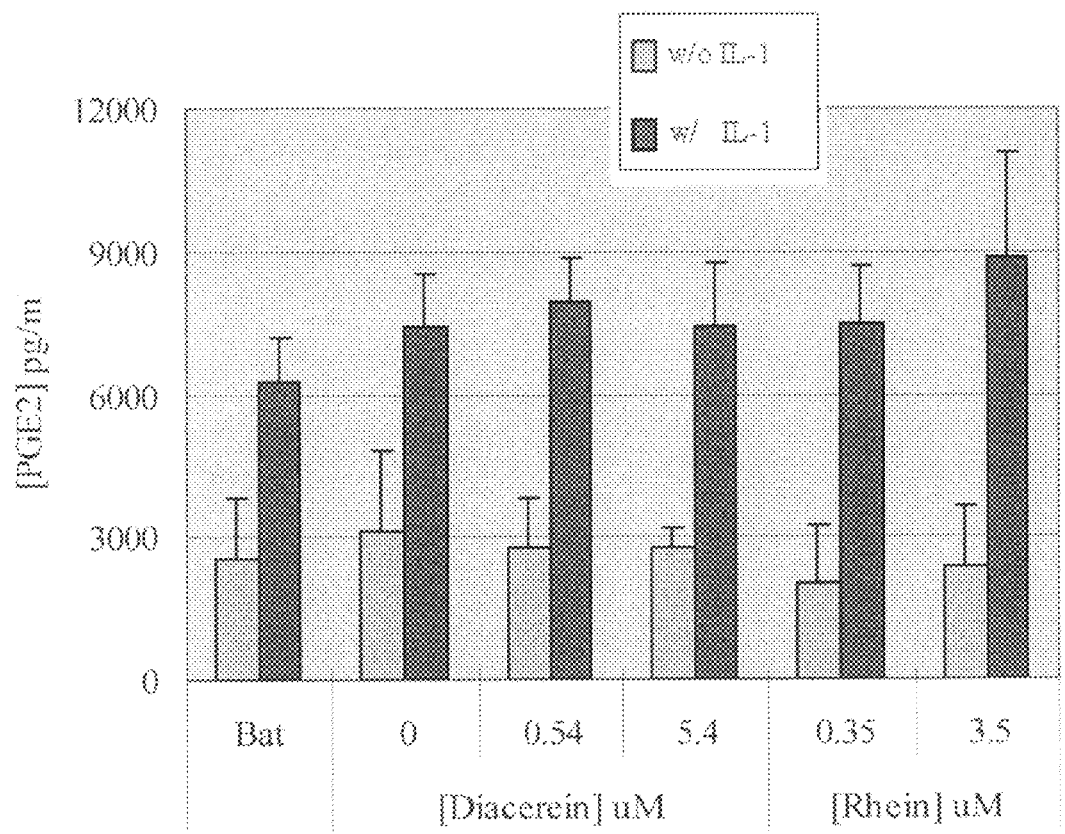
FIG. 1C is a bar graph of the effects of diacerein and rhein on inhibition of $PGE_2$ synthesis in the presence or absence of 10 ng/ml of IL-1β. The Y axis represents $PGE_2$ levels in pg/ml and the X axis represents diacerein and rhein in μM. In addition, non-treated (NT) and Batimastat (Bat) treated tissues were tested.
Figure 1D:
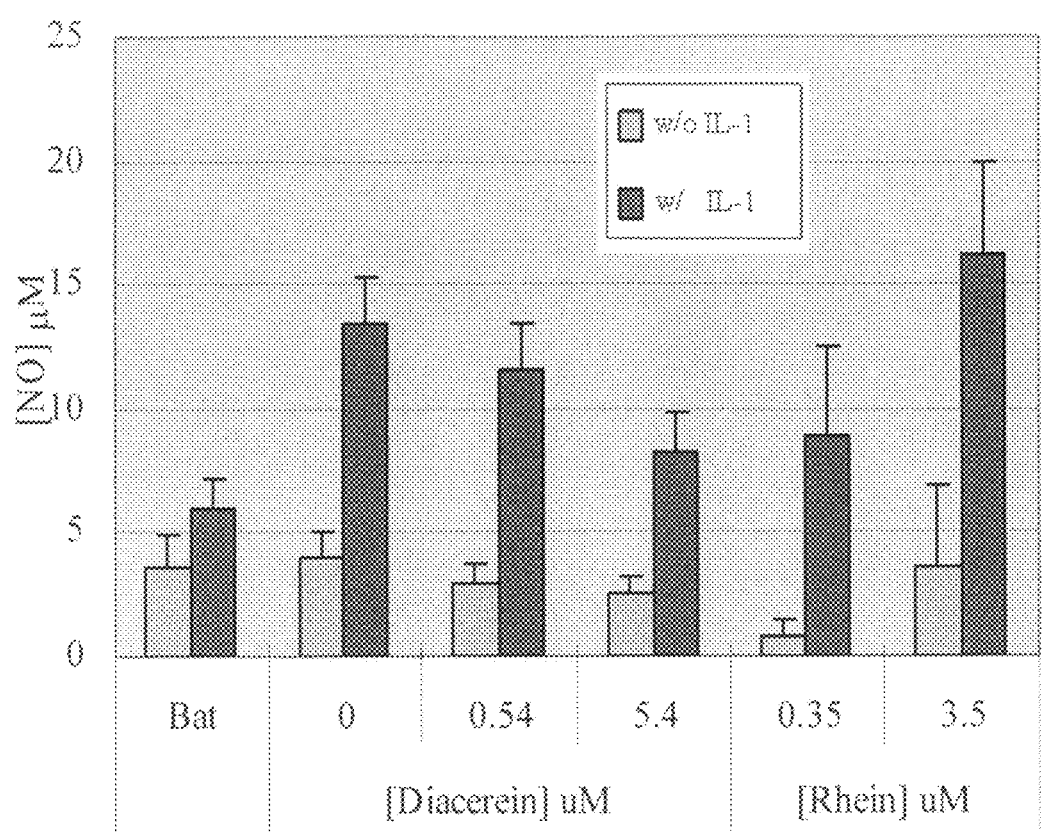
FIG. 1D is a bar graph of the effects of diacerein and rhein on inhibition of NO production in the presence or absence of 10 ng/ml of IL-1β. The Y axis represents NO levels in μM and the X axis represents diacerein and rhein in μM. In addition, non-treated (NT) and Batimastat (Bat) treated tissues were tested.

Both diacerein and rhein inhibited proteoglycan degradation at concentrations as low as 0.054 µM and 0.035 µM respectively (FIG. 1A). Diacerein at 5.4 µM and rhein at 0.35 µM also significantly inhibited NO production (FIG. 1D) yet had no effect on $PGE_2$ synthesis (FIG. 1C). Diacerein at 5.4 µM or rhein at 3.5 µM had a weaker inhibitory effect for GAG, and rhein at 3.5 µM had a weaker effect for NO than those at their lower concentrations. This might be attributed to their cytotoxicity at higher concentrations, with higher toxicity found for rhein (FIG. 1B). The fact that the mechanisms of action for diacerein or rhein are different from batimastat (an MMP inhibitor that inhibits GAG degradation), yet they also show efficacy in inhibition of GAG degradation and NO production, suggests that these parameters are good measures for therapeutic agents with different mechanisms of action.

Effects of Antiproliferative Compounds on $PGE_2$ Synthesis, NO Production and GAG Degradation and LDH Toxicity To test whether antiproliferative compounds have effects on inhibition of IL-1β stimulated responses in this in vitro model, chondrocyte pellets were treated with either JNJ 7706621 or rapamycin.

Rapamycin is a triene macrolide antibiotic, with anti-fungal, anti-inflammatory, anti-tumor and immunosuppressive properties. It blocks T-cell activation and proliferation, as well as the activation of p70 S6 kinase, and exhibits strong binding to FK-506 binding proteins. Rapamycin also inhibits the activity of the protein mTOR (mammalian target of rapamycin), which functions in a signaling pathway to promote tumor growth.

JNJ 7706621 is an inhibitor for cycline dependent kinase. Cyclin-dependent kinases (CDKs) are a family of protein serine/threonine kinases that play a central role in the molecular machinery that runs the cell cycle.

Figure 2A:
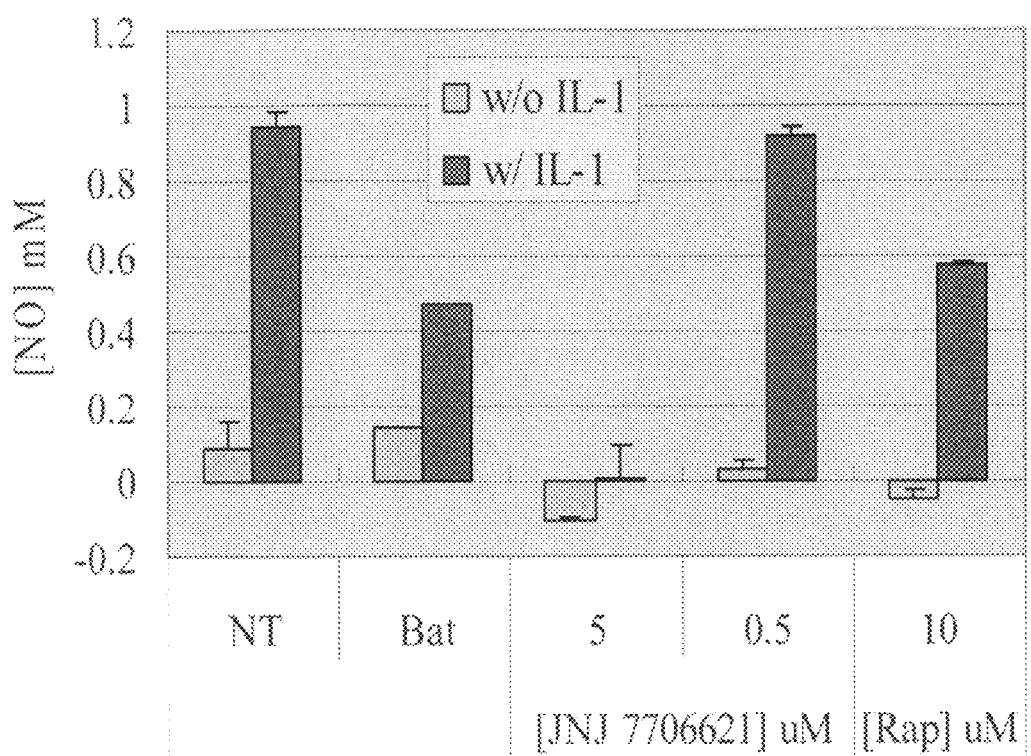
FIG. 2A is a bar graph of the effects of JNJ 7706621 and rapamycin (Rap) on inhibition of NO production in the presence or absence of 7.5 ng/ml of IL-1β. The Y axis represents NO levels in μM and the X axis represents JNJ 7706621 in μM. In addition, non-treated (NT) and Batimastat (Bat) treated tissues were tested.
Figure 2B:
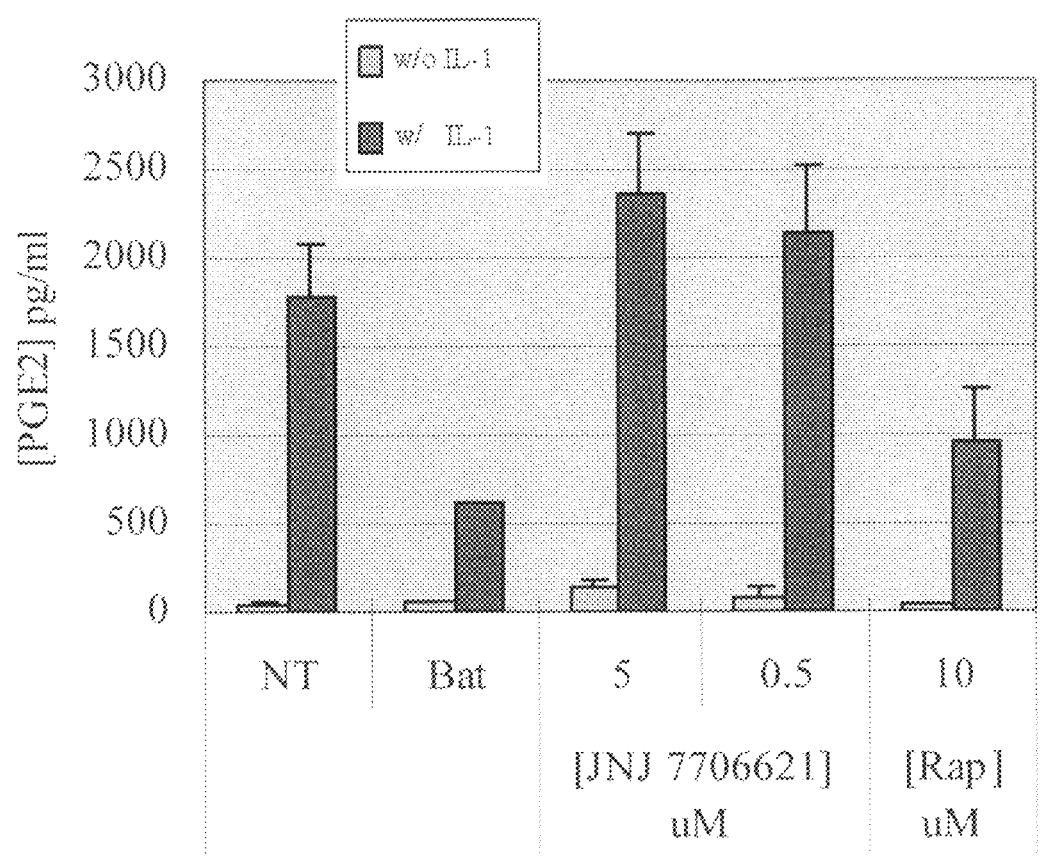
FIG. 2B is a bar graph of the effects of JNJ 7706621 and rapamycin (Rap) on inhibition of $PGE_2$ synthesis in the presence or absence of 7.5 ng/ml of IL-1β. The Y axis represents $PGE_2$ levels in pg/ml and the X axis represents JNJ 7706621 in μM. In addition, non-treated (NT) and Batimastat (Bat) treated tissues were tested.
Figure 2C:
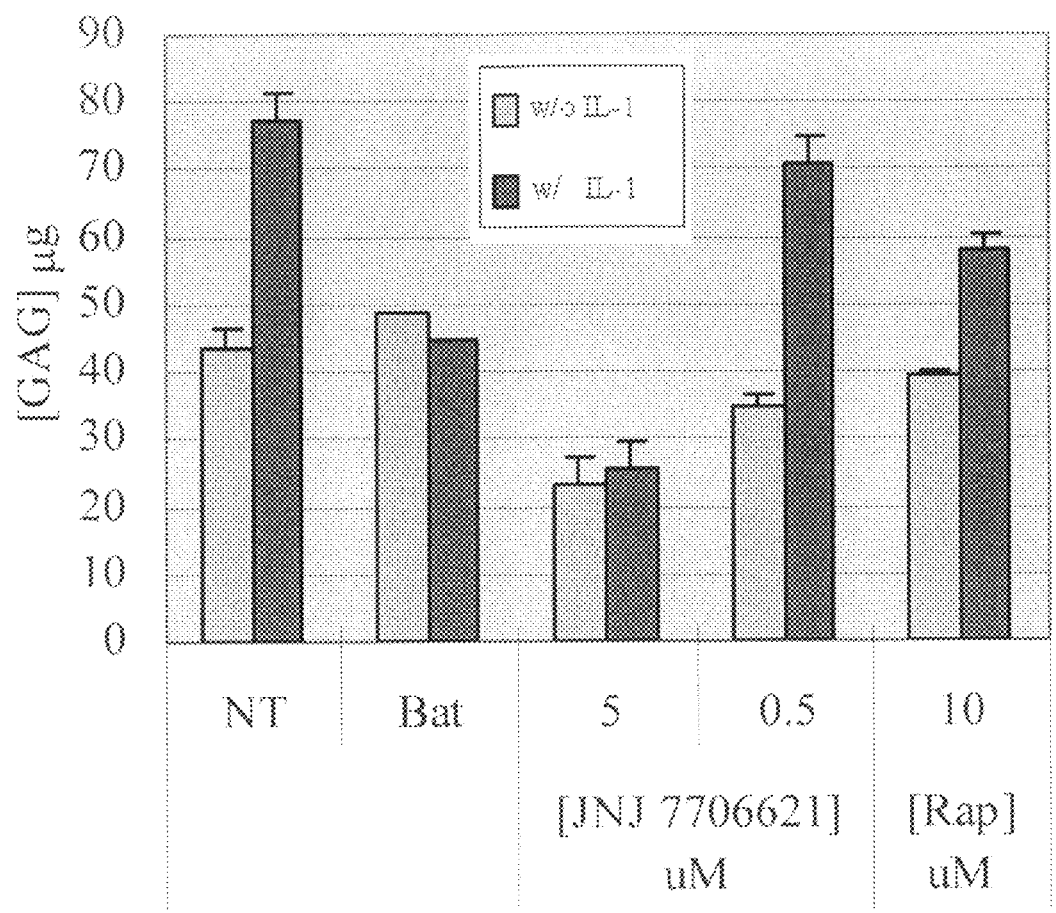
FIG. 2C is a bar graph of the effects of JNJ 7706621 and rapamycin (Rap) on inhibition of GAG degradation in the presence or absence of 7.5 ng/ml of IL-1β. The Y axis represents GAG μg and the X axis represents JNJ 7706621 in μM. In addition, non-treated (NT) and Batimastat (Bat) treated tissues were tested.
Figure 3A:
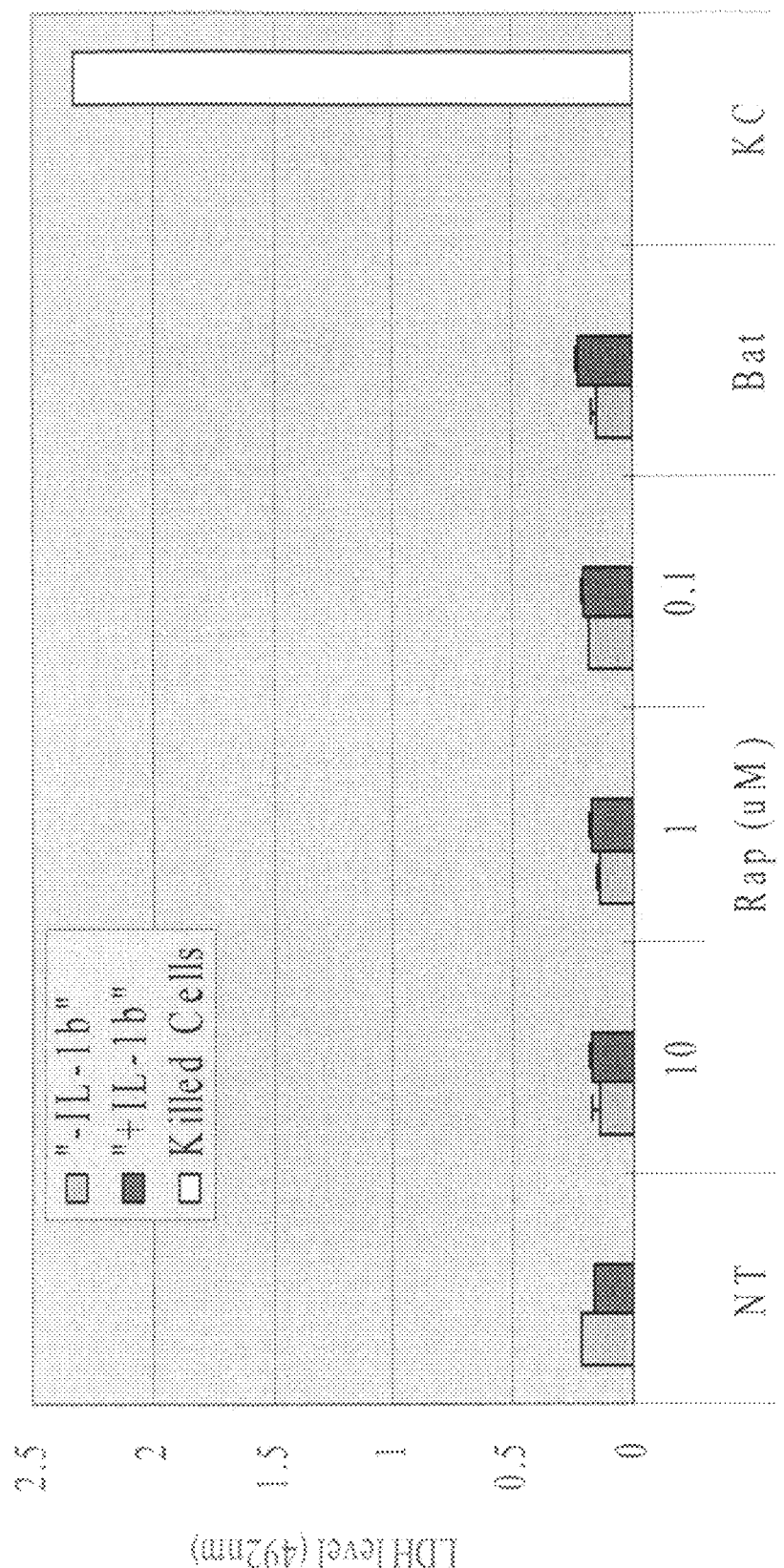
FIG. 3A is a bar graph of the effect of rapamycin (Rap) on cytotoxicity in the presence or absence of IL-1β. The Y axis represents LDH level (492 nm) and the X axis represents rapamycin in μM. In addition, non-treated (NT), Batimastat (Bat) and killed chondrocytes (KC) treated tissues were tested.
Figure 3B:
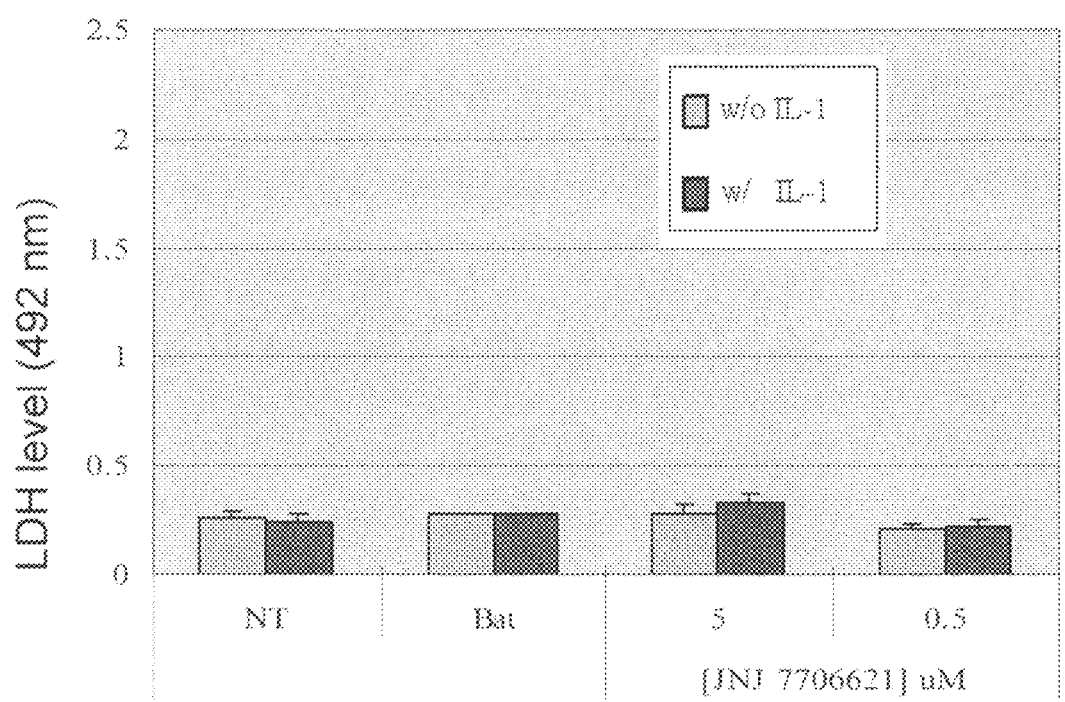
FIG. 3B is a bar graph of the effect of JNJ 7706621 on cytotoxicity in the presence or absence of IL-1β. The Y axis represents LDH level (492 nm) and the X axis represents JNJ 7706621 in μM. In addition, non-treated (NT) and Batimastat (Bat) treated tissues were tested.

ARC tissues were treated with JNJ 7706621 or rapamycin at the indicated concentrations in the presence or absence of 7.5 ng/ml of IL-1 for five days. Culture media were collected for NO production, $PGE_2$ synthesis and GAG release according to the methods described in the chondrocyte pellet model. The results show that rapamycin inhibited GAG release and NO production and $PGE_2$ synthesis. While JNJ 7706621 at 5 µM completely blocked GAG release and NO production, it had little effect on $PGE_2$ synthesis (FIGS. 2A-C). Both compounds had little toxicity to chondrocytes (FIGS. 3A and 3B).

Effects of REMICADE® on $PGE_2$ Synthesis, NO Production and GAG Degradation

Figure 4:
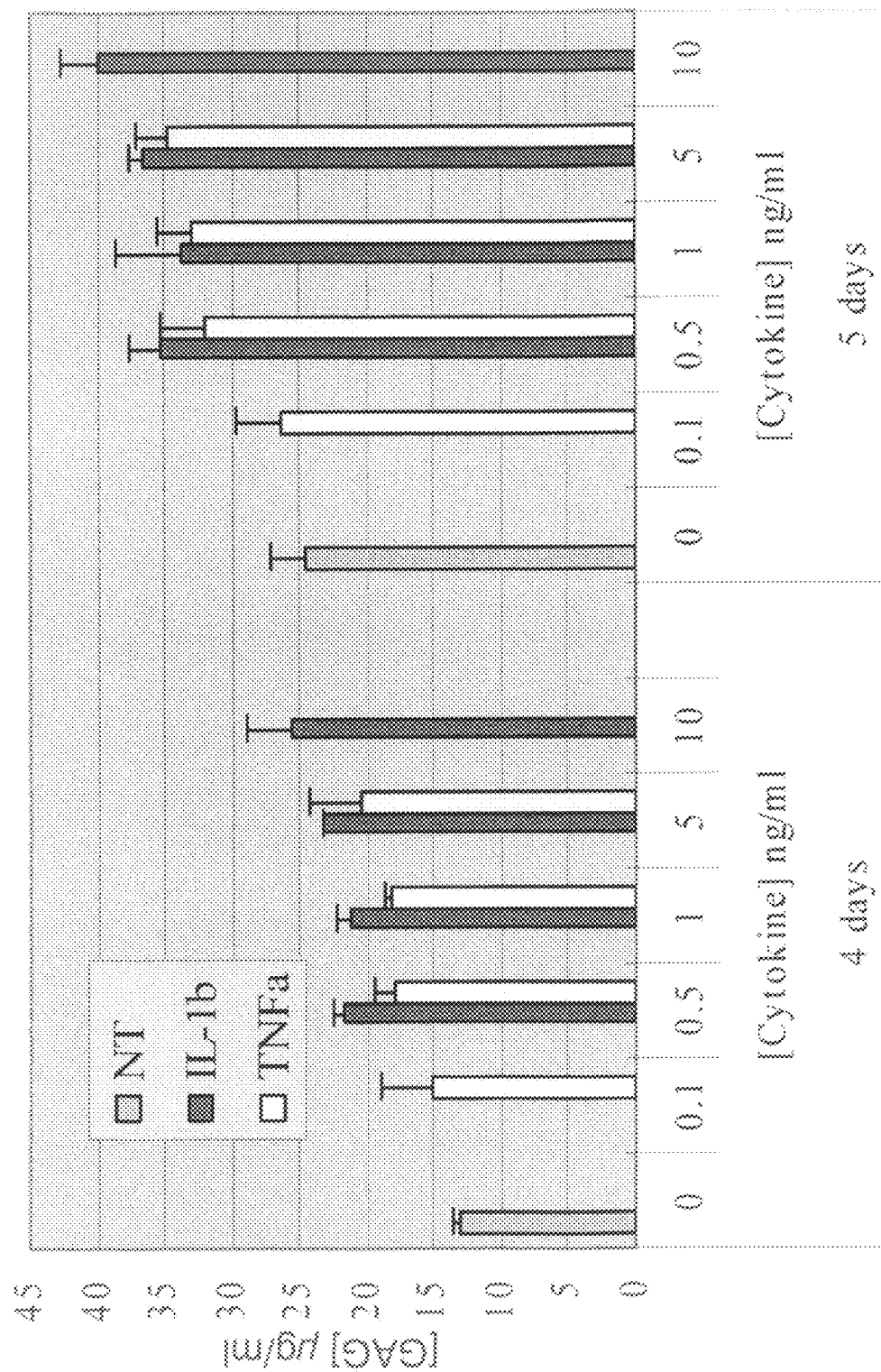
FIG. 4 is a bar graph of the effect of REMICADE® on inhibition of GAG degradation. ARC tissues prepared using human chondrocytes and were treated with REMICADE® in the presence or absence of 5 ng/ml of TNFα or IL-1β at four and five days. For studies testing the efficacy of antibodies, it was necessary to match the cells with the species that each antibody targets. The Y axis represents GAG levels in μg/ml and the X axis represents REMICADE® concentration in ng/ml.

REMICADE® infliximab is a monoclonal antibody against human TNFα. To test whether REMICADE® could modulate cytokine-stimulated responses in chondrocytes, human chondrocyte pellets were first tested for an optimal concentration for cytokine stimulation. Human ARC (i.e., ARCs generated using human chondrocytes) tissues were treated with various concentrations of either TNF or IL-1 for four and five days. The culture media was collected for measurement of GAG content as described above. Other assays were performed as described above. Cytokine dosage at 5 ng/ml and treatment for five days gave a reasonable treatment window, yet was not too challenging for compound efficacy (FIG. 4).

Figure 5A:
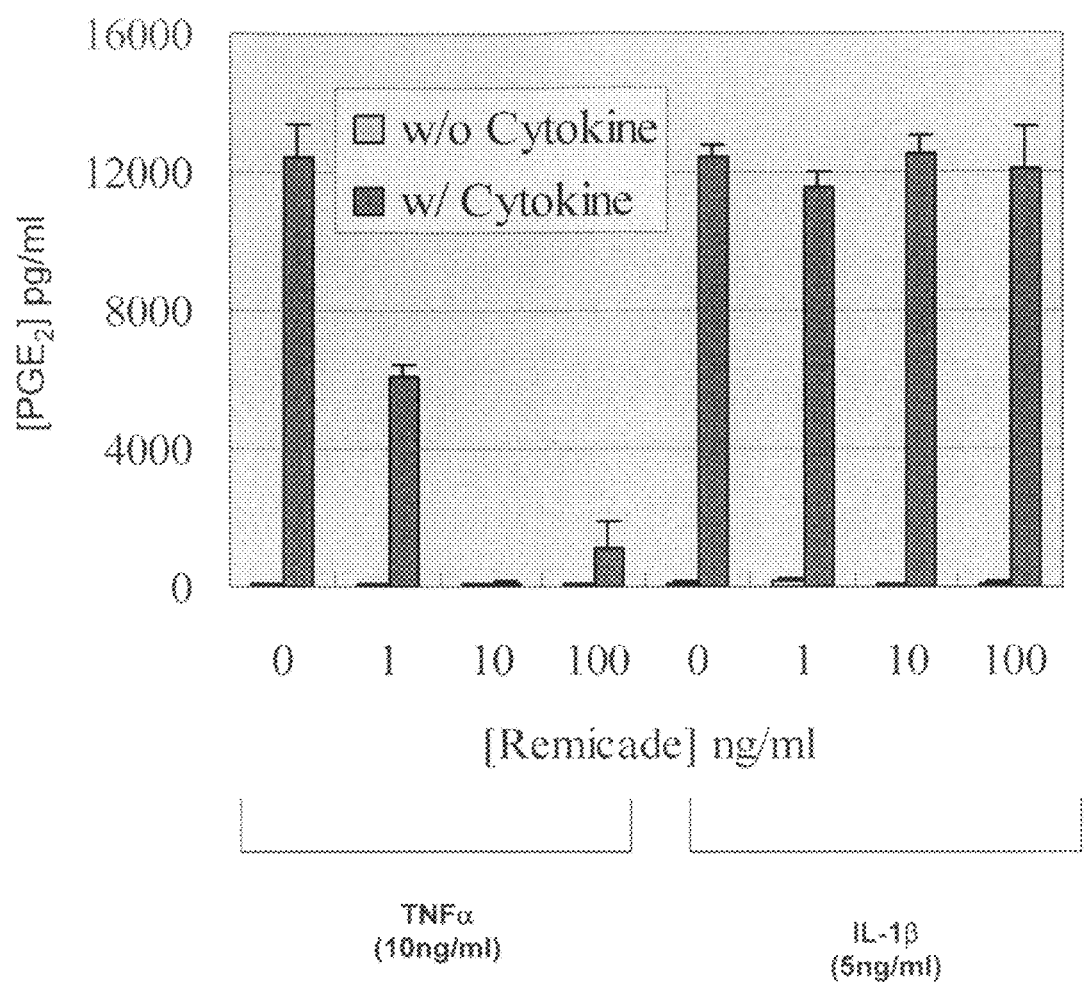
FIGS. 5A-C are bar graphs of the effects of REMICADE® on inhibition of $PGE_2$ synthesis, NO production and GAG degradation. Human chondrocyte generated ARC tissues were treated with REMICADE® in the presence or absence of 10 ng/ml of TNFα and 5 ng/ml of IL-1β.
Figure 5B:
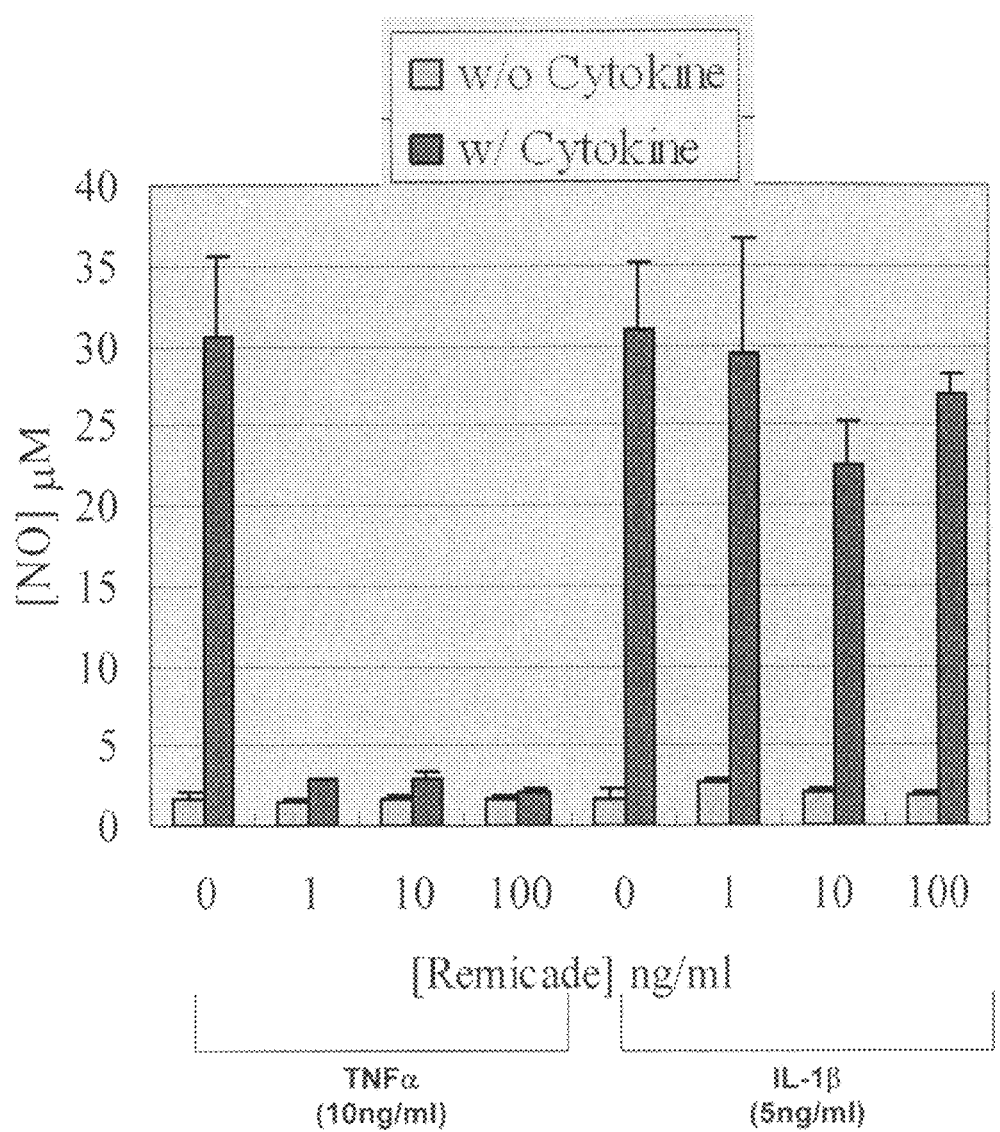
Figure 5C:
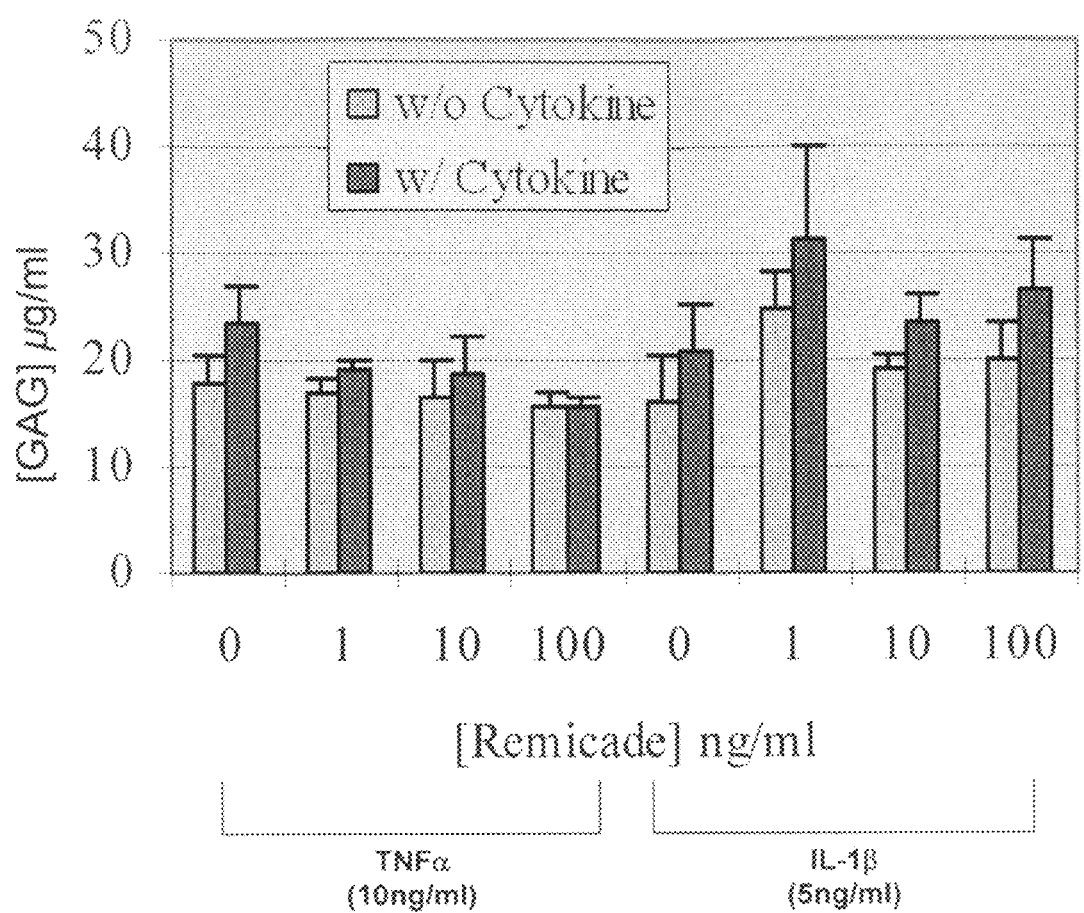

Human ARC tissues were then treated with various concentrations of REMICADE® in the presence or absence of either 10 ng/ml of TNFα or 5 ng/ml of IL-1β for four or five days. While REMICADE® strongly inhibited TNFα-induced PGE$_2$ synthesis, NO production and GAG release, it had little effect on IL-1β stimulated responses (FIG. 5A-C).
Effects of a Monoclonal Antibody Against IL-6 on PGE$_2$ Synthesis, NO Production and GAG Degradation The efficacy of a monoclonal antibody (mAb) against human IL-6 in inhibition of proteoglycan degradation, NO production and PGE$_2$ synthesis on human ARC tissues stimulated with IL-6 was also tested. Human ARC tissue were treated with 12.5, 25 and 250 ng/ml of IL-6 mAb diluted into chondrocyte stimulation medium. After one hour of treatment at 37° C., ARCs were stimulated with or without 25 ng/ml IL-6, 250 ng/ml IL-6 soluble receptor (IL-6SR) or IL-6 (25 ng/ml)+IL-6SR (250 ng/ml) and incubated for five days before the culture media were harvested for assays.

Figure 6A:
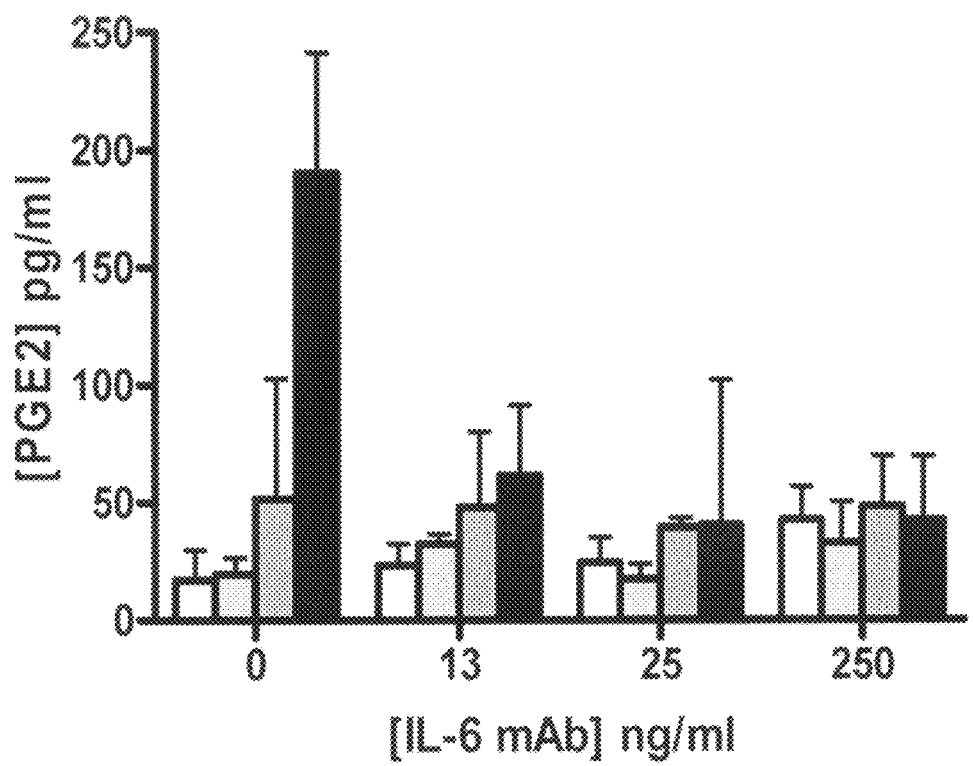
FIG. 6A is a bar graph of the effect of a human monoclonal antibody against Il-6 on inhibition of $PGE_2$ synthesis in human ARCs. The Y axis represents the $PGE_2$ concentration in pg/ml and the X axis represents the IL-6 monoclonal antibody in the following conditions: presence or absence of 25 ng/ml of IL-6, 250 ng/ml of IL-6 soluble receptor (SR) or IL-6 (25 ng/ml)+IL-6SR (250 ng/ml).
Figure 6B:
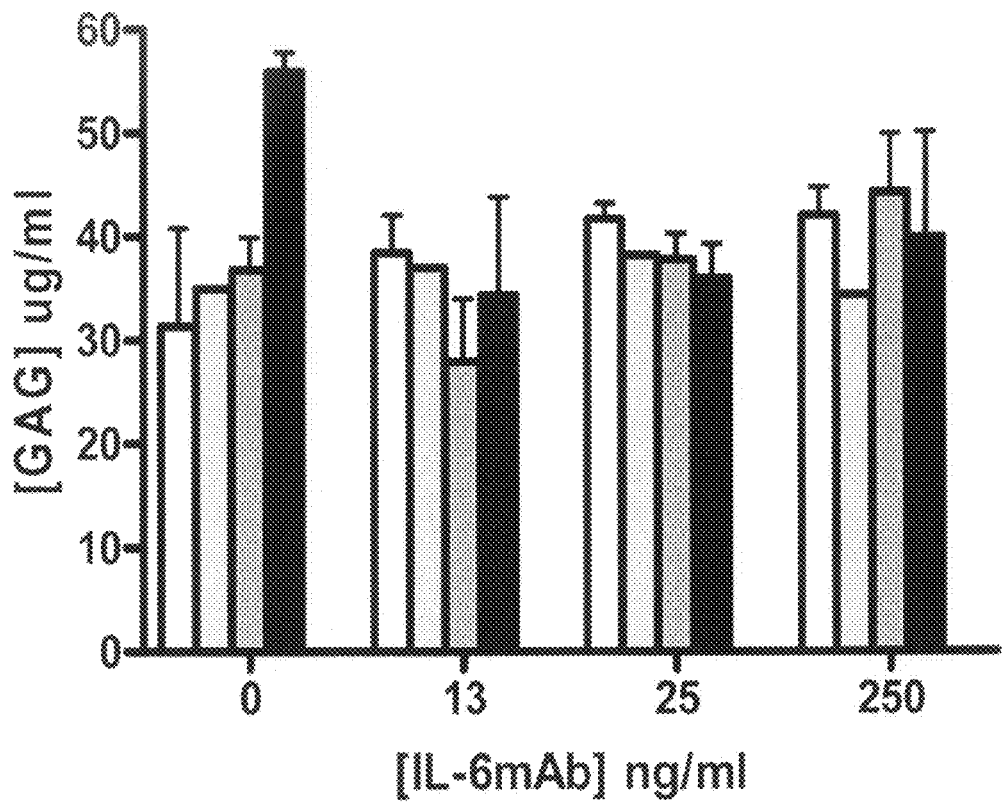
FIG. 6B is a bar graph of the effect of monoclonal antibody against Il-6 on inhibition of GAG degradation. The Y axis represents the GAG concentration in μg/ml and the X axis represents the IL-6 monoclonal antibody in the following conditions: presence or absence of 25 ng/ml of IL-6, 250 ng/ml of IL-6SR or IL-6 (25 ng/ml) plus IL-6SR (250 ng/ml).
Figure 6C:
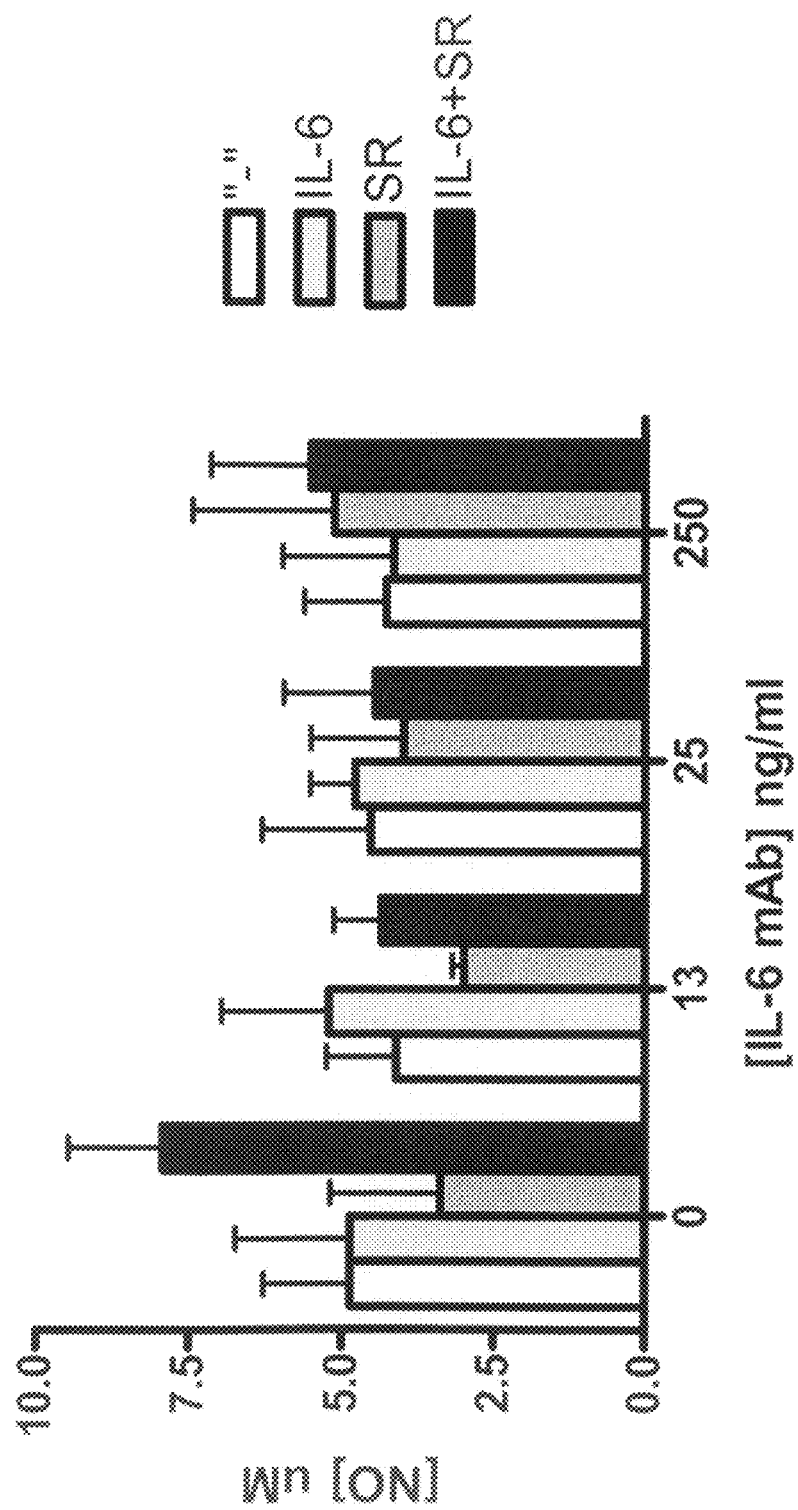
FIG. 6C is a bar graph of the effect of monoclonal antibody against IL-6 on inhibition of NO production. The Y axis represents the NO concentration in μM and the X axis represents the IL-6 monoclonal antibody in the following conditions: presence or absence of 25 ng/ml of IL-6, 250 ng/ml of IL-6SR or IL-6 (25 ng/ml)+IL-6SR (250 ng/ml).

As shown in FIG. 6A-C, neither IL-6 nor IL-6 soluble receptor (IL-6SR) stimulated an inflammatory reaction. However, the combination of IL-6 (25 ng/ml) and IL-6SR (250 ng/ml) at a ratio of 1:10 significantly (t test, P<0.02) stimulated GAG degradation, NO production and PGE$_2$ synthesis, indicating that the proinflammatory effect of IL-6 requires the presence of IL-6SR in this system. This inflammatory effect could be effectively blocked with monoclonal antibody against IL-6 at 12.5 ng/ml.
Effects of P38 MAP Kinase Inhibitors on PGE$_2$ Synthesis, NO Production, GAG Degradation and Toxicity The following p38 MAP kinase inhibitors were assessed for their effect on total nitric oxide (NO) production, PGE$_2$ levels (by ELISA) and GAG release in the media: JNJ 7583979 (RWJ 351958), JNJ 3026582 (RWJ 67657), JNJ 17089540 (RWJ 669307) SCIO-469 (SD 469) and SCIO-282 (SD 282). After five days of incubation, culture media were collected for measurement of these parameters as discussed above.

Bovine ARC tissues were treated with serial dilutions of JNJ 3026582 (RWJ 67657) (250 pM-10 μM), JNJ 17089540 (RWJ 669307) (25 nM-500 μM) and SCIO-282 (SD 282) (10 pM-10 μM) in the presence of 10 ng/ml of IL-1 or absence of IL-1β. All of these p38 MAP kinase inhibitors significantly inhibited PGE$_2$ synthesis with IC$_{50}$ ~0.5 μM and NO production with wider ranges of IC$_{50}$.

Figure 7A:
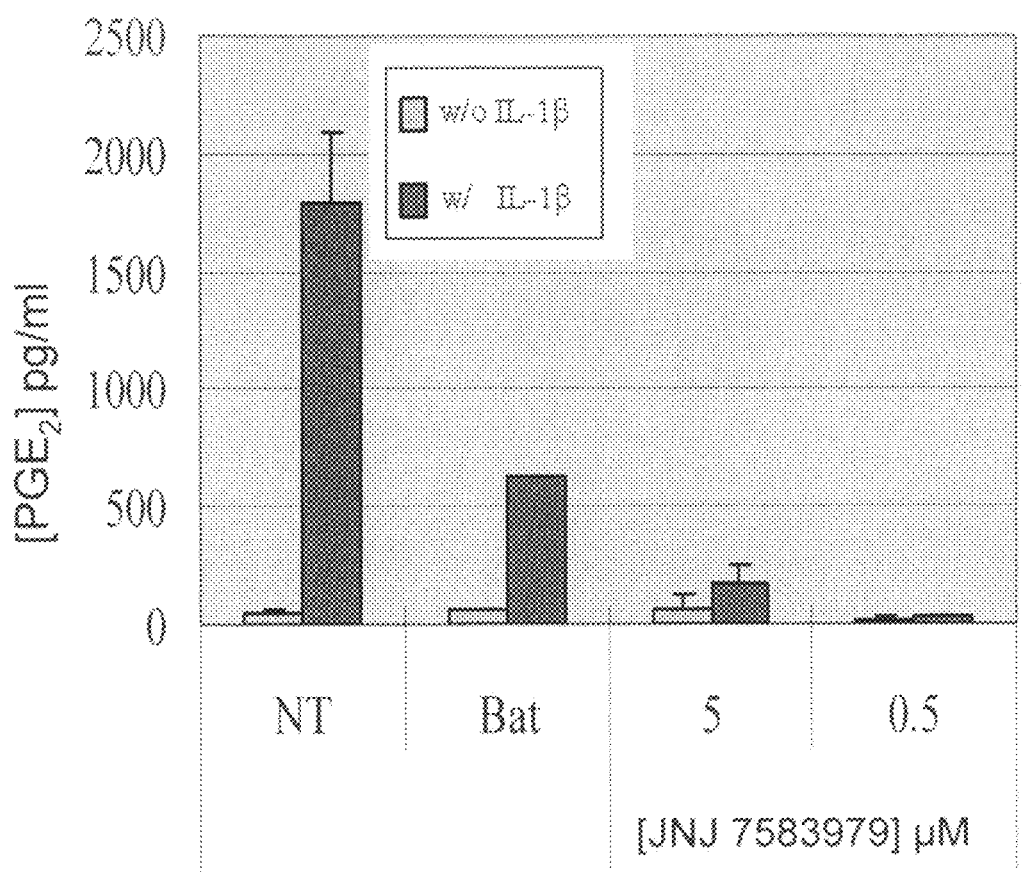
FIG. 7A is a bar graph of the effect of JNJ 7583979 (RWJ 351958) on inhibition of Prostaglandin $E_2$ ($PGE_2$) synthesis. Alginate Recovered Chondrocyte (ARC) tissues were treated with JNJ 7583979 (RWJ 351958) at indicated concentrations (μM) in the presence of 10 ng/ml of IL-1β or absence of IL-1β. The Y axis represents $PGE_2$ levels in pg/ml and the X axis represents JNJ 7583979 (RWJ 351958) in μM. In addition, non-treated (NT) and Batimastat treated (Bat) tissues were tested as controls. Error bars on all graphs indicate standard error.
Figure 7B:
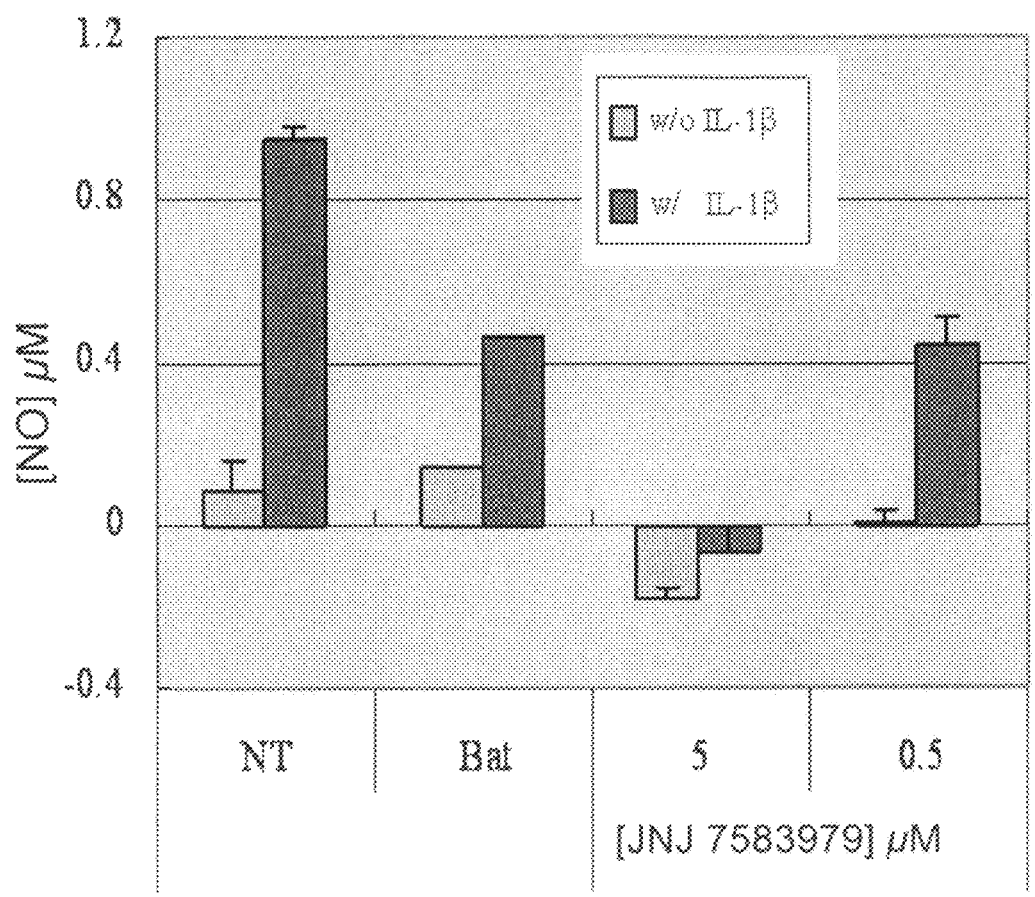
FIG. 7B is a bar graph of the effect of JNJ 7583979 (RWJ 351958) on inhibition of NO production. ARC tissues were treated with the test compound at indicated concentrations (μM) in the presence of 10 ng/ml of IL-1β or absence of IL-1β. The Y axis represents NO levels in μM and the X axis represents JNJ 7583979 (RWJ 351958) in μM. In addition, non-treated and Batimastat treated tissues were tested as controls.
Figure 8:
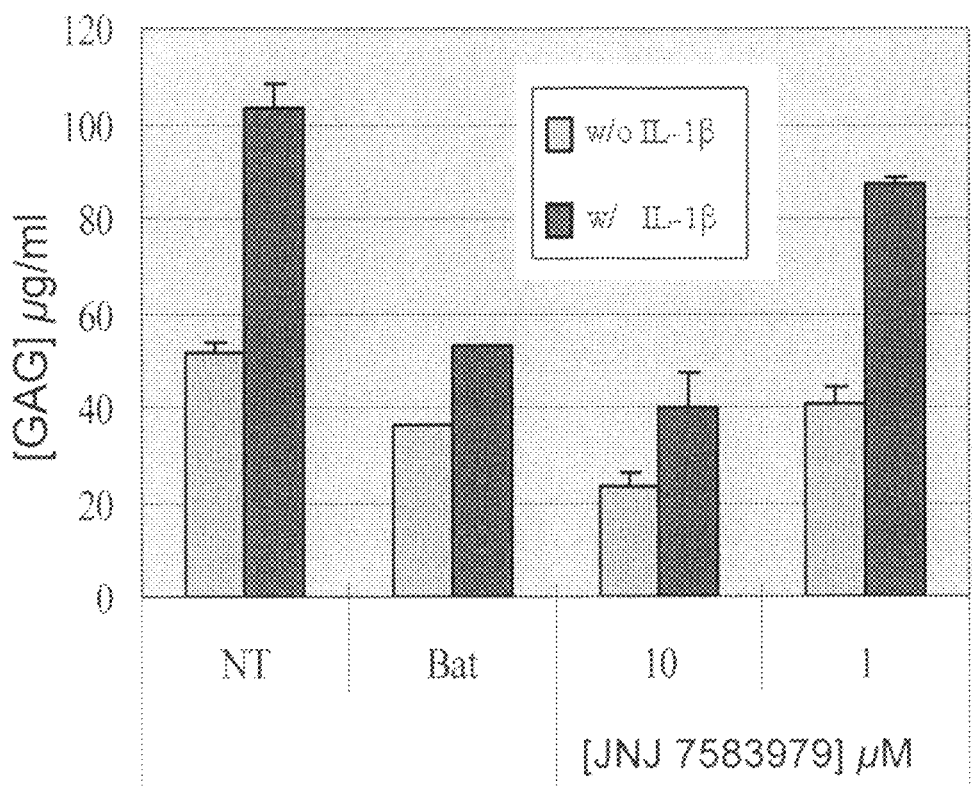
FIG. 8 is a bar graph of the effect of JNJ 7583979 (RWJ 351958) on inhibition of glycosaminoglycan (GAG) release. ARC tissues were treated with the test compound at indicated concentrations in the presence of 10 ng/ml of IL-1β or absence of IL-1β. The Y axis represents GAG levels in μg/ml and the X axis represents JNJ 7583979 (RWJ 351958) in μM. In addition, non-treated and Batimastat treated tissues were tested as controls.

As shown in FIG. 7A and FIG. 7B, JNJ 7583979 (RWJ 351958) significantly inhibited PGE$_2$ synthesis and NO production.

While JNJ 17089540 (RWJ 669307) and SCIO-282 (SD 282) had little effect on inhibition of GAG degradation, JNJ 7583979 (RWJ 351958) and JNJ 3026582 (RWJ 67657) showed significant effect, with stronger efficacy found for JNJ 3026582 (RWJ 67657) (FIG. 8, FIG. 9A, FIG. 9B and FIG. 9C). These results suggest that JNJ 17089540 (RWJ 669307) and SCIO-282 (SD 282) mainly modulate MAP kinase activity that might contribute to aberrant function of downstream transcription factors involved in NO and PGE$_2$ synthesis and some members also have activities in prevention of matrix degradation.

These compounds showed little cytotoxicity to chondrocytes within the tested concentrations (FIG. 10A, FIG. 10B and FIG. 10C).

Table 2 lists the results from a direct enzyme assay of SCIO-469 (SD 469) and SCIO-282 (SD 282). The assays were performed with human PBMC's stimulated with endotoxin. The information regarding SCIO-469 (SD 469) in comparison with SCIO-282 (SD 282) indicates that, while both compounds have selectivity for p38α, SCIO-282 (SD 282) is ~6 times more potent than SCIO-469 (SD 469) in inhibition of the enzyme.

TABLE 2

Comparison of Drug Activities on Inhibition of Different Enzymes SCIO-469 vs. SCIO-282

|  | SCIO-469 (SD 469) | SCIO-282 (SD 282) |
|---|---|---|
| h-p38α, IC$_{50}$ (nM) | 9 | 1.6 |
| h-p38β, IC$_{50}$ (nM) | 98 | 23 |
| Selectivity, p38β/α | ~10 | ~15 |
| 6 CYP450 (IC$_{50}$, μM) | >1 | CYP2C9, 0.5 μM |
| TNFα Inhibition | 1.6 | 0.07 |
| h-WBA (EC$_{50}$, μM) |  | (10x diluted) | h-WBA = human whole blood assay.
EC = effective concentration.

However, in contrast to the results from the direct enzyme assay in Table 2, Table 3A demonstrates that SCIO-469 (SD 469) is more potent than SCIO-282 (SD 282) in inhibition of both NO (18 nM vs 74 nM) and PGE$_2$ (107 nM vs 583 nM) production in the chondrocyte cell pellet model.

TABLE 3A

Comparison of NO and PGE$_2$ values SCIO-469 vs. SCIO-282

| IC$_{50}$ (nM) | SCIO-469 (SD 469) | JNJ 3026582 (RWJ 67657) | SCIO-282 (SD 282) | JNJ 17089540 (RWJ 669307) |
|---|---|---|---|---|
| NO | 18.01 | 119.3 | 74.39 | 4920 |
| PGE$_2$ | 106.8 | 421.2 | 582.5 | 29570 |

Figure 11A:
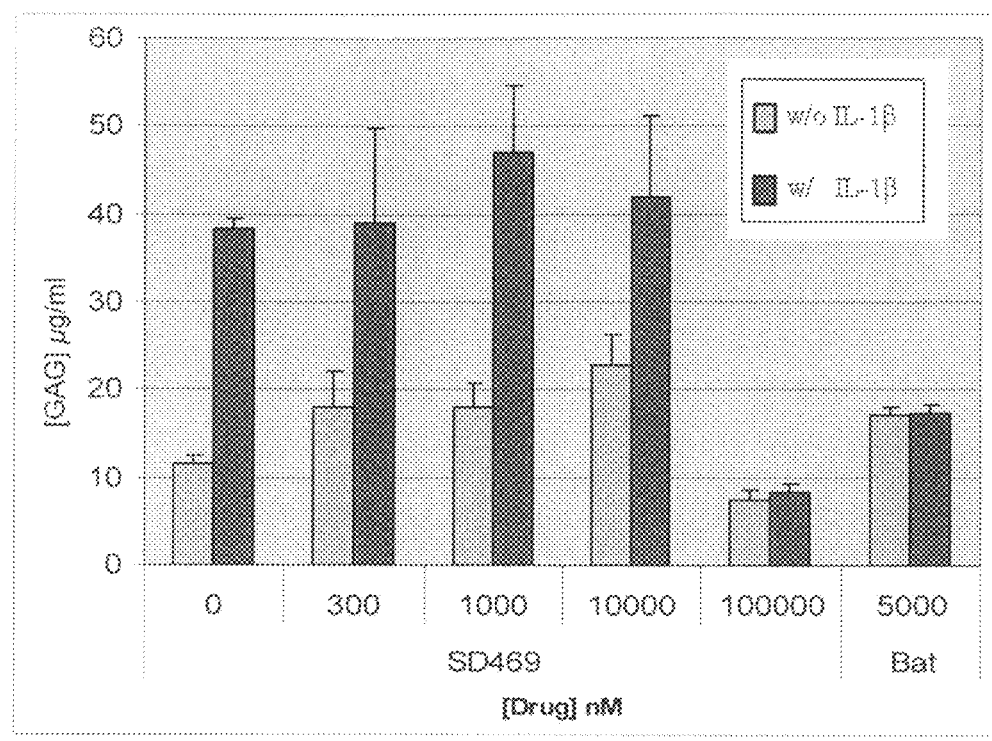
FIG. 11A is a bar graph of the effect of SCIO-469 (SD 469) on inhibition of GAG degradation in bovine ARC tissues stimulated with IL-1β in the presence of 10 ng/ml of IL-1β or absence of IL-1β. The Y axis represents GAG levels in μg/ml and the X axis represents SCIO-469 (SD 469) in nM concentrations in the presence or absence of IL-1β.
Figure 11B:
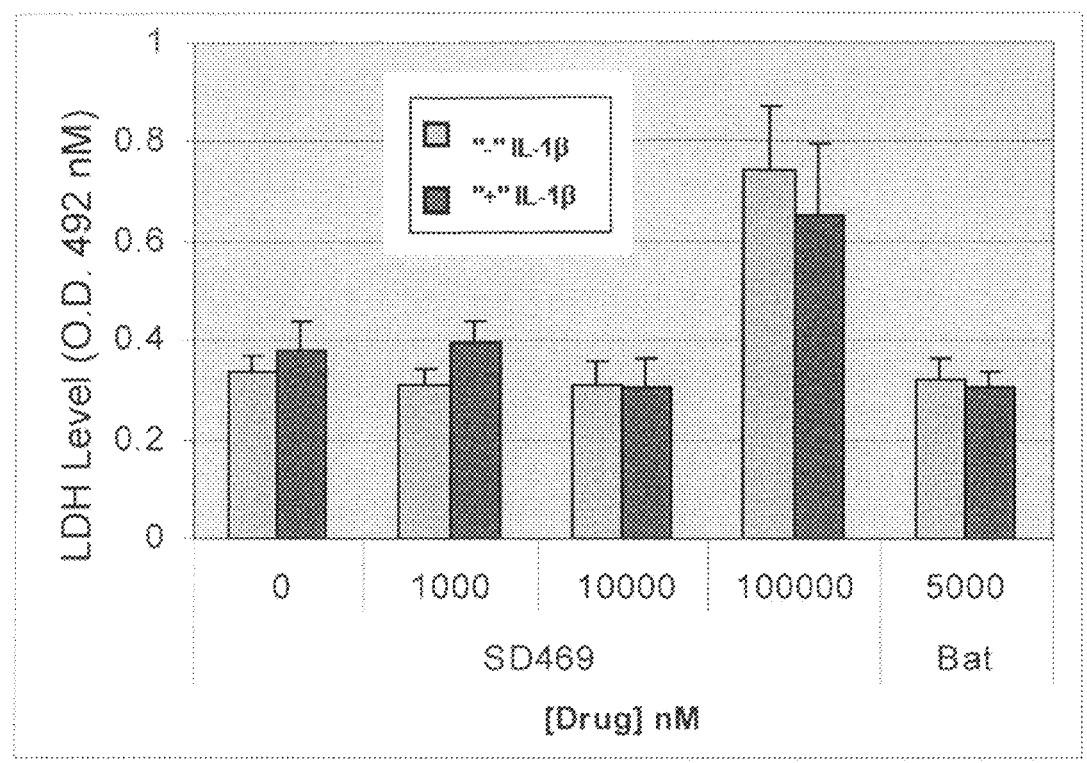
FIG. 11B is a bar graph of the effect of SCIO-469 (SD 469) on LDH level to assess cytotoxicity in bovine ARC tissues. The Y axis represents LDH levels in O.D. 492 nm and the X axis represents SCIO-469 (SD 469) in nM concentrations, in the presence of 10 ng/ml of Il-1β or absence of IL-1β.

SCIO-469 (SD 469) had no effect on inhibition of GAG degradation in ARC tissues stimulated with IL-1β (FIG. 1A). Cytotoxicity of SCIO-469 (SD 469) was assessed by measuring LDH level in the culture medium and the data indicated that SCIO-469 (SD 469) at 100,000 nM increased LDH level by 121% (FIG. 11B), indicating a mild toxicity at this high concentration to chondrocytes, consistent with the reduced GAG level in the same samples (FIG. 11A). These results suggest that the more water-soluble nature of SCIO-469 (SD 469) may allow better penetration into chondrocyte cells and, hence, that SCIO-469 (SD 469) is more potent than SCIO-282 (SD 282). However, the efficacy in inhibition of PGE$_2$ by SCIO-469 (SD 469) (maximum inhibition 62%) is lower than SCIO-282 (SD 282) (96%).

To characterize the relative efficacies among different p38 MAP kinase inhibitors, dose-response curves were generated for both PGE$_2$ and NO assays. Bovine ARCs were treated at 37° C. with serial dilutions of SCIO-469 (SD 469), SCIO-282 (SD 282), JNJ 3026582 (RWJ 67657) and JNJ 17089540 (RWJ 669307) in a range of 1 pM-100 μM. After one hour of treatment, ARCs were stimulated with or without 7.5 ng/ml IL-1β and continued to incubate for five days before assay. The IL-1β-stimulated PGE$_2$ synthesis or NO production was first calculated by subtraction of PGE$_2$/NO levels in the absence of IL-1β, from that in the presence of IL-1β. Percent of inhibition by compounds was then calculated by the decrease in PGE$_2$/NO levels in the presence of a compound divided by the IL-1β-stimulated PGE2/NO levels without a compound treatment. The IC$_{50}$ values in nM was then calculated using the Sigmoidal dose-response equation: Y=Bottom+(Top-Bottom)/(1+10^(logIC50-x)) created by Prizm program (Bottom: the lowest effect; Top: the maximum effect). In this plot, the drug concentration point at 0 nM was changed to 0.001 nM, which is ten times lower than the lowest dosage, to avoid the data point at 0 nM being problematic in the program, since Log zero is invalid.

While JNJ 3026582 (RWJ 67657) and SCIO-282 (SD 282) showed similar efficacy in inhibition of both NO and $PGE_2$, JNJ 17089540 (RWJ 669307) is a weaker inhibitor for NO (FIG. 12A) and even weaker in inhibition of $PGE_2$ synthesis (FIG. 12B), consistent with its different mechanism of action from those of JNJ 3026582 (RWJ 67657) and SCIO-282 (SD 282).

TABLE 3B

Summary for the compounds tested

| Compound category | Compound | Pellet Assay | | |
| --- | --- | --- | --- | --- |
| | | GAG Release | PGE2 Inhibition | NO Inhibition |
| Antiproliferatives | Rapamycin | 50% at 10 µM | 47% at 10 µM | 30% at 10 µM |
| | JNJ 7706621 (CDK Inhibitor) | 100% at 5 µM | No effect | 100% at 5 µM |
| NSAIDs | Suprofen | No effect | IC50 = 812pM | 20% at 10 µM |
| | Tolmetin | No effect | IC50 = 673 nM | No effect |
| | Tepoxalin | 15% at 10 µM | IC50 = 3.28 µM | 50% 10 µM |
| | Piroxicam | No effect | ND | ND |
| | Tiaprofenic Acid | No effect | ND | ND |
| P38 MAP Kinase Inhibitors | JNJ 3026582 (RWJ 67657) | ~90% inh at 10 µM | IC50 = 421 nM | IC50 = 119 nM |
| | JNJ 7583979 (RWJ 351958-000-A) | 64% at 10 µM, 10% at 1 µM | 100% at 0.5 µM | 50% at 0.5 µM |
| | JNJ 17089540 (RWJ669307) | No effect | IC50 = 29.6 µM | IC50 = 4.9 µM |
| | SD-282 | No effect | IC50 = 583 nM | IC50 = 74 nM |
| | SD-469 | No effect | IC50 = 18.01 nM | IC50 = 106.8 |
| Other anti-inflammatories | Anti-TNF* | 100% at 1 ng/ml | 100% at 10 ng/ml and 50% at 1 ng/ml | 100% at 1 ng/ml |
| | Topramax | No effect | No effect | No effect |
| | Feverfew | 50% at 0.1 mg/ml and 22% at 0.05 mg/ml | 62% at 0.1 mg/ml and 23% at 0.05 mg/ml | ND |
| | Centella (ETCA) | No effect | 25% at 10 µg/ml | 25% at 10 µg/ml |
| | Madecassoside | No effect | No effect | No effect |
| Protease Inhibitors | ORC (Interceed)** | ND | 100 at 0.8 mg/ml | ND |

*The effects of Remicade shown are on TNFα stimulated responses, with no effects on IL-1β stimulated reactions.
**The effects of ORC shown are those in HA solution.

Example IV

Drop Tower Design Model

In order to assess cartilage breakdown by inflammatory mediators and the effect of antagonists on those mediators, a cartilage impact model (the "drop tower model") was established using a drop tower device to apply a peak compressive stress to a cartilage sample of about 20-30 MPa over an area of about 11-15 mm². Advantages of this model included its clinical relevance due to its potential to mimic several key parameters of osteoarthritis such as inflammatory cell mediators (by co-culturing with inflammatory cells), and induction of trauma to create the cartilage damage.

Joint impact trauma frequently is sustained through accidents involving falls or direct blows to the joint. Even with careful early surgical reconstruction, development of post-traumatic osteoarthrosis is frequently a late consequence of joint impact trauma, leading to disability and requiring subsequent surgical intervention (such as joint arthroplasty and replacement by prostheses). Although links between a traumatic event and osteoarthrosis have been reported, the cellular pathways underlying progressive cartilage destruction are unknown. Some experimental animal studies reported structural changes in cartilage tissue and changes in cartilage metabolism similar to those found in early osteoarthrosis after impact trauma. Progressive degeneration after initial structural damage may be related to modifications of the mechanical environment or tissue properties. In addition, ongoing structural damage may be associated with biochemical processes after the traumatic event, which augment post-traumatic changes. These biochemical processes likely include inflammatory mediators that contribute to ultimate cartilage degeneration.

In the "drop tower design model" cartilage explants were first injured and then cultured in inflammatory medium to mimic the progression of joint impact trauma linked to cartilage degeneration and osteoarthritis. The approach of the model is to artificially produce cellular damage without gross structural alterations, and to determine how the cells respond to such an insult over the ensuing days when treated with or without potential therapeutic agents.

The drop tower design model was based on previously published papers (Jeffrey, J. E. et al., "Matrix Damage and Chondrocyte Viability Following a Single Impact Load on Articular Cartilage," *Archives of Biochem and Biophys,* 322 (1): 87-96 (1995); Duda G. N. et al., "Chondrocyte Death Precedes Structural Damage in Blunt Impact Trauma," *Clinc*

*Orth Res*, 393: 302-309 (2001); and David M G et al., "Inflammation Enlarges the Zone of Damage of Articular Cartilage After Acute Mechanical Trauma," *American Academy of Orthopaedic Surgeons* 393: 302-309 (2002)) with modifications. The contents of these references is incorporated by reference in their entirety.

The device comprises a vertical rail that guides a sliding weight from 0.1 kg to 3 kg directly onto a force transducer which is situated at the bottom of the device. A sphere-shaped 2 mm indenter resting on a specimen is located at the bottom of the vertical rail. The indenter is held by a stop screw. The specimen is rigidly attached to a tissue holder underneath the indenter, to avoid side movements, the specimen is rigidly attached to the tissue holder. In this manner, the force transducer transduces a force indirectly onto the specimen. Adjusting the weight of a mass and height from which the mass drops varies the magnitude of the intended impact. For example, a weight mass (e.g., 500 mg) held by a weight holder can be released from a height of e.g., 36 cm and dropped onto the force transducer.

For this model, the following in vitro parameters were evaluated:
a) histological scoring,
b) Glycosaminoglycan (GAG) release in the media—a measurement of proteoglycan degradation which indicates cartilage extracellular matrix breakdown,
c) GAG content in the tissues by histological stain,
d) $PGE_2$ levels by Enzyme-linked Immunosorbent Assay (ELISA)—a primary product of arachidonic acid metabolism that is synthesized and released upon cell activation, and whose presence indicates an inflammatory response, and
e) Total Nitric Oxide (NO) production—measurement of NO production indicates the presence of inflammatory response or mitogenic stimuli.

Pilot Studies:

Pilot studies were performed to determine optimal parameters to generate injury in explants. Blunt trauma to the knee joints of animals in vivo has been shown to induce degenerative changes in the cartilage and alterations in mechanical load are known to modulate matrix biosynthesis in vitro. To examine if cartilage matrix metabolism is also changed in response to injury in this model, the level of proteoglycan degradation in injured cartilage was determined.

Time course analyses of GAG release in response to various levels of severity of injury on cartilage specimens that were subsequently stimulated with or without PBMC-conditioned medium were performed. The level of GAG released was readily detectable at day three and was higher at day five of incubation. More importantly, the injured cartilage had more GAG degradation than non-injured specimens, which was proportional to the severity of an injury. After seven days in culture, however, cellularity per disc for both injured and non-injured specimens dropped to 14-30% of the cell number found at 1 day of incubation, indicating that there was tissue necrosis with time of culturing. Furthermore, longer incubation resulted in higher basal GAG release that narrowed down the treatment window in this model. Therefore, samples were harvested for assay at day five post treatment. In addition, since there was no gross damage to the cartilage samples even at highest impact energy tested, 1.96J was chosen as the impact energy for all subsequent experiments to ensure a maximal effect on cartilage.

The data demonstrated that cartilage injury resulted in increased GAG degradation (1.5-3 fold increase) and $PGE_2$ synthesis (1.7 fold) in an inflammatory environment.

Studies of the Effects of Therapeutic Compounds

Materials:

Dulbecco's Modified Eagle Medium (D-MEM) with high glucose (Cat. No 10564011), RPMI Medium 1640 (Cat. No. 11835030), Antibiotic-Antimycotic (100×) containing penicillin, streptomycin, amphotericin B, and neomycin (10000 U/ml, 10 µg/ml, 25 mg/ml and 5 µg/ml, respectively) (Cat. No. 15240062), and phosphate buffered saline (PBS, Cat. No. 14130-144) were purchased from Invitrogen Life Technology (Carlsbad, Calif.). Dimethylethylene (341088), ascorbic acid (A-4403), L-proline (P-5607), tolmetin sodium salt dihydrate (T-6779), Diacerein (D9302), Rhein (R-7269), indomethacin (1-7378), lipopolysaccharide (L-6529), insulin-transferrin-sodium selenite media supplement (Cat. No. I-1884), trypan blue (T-8154), and chondroitin 6-sulfate sodium salt from shark cartilage (C-4384) were purchased from Sigma-Aldrich (St. Louis, Mo.). Recombinant human interleukin-1β (IL-1β, Cat. No: 201-LB), recombinant human tissue necrosis factor α (TNF-α) (Cat. No. 210-TA), recombinant interferon-γ (Cat. No. 285-IF), recombinant human IL-6 (Cat. No. 1609-CL-025/CF) and Human IL-6 Quantikine ELISA Kit (Cat. No. D6050) were purchased from R&D Systems (Minneapolis, Minn.). A Nitrate/Nitrite Colorimetric Assay Kit (Cat. No. 780001), and a prostaglandin E2 detection kit (Cat. No. 514131) were purchased from Cayman Chemicals (Ann Arbor, Mich.). A 3 mm biopsy punch (VWR-21909-140) was purchased from VWR International (West Chester, Pa.). Peripheral blood mononuclear cells (PBMC) were purified from fresh bovine or human blood through ficoll gradient centrifugation by Lampire Biologics, Inc (Pipersville, Pa.). A Cytotoxicity Detection Kit (LDH) (Cat. No. 1 644 793) was purchased from Roche (Nutley, N.J.). Fetal calf serum (FCS), Cat. No. SH30070.03, Lot No. ANF19047) was purchased from Hyclone. Papain and a LIVE/DEAD Viability/Cytotoxicity Kit (L-3224) were purchased from Molecular Probes. Collagenase (3.4.24.3) and papain (3.4.22.2) were purchased from Worthington Biochemical Corp. (Lakewood, N.J.). A bone saw was purchased from Mar-med Inc. (Cleveland, Ohio).

Specimen Preparation and Treatment:

Bovine articular cartilage was obtained from the knee joints of adult, eighteen to twenty-four month old animals and processed within twenty-four hours after sacrifice. After removal of muscle and ligament, tibia plateau and trochlear groove areas were first cut into small pieces in a range of ~1-3×~2-5 $cm^2$ employing the least curved cartilage surface and ~1-1.5 cm of the subchondral bone underneath, since the presence of underlying bone has been shown to significantly limit the degree of matrix damage and cell death. Care was taken to consistently prepare the same thickness of bone layer. The cartilage-on-bone specimens were subjected to an impact. Since the contact area between cartilage surface and indenter during impact was about 1-2 mm in diameter, with a minimum of 0.4 cm apart between two adjacent loads, 3-5 impact loads could be performed on a piece of cartilage-on-bone with the above-mentioned dimensions. After each impact, the cartilage area with a visible indent of ~0.5-1 mm in the center was punched out with a 3 mm diameter puncher and immediately soaked in PBS with 1× Antibiotic-Antimycotic. Throughout the impact procedure and preparation of specimens, the cartilage was kept moist using PBS to prevent tissue dehydration. The cartilage discs were sterilized through 3× one hour wash in PBS with 10× Antibiotic-Antimycotic followed by 1×0.5 hour wash in PBS with 1× Antibiotic-Antimycotic. After wash, the specimens were incubated with conditioned medium harvested from peripheral blood mononuclear cells (PBMC) stimulated with or without LPS and at the same time, were treated with or without compounds for five days at 37° C., 5% $CO_2$. Culture medium was collected for GAG release, NO and $PGE_2$ assays, and assessment for cytotoxicity. The cartilage discs were digested with papain for GAG content.

Assessment of Cell Viability:

Cartilage discs were also processed to assess cell viability using Molecular Probe's Calcein-AM (C-1430) for live cells and ethidium homodimer-1 (E-1169) for dead cells, following previously described methods (Kim, Y J, Sah, R L, Doong J Y, Grodzinsky, A J, Fluorometric assay of DNA in cartilage explants using Hoechst 33258, *Analytical Biochemistry*, 174: 168-176 (1988)) with modifications. Briefly, the injured or non-injured explant disc was manually sliced vertically into slices of 0.1-0.5 mm in thickness and incubated in 2 µM calcein AM in PBS for 30-45 min at RT followed by incubation with 4 µM EthD-1 solution for five to ten minutes. The cell viability was assessed under the fluorescence microscope. The absorbance/emission wavelengths are 494/517 nm for Calcein and 528/617 nm for Ethidium homodimer-1 respectively.

To quantitatively assess relative cell death after injury at indicated time periods of incubation with conditioned media from PBMC, cartilage discs were digested with 0.2% collagenase in DMEM supplemented with 10% FCS and 1× Antibiotic-Antimycotic for four hours at 37° C. with gentle agitation. After filtering through a 40 µm Nylon Cell Strainer (Cat. No. REF 352340, BD Falcon) to remove tissue debris, chondrocytes were spun down, washed with 1×PBS and resuspended in 0.2-0.5 ml PBS. Viable and dead cells were counted under a light microscope in the presence of Trypan Blue. The percentage of cell death was calculated by dividing the number of blue stained cells by the total number of cells counted. In a series of digestions of normal bovine cartilage cultured for twenty-four hours, the viability of the cells extracted was found to be 90%. It was assumed that similar conditions prevail in impacted cartilage and that culturing and enzymatic extraction would result in a loss of 10% of the viable cells. The measured viabilities were, therefore, scaled by 100/90 to correct for this, so that the loss of viability shown was that due solely to the impact.

Induction of Inflammatory Conditions:

Samples for compound evaluation were tested using either of two different methods to induce inflammatory conditions. One method utilized media conditioned from peripheral blood mononuclear cells (PBMCs) stimulated with LPS ("+LPS") or non-inflammatory media without LPS ("−LPS"). Another method utilized the absence or presence of a cocktail of cytokines.

In the first method, bovine or human PBMCs were freshly prepared using Ficoll gradient by Lampire Biological Laboratories, Inc. PBMCs in RPMI w/10% FCS at delivery were spun down at 1500 rpm for twenty minutes and the cell pellet was washed twice with 1×PBS to wash off the residual Ficoll. The cells were then resuspended at a density of $1 \times 10^6$/ml in RPMI supplemented with 10% FCS, 1× Antibiotics-Antimycotics. The suspension was divided into two aliquots. One aliquot was stimulated with 10 µg/ml of LPS and the other was not stimulated. Both aliquots were then incubated at 37° C., 5% $CO_2$ for twenty-four to seventy-two hours. The conditioned media with or without LPS stimulation are collected, aliquoted, and stored in −80° C. for a maximum of three months. Each conditioned medium was assessed for levels of pro-inflammatory cytokines to ensure their secretion from PBMC. A representative cytokine, IL-6, was assayed by ELISA using a Human IL-6 Quantikine kit and it was shown that the LPS-stimulated medium had at least 10 ng/ml of IL-6, while IL-6 was undetectable in the unstimulated medium.

In the second method, the explants were cultured at 37° C., 5% $CO_2$ either in stimulated or non-stimulated conditioned medium as described above or in defined medium containing DMEM supplemented with 1% FCS, 1× insulin-transferrin-sodium selenite media supplement and Antibiotics-Antimycotics in the presence or absence of a cocktail of cytokines containing 10 ng/ml of IL-1β, 100 ng/ml of TNFα and 5 ng/ml of IFN-γ. The compounds were solubilized in $H_2O$, Ethanol or DMSO ($10^{-2}$ M) according to suppliers' instructions and further diluted with either conditioned medium stimulated with or without LPS to the required concentrations. DMSO concentrations in the culture media never exceeded 1%. This concentration of DMSO has no effect on cartilage proteoglycan metabolism in response to cytokines. The injured and noninjured cartilage explants were treated with compound-containing medium for three to five days. The specimens were first treated with compounds at desired concentrations at 37° C. for one hour and then incubated for three to five days in the absence or presence of the cocktail of cytokines. At the end of the incubation, media and cartilage samples were harvested and frozen for further analysis.

GAG Degradation Assay:

Glycosaminoglycan (GAG) levels in the culture media or cartilage were determined by measuring the amount of polyanionic material reacting with 1,9-dimethylmethylene blue (DME) as detected by absorbance at 525 nm, using shark chondroitin sulfate as a standard. The DME blue dye-binding solution was prepared by dissolving 16 mg of DME blue in a solution containing 0.304% glycine, 0.23% NaCl, 9.5 mM HCl, pH=3.0 with A525 equaling 0.31. Proteoglycans and proteoglycan metabolites in cartilage were released by digestion with 125 µg/ml of papain in 0.1M PBS, pH 6.0, 5 mM cysteine, 5 mM $Na_2EDTA$ at 50° C. for overnight (Farndale R. W. et al., "Improved Quantitation and Discrimination of Sulphated Glycosaminoglycans by use of Dimethylmethylene Blue," *Biochimica et Biophysica Acta*, 883: 173-177 (1986)). Results are reported as either micrograms of GAG per milliliter or percent of total GAG released into culture medium.

Total Nitrite and Nitrate Assay:

Nitrate/Nitrite was measured using the Griess reaction (Green L. C. et al., "Analysis of Nitrate, Nitrite, and [15N] nitrate in Biological Fluids," *Anal. Biochem.* 126: 131-138 (1982)) with a Nitrate/Nitrite Colorimetric Assay Kit (Cayman Chemicals), as described in Example III above.

Prostaglandin $E_2$ Assay:

$PGE_2$ was measured with STAT-Prostaglandin $E_2$ EIA ELISA kit (Cayman Biochemicals), as described in Example III above. The antibody-$PGE_2$ complex binds to a goat polyclonal anti-mouse IgG that has been previously attached to the well. After washing to remove any unbound reagents, para-nitrophenyl phosphate (pNPP) was added to the well. The product of this enzymatic reaction absorbs strongly at 412 nm. Because of the large range in response to IL-1β and other cytokines, $PGE_2$ values were converted to log scale prior to doing t-tests.

Assessment of Cytotoxicity:

Cell death was assessed by measuring the amount of lactate dehydrogenase (LDH) in the culture supernatant. 10-20 µl of culture medium was incubated with the reaction mixture from the Cytotoxicity Detection Kit (LDH, Roche), as described in Example III above. The amount of formazan formed was measured at 500 nm, which was proportional to the number of dead cells. Since no purified LDH was available for a standard curve at each measurement, an LDH level for 100% dead cells was measured in each experiment. The lysate for the dead cells was prepared as follows: Chondrocytes were enzymatically isolated as described earlier and about 0.1 million cells that were equivalent to the number of cells contained in a 3-mm punch of fresh cartilage explant were lysed in 1 ml of PBS with 1% Triton-100. Approximately 10-20 µl of the lysate was used in the assay as killed cell control.

All assays were done with triplicate or quadruplicate pellets for each dose. Negative and positive controls were included for specimens prepared from each knee.

Results

Effects of Diacerein and Rhein on Inhibition of GAG Release and LDH Toxicity

Figure 14A:
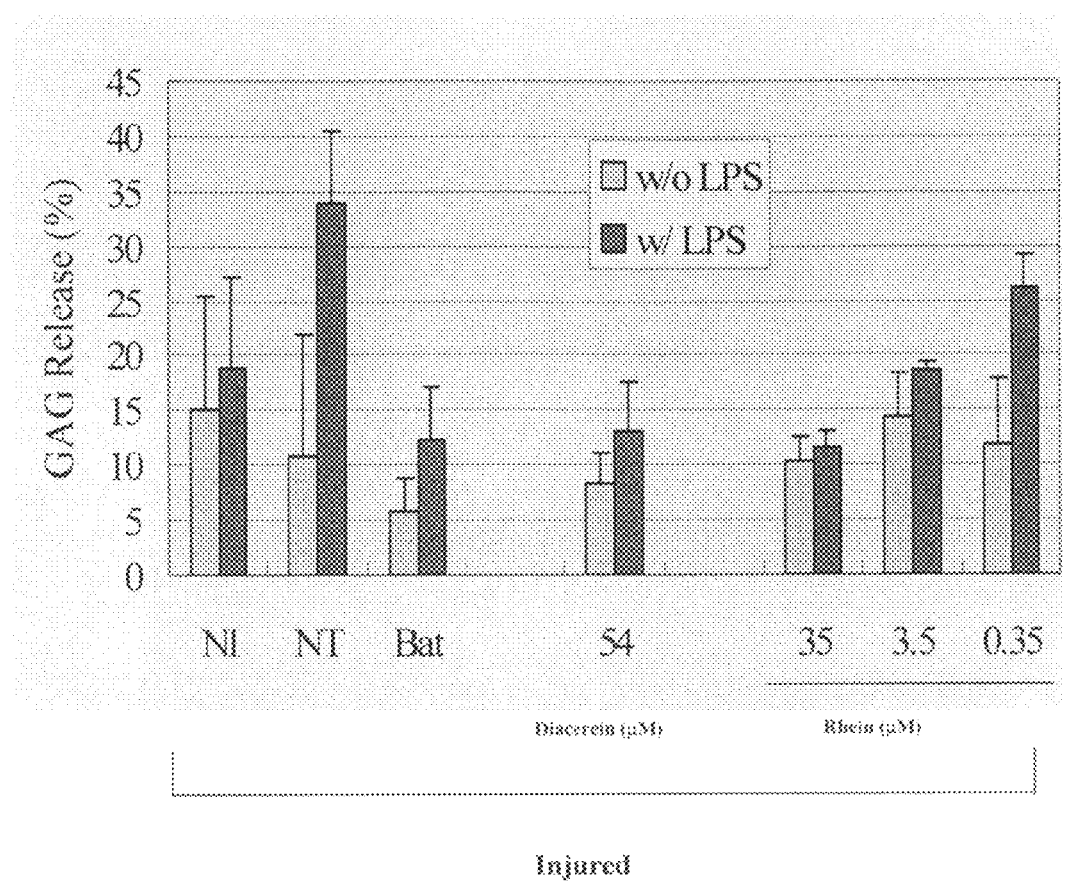
FIG. 14A is a bar graph demonstrating the effects of diacerein and rhein on inhibition of GAG degradation in injured cartilage explants with stimulated or non-stimulated LPS PBMC. The Y axis represents percent GAG inhibition and the X axis represents diacerein and rhein in μM. In addition, non-injured (NI), non-treated (NT), and Batimastat (Bat) treated data is shown.
Figure 14B:
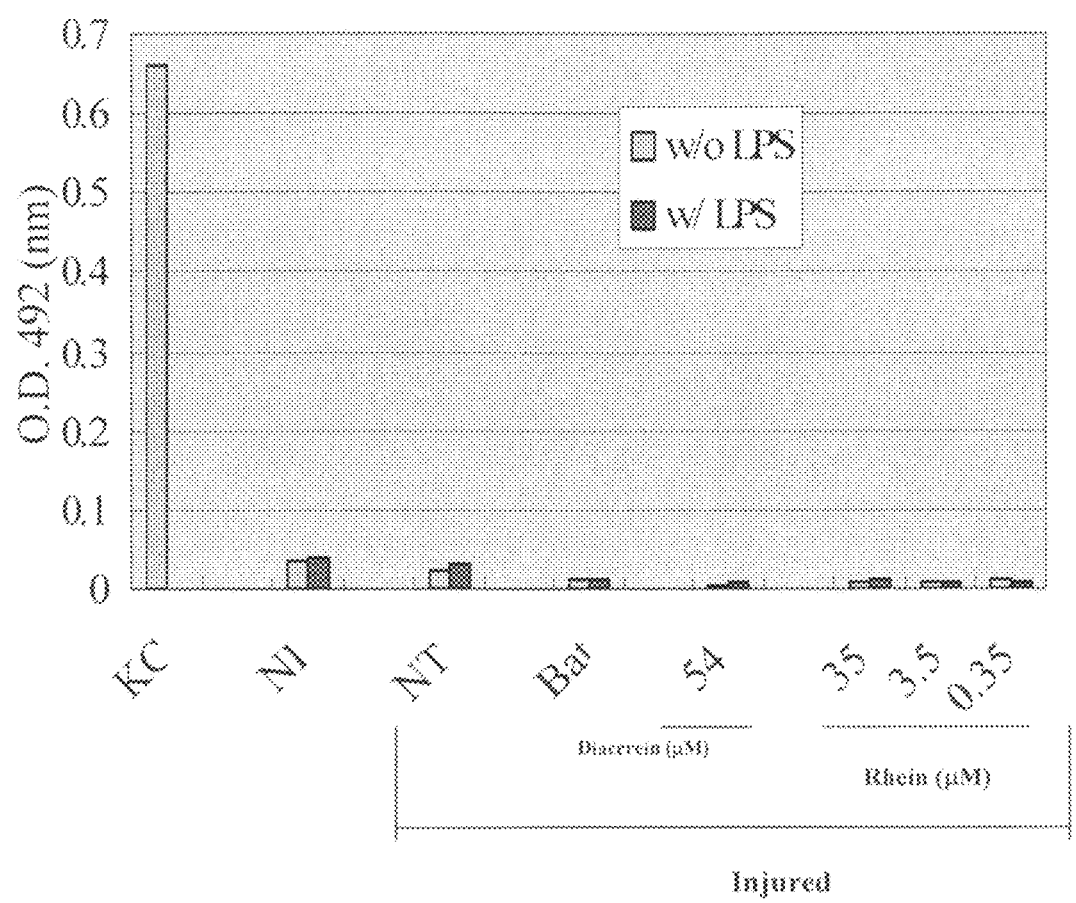
FIG. 14B is a bar graph demonstrating the effects of diacerein and rhein on cytotoxicity in injured cartilage explants with stimulated or non-stimulated LPS PBMC. The Y axis represents percent LDH level (492 nm) and the X axis represents diacerein and rhein in μM. In addition, non-injured (NI), non-treated (NT), Batimastat (Bat) treated, and killed chondrocyte (KC) data are shown.

The model was validated with known drugs diacerein and rhein (its active metabolite) as well as batimastat. Injured and non-injured cartilage samples were prepared as described above and incubated at 37° C., 5% $CO_2$ for five days with stimulated (w/LPS) or non-stimulated (w/o LPS) PBMC conditioned medium. Both diacerein and rhein, at high dosage, completely inhibited proteoglycan degradation in injured cartilage samples induced by inflammatory mediators. This inhibition was dose dependent (FIGS. 14A and 14B). These data suggest that proteoglycan degradation is a good indicator for a therapeutic effect of agents with different mechanisms of action.

The samples were also assayed for LDH levels in culture medium. Chondrocytes from non-injured cartilage explants were extracted according to the procedures described above and completely lysed with 1% Triton-100 in $H_2O$. The explants were tolerant to the cytotoxic effects of diacerein and rhein, even at high doses.

Effects of Batimastat on Inhibition of $PGE_2$ Synthesis and NO Production

Figure 15A:
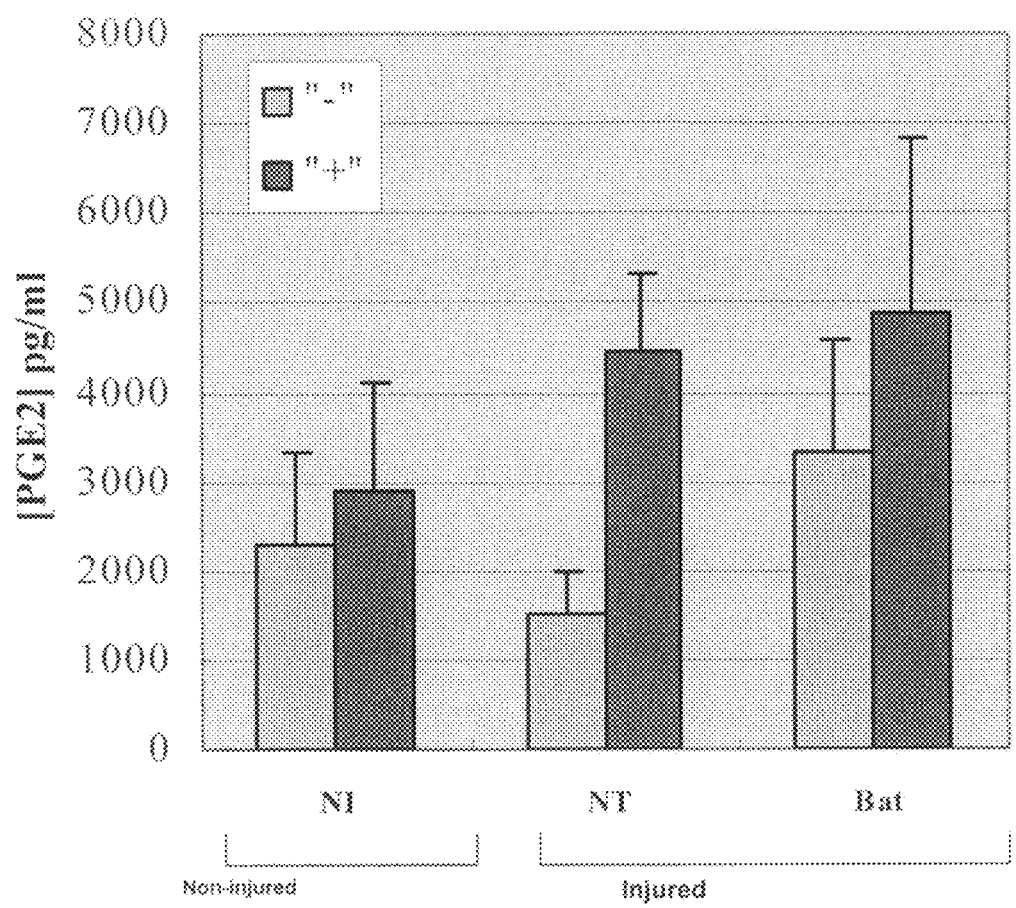
FIG. 15A is a bar graph demonstrating the effect of batimastat on inhibition of $PGE_2$ synthesis in injured cartilage explants in the presence or absence of a cocktail of cytokines (10 ng/ml of IL-1β, 100 ng/ml of TNF-α and 5 ng/ml of INF-γ) in the presence or absence of 10 μM of batimastat (Bat). The Y axis represents $PGE_2$ in pg/ml and the X axis represents batimastat (Bat) in μM. In addition, non-injured (NI) and non-treated (NT) data is shown.
Figure 15B:
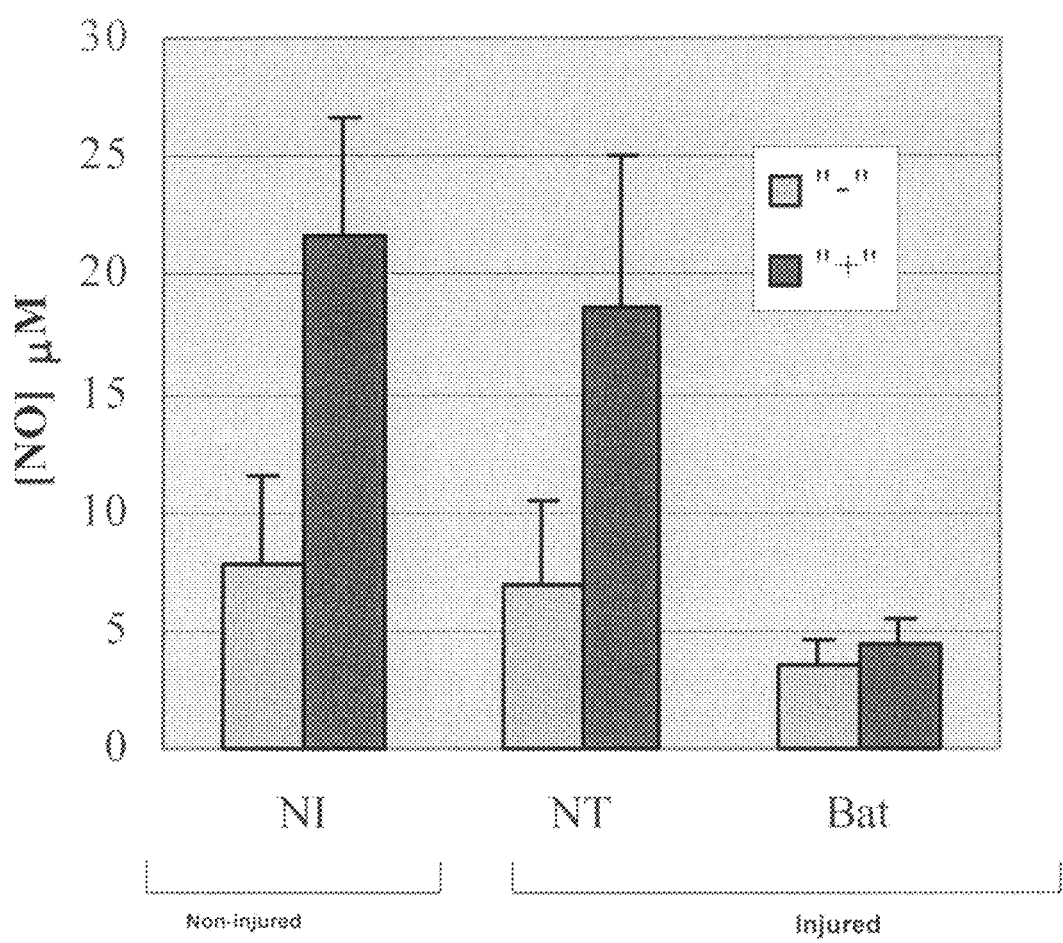
FIG. 15B is a bar graph demonstrating the effect of batimastat on inhibition of NO production in injured cartilage explants in the presence or absence of a cocktail of cytokines (10 ng/ml of IL-1β, 100 ng/ml of TNF-α and 5 ng/ml of INF-γ) in the presence or absence of 10 μM of batimastat (Bat). The Y axis represents NO in μM and the X axis represents batimastat (Bat) in μM. In addition, non-injured (NI) and non-treated (NT) data is shown.

Using the drop tower design model, non-injured and injured cartilage explants were prepared as described above and incubated for five days in defined medium with ("+") or without ("−") a cocktail of cytokines (10 ng/ml of IL-1β, 100 ng/ml of TNF-α and 5 ng/ml of INF-γ) in the presence or absence of 10 µM of batimastat (British Biotech Pharmaceuticals Ltd.). Culture media were harvested for measurement of $PGE_2$ and NO as described above. Batimastat did not inhibit $PGE_2$ synthesis, but did inhibit cytokine-stimulated NO production (FIGS. 15A and 15B). Batimastat was used as a positive control to inhibit GAG degradation since it is a known MMP inhibitor. For consistency, it was used throughout the experiments.

Effects of Rapamycin on Inhibition of GAG Release and LDH Toxicity

Using the drop tower design model, non-injured and injured cartilage specimens were prepared as described above and subjected to treatment with rapamycin at 0.01, 0.1 and 1 µM dosages for five days at 37° C., 5% $CO_2$. Both culture medium and cartilage discs were analyzed for GAG content and proteoglycan degradation was expressed as percent of GAG level released into the medium. The same culture medium was assayed for LDH level as above and a supernatant of killed chondrocytes with 10% Triton-X was used as a positive control for the assay.

Figure 16A:
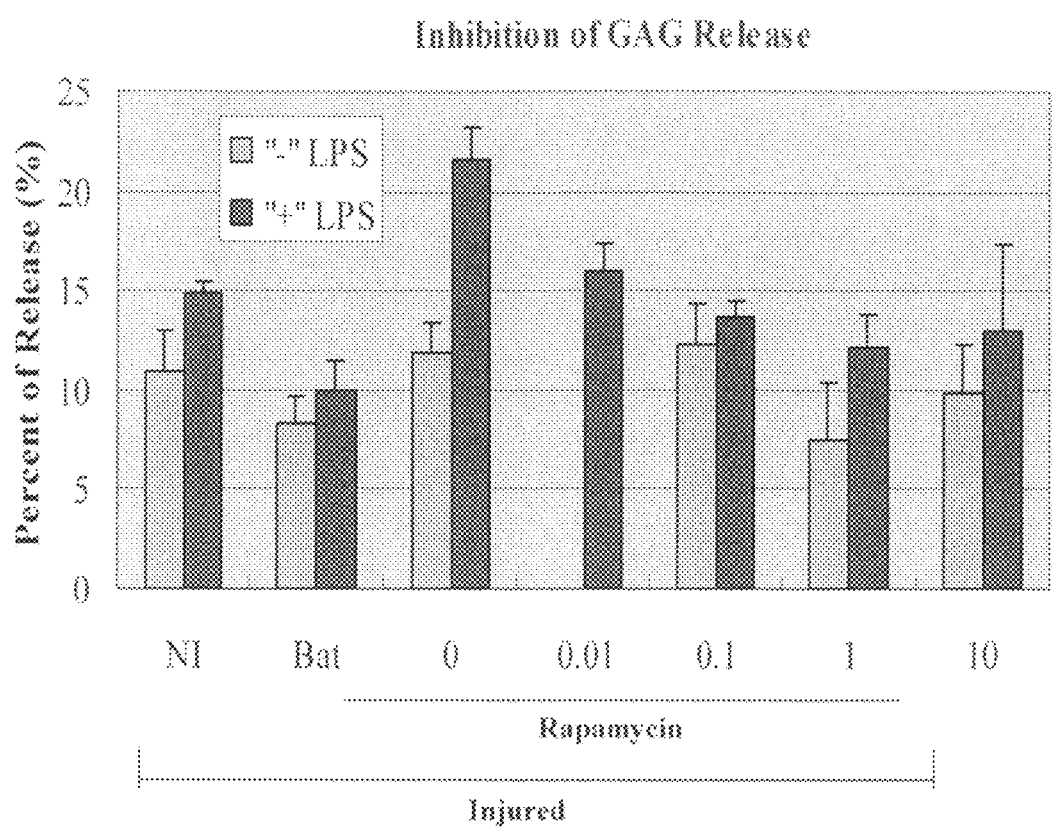
FIG. 16A is a bar graph demonstrating the effect of rapamycin on inhibition of GAG degradation in injured cartilage explants with stimulated and non-stimulated LPS The Y axis represents percent of GAG inhibition. The X axis represents rapamycin in μM. In addition, non-injured (NI) and Batimastat (Bat) treated data is shown.
Figure 16B:
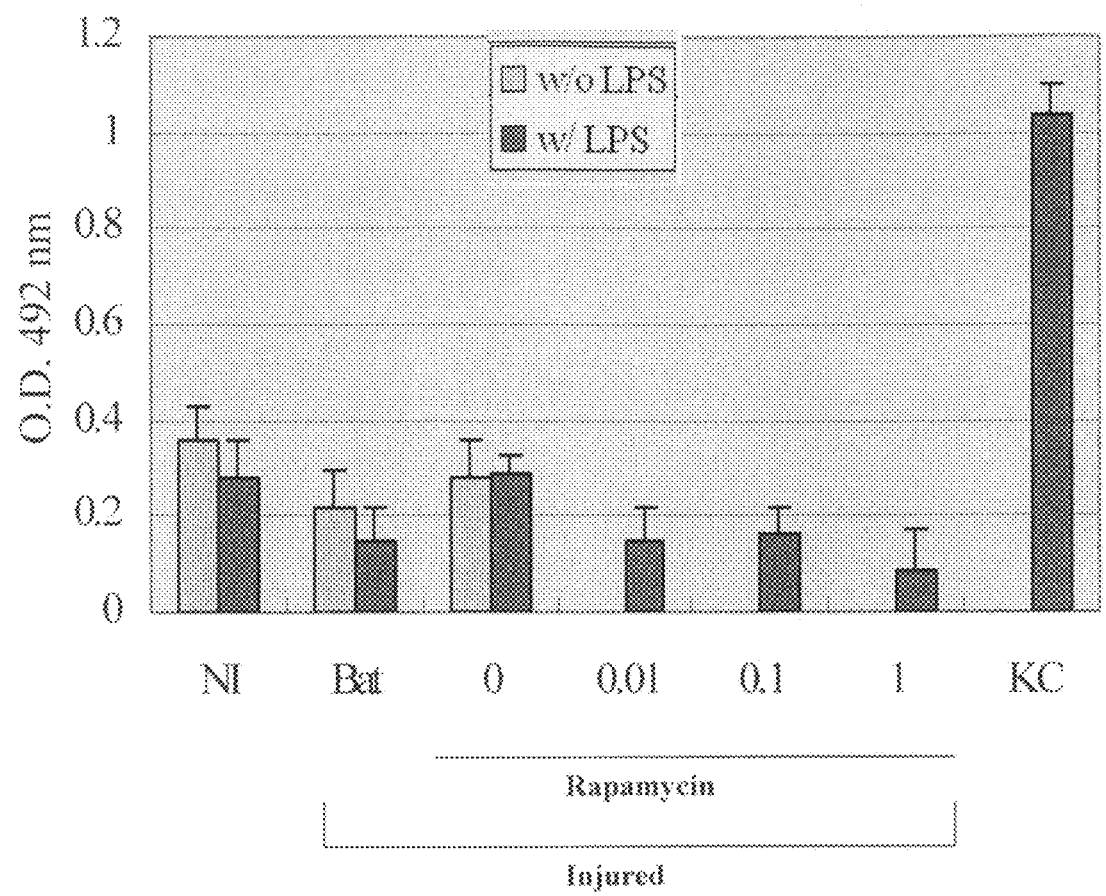
FIG. 16B is a bar graph demonstrating the effect of rapamycin on cytotoxicity in injured cartilage explants with stimulated and non-stimulated LPS. The Y axis represents LDH level on O.D. 492 nm. The X axis represents rapamycin in μM. The X axis represents Rapamycin in μM. In addition, non-injured (NI), Batimastat (Bat) and killed chondrocytes (KC) treated data is shown.

When compared to the "no treatment" explant, Rapamycin inhibited GAG release completely at as low as 0.1 µM and by 84% at 0.01 µM (FIG. 16A). At all testing dosages, rapamycin showed little cytotoxicity (FIG. 16B).

Figure 17A:
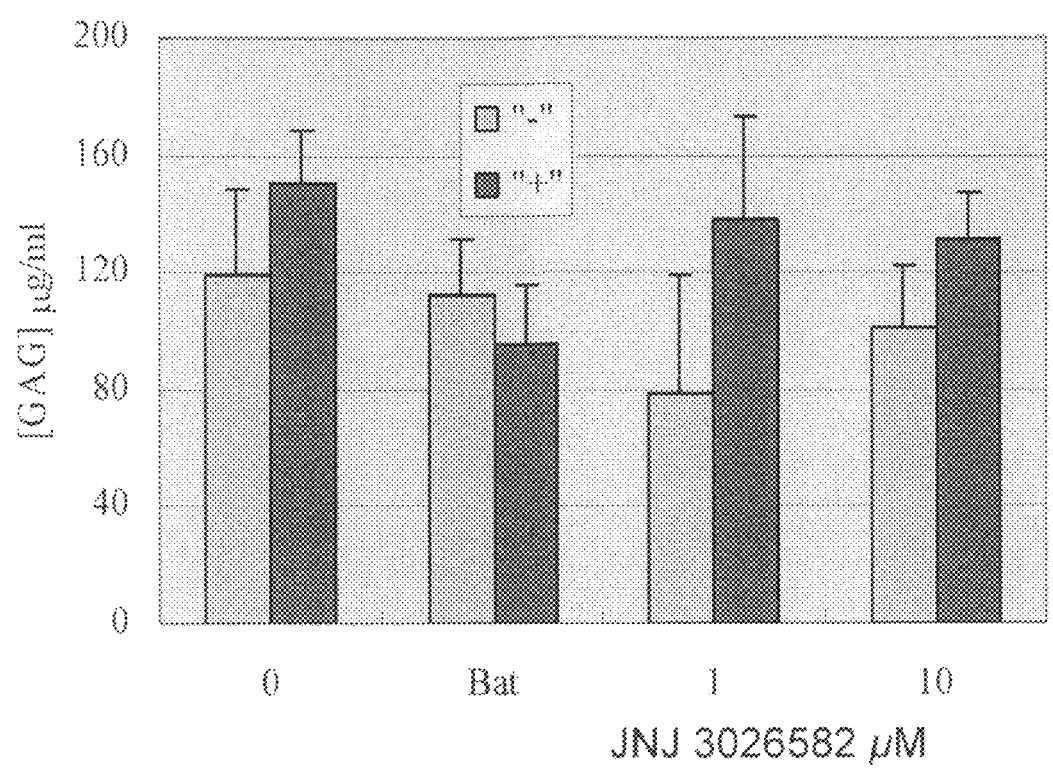
FIG. 17A is a bar graph demonstrating the effect of JNJ 3026582 μM (RWJ 67657) on inhibition of GAG degradation in injured cartilage explants which were cultured in the presence ("+") or absence ("−") of inflammatory conditions (10 ng/ml of IL-1β, 100 ng/ml of TNFα and 5 ng/ml of IFN-γ). The Y axis represents GAG in μg/ml and the X axis represents JNJ 3026582 (RWJ 67657) in μM concentrations.
Figure 17B:
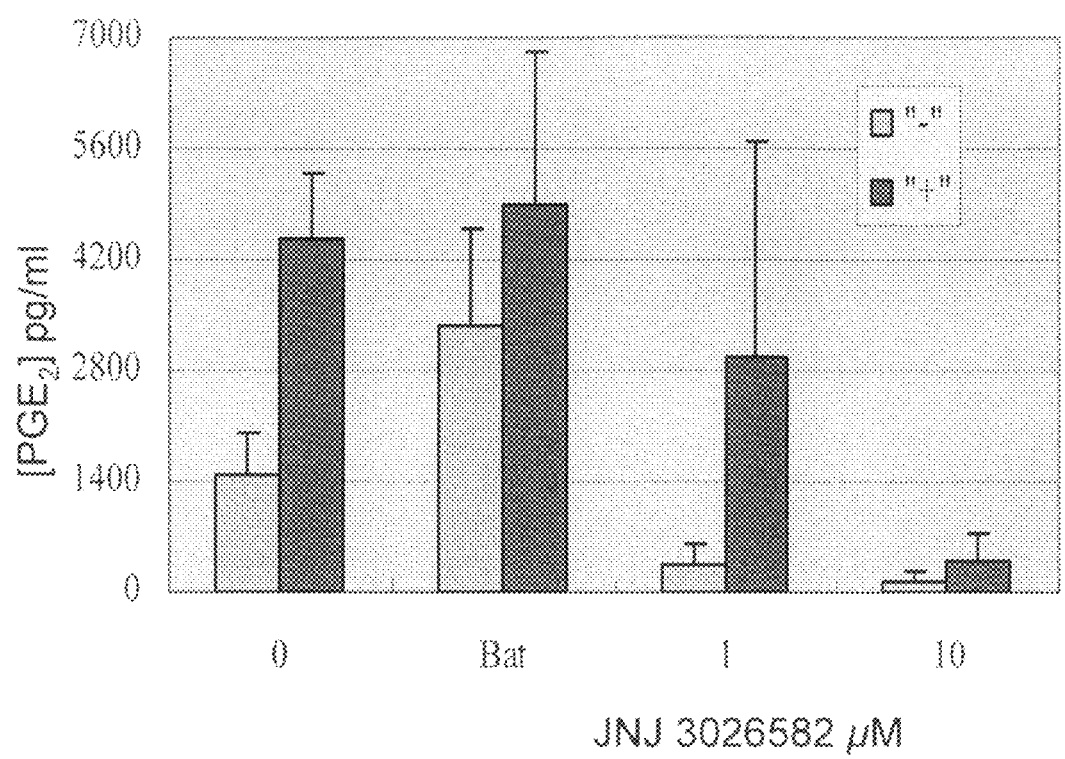
FIG. 17B is a bar graph demonstrating the effect of JNJ 3026582 (RWJ 67657) on inhibition of $PGE_2$ synthesis in injured cartilage explants which were cultured in the presence ("+") or absence ("−") of inflammatory conditions (10 ng/ml of IL-1β, 100 ng/ml of TNFα and 5 ng/ml of IFN-γ). The Y axis represents $PGE_2$ in pg/ml and the X axis represents JNJ 3026582 (RWJ 67657) in μM.
Figure 17C:
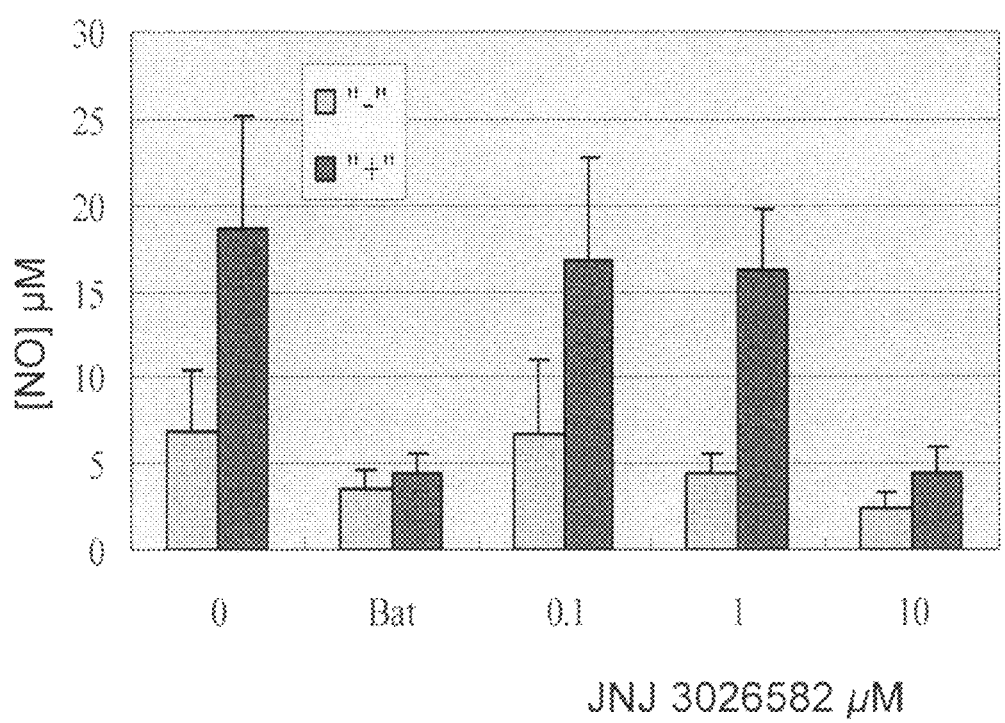
FIG. 17C is a bar graph demonstrating the effect of JNJ 3026582 (RWJ 67657) on inhibition of NO production in injured cartilage explants which were cultured in the presence ("+") or absence ("−") of inflammatory conditions (10 ng/ml of IL-1β, 100 ng/ml of TNFα and 5 ng/ml of IFN-β). The Y axis represents NO in μM and the X axis represents JNJ 3026582 (RWJ 67657) in μM.
Figure 17D:
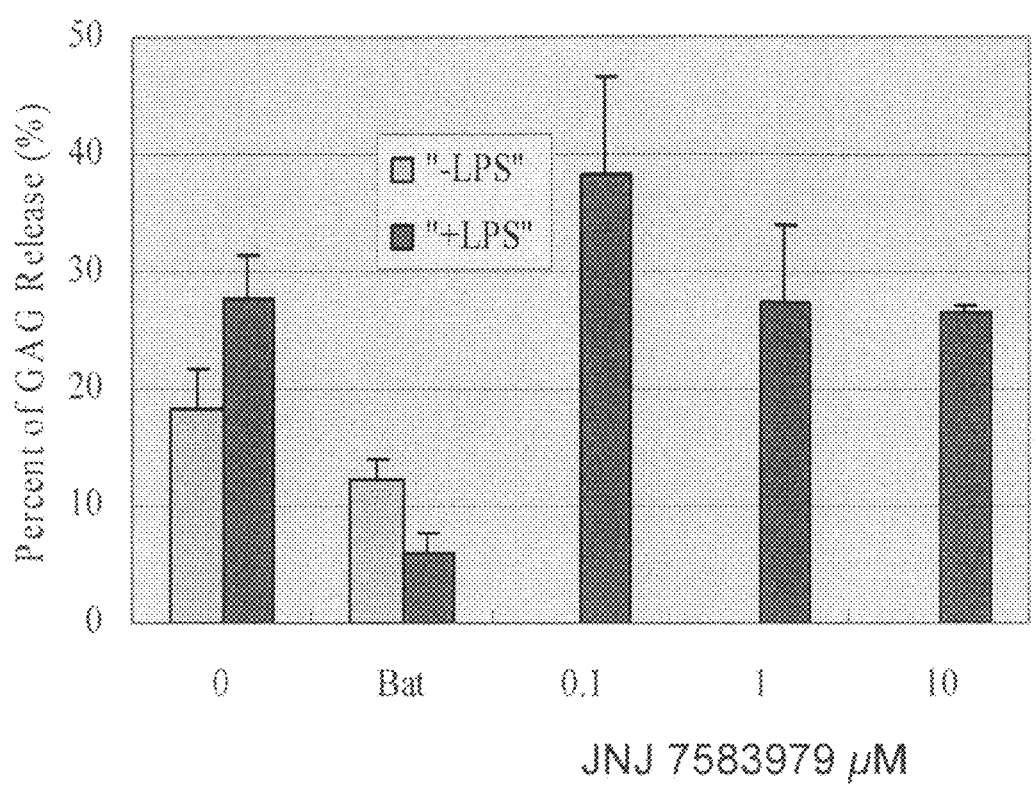
FIG. 17D is a bar graph demonstrating the effect of JNJ 7583979 (RWJ 351958) on inhibition of GAG release in injured cartilage explants with stimulated and non-stimulated LPS. The Y axis represents percent of GAG release and the X axis represents JNJ 7583979 (RWJ 351958) in μM. Data for "−LPS" not shown at 0.1, 1 and 10 due to sample contamination.

Effects of p38 MAP Kinase Inhibitors on Inhibition of GAG Release, NO Production and $PGE_2$ Synthesis Injured cartilage specimens were processed and treated with the compounds either in the presence ("+") or absence ("−") of cocktail of cytokines (10 ng/ml of IL-1β, 100 ng/ml of TNFα and 5 ng/ml of IFN-γ) (FIGS. 17A, B and C), or in PBMC-conditioned medium stimulated with ("+LPS") or without ("−LPS") LPS (FIG. 17D). Culture media were collected for assays. Batimastat was used as a positive control to inhibit GAG degradation because it is an MMP inhibitor.

As shown in FIGS. 17A, B and C, JNJ 3026582 (RWJ 67657) dose-dependently inhibited NO production and $PGE_2$ synthesis, but had little efficacy in inhibiting GAG release. As shown in FIG. 17D, JNJ 7583979 (RWJ 351958) also had little efficacy in inhibiting GAG release. The efficacies of the tested compounds, as well as additional compounds, on inhibition of GAG degradation, NO production and $PGE_2$ synthesis are summarized in Table 4.

TABLE 4

Efficacies of Tested Compounds on Inhibition of GAG Degradation, NO Production and $PGE_2$ Synthesis

| Compound | GAG | $PGE_2$ | NO |
| --- | --- | --- | --- |
| JNJ 3026582 (RWJ 67657) | little | 33% inh at 1 µM and 90% at 10 µM | 66% at 10 µM |
| JNK 7583979 (RWJ 351958) | little | | |
| Rapamycin | 100% inh at 0.1-1 µM | ND | ND |
| Suprofen | 100% inh at 0.1-1 µM | ND | ND |
| Tolmetin | 60% inh at 10 µM | ND | ND |
| Tepoxalin | 100% inh at 10 µM | 90% inh at 10 µM and 77% at 1 µM | 100% inh at 10 µM |
| Piroxicam | No effect | ND | ND |
| Tiaprofenic Acid | 70% inh at 10 µM | ND | ND |
| Rhein | 100% inh at 35 µM | | |
| Diacerein | 100% inh at 54 µM | | |
| Batimastat | 100% inh at 10 µM | No effect | 100% inh at 10 µM |

The effects of JNJ 17089540 (RWJ 669307) and SCIO-282 (SD 282) on inhibition of GAG release, NO production, and $PGE_2$ synthesis in injured cartilage explants were also assessed. Injured cartilage specimens were processed and treated with the compounds in the presence ("+") or absence ("−") of a cocktail of cytokines (10 ng/ml of IL-1β, 5 ng/ml of IFN-γ, 100 ng/ml of TNFα) (FIGS. 18A-F). Culture media were collected for assays as described above. A non-injured cartilage specimen was included as a negative control.

While the p38 MAP kinase inhibitors showed little efficacy in inhibition of GAG release (FIGS. 17A, 17D and 18A-B), they dose-dependently inhibited both NO production (FIGS. 17C and 18C-D) and $PGE_2$ synthesis (FIGS. 17B and 18E-F), indicating that this class of compounds mainly modulates MAP kinase activity that might contribute to aberrant function of downstream transcription factors involving in NO and $PGE_2$ synthesis.

The results from the chondrocyte pellet model and the drop tower design model may demonstrate different effects of the compounds tested because, while both models propagate osteoarthritis, the chondrocyte pellet culture model is more sensitive to treatment, including treatment by soluble factors and more control of variablility between samples, and the drop tower model is a better mimic of in vivo conditions than the chondrocyte pellet culture model, having a cellularity (0.2 M vs. 2 M for pellets) and percent of collagen more similar to actual tissue. For this reason, both models were used to obtain data.

Example V

Anterior Cruciate Ligament Transection (ACLT) Model

The rabbit anterior cruciate ligament transection (ACLT) model is a surgical model of mechanical instability, which mimics chronic traumatic osteoarthritis. The model provides a method for establishing and validating a small animal model of osteoarthritis for screening therapeutic agents delivered via local injection. Disease modification via cartilage preservation is the in vivo parameter evaluated. In this manner, substances which modify the structural progression of the osteoarthritic condition can be screened for use in the treatment of osteoarthritis.

New Zealand white rabbits (male, six to eight pounds) were anesthetized with ketamine (17 mg/kg) and xylazine (2.5 mg/kg). Supplementation was given during surgery, if needed, with an additional intramuscular injection of ketamine (35 mg/kg) and xylazine (5 mg/kg). The animals were given buprenorphine (0.01-0.05 mg/kg) for analgesia via a subcutaneous injection. The buprenorphine was administered every twelve hours for seventy-two hours. After induction of anesthesia, the right leg was clipped free of hair using electric animal clippers. The area around the site of surgery was scrubbed with chlorhexidine diacetate, rinsed with alcohol, dried, and painted with an aqueous iodophor solution of 1% available iodine and surgery was prepared using aseptic technique. In the right limb of each animal, the anterior cruciate ligament (ACL) was transected. A medial parapatellar incision was made and the patella was dislocated. The knee was flexed and the ACL visualized. A scalpel blade was positioned behind the ACL and brought anteriorly, thereby cutting the ACL while protecting the posterior cruciate ligament. The patella was returned to the normal anatomic position. The wound was closed in layers.

Following surgery, the animals were left untreated for six weeks. After six weeks, a series of five injections of the test compound were injected intra-articularly once weekly.

The animals were euthanized six weeks after initiation with an intravenous injection of pentobarbital (60 mg/kg). Following administration of the test compound, the animals were observed to ensure that respiratory function had ceased and that there was no palpable cardiac function. Immediately following euthanasia, gross observations of the knee joints were made and any abnormality was recorded. The joints were analyzed for disease state in the trochlear groove, the femoral condyles and the tibial plateau. Pathological assessments were performed on the sectioned tissue. Condylar structure, cellularity, presence of GAG and presence of cartilage were evaluated.

The examples that follow utilize the general ACLT model in testing agents including p38 MAP kinase inhibitors.

Example VI

Pilot Study: ACLT Model Validation Using JNJ 3026582 (RWJ 67657)

In a pilot study, the ACLT model was used to evaluate the ability of a pharmaceutical agent, JNJ 3026582 (RWJ 67657) (a p38 MAP kinase inhibitor), delivered directly to the knee, to reduce the incidence of osteoarthritic changes in an unstable joint.

JNJ 3026582 (RWJ 67657) is a potent dual inhibitor of p38 MAP kinase and JNK2. Both p38 MAP kinase and JNK are preferentially activated by pro-inflammatory cytokines such as those found in an osteoarthritic joint. Once activated, both p38 MAP kinase and JNK propagate several cellular processes such as, for example, cytokine production and chemokine production, which exacerbate the inflammatory response. By inhibiting these pathways, in particular the p38 MAP kinase pathway, modifying the disease of osteoarthritis can be accomplished.

Preparation of Test Compounds:

Sterile formulations of JNJ 3026582 (RWJ 67657) were prepared by gamma irradiation (1.5 mRAD) on dry ice. DMSO was sterile filtered and the remaining formulations were prepared aseptically. Specifically, 11.5 mg of JNJ 3026582 (RWJ 67657) was dissolved in 4 mL DMSO and the solution was thoroughly mixed with 5 mL of ARTHREASE® (Lot: 11840812) (Biotechnology General (Israel) Ltd.). The final concentration of JNJ 3026582 (RWJ 67657) in the formulation was 1.3 µg/µL and was considered the high dose. The mid dose was made by a 1:10 dilution of the high dose. The low dose was created in the same fashion as the mid dose i.e., by a 1:10 dilution of the mid dose.

Experimental Design:

TABLE 5

Experimental Design

| Test Agent | Dose/Treatment Group | Dose Category | Lot # |
|---|---|---|---|
| JNJ 3026582 (RWJ 67657) | 0.5 µg/kg | Low | Lot: NB3418-12L |
| JNJ 3026582 (RWJ 67657) | 5 µg/kg | Mid | Lot: NB3418-12M |
| JNJ 3026582 (RWJ 67657) | 50 µg/kg | High | Lot: NB3418-12H |
| No injection | | Surgical Control | |

A total of four rabbits (n=4) underwent ACLT of the right limb according to the ACLT model described above.

As discussed above, each formulation was injected once per week for five weeks. 160 µl was injected each time via a 26G (gauge) needle. The vehicle for the formulation was ARTHREASE® (Bio-Technology General (Israel) Ltd.).

The anesthesia and analgesia used in this experiment was slightly different from the ACLT model study described above. Animals were weighed and anesthesia was induced in each rabbit by using inhalation anesthesia (Isoflurane at 5.0%) via facemask. During surgery, the animal was maintained with Isoflurane at a level between 0.5 and 3.5%.

A prophylactic loading dose of antibiotic (penicillin; 37,500 IU/kg) was administered intramuscularly, prior to surgery.

Analgesia in these animals was accomplished with a fentanyl transdermal patch (25 µg/hr). The patch was applied to the shaved dorsum of the animal. The patch was applied twelve to twenty-four hours prior to the initiation of surgery so that fentanyl could become available to the systemic circulation for the post-operative period.

After induction of anesthesia, the right leg skin surface was clipped free of hair using electric animal clippers. The area around the site of surgery was scrubbed with chlorhexidine diacetate, rinsed with alcohol, dried, and painted with an aqueous iodophor solution of 1% available iodine. The anesthetized and surgically prepared animal was placed in the desired recumbent position. Sterile drapes were applied to the prepared area using aseptic technique.

The ACL was transected according to the ACLT model. However, in this experiment, the tendon from the long extensor muscle of the digits that attaches to the lateral condyle was also transected and excised about 3-4 mm in length from the joint to prevent restabilization.

The fentanyl patch was removed approximately forty-eight hours post-surgery. The animals were allowed to move freely as soon as they recovered from anesthesia.

After recovering from surgery and general anesthesia, each rabbit was observed for behavioral signs of discomfort or pain. No signs of discomfort or pain were observed. Animals were returned to their cage when fully conscious and ambulatory.

The health status of each rabbit was determined by general appearance and attitude, food consumption, fecal and urinary excretion and the presence of abnormal discharges. Each rabbit was observed twice daily during the first three days following surgery. Following this time period, the observations were reduced to once daily until the end of the study. The fentanyl patch was removed approximately forty-eight hours post-surgery.

The intra-articular injections were performed according to the ACLT model described above. However, anesthesia during injections was maintained via Isoflurane.

The animals were euthanized according to the ACLT model described above. However, the anesthesia was an intravenous injection of pentobarbital sodium and phenytoin sodium euthanasia solution (0.3 ml/kg body weight) via the marginal ear vein.

Observations following euthanasia were conducted according to the ACLT model. However, the joint was removed and fixed in 10% neutral buffered formalin. The joints were decalcified in appropriate acidic solutions. The joints were then trimmed. All samples were trimmed in approximately the same area of the condyle. Preference was given to sites containing lesions in order to assess the depth of erosions. The trimmed samples were embedded in paraffin, sectioned, and stained with hematoxylin and eosin for potential histological assessment. Histological processing was performed.

Surgery and anesthetic recovery were uneventful. All animals tolerated surgery well. Three animals developed clinical symptoms of skin fold dermatitis during the study. Animal 80 (no injection group) developed signs on day nine. 0.58 ml of penicillin (300,000 IU/ml) was administered intramuscularly and NEOSPORIN® was applied topically. NeoPredef with tetracaine powder was applied topically and 0.6 ml of penicillin was administered on days ten through thirteen. Animal 81 (no injection group) was treated with NeoPredef with Tetracaine and 0.6 ml penicillin on days nine through thirteen for similar signs. Animal 83 (high dose group) was administered 0.6 ml penicillin and topically applied NeoPredef with Tetracaine on days seventeen though nineteen; only powder was applied on days twenty-one through twenty-seven. This animal was also showing signs of a bladder infection although this diagnosis was never confirmed. Animal 75 (low dose group) demonstrated discoloration around the knee and the incision site was weeping. NeoPredef with tetracaine was administered for three days (days thirty-one through thirty-four). There was an n=4 per treatment group. The four animals that are listed received some additional care post surgery for signs of topical skin infection.

Clinical Observations:

At the time of sacrifice, the following parameters were evaluated grossly (the scale follows in parenthesis):
Anterior Surface of Femur (Trochlear Groove)
# of osteophytes (0-3)
Size (diameter) of osteophytes ((0-3)
Presence of trochlear groove thickening (0-1)
Erosion of cartilage (0-3)
Femoral Condyles (both medial and lateral condyle evaluated)
Erosion of cartilage (% surface area) (0-5)
Erosion of cartilage (depth) (0-3)
Presence of clefts (0-2)
Tibial Plateau (both medial and lateral evaluated)
# of Osteophytes (0-3)
Presence of clefts (0-1)
Erosion (% surface area) (0-5)
Erosion (depth) (0-3)
Appearance of Meniscus (both medial and lateral evaluated) (0-3)
Appearance of Patella (0-3)

Each parameter was given a score. The combination of all parameters gave a Total Score. A higher score indicates more damage to the joint. The most clinically relevant parameters are discussed in detail below. All other parameters are listed in Table 6.

Femoral Condyle (% Surface Area Erosion):

Percent surface area erosion was graded as follows: 0=no erosion; 1=less than or equal to 10% erosion; 2=11-25% erosion; 3=26-50% erosion; 4=51-75% erosion; 5=76-100% erosion of cartilage.

On the medial femoral condyle, the low dose group had an average score of 1.5, and no injection group demonstrated an average score of 4. The mid dose group and high dose group averaged 1.63 and 2.25, respectively. The no surgery control group averaged 0.12.

On the lateral femoral condyle, the average score for the low dose group was 1.23, 0.75 for the mid dose group, 2.5 for the high dose group and 3 for the no injection group. The no surgery control group averaged 0.06.

Femoral Condyle (depth of erosion):

Depth of cartilage erosion on the femoral condyle was graded as follows: 0=none; 0.5=barely perceptible; 1=slight; 2=significant; 3=severe.

On the medial femoral condyle, the low, mid and high treatment groups all averaged between 2.00 and 2.31 for their grade. The no injection group and no surgery control groups averaged 1.10 and 0.12, respectively.

On the lateral femoral condyle, the low, mid and high treatment groups all averaged between 1.50 and 1.63 for their grade. The no injection group and no surgery control groups averaged 0.70 and 0.06, respectively.

All Condylar Effects:

The score for All Condylar Effects ranged from 0 to 18. This score is a composite of grades from all criteria within this category. The grades that compose this parameter are the six criteria listed above under Femoral Condyles. The six criteria are the erosion of cartilage % (medial and lateral), erosion of cartilage depth (medial and lateral), and presence of clefts (medial and lateral).

The average score was 6.38 for the low dose, 5.88 for the mid dose group, and 8.69 for the high dose group. The no injection group and no surgery control groups averaged 8.80 and 0.38 respectively.

All Cartilage Effects:

The score for All Cartilage Effects ranged from 0 to 38. This score is a composite of grades from all criteria within this category: trochlear groove thickness and erosion, all the grades in All Condylar Effects, tibial plateau clefts (medial and lateral), tibial plateau erosion (medial and lateral) and tibial plateau depth (medial and lateral).

The average score was 12.75 for the low dose, 14.50 for the mid dose group, 19.19 for the high dose group. The no injection group and no surgery control groups averaged 16.50 and 2.15 respectively.

All Meniscal Effects:

Meniscal effects are a measurement of the degree of damage on both the medial and lateral meniscus. Scores ranged from 0-3 on each meniscus with 1=minor fibrillations, 2=moderate fibrillations and 3=marked fibrillations.

The score for All Meniscal Effects ranged from 0 to 6. This score is a composite of grades from the medial and lateral meniscal scores.

The average score was 2.50 for the low dose, 3.50 for the mid dose group, and 4.25 for the high dose group. The no injection group and no surgery control groups averaged 4.60 and 0.25 respectively.

Total Score:

The score for Total Score ranged from 0 to 59. This score is a composite of grades from all of the scoring criteria.

The average score was 25.00 for the low dose, 29.63 for the mid dose group, and 34.31 for the high dose group. The no injection group and no surgery control groups averaged 29.8 and 4.87 respectively.

TABLE 6

Mean and (SEM) of parameters.

| Parameter | Scale Description | Low | Mid | High | No Injection | No Surgery |
|---|---|---|---|---|---|---|
| Trochlear Groove | | | | | | |
| # of Osteophytes | 0 = 0, 1 = 1, 2 = 2, 3 = >2 | 3.00 (0) | 3.00 (0) | 3.00 (0) | 3.00 (0) | 0.88 (0.17) |
| Osteophyte Size | 0 = 0, 1 = ≤1 mm, 2 = 1-2 mm, 3 = ≥2 mm | 3.00 (0) | 3.00 (0) | 3.00 (0) | 3.00 (0) | 1.12 (0.22) |
| Thickening | 0 = Normal, 1 = Thickened Areas | 0.50 (0.25) | 0.75 (0.25) | 0.25 (0.25) | 0.20 (0.20) | 0 |
| Erosion of Cartilage | 0 = None, 1 = <25%, 2 = 25-50%, 3 = >50% | 1.00 (0) | 1.63 (0.38) | 1.25 (0.25) | 1.40 (0.40) | 0.47 (0.12) |
| Femoral Condyle | | | | | | |
| Presence of Clefts | 0 = Absent, 1 = Unicondylar, 2 = Both Condyles | 0 | 0 | 0 | 0 | 0 |
| Tibial Plateau (Medial) | | | | | | |
| # of Osteophytes | 0 = 0, 1 = 1, 2 = 2, 3 = >2 | 1.50 (0.50) | 2.00 (0.41) | 1.63 (0.38) | 1.00 (0.27) | 0.06 (0.06) |
| Presence of Clefts | 0 = Absent, 1 = Unicondylar, 2 = Both Condyles | 0 | 0 | 0 | 0 | 0 |
| Surface Area Erosion | 0 = None, 1 = ≤10%, 2 = 11-25%, 3 = 26-50%, 4 = 51-75%, 5 = 76-100% | 0.25 (0.25) | 2.00 (0.71) | 2.50 (0.50) | 1.80 (0.80) | 0.82 (0.31) |
| Depth of Erosion | 0 = None, 0.5 = Barely Perceptible, 1 = Slight, 2 = Significant, 3 = Severe | 0.50 (0.50) | 1.13 (0.52) | 1.94 (0.63) | 0.40 (0.19) | 0.18 (0.06) |
| Tibial Plateau (Lateral) | | | | | | |
| # of Osteophytes | 0 = 0, 1 = 1, 2 = 2, 3 = >2 | 1.75 (0.50) | 2.25 (0.25) | 2.00 (0.35) | 1.30 (0.30) | 0 |
| Presence of Clefts | 0 = Absent, 1 = Unicondylar, 2 = Both Condyles | 0 | 0 | 0 | 0 | 0 |
| Surface Area Erosion | 0 = None, 1 = ≤10%, 2 = 11-25%, 3 = 26-50%, 4 = 51-75%, 5 = 76-100% | 2.00 (0.41) | 2.25 (0.48) | 2.50 (0.65) | 2.00 (0) | 0.24 (0.14) |
| Depth of Erosion | 0 = None, 0.5 = Barely Perceptible, 1 = Slight, 2 = Significant, 3 = Severe | 2.13 (0.59) | 0.88 (0.38) | 2.06 (0.36) | 1.90 (0.40) | 0.09 (0.05) |
| Appearance of Meniscus | 0 = Normal, 1 = Minor Fibrillations, 2 = Moderate, 3 = Marked | | | | | |
| Medial | | 1.25 (0.63) | 2.5 (0.5) | 2.25 (0.25) | 3.00 (0) | 0.25 (0.17) |
| Lateral | | 1.25 (0.75) | 1.00 (0.71) | 2.00 (0.71) | 1.60 (0.68) | 0 |
| Appearance of Patella | 0 = Normal, 1 = <25%, 2 = 25-50%, 3 = >50% | 0.50 (0.29) | 1.38 (0.24) | 1.25 (0.25) | 0.40 (0.24) | 0.42 (0.21) |

Summary:

Erosion of cartilage from the femoral condyle was the most clinically relevant parameter. The low and mid dose groups demonstrated less surface area erosion of cartilage on both the medial and lateral femoral condyles compared to the no injection group. When depth of erosion was evaluated, the inverse was noted. No clefts on the femoral condyles were observed in this study. Although surface area erosion and depth of erosion on the medial and lateral femoral condyles was scored, depth of erosion was difficult to determine at necropsy. This parameter is best assessed by histology analysis. However, the preference was to take the sample at the worst lesion, thereby skewing the histological interpretation.

Based on the clinical findings, in general, there was a dose response curve favoring the low dose group compared to the no injection group among the composite grades. This was a pilot study (n=4) and, thus, statistical analysis was not warranted nor is appropriate. No statements about disease modulation can be made from this study alone.

Example VII

ACLT Model: P38 MAP Kinase Inhibitors (JNJ 3026582 (RWJ 67657), SCIO-282 (SD 282) and JNJ 17089540 (RWJ 669307))

The ACLT model was used to evaluate the ability of pharmaceutical agents JNJ 3026582 (RWJ 67657), SCIO-282 (SD 282) and JNJ 17089540 (RWJ 669307) (p38 MAP kinase inhibitors), which were delivered directly to the knee, to reduce the incidence of osteoarthritic changes in an unstable joint. These pharmaceutical agents are also known as cytokine-suppressive anti-inflammatory drugs (CSAIDs).

The purpose of this study was to evaluate the efficacy of these CSAIDs in a pre-clinical model of osteoarthritis. The etiology of osteoarthritis includes both a biomechanical and an inflammatory component. P38 MAP kinase inhibitors have been implicated as possible therapeutic agents for clinical osteoarthritis patients, due to their ability to modulate and affect pro-inflammatory cytokines. Particularly, TNFα and IL-1β have been identified as mediators of the inflammatory component of osteoarthritis and both are modulated by p38 MAP kinase. JNJ 3026582 (RWJ 67657) and SCIO-282 (SD 282) are potent p38 MAP kinase inhibitors, developed by Johnson & Johnson and SCIOS, respectively. JNJ 17089540 (RWJ 669307) is a weaker inhibitor of the kinase activity, however, it modulates the downstream responses by high affinity binding to the unactivated form of p38 MAP kinase, thus modulating TNFα synthesis. This study used direct dispersions of each drug into ARTHREASE®, and was given over a therapeutic course (1×/week for 5 weeks) to the animals after onset of disease (six weeks post-surgery).

Preparation of Test Compounds:

Sterile formulations of the test compounds were prepared by gamma irradiating (15 kGy) them on dry ice. Stability of the compounds post-irradiation was confirmed by high performance liquid chromatography (HPLC). All formulations were prepared in an aseptic manner by dispersing the drug into ARTHREASE®. 104 mg of each drug was weighed and dispersed in 2 ml of ARTHREASE® for a 40× solution (50.2 mg/ml). The stock was further diluted by using 0.5 mL of the stock in 20 mL of ARTHREASE® for a final concentration of 133 µg/ml. The drug was delivered in a volume of 160 µL at a concentration of 5 µg/kg. The low dose was made by diluting with ARTHREASE® to the final concentration.

HPLC Method:

Samples were stored in a refrigerator at 4° C. for the stability studies. Drug content was tested in duplicates by dissolving 1 ml of formulation in 10 ml DMSO under vigorous shaking on an arm-shaker for four hours. An aliquot of the solution was further diluted ten times in DMSO and injected on HPLC against external drug standards. Peak area was integrated and concentration calculated for drug recovery. Average drug content recovery is shown in Table 7.

TABLE 7

Average drug content recovery

| | | Concentration | Average Percent Drug Recovery | |
|---|---|---|---|---|
| Drug | Dosage | µg/µL | $T_0$ | 1 month |
| JNJ 3026582 (RWJ 67657) | High | 0.13 | 98.3 (1.6) | 99.7 (0.8) |
| | Low | 0.013 | 98.7 (1.2) | 98.5 (0.8) |
| JNJ 17089540 (RWJ 669307) | High | 0.13 | 99.7 (0.6) | 101.6 (0.3) |
| | Low | 0.013 | 102.1 (0.3) | 99.8 (0.3) |
| SCIO-282 (SD 282) | High | 0.13 | 99.8 (0.6) | 100.6 (0.4) |
| | Low | 0.013 | 98.7 (0.5) | 100.6 (1.2) |

Experimental Design:

TABLE 8

Experimental Design

| Test Agent | Dose/Treatment Group | Lot # |
|---|---|---|
| JNJ 17089540 (RWJ 669307) | 133 & 13.3 ng/µl | Lot # 15382-45-1A |
| JNJ 3026582 (RWJ 76757) | 133 & 13.3 ng/µl | Lot # MR2.1.70-1 |
| SCIO-282 (SD 282) | 133 & 13.3 ng/µl | Lot/Notebook |
| ARTHREASE ® | Vehicle Control | Lot # 11840812 |
| No Injection | Surgical Control | |
| No Surgery | Non-Surgical Control (contralateral limb) | |

Ninety-six (96) rabbits underwent ACLT on the right knee (n=ten per group) according to the ACLT model. Anesthesia, analgesia, surgical preparation, surgery, intra-articular injections, and euthanasia were conducted according to the ACLT model.

The joint was removed and fixed in 10% neutral buffered formalin. Digital images were taken of individual knee joints at the completion of the study. Samples were decalcified under acidic conditions and then processed for routine histological processing. Two sets of slides were stained with Hematoxylin and Eosin or Safranin O and were scored using a Modified Mankin Histological Scoring system. The histological scoring was used to measure the depth, since this parameter is the most difficult to discern by clinical observation. Effort was taken to identify the area on the condyle with the most severe lesion so that depth could be evaluated. Therefore, this parameter is skewed to reflect the most eroded area and is not representative of the overall joint health. Data for all histological scores is not shown.

Clinical Observations:

At the time of sacrifice, the following parameters were evaluated grossly (the scale follows in parentheses):

Anterior Surface of Femur (Trochlear Groove)
# of osteophytes (0-3)
Size (diameter) of osteophytes (0-3)
Presence of trochlear groove thickening (0-1)
Erosion of cartilage (0-3)
Femoral Condyles
Erosion of cartilage (% surface area) (0-5) (both medial and lateral condyle evaluated)
Erosion of cartilage (depth) (0-3) (both medial and lateral condyle evaluated)
Presence of clefts (0-2)
Tibial Plateau (both medial and lateral condyle evaluated)
# of osteophytes (0-3)
Presence of clefts (0-1)
Erosion of cartilage (% surface area) (0-5)
Erosion of cartilage (depth) (0-3)

Each parameter was given a score. The combination of all parameters gave a Total Score. A higher score indicates more damage to the joint. The means and standard error of the means (SEM)'s for all parameters, including those discussed in detail, are listed in Tables 9-13. Individual results for each parameter assessed were tabulated. Data for the individual scores is not shown.

Total Score in Table 9:
The score for total score ranges from 0 to 52. This score is a composite of grades from all of the scoring criteria.

All Trochlear Groove Effects in Table 10:
The score for all trochlear groove effects ranges from 1 to 10.

All Cartilage Effects in Table 11:
The score for all cartilage effects ranges from 0 to 40. The grades that compose this parameter are trochlear groove thickness and erosion, all the grades in all condylar effects, and all grades listed under tibial plateau.

Condylar Effects in Table 12:
The score for all condylar effects ranges from 0 to 18. This score is a composite of grades from all criteria within this category. The grades that compose this parameter are the 5 criteria listed above under Femoral Condyles. Each individual criterion was compared independently to the control groups, in addition to the overall effects of the composites score were compared to the controls.

All Tibial Plateau Effects in Table 13:
The score for All Tibial Plateau effects ranges from 0 to 24.

Figure 19:
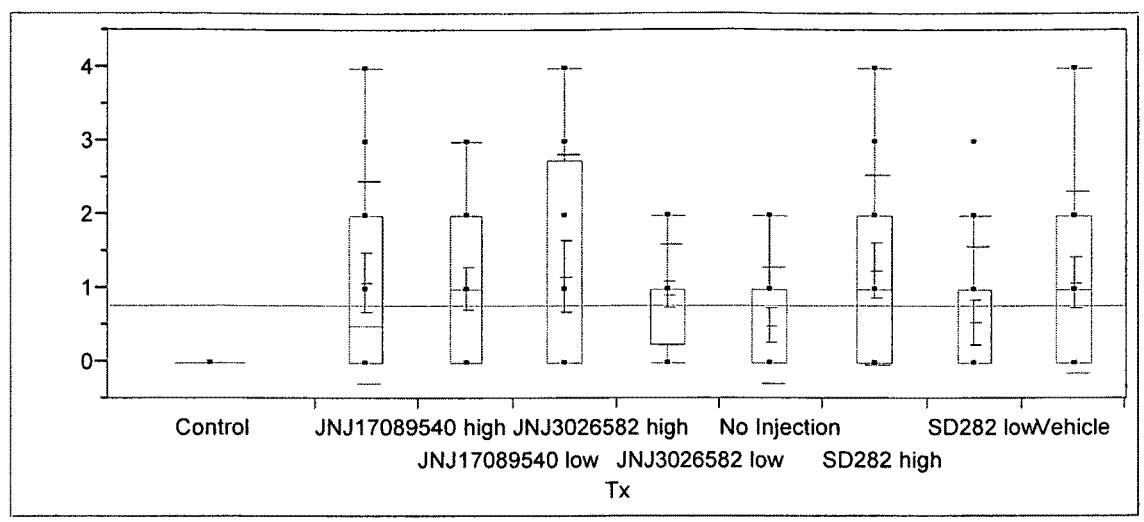
FIG. 19 depicts the depth of erosion on the medial femoral condyle for the following treatment groups: JNJ 3026582 (RWJ 67657), JNJ 17089540 (RWJ 669307), Scio-282, Vehicle, no injection, and no surgery. The Y axis represents the score for medial femoral condyle surface area erosion and the X axis represents for the following treatments: control, low and high dose for JNJ 17089540 (RWJ 669307), low and high dose for JNJ 3026582 (RWJ 67657), low and high dose for SCIO-282 (SD 282), no injection, and vehicle.

Femoral Condyle (% Surface Area Erosion):
In regard to the medial femoral condyle, none of the drug treated groups demonstrated an effect on surface erosion when compared to the no injection group (FIG. 19).

Figure 20:
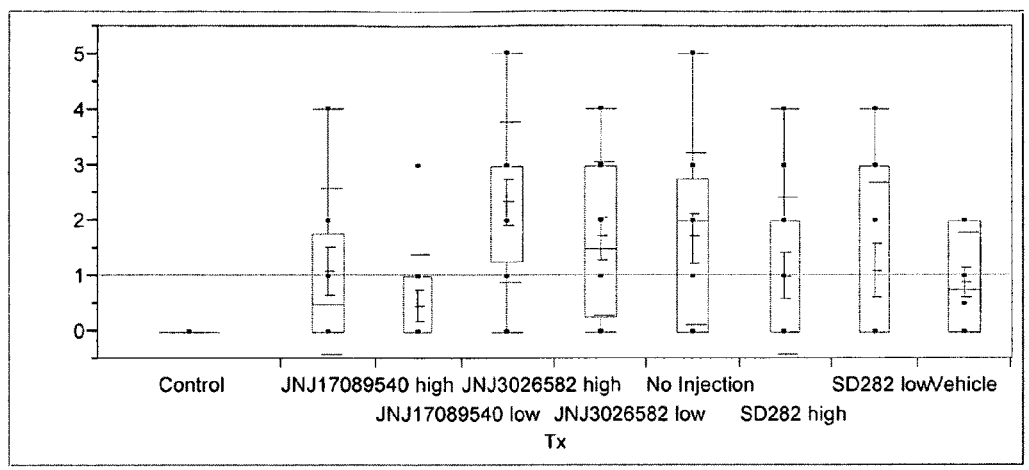
FIG. 20 depicts depicts the depth of erosion on the lateral femoral condyle for the following treatment groups: JNJ 3026582 (RWJ 67657), JNJ 17089540 (RWJ 669307), Scio-282, Vehicle, no injection, and no surgery. The Y axis represents the score for lateral femoral condyle surface area erosion and the X axis represents for the following treatments: control, low and high dose for JNJ 17089540 (RWJ 669307), low and high dose for JNJ 3026582 (RWJ 67657), low and high dose for SCIO-282 (SD 282), no injection, and vehicle.

With regard to the lateral femoral condyle, JNJ 17089540 (RWJ 669307) was efficacious in reducing the clinical score at both the high and the low dose, wherein the low dose reached a statistically significant level, and, in addition, SCIO-282 (SD 282) reduced the surface erosion, however, in a non-dose dependent manner FIG. 20. Also, JNJ 17089540 (RWJ 669307) tightened standard deviation over time when compared to the control groups. On the lateral femoral condyle, JNJ 3026582 (RWJ 67657) had no effect on surface erosion at either dose.

All Condylar Effects:
The score for All Condylar Effects ranges from 0 to 10. This score is a composite of grades from all criteria within this category. The grades that compose this parameter are the three criteria listed above under Femoral Condyles.

Figure 21:
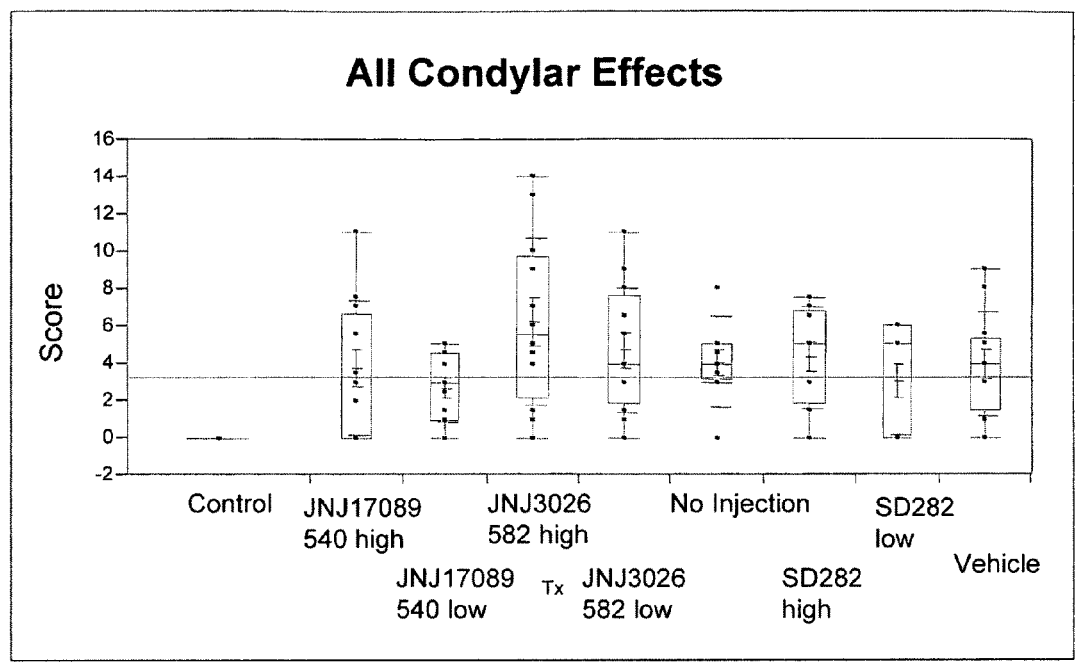
FIG. 21 depicts the score for All Condylar Effects. The Y axis represents the score for All Condylar Effects and the X axis represents for the following treatments: control, low and high dose for JNJ 17089540 (RWJ 669307), low and high dose for JNJ 3026582 (RWJ 67657), low and high dose for SCIO-282 (SD 282), no injection, and vehicle.

Both JNJ 17089540 (RWJ 669307) and SCIO-282 (SD 282) at the low dose demonstrated a decrease in overall clinical score for All Condylar Effects. JNJ 3026582 (RWJ 67657) had no effect on this clinical parameter (FIG. 21).

All Cartilage Effects:
The score for All Cartilage Effects ranges from 0 to 18. This score is a composite of grades from all criteria within this category. The grades that compose this parameter are trochlear groove thickness and erosion, all the grades in All Condylar Effects, and all grades listed under Tibial Plateau.

Figure 22:
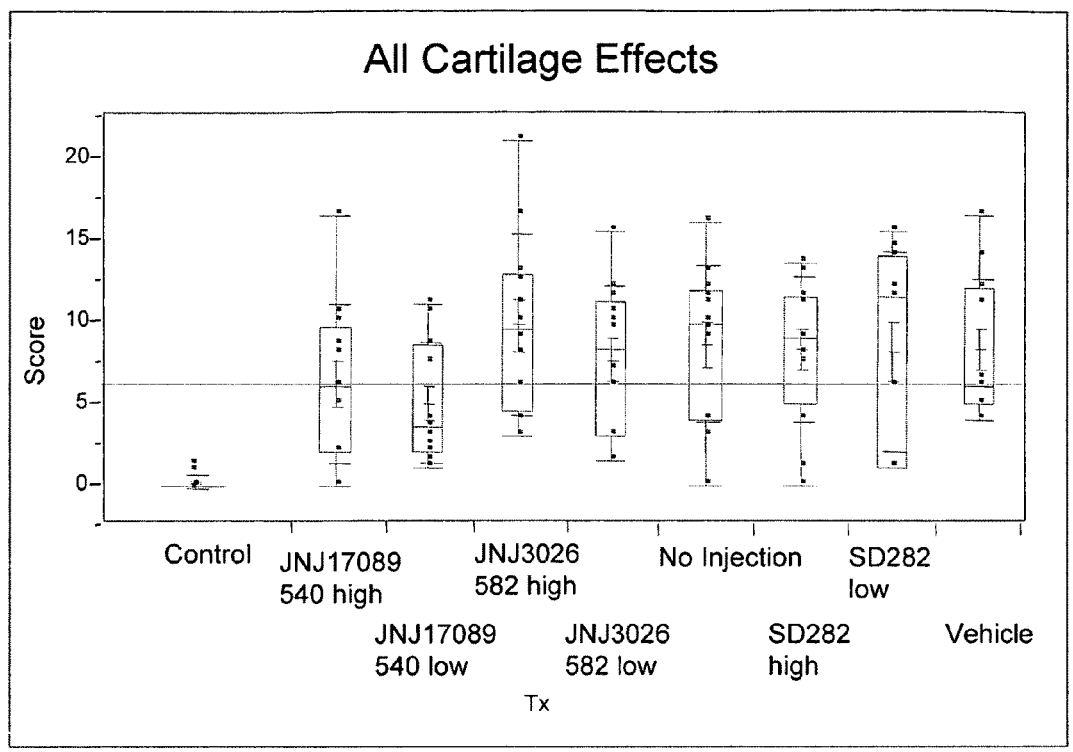
FIG. 22 depicts the score for All Cartilage Effects. The Y axis represents the score for All Cartilage Effects and the X axis represents the following treatments: control, low and high dose for JNJ 17089540 (RWJ 669307), low and high dose for JNJ 3026582 (RWJ 67657), low and high dose for SCIO-282 (SD 282), no injection, and vehicle.

JNJ 17089540 (RWJ 669307) exhibited a reduction in scores at both doses when compared to the non-injected control group. JNJ 3026582 (RWJ 67657) and SCIO-282 (SD 282) exhibited no efficacy at either concentration (FIG. 22).

Total Score:
The score for Total Score ranges from 0 to 24. This score is a composite of grades from all of the scoring criteria.

Figure 23:
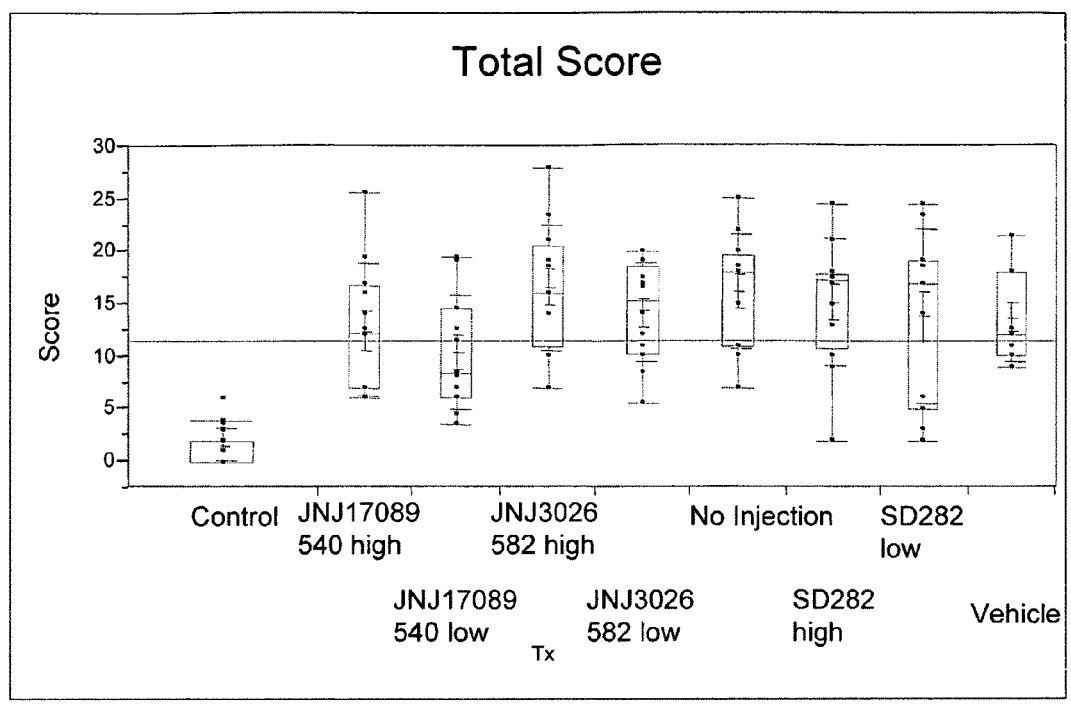
FIG. 23 depicts the Total Score, which is a composite of grades from all of the scoring criteria. The Y axis represents the Total Score and the X axis represents the following treatments: control, low and high dose for JNJ 17089540 (RWJ 669307), low and high dose for JNJ 3026582 (RWJ 67657), low and high dose for SCIO-282 (SD 282), no injection, and vehicle.
Figure 24A:
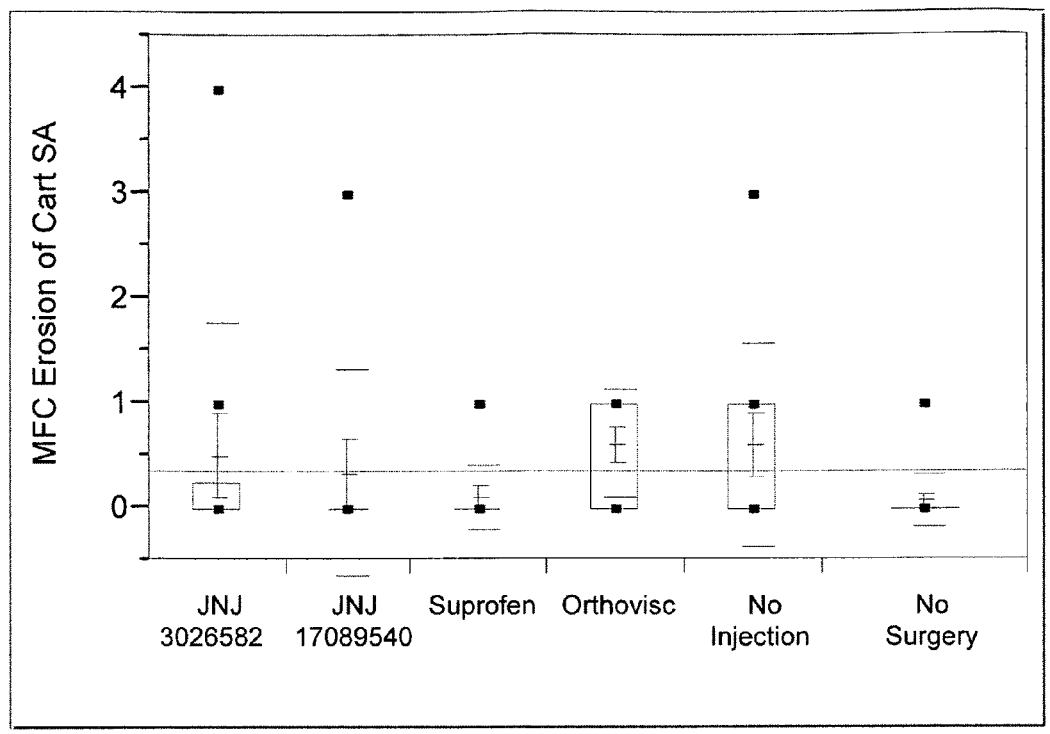
FIG. 24A depicts the percent surface area erosion on the medial femoral condyle (preventative dosing regimen) for the following treatment groups: JNJ 3026582 (RWJ 67657), JNJ 17089540 (RWJ 669307), Suprofen, ORTHOVISC®, no injection, and no surgery.
Figure 24B:
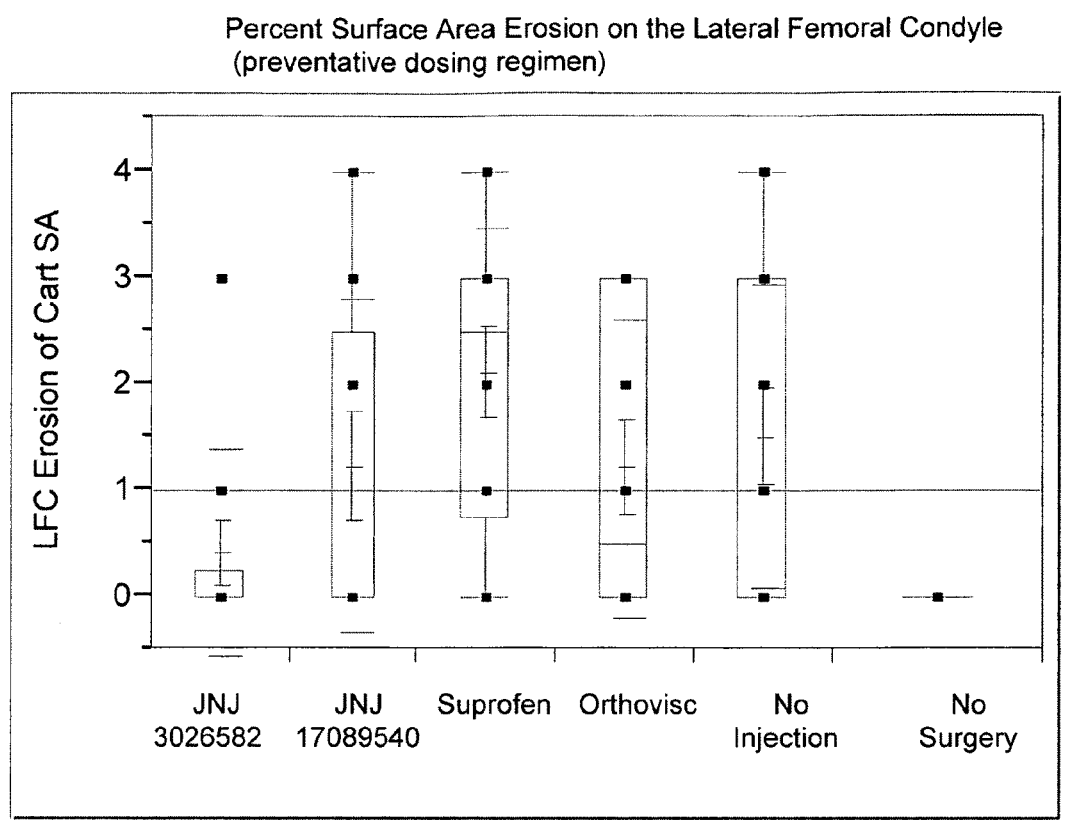
FIG. 24B depicts the percent surface area erosion on the lateral femoral condyle (preventative dosing regimen) for the following treatment groups: JNJ 3026582 (RWJ 67657), JNJ 17089540 (RWJ 669307), Suprofen, ORTHOVISC®, no injection, and no surgery.
Figure 24C:
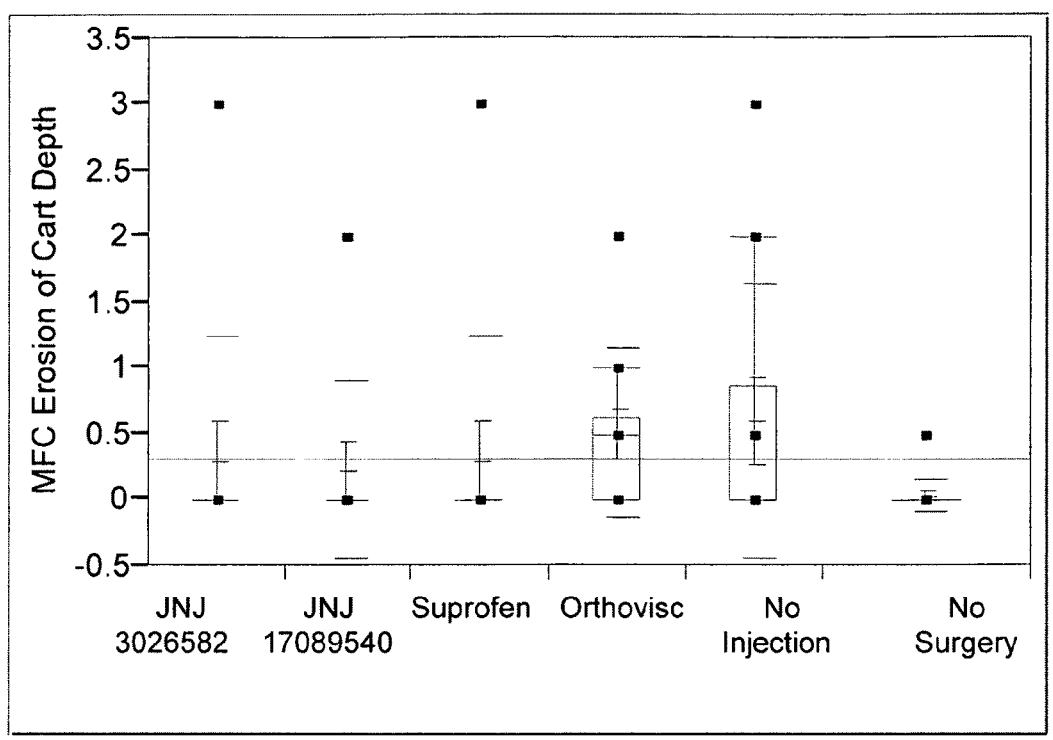
FIG. 24C depicts the depth of erosion on the medial femoral condyle (preventative dosing regimen) for the following treatment groups: JNJ 3026582 (RWJ 67657), JNJ 17089540 (RWJ 669307), Suprofen, ORTHOVISC®, no injection, and no surgery.
Figure 24D:
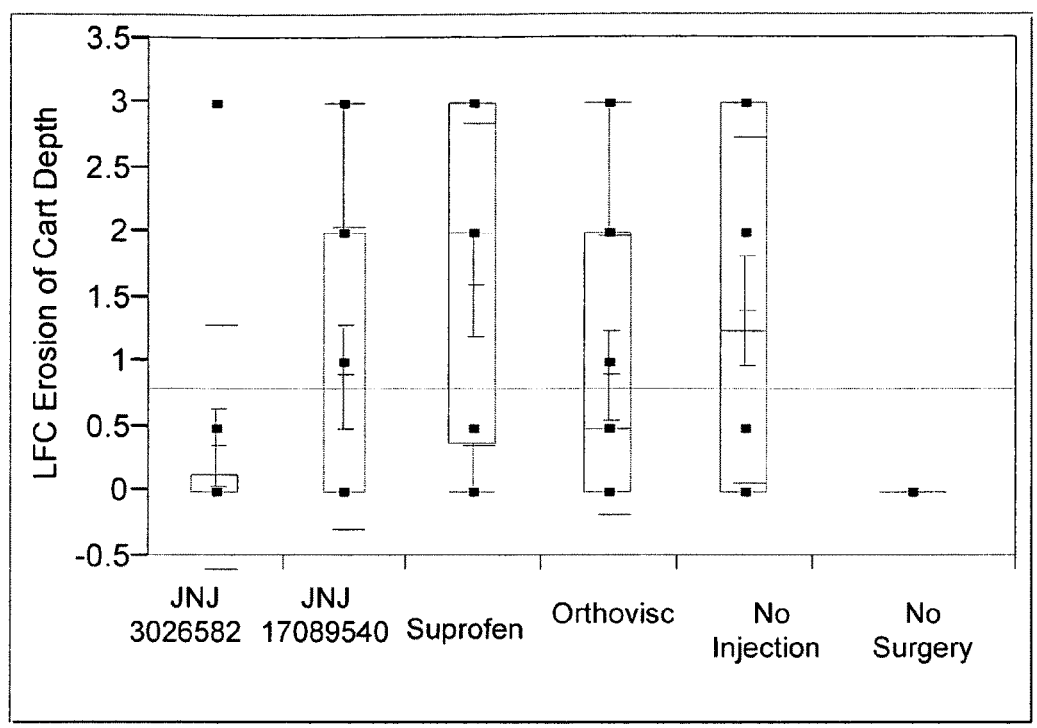
FIG. 24D depicts the depth of erosion of the lateral femoral condyle (preventative dosing regimen) for the following treatment groups: JNJ 3026582 (RWJ 67657), JNJ 17089540 (RWJ 669307), Suprofen, ORTHOVISC®, no injection, and no surgery.
Figure 24E:
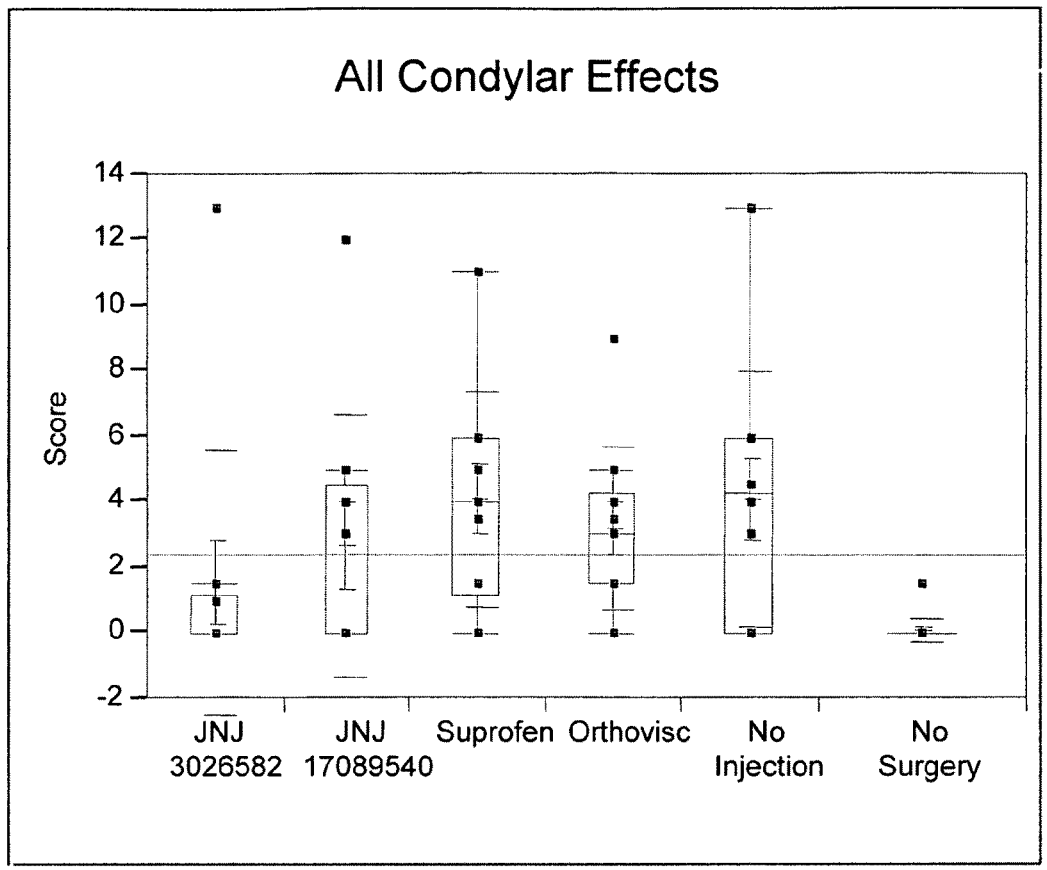
FIG. 24E depicts the All Condylar Effects (preventative dosing regimen) for the following treatment groups: JNJ 3026582 (RWJ 67657), JNJ 17089540 (RWJ 669307), Suprofen, ORTHOVISC®, no injection, and no surgery.

The data for JNJ 17089540 (RWJ 669307) trended downward for both doses, with the low dose have the greatest overall effect. Neither JNJ 3026582 (RWJ 67657) nor SCIO-282 (SD 282) had an effect on the clinical score when viewing all of the parameters in totality (FIG. 23).

TABLE 9

Clinical Scoring - Total Score

| Treatment | Mean | SEM |
|---|---|---|
| JNJ 3026582 (RWJ 67657): high dose | 16.58 | 1.73 |
| JNJ 3026582 (RWJ 67657): low dose | 14.17 | 1.36 |
| JNJ 17089540 (RWJ 669307): high dose | 12.46 | 1.8 |
| JNJ 17089540 (RWJ 669307): low dose | 10.41 | 1.66 |
| SCIO-282 (SD 282): high dose | 15.17 | 1.72 |
| SCIO-282 (SD 282): low dose | 13.77 | 2.5 |
| No injection | 16.17 | 1.56 |
| Vehicle | 13.73 | 1.3 |
| No surgery | 1.6 | 0.31 |

TABLE 10

Clinical Scoring - Trochlear Groove Effects

| Treatment | Mean | SEM |
|---|---|---|
| JNJ 3026582 (RWJ 67657): high dose | 7.92 | 0.42 |
| JNJ 3026582 (RWJ 67657): low dose | 7.75 | 0.52 |
| JNJ 17089540 (RWJ 669307): high dose | 6.25 | 0.55 |
| JNJ 17089540 (RWJ 669307): low dose | 5.55 | 0.71 |
| SCIO-282 (SD 282): high dose | 7.08 | 0.56 |
| SCIO-282 (SD 282): low dose | 6.09 | 0.78 |
| No injection | 7.08 | 0.45 |
| Vehicle | 6.67 | 0.51 |
| No surgery | 1.63 | 0.29 |

TABLE 11

Clinical Scoring - All Tibial Plateau Effects

| Treatment | Mean | SEM |
|---|---|---|
| JNJ 3026582 (RWJ 67657): high dose | 2.25 | 0.29 |
| JNJ 3026582 (RWJ 67657): low dose | 1.63 | 0.57 |

TABLE 11-continued

Clinical Scoring - All Tibial Plateau Effects

| Treatment | Mean | SEM |
|---|---|---|
| JNJ 17089540 (RWJ 669307): high dose | 2.38 | 0.43 |
| JNJ 17089540 (RWJ 669307): low dose | 1.95 | 0.69 |
| SCIO-282 (SD 282): high dose | 3.92 | 0.76 |
| SCIO-282 (SD 282): low dose | 4.68 | 1.08 |
| No injection | 5 | 0.75 |
| Vehicle | 2.41 | 0.78 |
| No surgery | 0.15 | 0.08 |

TABLE 12

Clinical Scoring - All Cartilage Effects

| Treatment | Mean | SEM |
|---|---|---|
| JNJ 3026582 (RWJ 67657): high dose | 9.75 | 1.59 |
| JNJ 3026582 (RWJ 67657): low dose | 7.58 | 1.33 |
| JNJ 17089540 (RWJ 669307): high dose | 6.21 | 1.41 |
| JNJ 17089540 (RWJ 669307): low dose | 5 | 1.11 |
| SCIO-282 (SD 282): high dose | 8.25 | 1.29 |
| SCIO-282 (SD 282): low dose | 8.14 | 1.86 |
| No injection | 8.58 | 1.38 |
| Vehicle | 8.27 | 1.3 |
| No surgery | 0.19 | 0.09 |

TABLE 13

Clinical Scoring - All Condylar Effects

| Treatment | Mean | SEM |
|---|---|---|
| JNJ 3026582 (RWJ 67657): high dose | 6.25 | 1.31 |
| JNJ 3026582 (RWJ 67657): low dose | 4.71 | 0.98 |
| JNJ 17089540 (RWJ 669307): high dose | 3.75 | 1.04 |
| JNJ 17089540 (RWJ 669307): low dose | 2.68 | 0.56 |
| SCIO-282 (SD 282): high dose | 4.33 | 0.8 |
| SCIO-282 (SD 282): low dose | 3.09 | 0.9 |
| No injection | 4.08 | 0.71 |
| Vehicle | 3.96 | 0.81 |
| No surgery | 0 | 0 |

Summary:

The TNF modulator, JNJ 17089540 (RWJ 669307) was efficacious in reducing the clinical scores across multiple endpoints, particularly at the low dose. However, based on the current data, JNJ 3026582 (RWJ 67657) had little to no efficacy in the study, at both the low and high doses across most clinical parameters. Likewise, SCIO-282 (SD 282), similar to JNJ 3026582 (RWJ 67657), had minimal efficacy on the clinical scores when compared to the non-treatment surgical group at both 0.5 and 5.0 µg/kg. Typically, three concentrations rather than two are tested for such a dose ranging study.

Of particular note when comparing these three p38 MAP kinase inhibitors is their solubility in aqueous solution. These drugs differ considerably in their solubility and these differences in solubility (and bioavailability) may strongly influence their performance. When delivering drugs via intrarticular injection there is limited volume of synovial fluid in which to solubilize the drug. Although no PK analysis was performed for this study, since Scios 282 has limited solubility, it is believed that it may have similar issues attributed to solubility as those attributed to JNJ 3026582 (RWJ 67657).

Example VIII

ACLT Model: P38 MAP Kinase Inhibitor

In another pilot study, the ACLT model was used to evaluate the ability of a pharmaceutical agent SCIO-469 (SD 469) (a p38 MAP kinase inhibitor), delivered directly to the knee, to reduce the incidence of osteoarthritic changes in an unstable joint.

Preparation of Test Compound:

SCIO-469 (SD 469) was gamma irradiated (15 kgy) on dry ice. The formulations were prepared in an aseptic manner by dispersing the drug into ORTHOVISC® at three concentrations of 1000 µg/mL, 100 µg/mL and 10 µg/mL. The formulation of the highest concentration was diluted into the lower concentrations using ORTHOVISC®. Once prepared, the formulations were stored at 4° C.

Experimental Design:

TABLE 14

Experimental Design

| Test agent | Dose/Treatment Group | Lot # |
|---|---|---|
| SCIO-469 (SD 469) | 50 µg/kg | Lot # NPC031469: 13 |
| SCIO-469 (SD 469) | 5 µg/kg | Lot # NPC031469: 13 |
| SCIO-469 (SD 469) | 0.5 µg/kg | Lot # NPC031469: 13 |
| Sham Injection | Surgical Control | |
| ORTHOVISC ® | 3 injections of 160 µl | Lot # NO40326 |

The study design consisted of an n=12 per group. The SCIO-469 (SD 469) was suspended in ORTHOVISC®. A total of 160 µl was injected at each administration.

Anesthesia, analgesia, surgical preparation and statistical analysis were performed according to the ACLT model.

The surgery was performed according to the ACLT model. However, a thin probe was passed between the ACL and the posterior cruciate ligament and drawn slowly forward to ensure that there were no uncut ligamental fibers. The patella was returned to the normal anatomic position. The wound was closed in layers.

The intra-articular injections were performed according to the ACLT model. However, control groups either received no injections or received the ORTHOVISC® vehicle delivered once weekly for three weeks.

Euthanasia was performed according to the ACLT model. However, the animals were euthanized nine weeks post ACLT with an intravenous injection of pentobarbital (60 mg/kg). After gross evaluation, eight of the twelve joints per treatment were fixed in 10% neutral buffered formalin.

For each treatment group, four animals were included to provide pharmacokinetic data (available drug levels in blood and tissue). Prior to treatment administration, blood samples were collected and frozen for analysis. After gross observation, the joints were removed and frozen for analysis.

SCIO-469 (SD 469) was dissolved prior to complete analysis being complete. Data on the drug content in the joints was collected (data not shown).

Immediately following euthanasia, gross observations of the knee joints were made and any abnormality was recorded. The joints were analyzed for disease state in the trochlear groove, the femoral condyles and the tibial plateau.

Clinical Observations:

At the time of sacrifice the following parameters were evaluated grossly (the scale follows in parenthesis):

Anterior Surface of Femur (Trochlear Groove)
# of osteophytes (0-3)
Size (diameter) of osteophytes ((0-3)
Presence of trochlear groove thickening (0-1)
Erosion of cartilage (0-3)
Femoral Condyles
Erosion of cartilage (% surface area) (0-5) (both medial and lateral condyle evaluated)
Erosion of cartilage (depth) (0-3) (both medial and lateral condyle evaluated)
Presence of clefts (0-2)
Tibial Plateau (both medial and lateral condyle evaluated)
# of osteophytes (0-3)
Presence of clefts (0-2)
Erosion of cartilage (% surface area) (0-5)
Erosion of cartilage (depth) (0-3)

Each parameter was given a score. The combination of all parameters gave a Total Score (0-52). Additionally, combinations of the three subsets of data yielded All Trochlear Groove Effects (0-10), All Condylar Effects (0-18) and All Tibial Plateau Effects (0-24). Lastly, an All Cartilage Effects Score was obtained. The score for All Cartilage Effects ranges from 0 to 40. The grades that compose this parameter are trochlear groove thickness and erosion, all the grades in All Condylar Effects, and all grades listed under tibial plateau. A higher score indicates more damage to the joint. A lower score indicates less damage or more cartilage preservation to the joint. Individual results for each parameter assessed were tabulated (data not shown).

The values obtained for the drug content of the joint were also determined (data not shown).

Table 15 lists the averages and SEM's of all parameters evaluated.

TABLE 15

Mean and SEM of all Parameters

| Parameter | Scale Description | SCIO-469 (SD 469) 50 µg/kg | SCIO-469 (SD 469) 5 µg/kg | SCIO-469 (SD 469) 0.5 µg/kg | ORTHOVISC ® | Sham Injection | No Surgery |
|---|---|---|---|---|---|---|---|
| Trochlear Groove | | | | | | | |
| # of Osteophytes | 0 = 0; 1 = 1; 2 = 2; 3 ≥ 2 | 2.64 (0.24) | 2.83 (0.17) | 3.00 (0) | 2.73 (0.19) | 3.00 (0) | 0.47 (0.17) |
| Osteophyte Size | 0 = 0; 1 = ≤1 mm; 2 = 1-2 mm; 3 = >2 mm | 2.91 (0.09) | 2.92 (0.08) | 3.00 (0) | 2.82 (0.18) | 3.00 (0) | 0.40 (0.13) |
| Thickening | 0 = Normal 1 = Thickened Areas | 0 (0) | 0.17 (0.11) | 0 (0) | 0.09 (0.09) | 0.08 (0.08) | 0.07 (0.07) |
| Erosion of Cartilage | 0 = 0; 1 = <25%; 2 = 25-50%; 3 = >50% | 1.36 (0.39) | 2.17 (0.32) | 2.40 (0.31) | 1.18 (0.30) | 2.17 (0.24) | 0 (0) |
| Femoral Condyle | | | | | | | |
| % Surface Area Erosion (Medial) | 0 = None; 1 ≤ 10% 1 2 = 11-25%; 3 = 26-50%; 4 = 51-75%; 5 = 76-100% | 1.27 (0.33) | 1.67 (0.43) | 0.90 (0.31) | 0.27 (0.14) | 0.83 (0.39) | 0 (0) |
| % Surface Area Erosion (Lateral) | 0 = None; 1 ≤ 10% 1 2 = 11-25%; 3 = 26-50%; 4 = 51-75%; 5 = 76-100% | 1.18 (0.46) | 1.67 (0.36) | 2.80 (0.36) | 0.73 (0.30) | 1.17 (0.46) | 0 (0) |
| Depth of Erosion (Medial) | 0 = no damage; 0.5 = barely perceptible; 1 = slight; 2 = significant; 3 = severe | 0.68 (0.22) | 1.21 (0.35) | 0.55 (0.22) | 0.27 (0.18) | 0.79 (0.32) | 0 (0) |
| Depth of Erosion (Lateral) | 0 = no damage; 0.5 = barely perceptible; 1 = slight; 2 = significant; 3 = severe | 1.05 (0.42) | 1.96 (0.40) | 2.00 (0.32) | 0.68 (0.35) | 0.79 (0.34) | 0 (0) |
| Presence of Clefts | 0 = absent; 1 = unicondylar; | 0 (0) | 0 (0) | 0.20 (0.13) | 0 (0) | 0.08 (0.08) | 0 (0) |

TABLE 15-continued

Mean and SEM of all Parameters

| Parameter | Scale Description | SCIO-469 (SD 469) 50 µg/kg | SCIO-469 (SD 469) 5 µg/kg | SCIO-469 (SD 469) 0.5 µg/kg | ORTHOVISC ® | Sham Injection | No Surgery |
|---|---|---|---|---|---|---|---|
| | 2 = both condyles | | | | | | |
| Tibial Plateau | | | | | | | |
| # of Osteophytes (Medial) | 0 = 0; 1 = 1; 2 = 2; 3 ≥ 2 | 1.73 (0.14) | 1.67 (0.14) | 1.80 (0.13) | 1.64 (0.20) | 1.33 (0.22) | 0.13 (0.09) |
| Presence of Clefts (Medial) | 0 = Absent; 1 = Present | 0 (0) | 0 (0) | 0 (0) | 0.09 (0.09) | 0 (0) | 0 (0) |
| % Surface Area Erosion (Medial) | 0 = None; 1 ≤ 10% 1 2 = 11-25%; 3 = 26-50%; 4 = 51-75%; 5 = 76-100% | 0.36 (0.15) | 0.58 (0.23) | 0 (0) | 0.45 (0.28) | 0.25 (0.13) | 0.20 (0.11) |
| Depth of Erosion (Medial) | 0 = no damage; 0.5 = barely perceptible; 1 = slight; 2 = significant; 3 = severe | 0.18 (0.08) | 0.63 (0.28) | 0 (0) | 0.18 (0.10) | 0.25 (0.17) | 0.13 (0.08) |
| # of Osteophytes (Lateral) | 0 = 0; 1 = 1; 2 = 2; 3 ≥ 2 | 0.91 (0.25) | 1.08 (0.19) | 1.50 (0.17) | 0.95 (0.20) | 0.58 (0.19) | 0.20 (0.11) |
| Presence of Clefts (Lateral) | 0 = Absent; 1 = Present | 0 (0) | 0 (0) | 0 (0) | 0 (0) | 0.08 (0.08) | 0 (0) |
| % Surface Area Erosion (Lateral) | 0 = None; 1 ≤ 10% 1 2 = 11-25%; 3 = 26-50%; 4 = 51-75%; 5 = 76-100% | 1.09 (0.39) | 1.50 (0.38) | 2.00 (0.45) | 0.91 (0.31) | 0.83 (0.32) | 0.47 (0.17) |
| Depth of Erosion (Lateral) | 0 = no damage; 0.5 = barely perceptible; 1 = slight; 2 = significant; 3 = severe | 1.14 (0.45) | 1.63 (0.40) | 1.90 (0.41) | 0.82 (0.35) | 0.54 (0.23) | 0.20 (0.07) |
| Combination Scores | | | | | | | |
| Total Score | 0-52 52 = max damage | 16.50 (2.59) | 21.67 (2.59) | 22.05 (1.54) | 13.82 (1.98) | 15.80 (2.04) | 2.27 (0.32) |
| All Trochlear Groove Effects | 0-10 10 = max damage | 6.91 (0.61) | 8.08 (0.51) | 8.40 (0.31) | 6.82 (0.62) | 8.25 (0.28) | 0.93 (0.28) |
| All Condylar Effects | 0-18 18 = max damage | 4.18 (1.21) | 6.50 (1.34) | 6.45 (0.80) | 1.95 (0.70) | 3.67 (1.28) | 0 (0) |
| All Tibial Plateau Effects | 0-24 24 = max damage | 5.41 (1.08) | 7.08 (0.94) | 7.20 (0.85) | 5.05 (1.10) | 3.88 (0.82) | 1.33 (0.28) |
| All Cartilage Effects | 0-40 40 = max damage | 8.32 (2.19) | 13.17 (2.38) | 12.75 (1.61) | 5.68 (1.59) | 7.88 (2.01) | 1.07 (0.29) |

Summary:

The appearance of osteoarthritis in this model can be seen at six weeks, and is characterized by erosion of cartilage on the trochlear groove and mild to serious cartilage erosion on the femoral condyle with damage visible on the tibial plateau. Although osteophyte formation is a hallmark to human osteoarthritis, rabbits readily form osteophytes from very minor manipulation. Scores from different subsets of data are combined into composite grades to gain insight into additional areas of efficacy (All Condylar Effects).

This is a very aggressive and severe model of osteoarthritis. Therefore, it is typically not the goal of these pilot studies to obtain statistical significance between the groups, but, rather, trends in improvement of the individual or composite scores are sought to identify therapies with clinical potential of offering chondroprotection.

The observations in this study did not demonstrate the utility of SCIO-469 (SD 469) at 0.5, 5 or 50 µg/kg, delivered via direct injection into a diseased joint. The most likely reason for this was due to the lack of a therapeutic amount of drug in the joint.

An analysis of the drug content in the joints, including calculated concentration (ng/ml) & calculated concentration (nM), showed that no drug could be detected in the joint at the time of analysis (data not shown). Thus, although the gross observations in this study did not demonstrate the utility of SCIO-469 at 0.5, 5 or 50 µg/kg, delivered via direct injection into a diseased joint, to offer possible disease modifying benefits by preserving cartilage in the joint space, the inventors believe that this p38 MAP kinase inhibitor would be efficacious.

Example IX

ACLT Model: P38 MAP Kinase Inhibitors (JNJ 17089540 (RWJ 669307) and JNJ 3026582 (RWJ 67657) and an NSAID (Suprofen)

The ACLT model was used to evaluate the ability of pharmaceutical agents, JNJ 17089540 (RWJ 669307) and JNJ 3026582 (RWJ 67657) (p38 MAP kinase inhibitors), delivered directly to the knee, to reduce the incidence of osteoarthritic changes in an unstable joint.

The purpose of this study was to evaluate the ability of a p38 MAP kinase inhibitor (JNJ 3026582 (RWJ 67657) and JNJ 17089540 (RWJ 669307)) or an NSAID (Suprofen) delivered in an HA (hyaluronic acid) solution administered directly to the knee to reduce effects of the osteoarthritic changes that occur and to prevent additional deterioration of the joint. The dosing schedule of these compounds was either as a preventative or a therapeutic regimen. Additionally, an evaluation of a microparticle carrier for sustained drug release was conducted.

The therapeutic and preventative models were chosen based upon recommendations from leading osteoarthritis experts. Previously, the therapeutic model was chosen because the model best represented the clinical endpoint targeted by the team. Since osteoarthritic pain is a subjective measure dependent on patient tolerance of pain, the desire was to mimic clinical symptoms upon presentation to a clinician. Therefore the preferred model to evaluate a chondroprotective effect was one which demonstrated significant lesions in the joint. With the success of earlier studies using the therapeutic mode, this study explored the use of p38 MAP kinase inhibitors or Suprofen delivered in a model which was less severe, the preventative model.

The gross observations in this study demonstrate the utility of JNJ 17089540 (RWJ 669307) or microparticles alone delivered via direct injection into a diseased joint to offer disease modifying benefits by preserving cartilage in the joint space. Additionally, this study demonstrated that microparticles could be used to deliver a therapeutic agent to the joint. Also, microparticles alone showed some chondroprotective effects. This treatment may be useful as a therapy either alone or in conjunction with drug.

Figure 26:
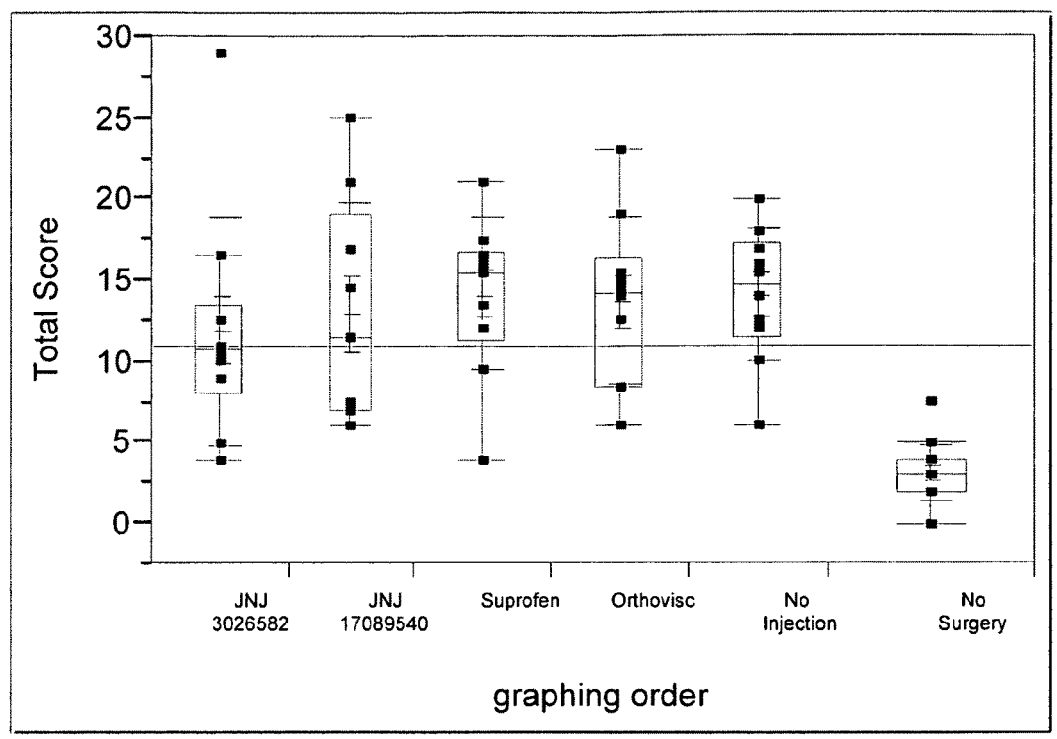
FIG. 26 depicts the Total Score (preventative dosing regimen) for the following treatment groups: JNJ 3026582 (RWJ 67657), JNJ 17089540 (RWJ 669307), Suprofen, ORTHOVISC®, Microparticle (control, 1× and 5×), no injection, and no surgery.
Figure 27A:
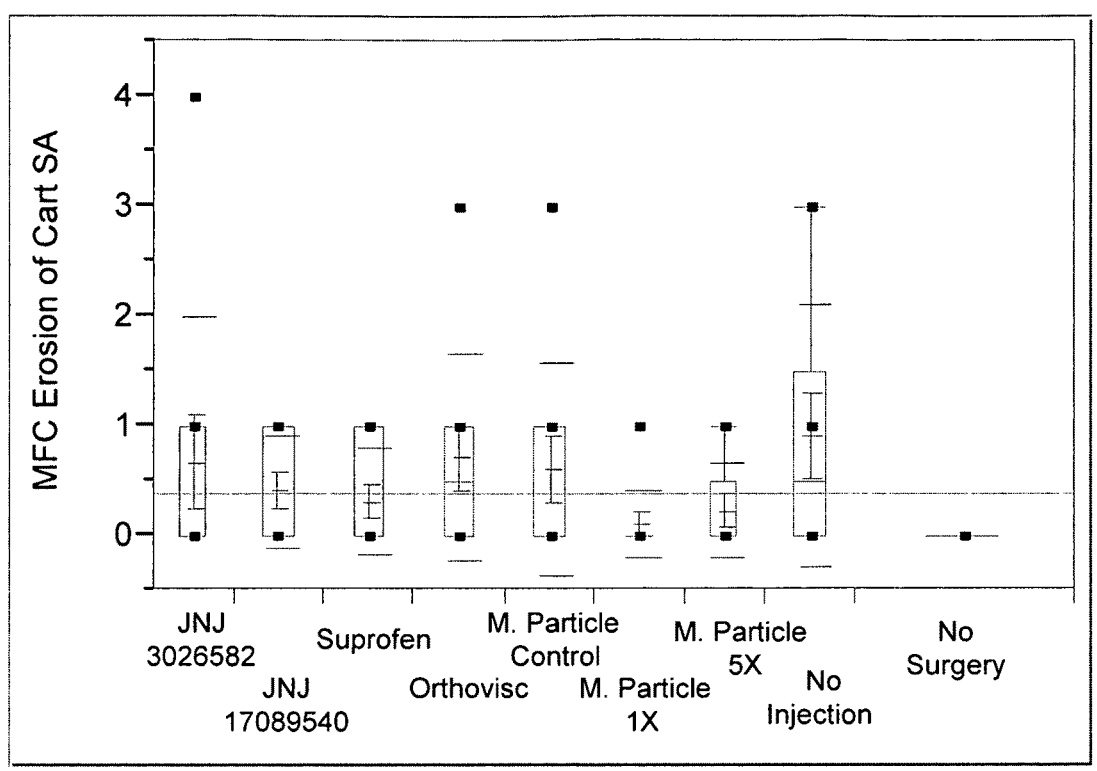
FIG. 27A depicts the percent surface area erosion on the medial femoral condyle (therapeutic dosing regimen) for the following treatment groups: JNJ 3026582 (RWJ 67657), JNJ 17089540 (RWJ 669307), Suprofen, ORTHOVISC®, Microparticle (control, 1× and 5×), no injection, and no surgery.
Figure 27B:
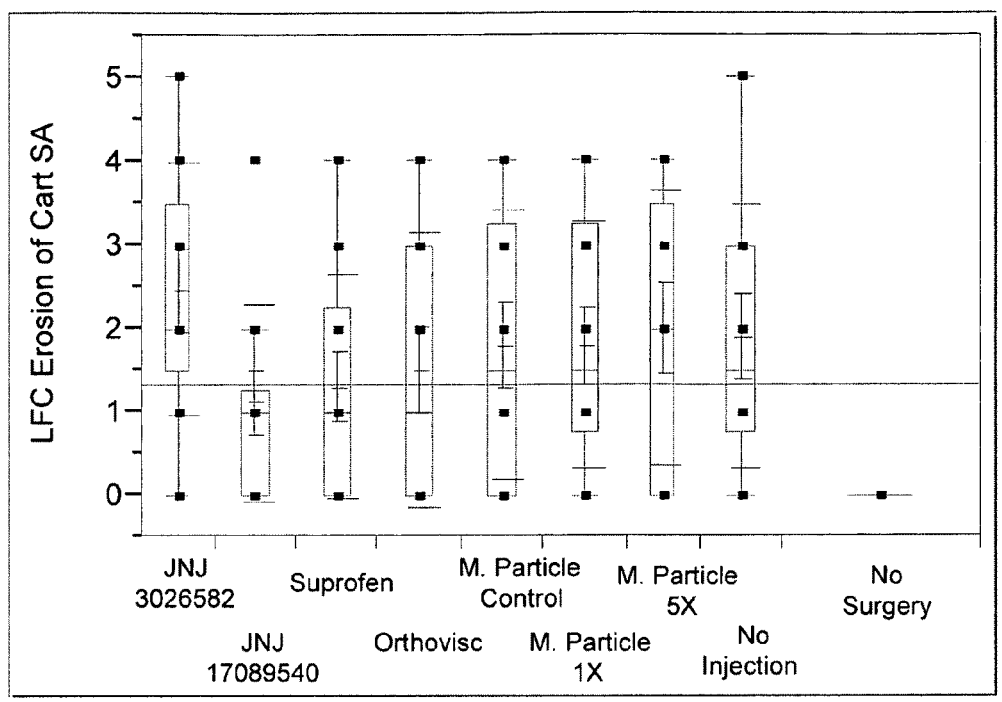
FIG. 27B depicts the percent surface area erosion on the lateral femoral condyle (therapeutic dosing regimen) for the following treatment groups: JNJ 3026582 (RWJ 67657), JNJ 17089540 (RWJ 669307), Suprofen, ORTHOVISC®, Microparticle (control, 1× and 5×), no injection, and no surgery.
Figure 27C:
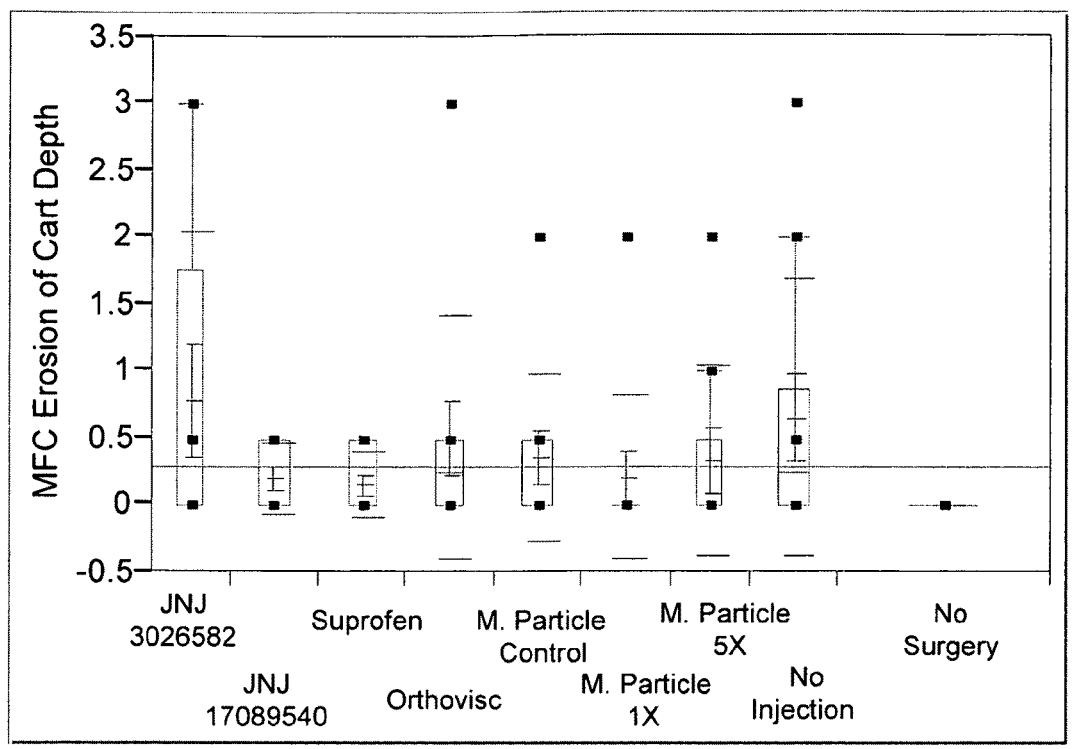
FIG. 27C depicts the depth of erosion on the medial femoral condyle (therapeutic dosing regimen) for the following treatment groups: JNJ 3026582 (RWJ 67657), JNJ 17089540 (RWJ 669307), Suprofen, ORTHOVISC®, Microparticle (control, 1× and 5×), no injection, and no surgery.
Figure 27D:
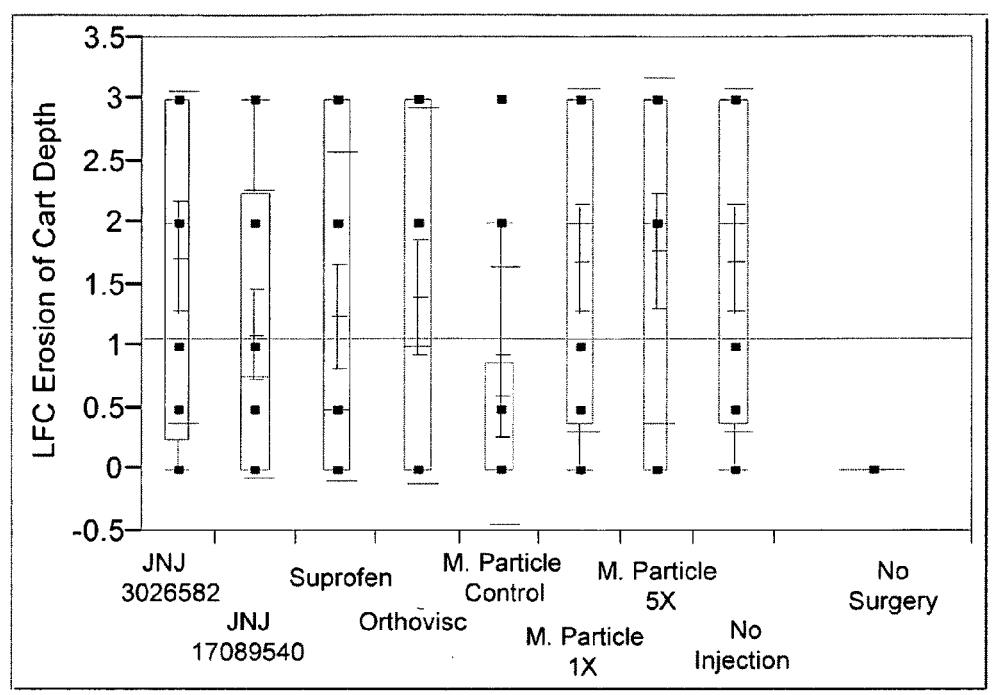
FIG. 27D depicts the depth of erosion of the lateral femoral condyle (therapeutic dosing regimen) for the following treatment groups: JNJ 3026582 (RWJ 67657), JNJ 17089540 (RWJ 669307), Suprofen, ORTHOVISC®, Microparticle (control, 1× and 5×), no injection, and no surgery.
Figure 27E:
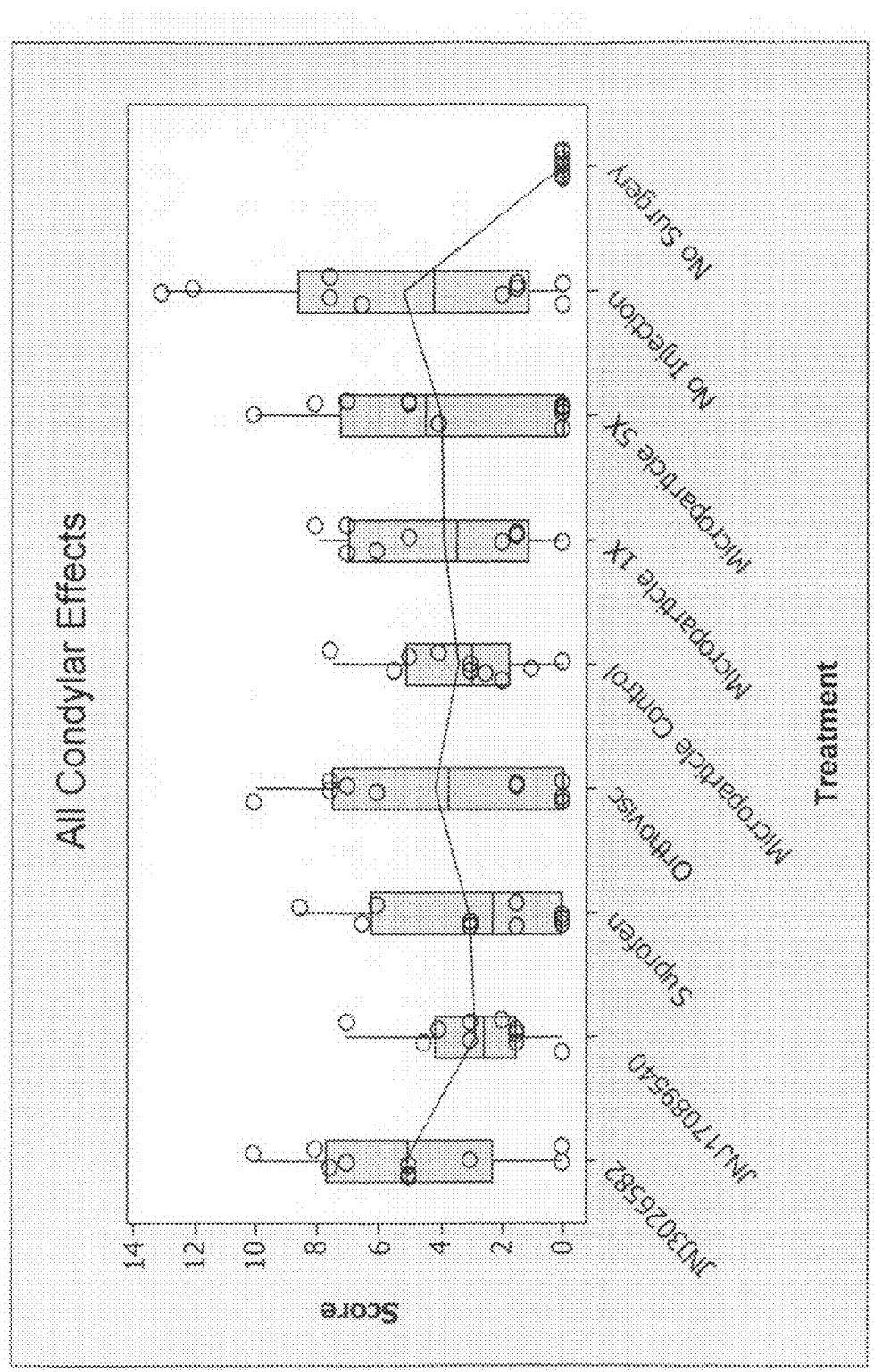
FIG. 27E depicts the All Condylar Effects (therapeutic dosing regimen) for the following treatment groups: JNJ 3026582 (RWJ 67657), JNJ 17089540 (RWJ 669307), Suprofen, ORTHOVISC®, Microparticle (control, 1× and 5×), no injection, and no surgery.

The results for total score for the preventative dosing regimen for JNJ 3026582 (RWJ 67657) are shown in FIG. 26. They show the potential utility of this compound for chondroprotection.

Preparation of Test Compounds:

JNJ 3026582 (RWJ 67657) was gamma irradiated on dry ice at a dose of 15 kgray. Then the sterile drug was aseptically mixed with ORTHOVISC® in the concentrations of 10 µg/mL and 100 µg/mL. Drug content uniformity was confirmed by reverse phase HPLC. There was approximately 100% drug stability.

JNJ 17089540 (RWJ 669307) was gamma irradiated on dry ice at a dose of 15 kgray. The sterile drug as aseptically mixed with ORTHOVISC® in the concentrations of 1 ug/uL and 10 ug/uL. Drug content uniformity was confirmed by reverse phase HPLC. There was approximately 100% drug stability.

Suprofen was gamma irradiated on dry ice at dose of 15 kgray. The sterile drug was aseptically mixed with ORTHOVISC® in the concentration of 1.3 ug/uL. Drug content uniformity at time of preparation and stability of 4 months at 4° C. was confirmed by reverse phase HPLC that there was around 100% drug stability.

Microparticle Preparations:

Polymer microparticles (Mean Size=35.1 micron; Inherent Viscosity (I.V.)=0.61 deciliters/gram in chloroform at 25° C.) were made using the emulsion/solvent evaporation procedure. Five grams of polymer were added to 125 grams of methylene chloride and mixed for 30 minutes. The polymer solution was added to 185 grams of Dow Corning Medical Fluid with a viscosity of 350 centistokes and agitated for approximately three minutes to form an emulsion. The emulsion was agitated for an additional three minutes, then transferred into 2500 grams of cyclomethicone and mixed for approximately one hour. Microspheres were then collected on a stainless steel screen and dried under vacuum with gradually elevated temperature. Microparticles were gamma irradiated on dry ice at 15 kgray.

Experimental Design:

130 Female New Zealand white rabbits underwent ACLT on the right knee. Intra-articular injections were administered to the operated knee once per week for five weeks beginning either one or six weeks after the ACLT. All animals were euthanized one week after the administration of the fifth injection. Gross observations were made on the knee joints according to a predetermined grading scale. The stifle joints were removed. Samples were preserved in 10% neutral buffered formalin. The stifle joints were photographed using high-resolution photography.

Preventative Dosing Regimen:

The ACLT was performed according to the ACLT model discussed above. Animals were group housed in pens on the floor and left untreated for one week to allow healing of the surgical site. Then, once weekly for five weeks, intra-articular injections were administered. One week following the last injection, the animals were sacrificed. The total in-life portion of the preventative dosing regimen was six weeks post-ACLT. Previous studies have confirmed that the six week time-point allows sufficient degeneration changes to occur. Thus, it was presumed that this dosing regimen would demonstrate prevention of osteoarthritic changes.

Therapeutic Dosing Regimen:

The ACLT was performed according to the ACLT model discussed above. Animals were group housed in pens on the floor and left untreated for six weeks to allow osteoarthritis to develop. Then, once weekly for five weeks, intra-articular injections were administered. One week following the last injection, the animals were sacrificed. The total in-life portion of this regimen was eleven weeks post-ACLT.

The preventative and therapeutic treatment groups are presented in Table 16 and Table 17.

TABLE 16

Preventative Dosing Regimen

| Compound | Dose | Lot # |
|---|---|---|
| JNJ 3026582 (RWJ 67657) | 0.5 µg/kg | 3418-60A |

TABLE 16-continued

Preventative Dosing Regimen

| Compound | Dose | Lot # |
|---|---|---|
| JNJ 17089540 (RWJ 669307) | 0.5 µg/kg | 3418-60B |
| Suprofen | 1.3 µg/µl | NSAID |
| ORTHOVISC ® | Vehicle | No 40326 |
| No Injection | N/A | N/A |

TABLE 17

Therapeutic Dosing Regimen

| Compound | Dose | Lot # |
|---|---|---|
| JNJ 3026582 (RWJ 67657) | 0.5 µg/kg | 3418-60A |
| JNJ 17089540 (RWJ 669307) | 0.5 µg/kg | 3418-60B |
| ORTHOVISC ® | Vehicle | No 40326 |
| No Injection | N/A | |
| Suprofen | 1.3 µg/µl | 3418-60 |
| Microparticle Control | | 3418-61A |
| Microparticle 1X Suprofen Loading | 1.3 µg/µl | 3418-61B |
| Microparticle 5X Suprofen Loading | 6.5 µg/µl | 3418-61B |

The study design consisted of an n=10 per group. A total of 160 µl was injected at each administration.

Anesthesia and intra-articular injections were performed according to the ACLT model. Surgery was performed according to the ACLT Model. However, a thin probe was passed between the two ligaments and drawn slowly forward to ensure there are no uncut ligamental fibers. The patella was returned to the normal anatomic position. The wound was closed in layers. Euthanasia was performed according to the ACLT model, but the animals were euthanized at either six or eleven weeks post ACLT.

Immediately following euthanasia, gross observations of the knee joints were made and any abnormality was recorded. The joints were analyzed for disease state in the trochlear groove, the femoral condyles and the tibial plateau. The joint was removed and fixed in 10% neutral buffered formalin. The joints were decalcified using appropriate acidic solutions. All samples were trimmed in approximately the same area of the condyle. The trimmed samples were embedded in paraffin and sectioned. Two sets of slides were stained with Hematoxylin and Eosin or Safranin O and were scored using a Modified Mankin Histological Scoring system. The histological scoring was used to measure the depth, since this parameter is the most difficult to discern by clinical observation. Effort was taken to identify the area on the condyle with the most severe lesion so that depth could be evaluated. Therefore, this parameter is skewed to reflect the most eroded area and is not representative of the overall joint health.

Results

Clinical Observations:

At the time of sacrifice the following parameters were evaluated grossly (the scale follows in parenthesis):

Anterior Surface of Femur (Trochlear Groove)
# of osteophytes (0-3)
Size (diameter) of osteophytes (0-3)
Presence of trochlear groove thickening (0-1)
Erosion of cartilage (0-3)
Femoral Condyles
Erosion of cartilage (% surface area) (0-5) (medial and lateral condyle evaluated separately)
Erosion of cartilage (depth) (0-3) (medial and lateral condyle evaluated separately)
Presence of clefts (0-2)
Tibial Plateau (medial and lateral evaluated separately)
# of osteophytes (0-3)
Presence of clefts (0-2)
Erosion of cartilage (% surface area) (0-5)
Erosion of cartilage (depth) (0-3)

Each parameter was given a score. The combination of all parameters gave a Total Score (0-52). Additionally, combinations of the three subsets of data yielded scores for All Trochlear Groove Effects (0-10), All Condylar Effects (0-18) and All Tibial Plateau Effects (0-24). Lastly, an All Condylar Effects Score was obtained. The score for All Condylar Effects ranges from 0 to 40. The grades that compose this parameter are trochlear groove thickness and erosion, all the grades in All Condylar Effects, and all grades listed under Tibial Plateau. A higher score indicates more damage to the joint. A lower score indicates less damage or more cartilage preservation in the joint. The means and SEM's for all parameters, including those discussed in detail, are listed in Tables 18 and 19. Individual results for each parameter assessed were tabulated.

TABLE 18

Preventative Dosing Regimen: Mean And SEM For All Parameters

| Parameter | Scale Description | JNJ 3026582 (RWJ 67657) | JNJ 17089540 (RWJ 669307) | Suprofen | Orthovisc | No Injection | No Surgery |
|---|---|---|---|---|---|---|---|
| Trochlear Groove | | | | | | | |
| # of Osteophytes | 0 = 0; 1 = 1; 2 = 2; 3 ≥ 2 | 2.8 (0.2) | 2.6 (0.2) | 2.8 (0.2) | 2.6 (0.2) | 2.6 (0.2) | 1.5 (0.2) |
| Osteophyte Size | 0 = 0; 1 ≤ 1 mm; 2 = 1-2 mm; 3 > 2 mm | 2.5 (0.3) | 2.7 (0.2) | 2.8 (0.2) | 2.8 (0.2) | 2.7 (0.2) | 1.4 (0.2) |
| Thickening | 0 = Normal 1 = Thickened Areas | 0 (0) | 0 (0) | 0 (0) | 0.2 (0.1) | 0.4 (0.2) | 0 (0) |

TABLE 18-continued

| Preventative Dosing Regimen: Mean And SEM For All Parameters | | | | | | | |
|---|---|---|---|---|---|---|---|
| Parameter | Scale Description | JNJ 3026582 (RWJ 67657) | JNJ 17089540 (RWJ 669307) | Suprofen | Orthovisc | No Injection | No Surgery |
| Erosion of Cartilage Femoral Condyle | 0 = 0; 1 < 25%; 2 = 25-50%; 3 > 50% | 1.3 (0.3) | 1.0 (0.2) | 1.5 (0.4) | 1.7 (0.3) | 0.6 (0.2) | 0 (0) |
| % Surface Area Erosion (Medial) | 0 = None; 1 ≤ 10%; 2 = 11-25%; 3 = 26-50%; 4 = 51-75%; 5 = 76-100% | 0.5 (0.4) | 0.3 (0.3) | 0.1 (0.1) | 0.6 (0.2) | 0.6 (0.3) | 0.1 (0.1) |
| % Surface Area Erosion (Lateral) | 0 = None; 1 ≤ 10% 1 2 = 11-25%; 3 = 26-50%; 4 = 51-75%; 5 = 76-100% | 0.4 (0.3) | 1.2 (0.5) | 2.1 (0.4) | 1.2 (0.4) | 1.5 (0.5) | 0 (0) |
| Depth of Erosion (Medial) | 0 = no damage; 0.5 = barely perceptible; 1 = slight; 2 = significant; 3 = severe | 0.3 (0.3) | 0.2 (0.2) | 0.3 (0.3) | 0.5 (0.2) | 0.6 (0.3) | 0 (0) |
| Depth of Erosion (Lateral) | 0 = no damage; 0.5 = barely perceptible; 1 = slight; 2 = significant; 3 = severe | 0.4 (0.3) | 0.2 (0.2) | 1.6 (0.4) | 0.9 (0.3) | 1.4 (0.4) | 0 (0) |
| Presence of Clefts Tibial Plateau | 0 = absent; 1 = unicondylar; 2 = both condyles | 0 (0) | 0 (0) | 0 (0) | 0 (0) | 0 (0) | 0 (0) |
| # of Osteophytes (Medial) | 0 = 0; 1 = 1; 2 = 2; 3 ≥ 2 | 1.7 (0.2) | 1.4 (0.2) | 1.1 (0.2) | 1.5 (0.2) | 1.3 (0.2) | 0 (0) |
| Presence of Clefts (Medial) | 0 = Absent; 1 = Present | 0 (0) | 0 (0) | 0 (0) | 0 (0) | 0 (0) | 0 (0) |
| % Surface Area Erosion (Medial) | 0 = None; 1 ≤ 10% 1 2 = 11-25%; 3 = 26-50%; 4 = 51-75%; 5 = 76-100% | 0 (0) | 0 (0) | 0 (0) | 0 (0) | 0.1 (0.1) | 0 (0) |
| Depth of Erosion (Medial) | 0 = no damage; 0.5 = barely perceptible; 1 = slight; 2 = significant; 3 = severe | 0 (0) | 0 (0) | 0 (0) | 0 (0) | 0.1 (0.1) | 0 (0) |
| # of Osteophytes (Lateral) | 0 = 0; 1 = 1; 2 = 2; 3 ≥ 2 | 0.6 (0.2) | 0.4 (0.2) | 0.5 (0.2) | 0.4 (0.2) | 0.7 (0.2) | 0.1 (0.1) |
| Presence of Clefts (Lateral) | 0 = Absent; 1 = Present | 0 (0) | 0 (0) | 0 (0) | 0 (0) | 0 (0) | 0 (0) |
| % Surface Area Erosion (Lateral) | 0 = None; 1 ≤ 10% 1 2 = 11-25%; 3 = 26-50%; 4 = 51-75%; 5 = 76-100% | 0.7 (0.2) | 1.3 (0.4) | 0.9 (0.2) | 0.7 (0.2) | 0.9 (0.2) | 0 (0) |
| Depth of Erosion (Lateral) | 0 = no damage; 0.5 = barely | 0.7 (0.2) | 0.8 (0.3) | 0.5 (0.1) | 0.7 (0.2) | 0.7 (0.2) | 0 (0) |

TABLE 18-continued

Preventative Dosing Regimen: Mean And SEM For All Parameters

| Parameter | Scale Description | JNJ 3026582 (RWJ 67657) | JNJ 17089540 (RWJ 669307) | Suprofen | Orthovisc | No Injection | No Surgery |
|---|---|---|---|---|---|---|---|
| | perceptible; 1 = slight; 2 = significant; 3 = severe | | | | | | |
| Combination Scores | | | | | | | |
| Total Score | 0-52 52 = max damage | 11.9 (2.2) | 12.9 (2.3) | 14.1 (1.5) | 13.7 (1.6) | 14.1 (1.3) | 3.0 (0.4) |
| All Trochlear Groove Effects | 0-10 10 = max damage | 6.6 (0.6) | 6.2 (0.4) | 7.1 (0.5) | 7.3 (0.6) | 6.3 (0.4) | 2.9 (0.4) |
| All Condylar Effects | 0-18 18 = max damage | 1.6 (1.3) | 2.7 (1.3) | 4.1 (1.0) | 3.2 (0.8) | 4.1 (1.2) | 0.1 (0.1) |
| All Tibial Plateau Effects | 0-24 24 = max damage | 3.7 (0.7) | 4.1 (0.9) | 3.1 (0.3) | 3.3 (0.5) | 3.7 (0.5) | 0.1 (0.1) |
| All Cartilage Effects | 0-40 40 = max damage | 4.3 (1.8) | 5.8 (2.0) | 6.8 (0.9) | 6.5 (1.4) | 6.8 (1.3) | 0.1 (0.1) |

TABLE 19

Therapeutic Dosing Regimen: Mean And SEM For All Parameters

| Parameter | Scale Description | JNJ 3026582 (RWJ 67657) | JNJ 17089540 (RWJ 669307) | Suprofen | Orthovisc | Microparticle Control | Microparticle 1X | Microparticle 5X | No Injection | No Surgery |
|---|---|---|---|---|---|---|---|---|---|---|
| Trochlear Groove | | | | | | | | | | |
| # of Osteophytes | 0 = 0; 1 = 1; 2 = 2; 3 ≥ 2 | 2.9 (0.1) | 3.0 (0) | 3.0 (0) | 2.8 (0.1) | 2.8 (0.2) | 2.9 (0.1) | 2.7 (0.2) | 3.0 (0) | 1.0 (0.2) |
| Osteophyte Size | 0 = 0; 1 ≤ 1 mm; 2 = 1-2 mm; 3 > 2 mm | 2.9 (0.1) | 3.0 (0) | 3.0 (0) | 2.9 (0.1) | 2.9 (0.1) | 2.9 (0.1) | 2.7 (0.2) | 2.8 (0.2) | 1.0 (0.2) |
| Thickening | 0 = Normal 1 = Thickened Areas | 0.3 (0.2) | 0 (0) | 0 (0) | 0 (0) | 0 (0) | 0 (0) | 0 (0) | 0 (0) | 0 (0) |
| Erosion of Cartilage | 0 = 0; 1 < 25%; 2 = 25-50%; 3 > 50% | 1.9 (0.3) | 1.6 (0.3) | 1.9 (0.3) | 2.0 (0.3) | 1.5 (0.4) | 1.1 (0.1) | 1.1 (0.3) | 1.9 (0.4) | 0 (0) |
| Femoral Condyle | | | | | | | | | | |
| % Surface Area Erosion (Medial) | 0 = None; 1 ≤ 10% 1 2 = 11-25%; 3 = 26-50%; 4 = 51-75%; 5 = 76-100% | 0.7 (0.4) | 0.4 (0.2) | 0.3 (0.2) | 0.7 (0.3) | 0.6 (0.3) | 0.1 (0.1) | 0.2 (0.1) | 0.9 (0.4) | 0 (0) |
| % Surface Area Erosion (Lateral) | 0 = None; 1 ≤ 10% 1 2 = 11-25%; 3 = 26-50%; 4 = 51-75%; 5 = 76-100% | 2.4 (0.5) | 1.1 (0.4) | 1.3 (0.4) | 1.5 (0.5) | 1.8 (0.5) | 1.8 (0.5) | 2.0 (0.6) | 1.9 (0.5) | 0 (0) |
| Depth of Erosion (Medial) | 0 = no damage; 0.5 = barely perceptible; | 0.8 (0.4) | 0.2 (0.1) | 0.2 (0.1) | 0.5 (0.3) | 0.4 (0.2) | 0.2 (0.2) | 0.3 (0.2) | 0.7 (0.3) | 0 (0) |

TABLE 19-continued

Therapeutic Dosing Regimen: Mean And SEM For All Parameters

| Parameter | Scale Description | JNJ 3026582 (RWJ 67657) | JNJ 17089540 (RWJ 669307) | Suprofen | Orthovisc | Micro-particle Control | Micro-particle 1X | Micro-particle 5X | No Injection | No Surgery |
|---|---|---|---|---|---|---|---|---|---|---|
| | 1 = slight; 2 = significant; 3 = severe | | | | | | | | | |
| Depth of Erosion (Lateral) | 0 = no damage; 0.5 = barely perceptible; 1 = slight; 2 = significant; 3 = severe | 1.7 (0.4) | 1.1 (0.4) | 1.3 (0.4) | 1.4 (0.5) | 0.6 (0.3) | 1.7 (0.4) | 1.8 (0.5) | 1.7 (0.4) | 0 (0) |
| Presence of Clefts | 0 = absent; 1 = unicondylar; 2 = both condyles | 0 (0) | 0 (0) | 0 (0) | 0 (0) | 0 (0) | 0 (0) | 0 (0) | 0 (0) | 0 (0) |
| Tibial Plateau | | | | | | | | | | |
| # of Osteophytes (Medial) | 0 = 0; 1 = 1; 2 = 2; 3 ≥ 2 | 1.4 (0.2) | 1.5 (0.2) | 1.6 (0.2) | 1.3 (0.2) | 1.9 (0.1) | 1.8 (0.1) | 1.9 (0.1) | 2.2 (0.2) | 0 (0) |
| Presence of Clefts (Medial) | 0 = Absent; 1 = Present | 0 (0) | 0 (0) | 0 (0) | 0 (0) | 0 (0) | 0 (0) | 0 (0) | 0 (0) | 0 (0) |
| % Surface Area Erosion (Medial) | 0 = None; 1 ≤ 10% 1 2 = 11-25%; 3 = 26-50%; 4 = 51-75%; 5 = 76-100% | 0.4 (0.2) | 0 (0) | 0 (0) | 0.2 (0.1) | 0.3 (0.2) | 0 (0) | 0 (0) | 0 (0) | 0 (0) |
| Depth of Erosion (Medial) | 0 = no damage; 0.5 = barely perceptible; 1 = slight; 2 = significant; 3 = severe | 0.2 (0.1) | 0 (0) | 0 (0) | 0.1 (0.1) | 0.5 (0.3) | 0 (0) | 0 (0) | 0.1 (0.1) | 0 (0) |
| # of Osteophytes (Lateral) | 0 = 0; 1 = 1; 2 = 2; 3 ≥ 2 | 0.9 (0.2) | 0.7 (0.2) | 0.8 (0.2) | 0.5 (0.2) | 1.2 (0.2) | 1.3 (0.3) | 1.2 (0.3) | 1.1 (0.2) | 0 (0) |
| Presence of Clefts (Lateral) | 0 = Absent; 1 = Present | 0 (0) | 0 (0) | 0 (0) | 0 (0) | 0 (0) | 0 (0) | 0 (0) | 0 (0) | 0 (0) |
| % Surface Area Erosion (Lateral) | 0 = None; 1 ≤ 10% 1 2 = 11-25%; 3 = 26-50%; 4 = 51-75%; 5 = 76-100% | 1.3 (0.3) | 1.4 (0.2) | 1.6 (0.2) | 1.2 (0.1) | 1.8 (0.4) | 1.0 (0.3) | 1.0 (0.2) | 2.2 (0.2) | 0.3 (0.1) |
| Depth of Erosion (Lateral) | 0 = no damage; 0.5 = barely perceptible; 1 = slight; 2 = significant; 3 = severe | 0.9 (0.3) | 1.2 (0.3) | 1.4 (0.3) | 0.7 (0.1) | 1.4 (0.3) | 1.2 (0.3) | 1.0 (0.4) | 2.0 (0.3) | 0.1 (0) |
| Combination Scores | | | | | | | | | | |
| Total Score | 0-52 52 = max damage | 18.9 (1.6) | 15.2 (1.2) | 16.3 (1.5) | 15.8 (1.4) | 17.6 (1.9) | 16.0 (1.3) | 15.9 (2.2) | 20.4 (2.4) | 2.4 (0.4) |
| All Trochlear Groove Effects | 0-10 10 = max damage | 8.0 (0.4) | 7.6 (0.3) | 7.9 (0.3) | 7.7 (0.3) | 7.2 (0.5) | 6.9 (0.1) | 6.4 (0.6) | 7.7 (0.5) | 1.9 (0.3) |
| All Condylar Effects | 0-18 18 = max damage | 5.6 (1.0) | 2.8 (0.6) | 3.0 (1.0) | 4.1 (1.2) | 3.4 (0.7) | 3.8 (1.0) | 4.3 (1.2) | 5.2 (1.5) | 0 (0) |
| All | 0-24 | 5.3 | 4.8 | 5.4 | 4.0 | 7.0 | 5.3 | 5.1 | 7.6 | 0.5 |

TABLE 19-continued

Therapeutic Dosing Regimen: Mean And SEM For All Parameters

| Parameter | Scale Description | JNJ 3026582 (RWJ 67657) | JNJ 17089540 (RWJ 669307) | Suprofen | Orthovisc | Micro-particle Control | Micro-particle 1X | Micro-particle 5X | No Injection | No Surgery |
|---|---|---|---|---|---|---|---|---|---|---|
| Tibial Plateau Effects | 24 = max damage | (0.5) | (0.6) | (0.6) | (0.5) | (1.0) | (0.6) | (0.7) | (0.7) | (0.2) |
| All Cartilage Effects | 0-40<br>40 = max damage | 10.8<br>(1.4) | 7.0<br>(1.0) | 7.9<br>(1.5) | 8.3<br>(1.4) | 8.8<br>(1.5) | 7.1<br>(1.1) | 7.4<br>(1.6) | 11.3<br>(2.1) | 0.4<br>(0.2) |

Photographic Documentation:

Digital images were taken of individual knee joints at the completion of the study (data not shown). No photographic images were taken and no histology analysis is available for the joints from the No Injection group of the Therapeutic Dosing Regimen.

Preventative Dosing Regimen

All Condylar Effects:

The JNJ 3026582 (RWJ 67657) treated group, the JNJ 17089540 (RWJ 669307) treated group and the Suprofen treated group demonstrated numerically lower mean scores (0.5+0.4, 0.3+0.3, and 0.1+0.1 respectively) than the ORTHOVISC® treated group (0.6+0.2) or the No Injection group (0.6+0.3) for percent surface area erosion of the medial femoral condyle. The JNJ 3026582 (RWJ 67657) treated group demonstrated a numerically lower mean score (0.4+0.3) than either the ORTHOVISC® treated group (1.2+0.4) or the No Injection group (1.5+0.5) for percent surface area erosion of the lateral femoral condyle. The JNJ 3026582 (RWJ 67657) treated group, the JNJ 17089540 (RWJ 669307) treated group and the Suprofen treated group demonstrated numerically lower mean scores (0.3+0.3, 0.2+0.2, 0.3+0.3 respectively) than both the ORTHOVISC® treated group (0.5+0.2) or the No Injection group (0.6+0.3) for the depth of the erosion on the medial femoral condyle. The JNJ 3026582 (RWJ 67657) treated group and the JNJ 17089540 (RWJ 669307) treated group demonstrated numerically lower mean scores (0.4+0.3 and 0.2+0.2 respectively) than the ORTHOVISC® treated group (0.9+0.3) and the No Injection group (1.4+0.4) for the depth of the erosion on the lateral femoral condyle. Similarly, the JNJ 3026582 (RWJ 67657) treated group and the JNJ 17089540 (RWJ 669307) treated group demonstrated numerically lower mean scores (1.6+1.3 and 2.7+1.3 respectively) than the ORTHOVISC® treated group (3.2+0.8) and the No Injection group (4.1+1.2) for All Condylar Effects (FIGS. 24A-E).

Figure 25:
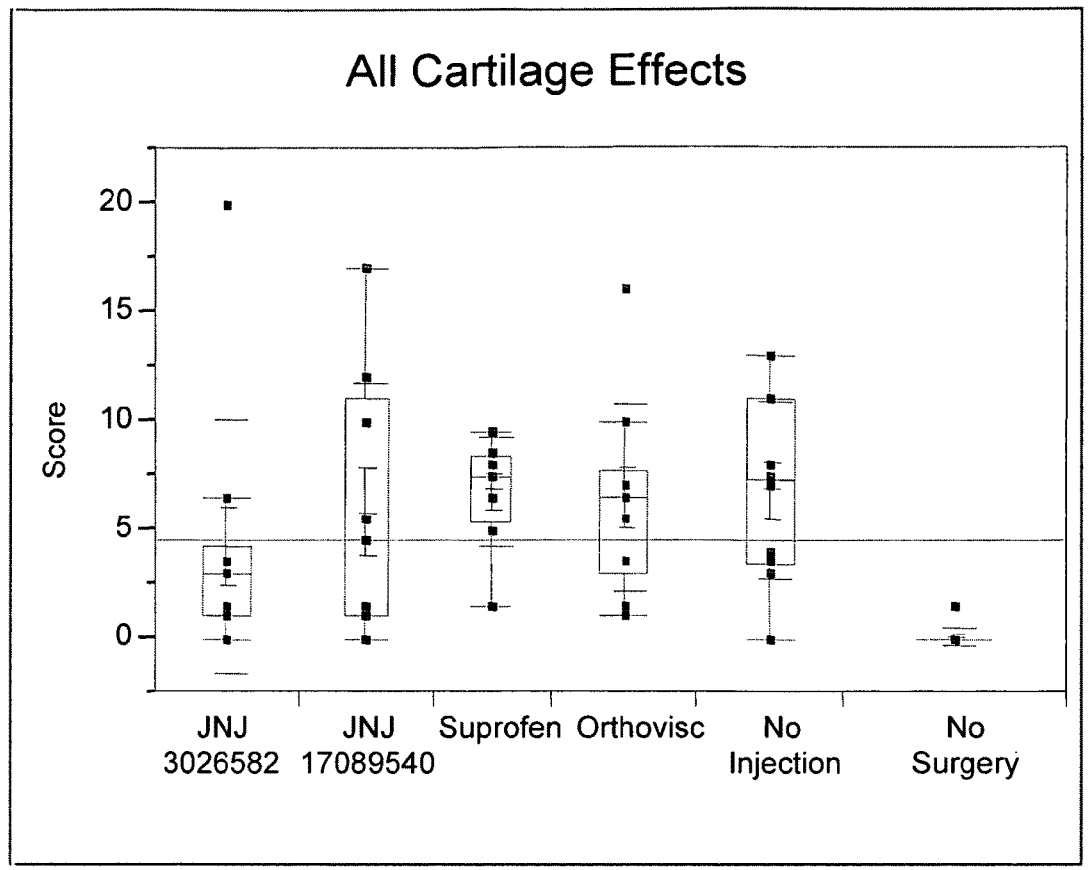
FIG. 25 depicts the All Cartilage Effects (preventative dosing regimen) for the following treatment groups: JNJ 3026582 (RWJ 67657), JNJ 17089540 (RWJ 669307), Suprofen, ORTHOVISC®, no injection, and no surgery.

All Cartilage Effects:

The JNJ 3026582 (RWJ 67657) treatment group and the JNJ 17089540 (RWJ 669307) treatment group demonstrated numerically lower mean scores (4.3+1.8 and 5.8+2.0, respectively) than either the ORTHOVISC® treated group (6.5+1.4) or the No Injection group (6.8+1.3) for all cartilage effects (FIG. 25).

Total Score:

The JNJ 3026582 (RWJ 67657) treatment group and the JNJ 17089540 (RWJ 669307) treatment group demonstrated numerically lower mean scores (11.9+2.2 and 12.9+2.3, respectively) than either the ORTHOVISC® treated group (13.7+1.6) or the No Injection group (14.1+1.3) for total score. The JNJ 3026582 (RWJ 67657) and the JNJ 17089540 (RWJ 669307) treated animals demonstrated greater overall health of the joint when compared to the control groups (FIG. 26).

Therapeutic Dosing Regimen

All Condylar Effects:

The JNJ 17089540 (RWJ 669307) treated group, the Suprofen treated group, the Microparticle 1× and the Microparticle 5× treated groups demonstrated numerically lower mean scores (0.4+0.2, 0.3+0.2, 0.1+0.1 and 0.2+0.1 respectively) than the Microparticle Control treated group (0.6+0.3), the ORTHOVISC® treated group (0.7+0.3) or the No Injection group (0.9+0.4) for percent surface area erosion of the medial femoral condyle. The JNJ 17089540 (RWJ 669307) treated group and the Suprofen treated group demonstrated numerically lower mean scores (1.1+0.4 and 1.3+0.4 respectively) than either the ORTHOVISC® treated group (1.5+0.5) or the No Injection group (1.9+0.5) for percent surface area erosion of the lateral femoral condyle. The JNJ 17089540 (RWJ 669307) treated group, the Suprofen treated group, the Microparticle 1× and the Microparticle 5× treated groups demonstrated numerically lower mean scores (0.2+0.1, 0.2+0.1, 0.2+0.2 and 0.3+0.2 respectively) than the Microparticle Control treated group (0.4+0.2), the ORTHOVISC® treated group (0.5+0.3) or the No Injection group (0.7+0.3) for the depth of the erosion on the medial femoral condyle. The JNJ 17089540 (RWJ 669307) treated group, the Suprofen treated group and the Microparticle Control group demonstrated numerically lower mean scores (1.1+0.4, 1.3+0.4 and 0.6+0.3 respectively) than either the ORTHOVISC® treated group (1.4+0.5) or the No Injection group (1.7+0.4) for the depth of the erosion on the lateral femoral condyle. The JNJ 17089540 (RWJ 669307) treated group, the Suprofen treated group and the Microparticle Control treated group (3.4+0.7) treated groups demonstrated numerically lower mean scores (2.8+0.6, 3.0+1.0 and 3.4+0.7 respectively) than the ORTHOVISC® treated group (4.1+1.2) or the No Injection group (5.2+1.5) for all condylar effects (FIGS. 27A-E).

Figure 28:
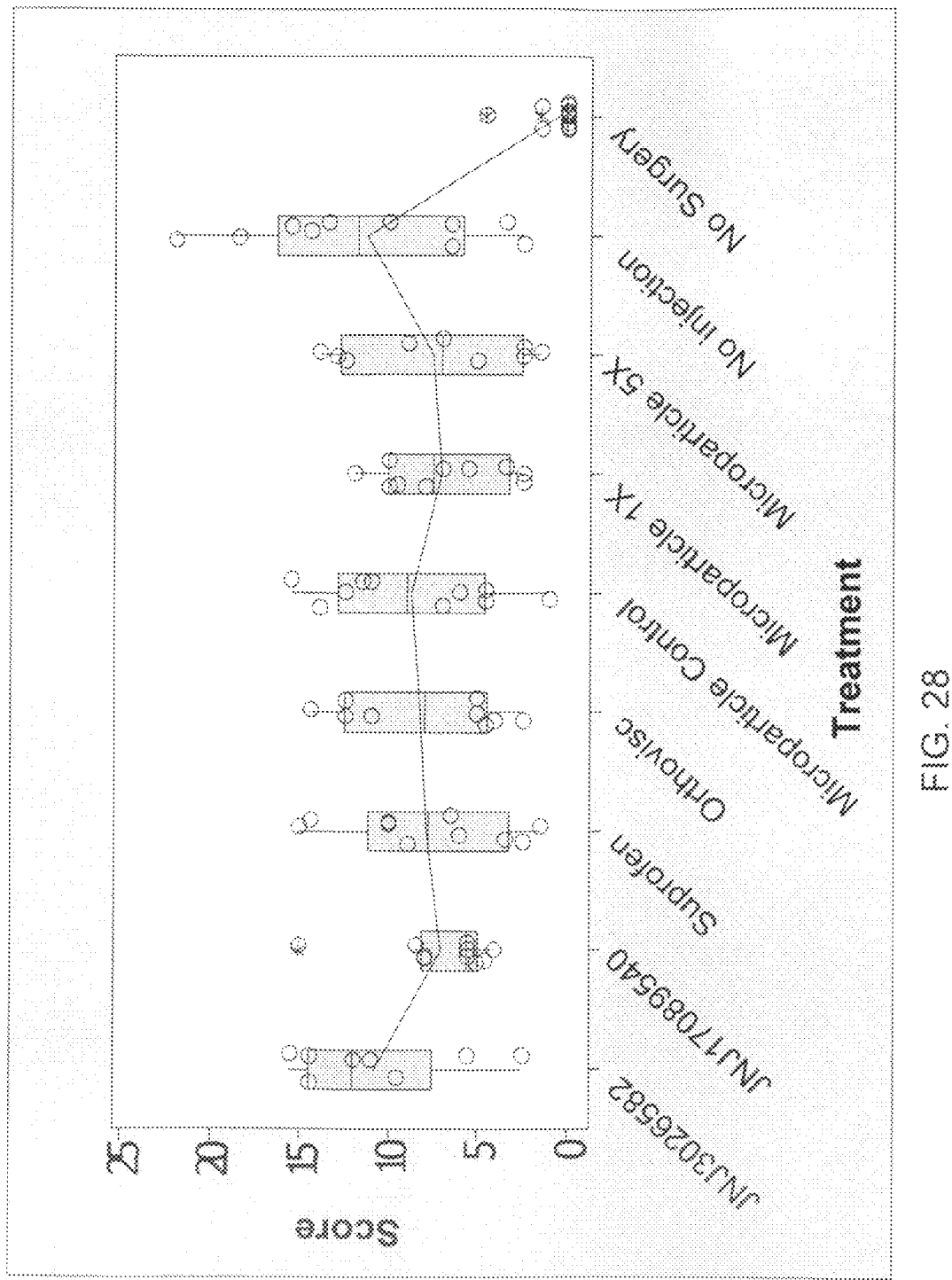
FIG. 28 depicts the All Cartilage Effects (therapeutic dosing regimen) for the following treatment groups: JNJ 3026582 (RWJ 67657), JNJ 17089540 (RWJ 669307), Suprofen, ORTHOVISC®, Microparticle (control, 1× and 5×), no injection, and no surgery.

All Cartilage Effects:

The JNJ 17089540 (RWJ 669307) treated group, the Suprofen treated group, the Microparticle 1× and the Microparticle 5× treated groups demonstrated numerically lower mean scores (7.0+1.0, 7.9+1.5, 7.1+1.1 and 7.4+1.6 respectively) than the Microparticle Control treated group (8.8+1.5), the ORTHOVISC® treated group (8.3+1.4) or the No Injection group 11.3+2.1) for All Cartilage Effects (FIG. 28).

Figure 29:
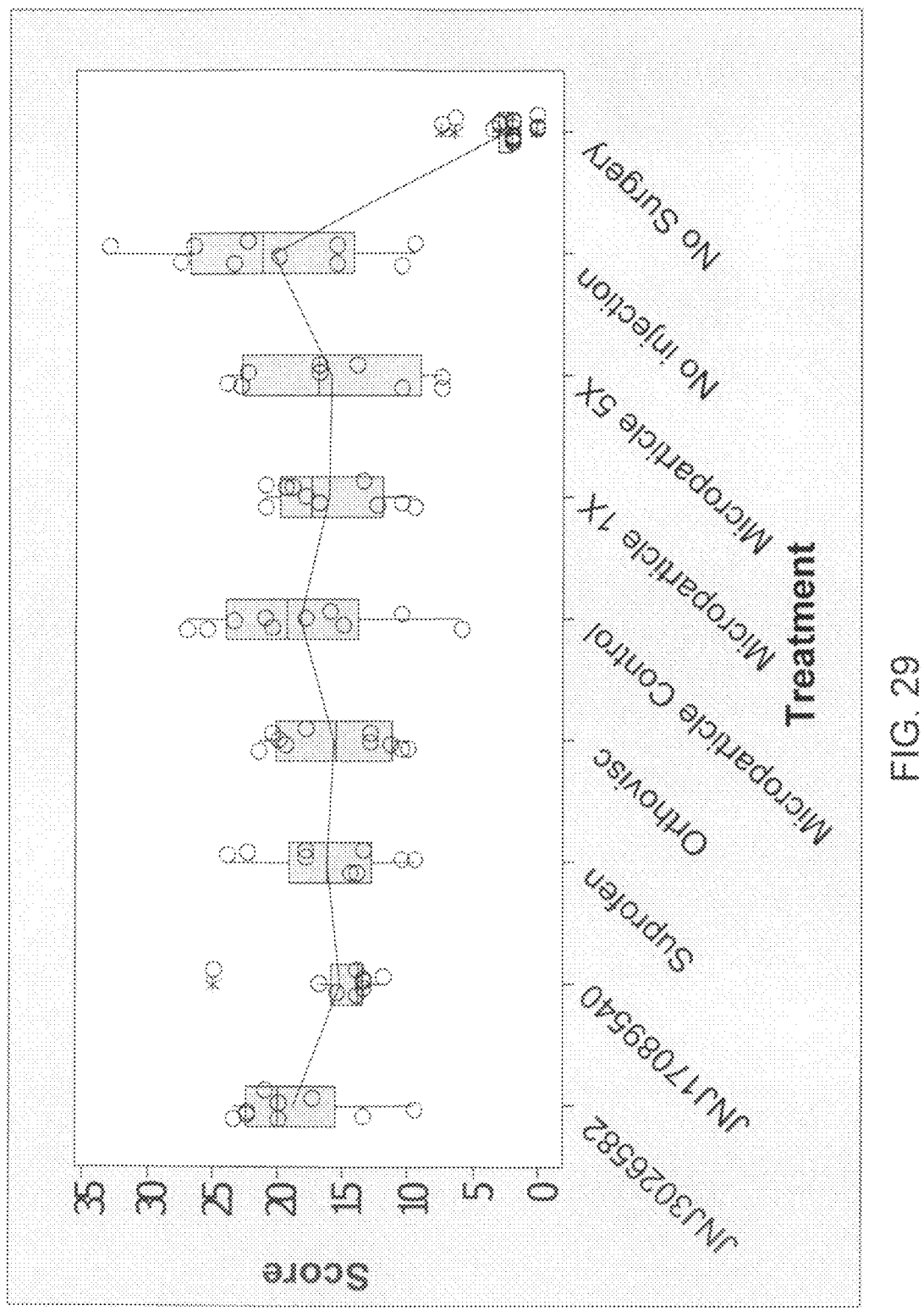
FIG. 29 depicts the Total Score (therapeutic dosing regimen) for the following treatment groups: JNJ 3026582 (RWJ 67657), JNJ 17089540 (RWJ 669307), Suprofen, ORTHOVISC®, Microparticle (control, 1× and 5×), no injection, and no surgery.

Total Score:

The JNJ 17089540 (RWJ 669307) treated group demonstrated a numerically lower mean score (15.2+1.2) than the ORTHOVISC® treated group (15.8+1.4) or the No Injection group (20.4+2.4) for total score (FIG. 29).

Summary:

The appearance of osteoarthritis in this model could be seen at six weeks, and was characterized by erosion of cartilage on the trochlear groove and mild to serious cartilage erosion on the femoral condyle with damage visible on the tibial plateau. Although osteophyte formation is a hallmark to human osteoarthritis, rabbits readily form osteophytes from very minor manipulation. Scores from different subsets of data are combined into composite grades to gain insight into additional areas of efficacy (for example, All Condylar Effects). The therapeutic model is a very aggressive and severe model of osteoarthritis. Therefore, it is typically not the goal of these studies to obtain statistical significance between the groups, but, rather, trends in improvement of the individual or composite scores are used to identify therapies with clinical potential, which may offer chondroprotection.

In the preventative model, JNJ 3026582 (RWJ 67657) showed a trend towards improvement in All Condylar Effects. This parameter is most heavily weighted in this analysis since it is the most clinically relevant. However, in the therapeutic model, this positive effect was not observed. One possible explanation is that when an anti-inflammatory compound is given at a time point immediately post-ACL transection surgery, the normal post-surgical healing process may be altered. Inflammation, immediately post injury, is essential to complete the healing process. The therapeutic model has successfully been used previously to test other classes of compounds such as MMP inhibitors. Another consideration is that since JNJ 3026582 (RWJ 67657) is insoluble in the vehicle, it is unclear whether the bioavailability of the drug differs based on the surface interactions between the drug and an intact cartilage surface versus the drug with an osteochondral defect (as in the therapeutic model).

When evaluating joint preservation, two key factors were measured: the percent surface area affected and the depth of the lesion. It is believed that clinical presentation of a patient with pain is caused by a combination of the percent of surface area affected and the depth of the lesion. When both surface area and depth of erosion across all of the cartilage surfaces of the joint capsule were considered, a trend towards improvement in scoring was demonstrated for the JNJ 17089540 (RWJ 669307) and the Suprofen treated groups.

In addition, JNJ 17089540 (RWJ 669307) tightened the standard deviation when compared to the ORTHOVISC® and the No Injection control groups, demonstrating an overall improvement in the health of the joint.

The microparticle control group also showed improved scores compared to the ORTHOVISC® and No Injection control groups with regard to All Condylar Effects. In addition, the microparticles alone also showed improvement in the overall standard deviation of scores when compared to either the ORTHOVISC® or the no injection controls. The Microparticle groups (1× and 5×) demonstrated trends toward improvement, but the effects were not universal. SEM images of the microparticle control group and Suprofen containing microparticle group indicate that, during the encapsulation process, the drug may recrystallize on the surface of the microparticles, changing the drug solubility and drug release kinetics, which may account for the increased standard deviation seen in the groups treated with microparticle-loaded suprofen.

The results for JNJ 17089540 (RWJ 669307) demonstrate its chondroprotective effects. The results for JNJ 3026582 (RWJ 67657) appear to be less conclusive, most likely due to the solubility of the compound in the vehicle. JNJ 17089540 has been repeatedly shown to have chondroprotective effects in multiple studies. JNJ 3026582 has shown efficacy in several studies, however, it has had mixed results in this study. This could be due to compound specificity but it is most likely due simply to compound solubility since this compound is extremely insoluble and was delivered in an aqueous (HA) vehicle. It was believed that if the formulation was optimized to maintain solubility and bioavailability that the results would have shown consistent performance.

Example X

ACLT: Rabbit Anti-TNFα Antibody

Objective:
The purpose of this study was to evaluate the ability of rabbit anti-TNF-α antibody delivered directly to the knee to reduce effects of the osteoarthritic changes that occur and to prevent additional deterioration of the joint.

Experimental Design:
Forty female New Zealand White Rabbits underwent ACLT on the right knee. Intra-articular injections for the rabbit anti-TNF-α antibody and saline treated groups were administered to the operated knee once per week for five weeks beginning six weeks after the ACLT. All animals were euthanized 12 weeks after the ACLT. Gross observations were made on the knee joints. The stifle joints were removed. Samples were preserved in 10% neutral buffered formalin. The stifle joints were photographed using high-resolution photography.

Before testing the efficacy of anti-rabbit TNFα monoclonal antibody (mAb) in this model, the effect of anti-rabbit TNFα mAb was first examined in vitro using the chondrocyte pellet culture model. In this study, chondrocytes isolated from rabbits were used to make alginate recovered cartilage tissues (ARC). Rabbit TNFα was also used to avoid possible species specificity between this cytokine and anti-rabbit TNFα mAb. Rabbit ARC punches were treated with 10 or 100 ng/ml mAb (anti-rabbit TNFα, from Centocor, Inc.) diluted into chondrocyte stimulation medium [DMEM supplemented with 1% FCS, 1× insulin (5 µg/ml)-transferrin (5 µg/ml)-sodium selenite (5 µg/ml) media supplement and 1× Antibiotics-Antimycotics (Penicillin G Sodium, 100 units/ml, Steptomycin Sulfate, 100 µg/ml and Amphotericin B, 0.25 µg/ml)]. After one hour treatment at 37° C., ARCs were stimulated with or without the indicated cytokines at indicated concentrations (IL-β, 5 µg/ml) and continued to incubate for 5 days before the culture media was collected for assays as described.

Figure 30A:
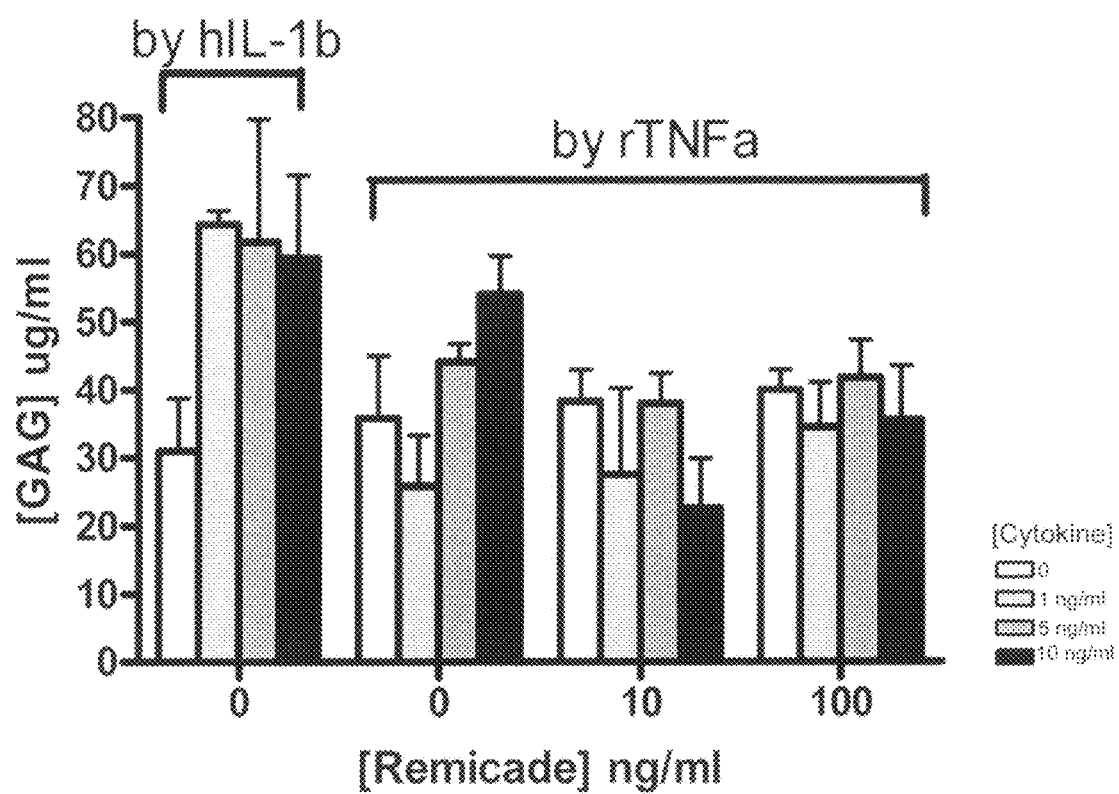
FIGS. 30A and 30B (FIG. 30A) depict the effects of an anti-TNFα monoclonal antibody on inhibition of GAG degradation and NO production (FIG. 30B) on ARCs stimulated with cytokines IL-1β and TNFα, in amounts of 0, 1 ng/ml, 5 ng/ml and 10 ng/ml.
Figure 30B:
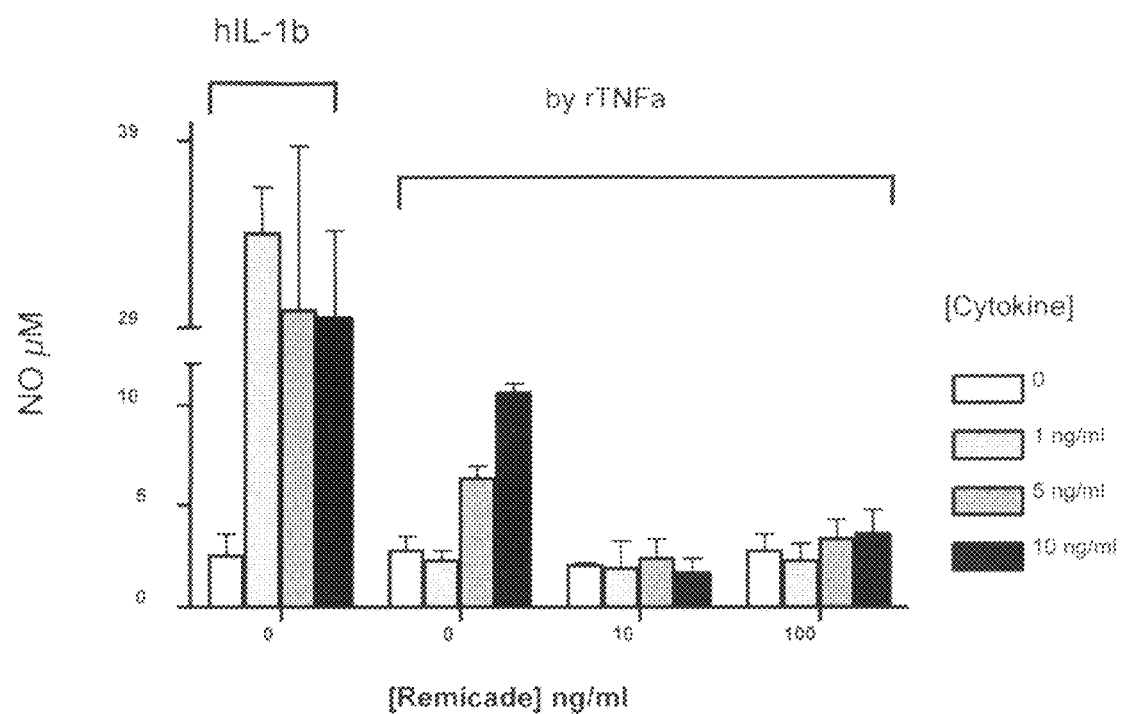

As shown in FIG. 30, TNFα at 5 and 10 ng/ml dose-dependently stimulated both GAG degradation and NO production that was effectively inhibited by 10 ng/ml of anti-TNFα mAb. TNFα at 1 ng/ml showed no stimulation and the effect of TNFα is much weaker than IL-1β.

Treatment Groups:
The rabbit anti-TNF-α antibody was prepared and received from Centocor, Inc. (Radnor, Pa.).

TABLE 20

| Dosing | | | |
|---|---|---|---|
| Rabbit anti-TNF-α antibody | | 50 µg/kg | Five injections |
| Saline (PBS) (Lot # 14190-144) | Vehicle Control | | Five injections |
| No Injection | Surgical Control | | |
| No Surgery | Non-Surgical Control | | |

There were ten rabbits per group; the antibody were suspended in PBS. 160 µl total volume was injected for each administration.

Materials and Methods:

Housing and Care:

This study was conducted in accordance with the rules and regulations of the Institutional Animal Care and Use Committee of State University of New York (SUNY) Health Science Center at Brooklyn. The animals were group housed in pens. Diet consisted of a commercially available rabbit chow and tap water. The animals utilized in this study were handled and maintained in accordance with the current requirements of the Department of Animal Laboratory Resources and Maimonides at SUNY.

Anesthesia, Analgesia and Surgical Preparation:

Animals were weighed and anesthesia was induced in each rabbit via an intra-muscular injection of Ketamine (17 mg/kg) and Xylazine (2.5 mg/kg). Supplementation, during surgery, was given if needed with additional intra-muscular injections of Ketamine (35 mg/kg) and Xylazine (5 mg/kg).

Analgesia in these animals was accomplished with Buprenorphine (0.01-0.05 mg/kg) via a subcutaneous injection. Buprenorphine was administered every 12 hours for 72 hours.

After induction of anesthesia, the right leg skin surface was clipped free of hair using electric animal clippers. The area around the site of surgery was scrubbed with Chlorhexidine diacetate, rinsed with alcohol, dried, and painted with an aqueous iodophor solution of 1% available iodine. The anesthetized and surgically prepared animal was placed in the desired recumbent position. Sterile drapes were applied to the prepared area using aseptic technique.

Surgical Approach:

In the right limb of each animal, the ACL was transected. A medial parapatellar incision was made and the patella dislocated. The knee was flexed and the ACL visualized. A scalpel blade was positioned behind the ACL and brought anteriorly, thereby cutting the ACL while protecting the posterior cruciate ligament. A thin probe was passed between the two ligaments and drawn slowly forward to ensure there are no uncut ligamental fibers. The patella was returned to the normal anatomic position. The wound was closed in layers. Animals were allowed to move freely as soon as they recovered from anesthesia.

Rabbit Anti-TNF-α Antibody Preparation:

Twenty-week old Sprague Dawley rats were immunized subcutaneously with recombinant rabbit TNF (lot # JG111397), cloned and expressed. Each rat received a total of six injections at three week intervals. Blood collections were performed by retro-orbital puncture and serum was collected for titer determination by rabbit TNF solid phase EIA. One rat spleen was fused with murine myeloma cells utilizing PEG1450. Three antibodies reactive to rabbit TNF were identified and further characterized. All three antibodies (C384A, C385A, and C386A) were of isotype IgG2b, and were able to neutralize rabbit TNF.

Once the rabbit anti-TNF-α was received at CBAT, it was stored at 4° C. To prepare the antibody for injection, antibody stock solution with concentration of 3.16 mg/mL was diluted to 1.25 mg/mL, with Dulbecco's phosphate-buffered saline (PBS) (manufactured by GIBCO, Invitrogen Corporation, Carlsbad, Calif., without $Ca^{++}/Mg^{++}$, Lot #14190-144). Due to the low viscosity of the vehicle, vials of treatment were prepared so that at the time of injection, the appropriate amount of solution was drawn into a syringe for injection. This treatment was shipped on wet ice. The final preparation was stored at 4° C.

Intra-Articular Injections:

Following surgery, animals were untreated for six weeks to allow for joint degeneration. Previous studies have confirmed that the six week time-point allows sufficient degeneration changes to occur. Control groups either received no injections or received the saline vehicle delivered once weekly for five weeks. This dosing regimen corresponds to the clinical dosing regimen for local delivery of viscosupplements. The rabbit anti-TNF-α antibody was administered once weekly for five weeks.

Euthanasia:

The animals were euthanized 12 weeks post ACLT with an intravenous injection of pentobarbital (60 mg/kg).

Results

Immediately following euthanasia, gross observations of the knee joints were made and any abnormality was recorded. The joints were analyzed for disease state in the trochlear groove, the femoral condyles and the tibial plateau.

At the time of sacrifice, the following parameters were evaluated grossly (the scale follows in parenthesis):

Anterior Surface of Femur (Trochlear Groove)
  # of osteophytes (0-3)
  Size (diameter) of osteophytes (0-3)
  Presence of trochlear groove thickening (0-1)
  Erosion of cartilage (0-3)

Femoral Condyles
  Erosion of cartilage (% surface area) (0-5) (both medial and lateral condyle evaluated)
  Erosion of cartilage (depth) (0-3) (both medial and lateral condyle evaluated)
  Presence of clefts (0-2)

Tibial Plateau (both medial and lateral condyle evaluated)
  # of osteophytes (0-3)
  Presence of clefts (0-2)
  Erosion of cartilage (% surface area) (0-5)
  Erosion of cartilage (depth) (0-3)

Each parameter was given a score. The combination of all parameters gave a Total Score (0-52). Additionally, combinations of the three subsets of data yielded All Trochlear Groove Effects (0-10), All Condylar Effects (0-18) and All Tibial Plateau Effects (0-24). Lastly, an All Cartilage Score was obtained. The score for All Cartilage Effects ranges from 0 to 40. The grades that compose this parameter are trochlear groove thickness and erosion, all the grades in All Condylar Effects, and all grades listed under tibial plateau. A higher score indicates more damage to the joint. A lower score indicates less damage or more cartilage preservation to the joint. The means and SEM's for all parameters, including those discussed in detail, are listed in Table 21.

Treatments were assigned in a blocked fashion. Visual assessments were analyzed using JMP (SAS Institute Incorporated, Cary, N.C.) 4.0.4 software. A Shapiro-Wilk-W Test was performed prior to data analysis to determine normality. Nominal and Ordinal data were analyzed using Chi-Square. Continuous data was analyzed using One-way ANOVA. A Tukey-Kramer or Student-Newman-Keuls (SNK) test for multiple comparisons was performed to determine differences between groups following One-way ANOVA. A value of $p<0.05$ was used as the level of significance.

Data is graphically represented using JMP 4.0.4 software. For each graph, each point represents a data point given by an independent pathologist blinded to the treatments (the statistical program stacks data points, thus, several animals with the same score are represented as a single point). The centermost horizontal "short" line in each treatment group represents the mean of the data. The next set of horizontal short lines that are connected to the mean by a vertical line represent the standard error of the mean (SEM). The last set of horizontal short lines represent the standard deviation. The centermost horizontal "longer" line running from one edge of the box (or which is the width of the box) to the other represents the median of the data. The box depicts the lower and upper 95$^{th}$ percentiles of the data. The line running horizontally across the entire graph is the mean of the entire data set. Note that the entire data set includes data from healthy joints (the n of this group is twice the treatment groups) thereby making this score relatively low.

In addition to using JMP 4.0.4 software, statistical analysis was performed using Minitab 14 software in order to enhance visualization of the data. For this analysis, each circle represents an individual data point given by an independent pathologist blinded to the treatments. Each circle enclosing a cross represents the mean of the data; each of the means of the treatment groups is connected.

Trochlear Groove Effects:

The rabbit anti-TNF-α antibody treatment group demonstrated a numerically lower mean score (0.78+0.36) than the saline treated group (1.67+0.41) for trochlear groove surface area erosion. The rabbit anti-TNF-α antibody treatment group demonstrated a numerically lower mean score (0.11±0.11) than the No Injection treated group (0.20±0.13) for thickening. Additionally, the rabbit anti-TNF-α antibody treatment group demonstrated a numerically lower mean score (6.67±0.55) than the saline treated group (7.33±0.58) for all trochlear groove effects.

Condylar Effects:

The rabbit anti-TNF-α antibody treatment group demonstrated a numerically lower mean score (4.0±1.55) than the saline treated group (4.22±0.99) and the No Injection group (5.00±1.23) for all condylar effects. In addition, the rabbit anti-TNF-α antibody treatment group demonstrated a numerically lower mean score (0.78±0.43) than the Saline treated group (1.28±0.41) and the No Injection group (1.80±0.39) for depth of cartilage erosion on the lateral condyle. The rabbit anti-TNF-α antibody treatment group demonstrated a numerically lower mean score (1.00±0.50) than the Saline treated group (1.56±0.47) and the No Injection group (2.30±0.58) for percent area cartilage erosion on the lateral condyle.

Tibial Plateau Effects:

The rabbit anti-TNF-α antibody treatment group demonstrated numerically lower mean scores than the saline treated group and the No Injection group for all parameters under tibial plateau (see Table 21). Presence of clefts, both medial and lateral, was the same for these three groups. Additionally the rabbit anti-TNF-α antibody treatment group demonstrated a numerically lower mean score (3.94±0.54) than the saline treated group (6.56±0.99) and the No Injection group (6.50±1.11) for all tibial plateau effects.

All Cartilage Effects:

The rabbit anti-TNF-α antibody treatment group demonstrated a lower average score (6.94±2.21) than the saline treated group (9.33±1.65) and the No Injection group (9.60±2.13).

Total Score:

The rabbit anti-TNF-α antibody treatment group demonstrated a lower average score (14.61±2.23) than the saline treated group (18.11±2.22) and the No Injection group (17.50±2.64). The rabbit anti-TNF-α antibody tested animals demonstrated greater overall health of the joint when compared to the control groups.

Summary:

The purpose of this study was to evaluate the ability of rabbit anti-TNF-α delivered directly to the knee, to reduce the incidence of osteoarthritic changes in an unstable joint.

The appearance of OA in this model can be seen at 6 weeks, and is characterized by erosion of cartilage on the trochlear groove and mild to serious cartilage erosion on the femoral condyle with damage visible on the tibial plateau. Although osteophyte formation is a hallmark to human OA, rabbits readily form osteophytes from very minor manipulation. Scores from different subsets of data are combined into composite grades to gain insight into additional areas of efficacy (i.e., All Condylar Effects).

Summary:

The purpose of this study was to evaluate rabbit anti-TNF-α, delivered directly to the knee, to reduce the incidence of osteoarthritic changes in a recognized model of osteoarthritis. The primary endpoint of this study was the clinical evaluation of cartilage preservation scored by a pathologist at the time of necropsy.

Gross observations indicated that local injection of the rabbit anti-TNF-α to rabbit knees, which have significant degenerative changes due to osteoarthritis, offered a trend towards improvement of cartilage scoring of the trochlear groove, tibial plateau and femoral condyles. At the concentrations tested, no detrimental effects were observed.

The rabbit anti-TNF-α treatment group demonstrated lower mean scores than the saline treated group for the trochlear groove surface area erosion and lower average scores for percent lateral surface area erosion, depth of lateral condyle erosion when compared to the Saline and No Injection groups.

The combined scores constituting the all tibial plateau effects indicate that the rabbit anti-TNF-α treatment group demonstrated lower average scores that the saline and No Injection groups. This is indicative of a trend towards improvement as compared to the control groups. In addition, osteophytes are known to be rapidly generated in rabbits which undergo minimal procedural intervention or may form as a result from slight changes in gait. The osteophyte average score for both the rabbit anti-TNF-α treatment group were lower than both control groups, perhaps indicating general improvement in the overall health of the joint.

This is a very aggressive and severe model of osteoarthritis. Therefore, it is typically not the goal of these pilot studies to obtain statistical significance between the groups. Traditionally, trends in improvement of the individual or composite scores are sought to identify therapies with clinical potential which may offer chondroprotection.

When evaluating joint preservation, two key factors are measured, the percent surface area affected as well as the depth of the lesion. It is unknown which of these parameters is responsible for clinical presentation of a patient with pain as it is speculated that pain is a combination of the percent of surface area affected as well as the depth of the lesion. When considering both surface area and depth of erosion across all of the cartilage surfaces of the joint capsule, a trend towards improvement in scoring was demonstrated for the rabbit anti-TNF-α treated group.

The gross observations in this study demonstrate the utility of rabbit anti-TNF-α delivered via direct injection into a diseased joint to offer possible disease modifying benefits by preserving cartilage in the joint space.

TABLE 21

| | | Mean and (SEM) of all parameters. | | | |
|---|---|---|---|---|---|
| Parameter | Scale Description | Rabbit Anti-TNF-α Antibody | Saline | No Injection | No Surgery |
| Trochlear Groove | | | | | |
| # of Osteophytes | 0 = 0; 1 = 1; 2 = 2; 3 ≥ 2 | 2.78 (0.22) | 2.56 (0.24) | 2.6 (0.22) | 0.50 (0.15) |
| Osteophyte Size | 0 = 0; 1 ≤ 1 mm; 2 = 1-2 mm; 3 > 2 mm | 3.00 (0) | 3.00 (0) | 2.6 (0.31) | 1.25 (0.35) |
| Thickening | 0 = Normal 1 = Thickened Areas | 0.11 (0.11) | 0.11 (0.11) | 0.20 (0.13) | 0 (0) |
| Erosion of Cartilage | 0 = 0; 1 < 25%; 2 = 25-50%; 3 > 50% | 0.78 (0.36) | 1.67 (0.41) | 0.60 (0.27) | 0 (0) |
| Femoral Condyle | | | | | |
| % Surface Area Erosion (Medial) | 0 = None; 1 ≤ 10% 1 2 = 11-25%; 3 = 26-50%; 4 = 51-75%; 5 = 76-100% | 1.33 (0.41) | 0.56 (0.29) | 0.50 (0.31) | 0 (0) |
| % Surface Area Erosion (Lateral) | 0 = None; 1 ≤ 10% 1 2 = 11-25%; 3 = 26-50%; 4 = 51-75%; 5 = 76-100% | 1.00 (0.50) | 1.56 (0.47) | 2.30 (0.58) | 0 (0) |
| Depth of Erosion (Medial) | 0 = no damage; 0.5 = barely perceptible; 1 = slight; 2 = significant; 3 = severe | 0.89 (0.33) | 0.83 (0.39) | 0.40 (0.30) | 0 (0) |
| Depth of Erosion (Lateral) | 0 = no damage; 0.5 = barely perceptible; 1 = slight; 2 = significant; 3 = severe | 0.78 (0.43) | 1.28 (0.41) | 1.80 (0.39) | 0 (0) |
| Presence of Clefts | 0 = absent; 1 = unicondylar; 2 = both condyles | 0 (0) | 0 (0) | 0 (0) | 0.08 (0.08) |
| Tibial Plateau | | | | | |
| # of Osteophytes (Medial) | 0 = 0; 1 = 1; 2 = 2; 3 ≥ 2 | 1.44 (0.18) | 1.78 (0.15) | 1.80 (0.13) | 0 (0) |
| Presence of Clefts (Medial) | 0 = Absent; 1 = Present | 0 (0) | 0 (0) | 0 (0) | 0 (0) |
| % Surface Area Erosion (Medial) | 0 = None; 1 ≤ 10% 1 2 = 11-25%; 3 = 26-50%; 4 = 51-75%; 5 = 76-100% | 0.11 (0.11) | 0.22 (0.15) | 0.20 (0.13) | 0.08 (0.08) |
| Depth of Erosion (Medial) | 0 = no damage; 0.5 = barely perceptible; 1 = slight; 2 = significant; 3 = severe | 0.06 (0.06) | 0.17 (0.12) | 0.15 (0.11) | 0 (0) |
| # of Osteophytes (Lateral) | 0 = 0; 1 = 1; 2 = 2; 3 ≥ 2 | 0.44 (0.18) | 1.44 (0.29) | 0.90 (0.18) | 0.04 (0.04) |
| Presence of Clefts (Lateral) | 0 = Absent; 1 = Present | 0 (0) | 0 (0) | 0 (0) | 0 (0) |
| % Surface Area Erosion (Lateral) | 0 = None; 1 ≤ 10% 1 2 = 11-25%; 3 = 26-50%; 4 = 51-75%; 5 = 76-100% | 1.11 (0.31) | 1.67 (0.41) | 1.90 (0.41) | 0.08 (0.08) |
| Depth of Erosion (Lateral) | 0 = no damage; 0.5 = barely perceptible; 1 = slight; | 0.78 (0.25) | 1.28 (0.42) | 1.55 (0.38) | 0.13 (0.09) |

TABLE 21-continued

Mean and (SEM) of all parameters.

| Parameter | Scale Description | Rabbit Anti-TNF-α Antibody | Saline | No Injection | No Surgery |
|---|---|---|---|---|---|
| | 2 = significant; 3 = severe | | | | |
| Combination Scores | | | | | |
| Total Score | 0-52 | 14.61 | 18.11 | 17.50 | 2.17 |
| | 52 = max damage | (2.23) | (2.22) | (2.64) | (0.40) |
| All Trochlear | 0-10 | 6.67 | 7.33 | 6.00 | 1.75 |
| Grove Effects | 10 = max damage | (0.55) | (0.58) | (0.63) | (0.41) |
| All Condylar | 0-18 | 4.00 | 4.22 | 5.00 | 0.08 |
| Effects | 18 = max damage | (1.55) | (0.99) | (1.23) | (0.08) |
| All Tibial | 0-24 | 3.94 | 6.56 | 6.50 | 0.33 |
| Plateau | 24 = max damage | (0.54) | (0.99) | (1.11) | (0.18) |
| Effects | | | | | |
| All Cartilage | 0-40 | 6.94 | 9.33 | 9.60 | 0.38 |
| Effects | 40 = max damage | (2.21) | (1.65) | (2.13) | (0.16) |

While this invention has been particularly shown and described with references to preferred embodiments thereof, it will be understood by those skilled in the art that various changes in form and details may be made therein without departing from the scope of the invention encompassed by the appended claims.

All references cited herein are incorporated by reference in their entirety.

What is claimed is:

1. A method of treating an inflamed orthopedic joint in a human or an animal, said joint comprising: i) opposing hyaline cartilage articular surfaces; ii) peripheral to the surfaces, a central joint space comprising a collagenous capsule; and iii) synovial fluid contained within the joint space, the method comprising directly administering into the joint space by trans-capsular administration a formulation comprising an effective amount of a compound of one of the following structural formulas:

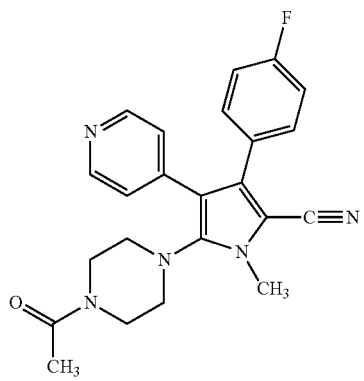

or

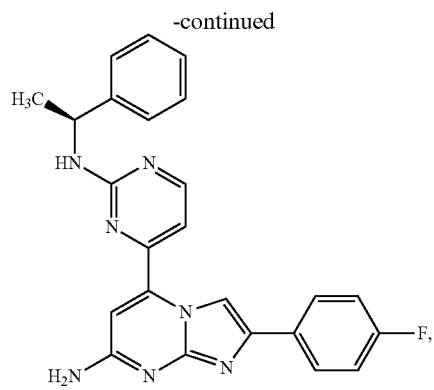

or a salt thereof.

2. The method of claim 1, wherein the administration is through a needle.
3. The method of claim 1, wherein the administration is through a drug pump.
4. The method of claim 1, wherein the administration is by injection into the synovial fluid.
5. The method of claim 1, wherein a portion of the synovial fluid is removed prior to administering the formulation.
6. The method of claim 1, wherein the formulation further comprises at least one additional therapeutic agent.
7. The method of claim 6, wherein the additional therapeutic agent is selected from the group consisting of:
   i) a growth factor,
   ii) mesenchymal stem cells, adult stem cells and embryonic stem cells,
   iii) an MMP antagonist,
   iv) a monoclonal anti-TNFα antibody,
   v) rapamycin,
   vi) a COX-2 antagonist,
   vii) an antagonist of nitric oxide synthase,
   viii) an anti-oxidant,
   ix) an anti-proliferative agent,
   x) an anti-apoptotic agent,
   xi) a non-steroidal anti-inflammatory agent,
   xii) glycosaminoglycans,
   xiii) microparticles,
   xiv) a caspase inhibitor,
   xv) an inhibitor of pro-inflammatory interleukin, xvi) an inhibitor of PLA₂ viscosupplement,
xvii) tetracycline analogs, and
xviii) IGFI and II.

8. The method of claim 6, wherein the additional therapeutic agent is a non-steroidal anti-inflammatory agent.

9. The method of claim 8, wherein the non-steroidal anti-inflammatory agent is selected from the group consisting of rhein, diacerein, tolmetin, and tepoxalin.

10. The method of claim 1, wherein the administration comprises releasing the formulation from a sustained delivery device.

11. The method of claim 1, wherein the inflamed orthopedic joint is an inflamed sacro-iliac joint.

12. A method of treating a degenerative joint disease in an inflamed orthopedic joint in a human or an animal, said joint comprising: i) opposing hyaline cartilage articular surfaces; ii) peripheral to the surfaces, a central joint space comprising a collagenous capsule; and iii) synovial fluid contained within the joint space, the method comprising directly administering into the joint space by trans-capsular administration a formulation comprising an effective amount of a compound of one of the following structural formulas:

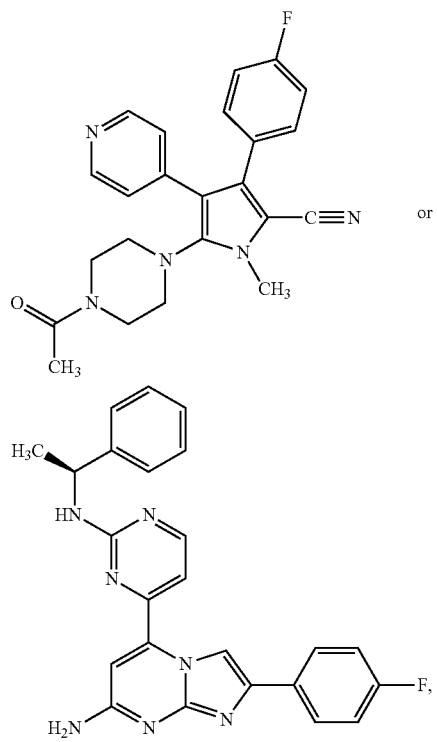

or a salt thereof.

* * * * *